United States Patent
Rogers et al.

(10) Patent No.: US 10,478,331 B2
(45) Date of Patent: Nov. 19, 2019

(54) SYSTEM, METHODS AND APPARATUS FOR DELIVERING NERVE STIMULATION TO A PATIENT WITH PHYSICIAN OVERSIGHT

(71) Applicant: Scion Neurostim, LLC, Raleigh, NC (US)

(72) Inventors: Lesco L. Rogers, Raleigh, NC (US); Lanty L. Smith, Raleigh, NC (US); Robert D. Black, Chapel Hill, NC (US)

(73) Assignee: Scion NeuroStim, LLC, Raleigh, NC (US)

( * ) Notice: Subject to any disclaimer, the term of this patent is extended or adjusted under 35 U.S.C. 154(b) by 169 days.

(21) Appl. No.: 15/379,612

(22) Filed: Dec. 15, 2016

(65) Prior Publication Data

US 2017/0135854 A1    May 18, 2017

Related U.S. Application Data

(63) Continuation of application No. 13/994,276, filed as application No. PCT/US2011/065456 on Dec. 16, 2011, now Pat. No. 9,526,653, which is a continuation-in-part of application No. 12/970,347, filed on Dec. 16, 2010, now Pat. No. 8,603,152, and a continuation-in-part of application No. 12/970,312, filed on Dec. 16, 2010, now Pat. No. 8,460,356.

(60) Provisional application No. 61/498,911, filed on Jun. 20, 2011, provisional application No. 61/498,943, filed on Jun. 20, 2011, provisional application No. 61/498,080, filed on Jun. 17, 2011, provisional application No. 61/498,096, filed on Jun. 17, 2011, provisional application No. 61/498,131, filed on Jun. 17, 2011, provisional application No. 61/497,761, filed on Jun. 16, 2011, provisional application No. 61/424,326, filed on Dec. 17, 2010, provisional application No. 61/424,474, filed on Dec. 17, 2010, provisional application No. 61/424,132, filed on Dec. 17, 2010.

(51) Int. Cl.
*A61B 18/18* (2006.01)
*A61F 7/00* (2006.01)
*A61F 7/12* (2006.01)
*A61F 7/02* (2006.01)

(52) U.S. Cl.
CPC ............... *A61F 7/007* (2013.01); *A61F 7/12* (2013.01); *A61F 2007/0005* (2013.01); *A61F 2007/0075* (2013.01); *A61F 2007/0093* (2013.01); *A61F 2007/0096* (2013.01); *A61F 2007/0295* (2013.01); *A61F 2007/0296* (2013.01)

(58) Field of Classification Search
CPC ...... A61F 2007/0005; A61F 2007/0075; A61F 2007/0093; A61F 2007/0096; A61F 2007/0295; A61F 2007/0296; A61F 7/007; A61F 7/12
See application file for complete search history.

(56) References Cited

U.S. PATENT DOCUMENTS

2009/0182399 A1*  7/2009  Sylvestre .................. A61F 7/12
                                                          607/99

* cited by examiner

*Primary Examiner* — Michael F Peffley
*Assistant Examiner* — Amanda L Zink
(74) *Attorney, Agent, or Firm* — Myers Bigel, P.A.

(57) ABSTRACT

The present invention provides devices, systems and methods for delivering one or more thermal waveforms to the vestibular system and/or the nervous system of a patient. In some embodiments, the present invention provides a vestibular stimulation device configured both to generate a prescription for delivering one or more thermal waveforms and to deliver the prescribed thermal waveforms.

20 Claims, 47 Drawing Sheets

Figure 6

SYSTEM, METHODS AND APPARATUS FOR DELIVERING NERVE STIMULATION TO A PATIENT WITH PHYSICIAN OVERSIGHT

RELATED APPLICATIONS

This application is a continuation of U.S. patent application Ser. No. 13/994,276, filed on Jul. 25, 2013, which is a is a 35 U.S.C. § 371 national phase entry of PCT Application No. PCT/US2011/065456, filed Dec. 16, 2011 and published in English on Jun. 21, 2012 as International Publication No. WO 2012/083151, which claims priority to U.S. Provisional Patent Application Nos. 61/424,474, filed Dec. 17, 2010; 61/498,131, filed Jun. 17, 2011; 61/497,761, filed Jun. 16, 2011; 61/424,132, filed Dec. 17, 2010; 61/498,096, filed Jun. 17, 2011; 61/424,326, filed Dec. 17, 2010; 61/498,080, filed Jun. 17, 2011; 61/498,911, filed Jun. 20, 2011 and 61/498,943, filed Jun. 20, 2011; PCT Application No. PCT/US2011/065456 is a continuation of U.S. patent application Ser. No. 12/970,312, filed Dec. 16, 2010 and Ser. No. 12/970,347, filed Dec. 16, 2010 and PCT Application No. PCT/US2011/065456 claims priority to PCT Application Nos. PCT/US2010/060764, filed Dec. 16, 2010 and PCT/US2010/060771, filed Dec. 16, 2010, the disclosure of each of which is incorporated herein by reference in its entirety.

FIELD OF THE INVENTION

The present invention concerns apparatuses and associated methods useful for delivering stimulation to the vestibular system and/or the nervous system of an individual, thereby inducing physiological changes in the individual and/or treating a disorder or symptom of the individual.

BACKGROUND

Caloric vestibular stimulation (CVS) has been widely and safely utilized for more than a century for diagnostic purposes, particularly in the emergency room to detect brain function after injury and in ear, nose and throat practice to assess balance.

CVS activates the sensory organs of the vestibular system located within the inner ear. The core elements consist of the semi-circular canals, which sense rotational motion, and the otoliths, which sense linear acceleration. Motion within the semi-circular canals is detected through motion of internal fluid (endolymph), which in turn activates hair cells that generate electrical signals, which are then transmitted via the 8th cranial nerve to the brainstem and widely throughout the cerebellum and cortical regions. In traditional CVS, irrigation of the external auditory canal (the ear canal) with warm or cold water/air changes the density of the endolymph in the semi-circular canal of the inner ear, which in turn activates the pathways noted above. Nystagmus, or the vestibulo-ocular reflex, is an easily observed result of CVS, wherein the eyes move spontaneously, even if the patient is unconscious.

There have been intriguing (but largely anecdotal) reports of using CVS as a therapeutic measure. Survey articles document a variety of outcomes and discuss some of the mechanisms involved (Miller et al., ACTA NEUROPSYCHIATRIA 19:183-203 (2007); Been, et al., BRAIN RES. REV. 56:346-36 (2007)). Squirting or blowing warm/cold water/air into a patient's ear, however, is crude, does not provide closely controlled thermal activity and is not consistent with medical dosing. Nevertheless, CVS is known to activate specific brainstem, cerebellar and cortical sites, which have therapeutic potential, as demonstrated through functional imaging (Bottini et al., EXP. BRAIN. RES. 99:164-169 (1994); Bense et al., ANN. N.Y. ACAD. SCI. 1004:440-445 (2003); Dieterich et al., BRAIN 131:2538-2552 (2008); Baier et al., HUM. BRAIN MAPPING (Sep. 2, 2009) [e-published ahead of print]; Naito et al., BRAIN 126 (2003)).

In addition, vestibular stimulation is also known to release important neurotransmitters (e.g., serotonin, acetylcholine, histamine, endorphins, vasopressin and dopamine) (Fu-rong et al., CHIN. MED. J. 120(2):120-124 (2007); Horii et al., J. NEUROPHYSIOL. 72:605-611 (1994); Tabet, AGE AND AGING 35:336-338 (2006); Horii et al., J. NEUROPHYSIOL. 70:1822-1826 (1993); Horii et al., BRAIN RES. 914:179-184 (2001)).

In contrast to both pharmaceutical treatment and neurostimulation devices which employ electrical signals, CVS appears to have an advantage: although nystagmus habituates with repetition of CVS (Naito et al., BRAIN 126 (2003), the vestibular neurological response appears not to be patient to such habituation or accommodation (Emani-Nouri, ACTA OTOLARYNGOLOGICA 76:183-189 (1973)). In addition, CVS does not have the same potential for side effects like a drug. Yet, CVS has not attained wide-spread use for therapeutic purposes. Hence, there remains a need for new ways to carry out CVS for therapeutic purposes.

SUMMARY OF THE INVENTION

A first aspect of the present invention is a vestibular stimulation device for delivering one or more thermal waveforms to the vestibular system and/or the nervous system of a patient. In some embodiments, the vestibular stimulation device comprises, consists essentially of or consists of an earpiece, a thermoelectric device (TED) and a controller, wherein said TED is thermally coupled to said earpiece and wherein said controller is operatively connected to said TED and is configured to activate said TED to deliver one or more thermal waveforms to the vestibular system and/or the nervous system of a patient (i.e., to activate the TED such that the earpiece is warmed and/or cooled so as to deliver the thermal waveform(s) to the vestibular system and/or the nervous system of the patient). In some such embodiments, the vestibular stimulation device further comprises a heat sink, and the TED is thermally coupled between the earpiece and the heat sink such that activation of the TED facilitates the transfer or heat between the earpiece and the heat sink. In some embodiments, the controller is configured to generate a prescription comprising a set of instructions for delivering one or more thermal waveforms to the vestibular system and/or the nervous system of a patient and to activate the TED to deliver the prescribed thermal waveform(s).

A second aspect of the present invention is a physician control device for generating and/or modifying the parameters, indications and/or approvals of one of more thermal waveforms; for generating, modifying, updating and/or extending one or more prescriptions and/or for receiving, analyzing and/or transmitting data. In some embodiments, the physician control device is configured to generate and/or modify the parameters, indications and/or approvals of one or more idealized thermal waveforms. In some embodiments, the physician control device is configured to generate a prescription comprising a set of instructions for delivering one or more thermal waveforms to the vestibular system and/or the nervous system of a patient. In some embodiments, the physician control device is configured to transmit the parameters, indications and/or approvals of one or more thermal waveforms to one or more vestibular stimulation devices and/or one or more patient control devices. In some embodiments, the physician control device is configured to transmit one or more prescriptions to one or more vestibular stimulation devices and/or one or more patient control devices. In some embodiments, the physician control device is configured to receive data from one or more vestibular stimulation devices and/or one or more patient control devices. In some embodiments, the physician control device is configured to transmit data to one or more physician support devices.

A third aspect of the present invention is a patient control device for receiving, analyzing and/or transmitting data. In some embodiments, the patient control device is configured to receive the parameters, indications and/or approvals of one or more thermal waveforms from a physician control device. In some embodiments, the patient control device is configured to transmit the parameters, indications and/or approvals of one or more thermal waveforms to one or more vestibular stimulation devices. In some embodiments, the patient control device is configured to receive a prescription comprising a set of instructions for delivering one or more thermal waveforms to the vestibular system and/or the nervous system of a patient from a physician control device. In some embodiments, the patient control device is configured to transmit a prescription comprising a set of instructions for delivering one or more thermal waveforms to the vestibular system and/or the nervous system of a patient to a vestibular stimulation device. In some embodiments, the patient control device is configured to receive data from one or more vestibular stimulation devices. In some embodiments, the physician control device is configured to transmit data to one or more physician control devices.

A fourth aspect of the present invention is a physician support device for generating and/or modifying the parameters, indications and/or approvals of one of more thermal waveforms; for generating, modifying, updating and/or extending one or more prescriptions and/or for receiving, analyzing and/or transmitting data. In some embodiments, the physician support device is configured to generate and/or modify the parameters, indications and/or approvals of one or more idealized thermal waveforms. In some embodiments, the physician support device is configured to generate a prescription comprising a set of instructions for delivering one or more thermal waveforms to the vestibular system and/or the nervous system of a patient. In some embodiments, the physician support device is configured to transmit the parameters, indications and/or approvals of one or more thermal waveforms to one or more vestibular stimulation devices, one or more patient control devices and/or one or more physician control devices. In some embodiments, the physician support device is configured to transmit one or more prescriptions to one or more vestibular stimulation devices, one or more patient control devices and/or one or more physician control devices. In some embodiments, the physician support device is configured to receive data from one or more vestibular stimulation devices, one or more patient control devices and/or one or more physician control devices.

A fifth aspect of the present invention is a registry for receiving, storing and/or transmitting data. In some embodiments, the registry is configured to receive data associated with the parameters, indications and/or approvals of one or more thermal waveforms (e.g., idealized thermal waveforms) from one or more vestibular stimulation devices, one or more patient control devices, one or more physician control devices and/or one or more physician support devices. In some embodiments, the registry is configured to transmit data associated the parameters, indications and/or approvals of one of more idealized thermal waveforms to one or more vestibular stimulation devices, one or more patient control devices, one or more physician control devices and/or one or more physician support devices.

A sixth aspect of the present invention is a telemedicine module for facilitating and/or controlling communications between vestibular stimulation devices, patient control devices, physician control devices and/or physician support devices. In some embodiments, the telemedicine module is configured to facilitate and/or control communications between a vestibular stimulation device, ad patient control device, a physician control device and/or a physician support device by ensuring that data is transmitted between the devices in a manner that complies with any and all applicable laws and/or regulations (e.g., the Health Insurance Portability and Accountability Act of 1996 (P.L. 104-191; "HIPAA")).

A seventh aspect of the present invention is a vestibular stimulation system for delivering one or more thermal waveforms to the vestibular system and/or the nervous system of a patient. In some embodiments, the vestibular stimulation system comprises a physician control device configured to generate a prescription comprising a set of instructions for delivering one or more thermal waveforms to the vestibular system and/or the nervous system of a patient and a vestibular stimulation device configured to deliver the prescribed thermal waveforms to the patient.

An eighth aspect of the present invention is a method of delivering one or more thermal waveforms to the vestibular system and/or the nervous system of a patient. In some embodiments, the method comprises generating a prescription comprising a set of instructions for delivering one or more thermal waveforms to the vestibular system and/or the nervous system of a patient and delivering the prescribed thermal waveform(s) to the patient using a vestibular stimulation device.

A ninth aspect of the present invention is a method of updating a waveform database. In some embodiments, the method comprises analyzing physician feedback data and modifying one or more thermal waveforms in the waveform database responsive to analyzing the physician feedback data.

The foregoing and other objects and aspects of the present invention are explained in greater detail in the drawings herein and the specification set forth below. All patent references cited herein are specifically intended to be incorporated herein by reference in their entirety.

BRIEF DESCRIPTION OF THE DRAWINGS

FIGS. 2-12 are screenshots illustrating various functionalities of a controller according to some embodiments of the present invention, wherein the controller comprises an interactive touchscreen.

FIG. 2 depicts a startup screen wherein the current time is shown in the upper right-hand corner of the screen.

FIG. 3 depicts a waveform module screen wherein the user has generated a thermal waveform by drawing the desired waveform on the interactive touch screen and wherein the waveform module has identified fourteen waveform modulation points (gray diamonds).

FIG. 4 depicts a waveform module screen wherein the thermal waveform depicted in FIG. 3 has been modified by selecting the third waveform modulation point of the thermal waveform and moving it to a higher temperature.

FIG. 5 depicts a treatment module screen that enables a user to provide instructions as to how many days are to be in a treatment schedule and how many treatments may be administered per day.

FIG. 6 depicts a treatment module screen that enables a user to authorize delivery of one or more prescribed thermal waveform(s) during one or more specified time periods by touching an available treatment window (represented by a grey rectangle with a black dash in its center) and then providing instructions as to which thermal waveform(s) is/are to be delivered during that treatment window (as shown in FIGS. 7-8) and instructions as to when the treatment window is to begin and end (as shown in FIG. 9).

FIG. 7 depicts a treatment module screen that enables a user to provide instructions to apply an idealized thermal waveform to the ear canal of a patient by touching the circular selection indicator to the right of the desired waveform.

FIG. 8 depicts a treatment module screen that enables a user to provide instructions to apply the selected thermal waveform to the left or right ear canal of a patient by touching the upper or lower graph, respectively.

FIG. 9 depicts a treatment module screen that enables a user to provide instructions as to when a given treatment window is to begin and end (i.e., to provide instructions as to the window of time in which one or more prescribed thermal waveforms may be administered to a patient).

FIG. 10 depicts a treatment module screen that enables a user to modify a treatment schedule by editing and/or copying previously established treatment sessions (e.g., by changing which thermal waveform(s) are to be delivered during a given treatment session (as shown in FIGS. 7-8), by changing the start and/or end time for one or more treatment sessions (as shown in FIG. 9), by deleting one or more treatment sessions, etc.).

FIG. 11 depicts a control module screen wherein a thermal waveform delivered to the left ear canal and a thermal waveform being delivered to the right ear canal of a patient are graphically represented, with the current progress of each waveform represented by the changing of the depicted waveform from light gray to dark grey (i.e., the elapsed time is represented by the dark gray portion of each waveform and the time remaining is represented by the light gray portion of each waveform), and wherein the user may stop the treatment session by touching the "X" in the lower left-hand corner of the screen.

FIG. 12 depicts a password protection screen.

DETAILED DESCRIPTION

Figure 1:
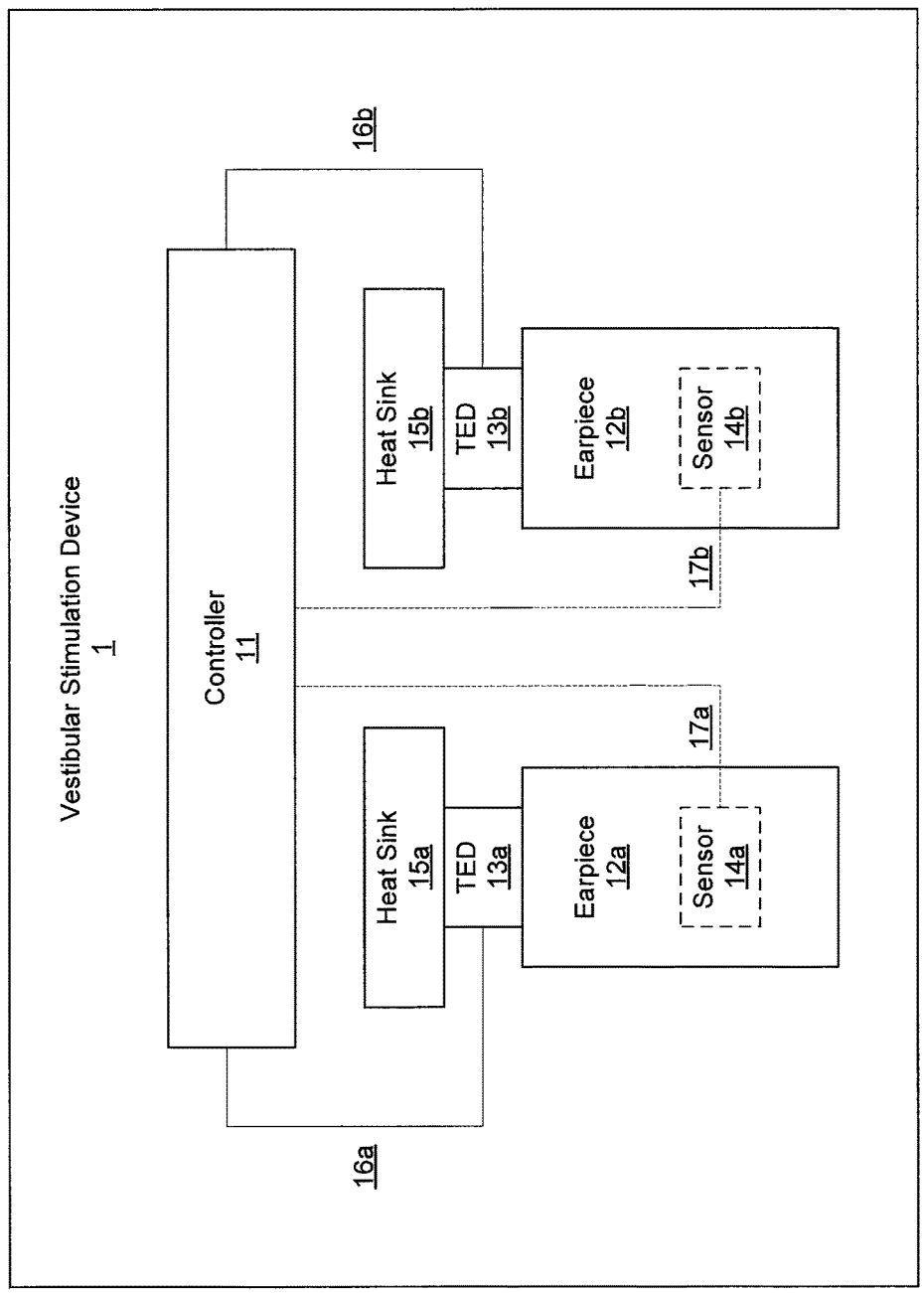
FIG. 1 is a block diagram of a vestibular stimulation device according to some embodiments of the present invention.
Figure 2:
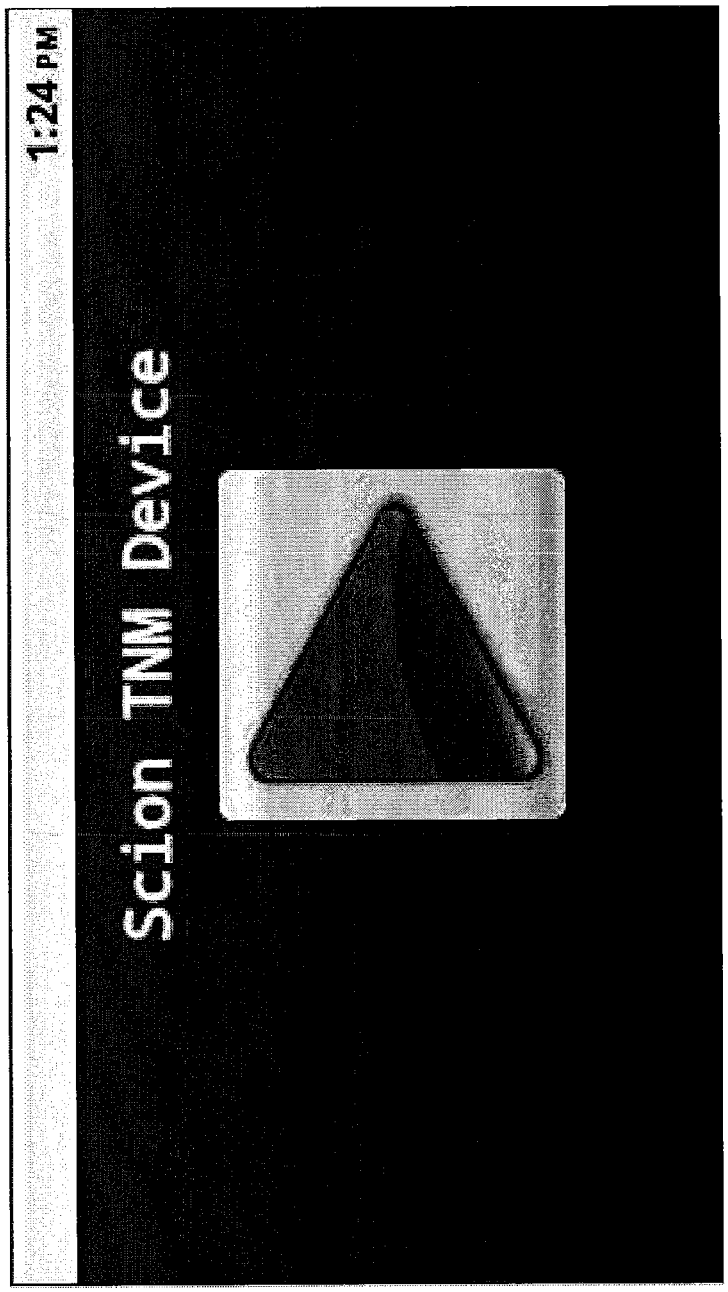

The present invention is explained in greater detail below. This description is not intended to be a detailed catalog of all the different ways in which the invention may be implemented or of all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein, which do not depart from the instant invention, will be apparent to those skilled in the art in light of the instant disclosure. Hence, the following specification is intended to illustrate some particular embodiments of the invention, and not to exhaustively specify all permutations, combinations and variations thereof.

It will be understood that when an element or layer is referred to as being "on", "attached to", "connected to", "coupled to", "coupled with" or "contacting" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. It will also be appreciated by those of skill in the art that references to a structure or feature that is disposed "adjacent" another structure or feature may have portions that overlap or underlie the adjacent structure or feature.

The present invention is described below with reference to block diagrams and/or flowchart illustrations of methods, systems and/or computer program products according to embodiments of the invention.

It is understood that various blocks of the block diagrams and/or flowchart illustrations, and combinations of blocks in the block diagrams and/or flowchart illustrations, can be implemented by computer program instructions. These computer program instructions may be provided to a processor of a general purpose computer, special purpose computer and/or other programmable data processing apparatus to produce a machine, such that the instructions, which execute via the processor of the computer or other programmable data processing apparatus, create means for implementing the functions/acts specified in the block diagrams and/or flowchart illustrations. The computer program instructions may also be stored in a computer-readable memory that can direct a computer or other programmable data processing apparatus to function in a particular manner, such that the instructions stored in the computer-readable memory produce an article of manufacture including instructions which implement the function/act specified in the block diagram and/or flowchart illustrations. The computer program instructions may also be loaded onto a computer or other programmable data processing apparatus to cause a series of operational steps to be performed on the computer or other programmable data processing apparatus to produce a computer-implemented process such that the instructions which execute on the computer or other programmable data processing apparatus provide steps for implementing the functions/acts specified in the block diagrams and/or flowchart illustrations.

Accordingly, the present invention may be embodied in hardware and/or software (including firmware, resident software, micro-code, etc.). Furthermore, embodiments of the present invention may take the form of a computer program product on a computer-usable or computer-readable non-transient storage medium having computer-usable or computer-readable program code embodied in the medium for use by or in connection with an instruction execution system. In the context of this document, a computer usable or computer-readable non-transient storage medium may be any medium that can contain and/or store the program for use by or in connection with the instruction execution system, apparatus or device. For example, the computer-usable or computer-readable medium may be an electronic, optical, electromagnetic, infrared or semiconductor system, apparatus or device.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

As used herein, the terms "actively controlled waveform" and "actively controlled, time-varying thermal waveform" refer to a thermal waveform in which the intensity and/or the directionality of the activation signal used to deliver the thermal waveform and/or the temperature of the earpiece used to deliver the thermal waveform is repeatedly adjusted (e.g., continuously adjusted or substantially continuously adjusted) during delivery of the thermal waveform. For example, the activation signal driving the TED(s) used to deliver the thermal waveform may be continuously adjusted in response to feedback data from one or more sensors (e.g., a temperature sensor configured to sense the temperature of the earpiece with which the TED(s) is/are associated). Such active control may be used to minimize errors in the delivery of a prescribed thermal waveform (e.g., by minimizing thermal drift, which may otherwise allow the patient's body temperature to adversely affect the accuracy).

As used herein, the term "adjuvant treatment" refers to a treatment session in which the delivery of one or more thermal waveforms to the vestibular system and/or the nervous system of a patient modifies the effect(s) of one or more active agents and/or therapies. For example, the delivery of one or more thermal waveforms to the vestibular system and/or the nervous system of a patient may enhance the effectiveness of a pharmaceutical agent (by restoring the therapeutic efficacy of a drug to which the patient had previously become habituated, for example). Likewise, the delivery of one or more thermal waveforms to the vestibular system and/or the nervous system of a patient may enhance the effectiveness of counseling or psychotherapy. In some embodiments, delivery of one or more thermal waveforms to the vestibular system and/or the nervous system of a patient may reduce or eliminate the need for one or more active agents and/or therapies. Adjuvant treatments may be effectuated by delivering one or more thermal waveforms to the vestibular system and/or the nervous system of a patient prior to, currently with and/or after administration of one or more active agents and/or therapies.

As used herein, the term "and/or" includes any and all combinations of one or more of the associated listed items.

As used herein, the terms "chronic treatment," "chronically treating" and the like refer to a therapeutic treatment carried out at least once per week (e.g., two or three times per week, daily, etc.) over an extended period of time. Chronic treatment typically lasts at least one to two weeks (and, in some embodiments, at least one to two months), but may last as long as required to achieve and/or maintain therapeutic efficacy for the particular condition or disorder for which the treatment is carried out (i.e., the device may be used periodically throughout the patient's life).

As used herein, the term "controller feedback data" refers to data that is transmitted to the controller by one or more TEDs and/or one or more sensors and is used by the controller to verify the accuracy of the thermal waveform(s) being delivered, to modulate the activation of one or more TEDs so as to deliver the appropriate thermal waveform(s) and/or to enable the controller to activate safety precautions in the event of a system failure. For example, controller feedback data may comprise data associated with the temperature of an earpiece, wherein said data is used to verify that the appropriate temperature is being delivered to the ear canal of a patient, to enable the controller to increase/decrease the activation of one or more TEDs to ensure that the appropriate temperature is delivered to the ear canal of a patient and/or to trigger a system shutdown if the temperature of the earpiece drops below a low temperature threshold (e.g., about 10 degrees Centigrade) or exceeds a high temperature threshold (e.g., about 50 degrees Centigrade). Likewise, controller feedback data may comprise data associated with the temperature of a heat sink that is thermally coupled to one or more TEDs, wherein said data is used to trigger a system shutdown if the temperature of the heat sink exceeds a high temperature threshold (e.g., about 50 degrees Centigrade).

As used herein, the term "data associated with the delivery of one or more thermal waveforms" refers to information associated with the delivery of one or more thermal waveforms and may include, but is not limited to, data associated with the target time/temperature parameters of the thermal waveform(s), the time/temperature parameters of the thermal waveform(s) delivered; the date/time of delivery of the thermal waveform(s), the temperature of the patient's ear canal(s) at various time points before, during and/or after delivery of the thermal waveform(s); the temperature of the patient's inner ear(s) at various time points before, during and/or after delivery of the thermal waveform(s); the fit of the earpiece(s) at various time points before, during and/or after delivery of the thermal waveform(s); an estimate of the thermal contact between the earpiece(s) and the patient's ear canal(s) at various time points before, during and/or after delivery of the thermal waveform(s); patient-specific time constants (e.g., a time constant associated with the transduction of heat from the ear canal to the inner ear); reaction time (i.e., how long it took for the patient to react to the thermal waveform(s)); effectiveness of the thermal waveform(s) (e.g., whether and to what extent symptoms were relieved, whether the thermal waveform(s) enhanced the effectiveness of another agent/therapy, etc.); stability of the treatment (i.e., how long the effects of the treatment lasted); instability of the treatment (i.e., which condition(s) and/or symptom(s) returned and when did it/they return); the presence or absence of comorbid disorders, injuries and/or diseases; disorder, injury and/or disease modulation(s) and/or other modification(s) that occurred as a result of treatment; the cognitive effect(s) of one or more thermal waveforms; patient compliance (e.g., whether the patient initiated delivery at the prescribed time, whether the patient completed the prescribed treatment session, whether the earpiece(s) remained properly fitted in the patient's ear canal(s) for the duration of the treatment session, etc.); the mood of the patient before, during and/or after his/her treatment session(s) (e.g., videos/images of a patient that may be used to assess mood); objectives measures of efficacy (e.g., nystamography data, EEG data, MRI data, heart rate data, blood pressure data); subjective measures of efficacy (e.g., a patient-reported pain score); blood chemistry data (e.g., blood A1c levels, blood glucose levels and blood cortisol levels); saliva chemistry data (e.g., saliva cortisol levels); urine chemistry data (e.g., urine cortisol levels)) and comments the patient made about his/her treatment session(s) (e.g., comments made to a physician, submitted in response to an automated survey and/or recorded in a treatment diary). In some embodiments, data associated with the delivery of one or more thermal waveforms comprises controller feedback data, patient feedback data and/or physician feedback data. In some embodiments, data associated with the delivery of one or more thermal waveforms comprises, consists essentially of or consists of data associated with the precise time/temperature parameters of the thermal waveform(s) delivered to the patient and a subjective measure of efficacy (e.g., a patient-reported pain score).

As used herein, the term "data associated with the fit of the earpiece(s)" may include, but is not limited to, data associated with the impedance between an earpiece inserted into the ear canal of a patient and an electrode affixed to a second location on/in said patient's body (e.g., an electrode placed in or adjacent to the patient's other ear canal), data associated with the rate at which the ear canal and/or the inner ear cooled in response to a cooling stimulus (e.g., data from a temperature sensor, such as thermistor, that monitors how quickly the ear canal and/or the inner ear cools in response to a cooling waveform), data associated with the rate at which the ear canal and/or the inner ear warmed in response to a warming stimulus (e.g., data from a temperature sensor, such as a thermistor, that monitors how quickly the ear canal and/or the inner ear warms in response to a warming waveform) and patient comments regarding the subjective fit of the earpiece(s). In some embodiments, data associated with the fit of the earpiece(s) comprises, consists essentially or consists of data associated with the impedance between an earpiece inserted into the right ear canal of a patient and an earpiece inserted into the left ear canal of said patient.

As used herein, the terms "idealized thermal waveform" and "idealized waveform" refer to a thermal waveform that has been indicated and/or approved for use in the treatment of one or more diseases/disorders/injuries and/or for use in the provision of neuroprotection, enhanced cognition and/or increased cognitive reserve. For example, a thermal waveform may be indicated for use in the treatment of migraines if it has effectively treated migraines in the past or if it belongs to a class of thermal waveforms that are known to treat migraines. Likewise, a thermal waveform may be approved for use in the treatment of a given disorder if it has received regulatory approval (e.g. FDA approval) for such use, or if it belongs to a class of thermal waveforms that have been approved for the treatment of that disorder. An idealized thermal waveform may be indicated/approved for use in the treatment of multiple diseases/disorders/injuries.

As used herein, the term "patient" refers to both human subjects and animal subjects, including, but not limited to, mice, rats, rabbits, cats, dogs, pigs, horses, monkeys, apes, etc. The patient may be male or female. That patient may be of any suitable age, including infant, juvenile, adolescent, adult and geriatric ages. In some embodiments, the methods, devices and systems of the present invention may be used to induce physiological and/or psychological responses in a patient for medically diagnostic and/or therapeutic purposes. For example, the methods, devices and systems of the present invention may be used to diagnose and/or treat mammalian subjects, such as mice, rats, pigs and monkeys, for medical research or veterinary purposes.

As used herein, the term "patient information" refers to data associated with one or more patients. Patient information may comprise, but is not limited to, information related to a patient's identity, a patient's cognitive abilities, a patient's medical history, a patient's current symptoms (if any), a patient's present diagnosis (if any), a patient's current prescriptions (if any) and data associated with the delivery of one or more thermal waveforms to the vestibular system and/or the nervous system of a patient.

As used herein, the term "patient feedback data" refers to data associated with patient feedback regarding the delivery of one or more thermal waveforms. Patient feedback data may comprise, but is not limited to, a patient's evaluation of their pain level before, during and/or after delivery of the thermal waveform(s) (e.g., patient-reported pain scores given before, during and after a treatment session) and patient comments (e.g., comments regarding a patient's opinion as to the efficacy of a given waveform or the effect(s) of certain waveform modifications, etc.).

As used herein, the term "physician feedback data" refers to data associated with physician feedback regarding the delivery of one or more thermal waveforms. Physician feedback data may comprise, but is not limited to, patient information from the patient history database of one or more physician control devices and comments from one or more physicians (e.g., comments regarding a physician's opinion as to the efficacy of a given waveform or the effect(s) of certain waveform modifications, etc.).

As used herein, the terms "prescription" and "prescription protocol" refer to a set of instructions and/or limitations associated with stimulation of the vestibular system and/or the nervous system of a patient. In some embodiments, a prescription comprises, consists essentially of or consists of a set of instructions for delivering of one or more thermal waveforms (e.g., one or more actively controlled, time-varying thermal waveforms) to the vestibular system and/or the nervous system of a patient (e.g., by warming and/or cooling an earpiece positioned in the ear canal of the patient). A prescription may comprise a set of instructions for delivering one or more thermal waveforms to the left vestibular system of a patient (by delivering one or more thermal waveforms to the left ear canal of the patient) and/or a set of instructions for delivering one or more thermal waveforms to the right vestibular system of a patient (by delivering one or more thermal waveforms to the left ear canal of the patient) (i.e., one prescription may comprise instructions for stimulating both the right and left vestibular systems). A prescription may comprise any suitable instructions and/or limitations, including, but not limited to, the parameters of the waveform(s) to be delivered to the patient, the number and frequency of treatment sessions (e.g., X treatment sessions over Y time period), a limitation as to how many treatment sessions may be administered during a given time period (e.g., no more than X treatment sessions within Y time period), instructions as to which thermal waveform(s) will be administered during a given treatment session (and in what order they are to be administered), instructions as to which vestibular system will receive a given waveform (e.g., right, left or both) and an expiration date. In some embodiments, a prescription comprises instructions for delivering a placebo (i.e., for fooling a patient into believing one or more thermal waveforms has been delivered even though no such deliver has occurred). In some embodiments, the prescription is generated by a physician. Any conventional security means may be provided to prevent unauthorized modification of the prescription (e.g., the prescription may be password protected, with only the prescribing physician having knowledge of and/or access to the password).

As used herein, the terms "treatment," "treat," and "treating" refer to reversing, alleviating, reducing the severity of, delaying the onset of, inhibiting the progress of or preventing a disease or disorder as described herein, or at least one symptom of a disease or disorder as described herein (e.g., treating one or more of tremors, bradykinesia, rigidity or postural instability associated with Parkinson's disease; treating one or more of intrusive symptoms (e.g., dissociative states, flashbacks, intrusive emotions, intrusive memories, nightmares, and night terrors), avoidant symptoms (e.g., avoiding emotions, avoiding relationships, avoiding responsibility for others, avoiding situations reminiscent of the traumatic event) or hyperarousal symptoms (e.g., exaggerated startle reaction, explosive outbursts, extreme vigilance, irritability, panic symptoms, sleep disturbance) associated with post-traumatic stress disorder). In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved—for example, to prevent or delay their recurrence. Treatment may comprise providing neuroprotection, enhancing cognition and/or increasing cognitive reserve. Treatment may be as an adjuvant treatment as further described herein.

The present invention may be used to treat a patient for any reason. In some embodiments, the present invention is used to treat one or more disorders. Disorders for which treatment may be carried out include, but are not limited to, headaches, depression, anxiety (e.g., as experienced in post-traumatic stress disorder ("PTSD") or other anxiety disorders), dementia, spatial neglect, Parkinson's disease, seizures (e.g., epileptic seizures) and diabetes (e.g., type II diabetes).

Additional disorders and conditions that can be treated by the methods and systems of the present invention include, but are not limited to, tinnitus, neuropathic pain (e.g., migraine headaches), brain injury (acute brain injury, excitotoxic brain injury, traumatic brain injury, etc.), spinal cord injury, body image or integrity disorders (e.g., spatial neglect), visual intrusive imagery, neuropsychiatric disorders (e.g., depression), bipolar disorder, neurodegenerative disorders (e.g., Parkinson's disease), asthma, dementia, insomnia, stroke, cellular ischemia, metabolic disorders, (e.g., diabetes), PTSD, addictive disorders, sensory disorders, motor disorders, and cognitive disorders.

Headaches that may be treated by the methods and apparatuses of the present invention include, but are not limited to, primary headaches (e.g., migraine headaches, tension-type headaches, trigeminal autonomic cephalagias and other primary headaches, such as cough headaches and exertional headaches) and secondary headaches. See, e.g., International Headache Society Classification ICHD-II.

Migraine headaches that may be treated by the methods and apparatuses of the present invention may be acute/episodic/chronic and unilateral/bilateral. The migraine headache may be of any type, including, but not limited to, migraine with aura, migraine without aura, hemiplegic migraine, opthalmoplegic migraine, retinal migraine, basilar artery migraine, abdominal migraine, vestibular migraine and probable migraine. As used herein, the term "vestibular migraine" refers to migraine with associated vestibular symptoms, including, but not limited to, head motion intolerance, unsteadiness, dizziness and vertigo. Vestibular migraine includes, but is not limited to, those conditions sometimes referred to as vertigo with migraine, migraine-associated dizziness, migraine-related vestibulopathy, migrainous vertigo and migraine-related vertigo. See, e.g., Teggi et al., HEADACHE 49:435-444 (2009).

Tension-type headaches that may be treated by the methods and apparatuses of the present invention, include, but are not limited to, infrequent episodic tension-type headaches, frequent episodic tension-type headaches, chronic tension-type headache and probable tension-type headache.

Trigeminal autonomic cephalagias that may be treated by the methods and apparatuses of the present invention, include, but are not limited to, cluster headaches, paroxysmal hemicranias, short-lasting unilateral neuralgiform headache attacks with conjunctival injection and tearing and probable trigeminal autonomic cephalagias. Cluster headache, sometimes referred to as "suicide headache," is considered different from migraine headache. Cluster headache is a neurological disease that involves, as its most prominent feature, an immense degree of pain. "Cluster" refers to the tendency of these headaches to occur periodically, with active periods interrupted by spontaneous remissions. The cause of the disease is currently unknown. Cluster headaches affect approximately 0.1% of the population, and men are more commonly affected than women (in contrast to migraine headache, where women are more commonly affected than men).

Other primary headaches that may be treated by the methods and apparatuses of the present invention, include, but are not limited to, primary cough headache, primary exertional headache, primary headache associated with sexual activity, hypnic headache, primary thunderclap headache, hemicranias continua and new daily-persistent headache. Sensory disorders that may be treated by the methods and apparatuses of the present invention include, but are not limited to, vertigo, dizziness, seasickness, travel sickness cybersickness, sensory processing disorder, hyperacusis, fibromyalgia, neuropathic pain (including, but not limited to, complex regional pain syndrome, phantom limb pain, thalamic pain syndrome, craniofacial pain, cranial neuropathy, autonomic neuropathy, and peripheral neuropathy (including, but not limited to, entrapment-, heredity-, acute inflammatory-, diabetes-, alcoholism-, industrial toxin-, Leprosy-, Epstein Barr Virus-, liver disease-, ischemia-, and drug-induced neuropathy)), numbness, hemianesthesia, and nerve/root plexus disorders (including, but not limited to, traumatic radiculopathies, neoplastic radiculopathies, vaculitis, and radiation plexopathy).

Motor disorders that may be treated by the method and apparatuses of the present invention include, but are not limited to, upper motor neuron disorders such as spastic paraplegia, lower motor neuron disorders such as spinal muscular atrophy and bulbar palsy, combined upper and lower motor neuron syndromes such as familial amyotrophic lateral sclerosis and primary lateral sclerosis, and movement disorders (including, but not limited to, Parkinson's disease, tremor, dystonia, Tourette Syndrome, myoclonus, chorea, nystagmus, spasticity, agraphia, dysgraphia, alien limb syndrome, and drug-induced movement disorders).

Cognitive disorders that may be treated by the method and apparatuses of the present invention include, but are not limited to, schizophrenia, addiction, anxiety disorders, depression, bipolar disorder, dementia, insomnia, narcolepsy, autism, Alzheimer's disease, anomia, aphasia, dysphasia, parosmia, spatial neglect, attention deficit hyperactivity disorder, obsessive compulsive disorder, eating disorders, body image disorders, body integrity disorders, post-traumatic stress disorder, intrusive imagery disorders, and mutism.

Metabolic disorders that may be treated by the present invention include diabetes (particularly type II diabetes), hypertension, obesity, etc.

Addiction, addictive disorders, or addictive behavior that may be treated by the present invention includes, but is not limited to, alcohol addiction, tobacco or nicotine addiction (e.g., using the present invention as a smoking cessation aid), drug addictions (e.g., opiates, oxycontin, amphetamines, etc.), food addictions (compulsive eating disorders), etc.

In some embodiments, the patient has two or more of the above conditions, and both conditions are treated concurrently with the methods and systems of the invention. For example, a patient with both depression and anxiety (e.g., PTSD) can be treated for both disorders, concurrently, with the methods and systems of the present invention.

As used herein, the term "vestibular system" has the meaning ascribed to it in the medical arts and includes, but is not limited to, those portions of the inner ear known as the vestibular apparatus and the vestibulocochlear nerve. The vestibular system, therefore, further includes, but is not limited to, those parts of the brain that process signals from the vestibulocochlear nerve.

As used herein, the terms "waveform," "waveform stimulus" and "thermal waveform" refer to a thermal stimulus (heating and/or cooling) delivered to the ear canal of a patient. "Waveform" is not to be confused with "frequency," the latter term concerning the rate of delivery of a particular waveform. The term "waveform" is used herein to refer to one complete cycle thereof, unless additional cycles (of the same, or different, waveform) are indicated. As discussed further below, time-varying thermal waveforms are preferred over square waveforms in carrying out the present invention.

In general, a waveform of the present invention comprises a leading edge, a peak, and a trailing edge.

The waveform leading edge is preferably ramped or time-varying: that is, the amplitude of the waveform increases through a plurality of different temperature points over time (e.g., at least 5, 10, or 15 or more distinct temperature points, and in some embodiments at least 50, 100, or 150 or more distinct temperature points, from start to peak). The shape of the leading edge may be a linear ramp, a curved ramp (e.g., convex or concave; logarithmic or exponential), or a combination thereof. A vertical cut may be included in the waveform leading edge, so long as the remaining portion of the leading edge progresses through a plurality of different temperature points over time as noted above.

The peak of the waveform represents the amplitude of the waveform as compared to the patient's body temperature. In general, an amplitude of at least 5 or 7 degrees Centigrade is preferred for both heating and cooling waveform stimulation. In general, an amplitude of up to 25 degrees Centigrade is preferred for cooling waveform stimulation (e.g., 15 degrees Centigrade). In general, an amplitude of up to 8 or 10 degrees Centigrade is preferred for heating waveform stimulus (e.g., 6 degrees Centigrade). The peak of the waveform may be truncated (that is, the waveform may reach an extended temperature plateau), as long as the desired characteristics of the leading edge, and preferably trailing edge, are retained. For heating waveforms, truncated peaks of long duration (that is, maximum heat for a long duration) are less preferred, particularly at higher heats, because of the potential that the patient may experience a burning sensation.

The waveform trailing edge is preferably ramped or time-varying: that is, the amplitude of the waveform decreases through a plurality of different temperature points over time (e.g., at least 5, 10, or 15 or more distinct temperature points, or in some embodiments at least 50, 100, or 150 or more distinct temperature points, from peak to trough). The shape of the trailing edge may be a linear ramp, a curved ramp (e.g., convex or concave; logarithmic or exponential), or a combination thereof. A vertical cut may again be included in the waveform trailing edge, as long as the remaining portion of the trailing edge progresses through a plurality of different temperature points over time as noted above.

The duration of a waveform (or the frequency of that waveform stimulus) is the time from the onset of the leading edge to either the conclusion of the trailing edge or (in the case of a vertically cut waveform) the onset of a subsequent waveform. In general, each waveform has a duration, or frequency, of from one or two minutes up to ten or twenty minutes.

If a first waveform is followed by a second waveform, the minimal stimulus point therebetween (i.e., the point of minimal heating or minimal cooling) is referred to as a trough. Like a peak, the trough may be truncated, as long as the desired characteristics of the trailing edge and the following leading edge are retained. While the trough may represent a return to the patient's current body temperature, in some embodiments minor thermal stimulation (e.g., cooling or heating by 1 or 2 degrees up to 4 or 5 degrees Centigrade) may continue to be applied at the trough (or through a truncated trough).

In a treatment session, a plurality of waveforms may be delivered in sequence. In general, a treatment session will comprise 1, 2 or 3 waveforms, up to about 10 or 20 or more waveforms delivered sequentially. Each individual waveform may be the same, or different, from the other waveform(s).

The first waveform of a treatment session is initiated at a start point, which start point may be at or about the patient's body temperature at the time the treatment session is initiated (typically a range of about 34 to 38 degrees Centigrade, around a normal body temperature of about 37 degrees Centigrade. The lower point, 34, is due to the coolness of the ear canal in comparison with the rest of the body. It typically will not be above about 37 unless the patient is febrile). Note that, while the patient's ear canal may be slightly less than body temperature (e.g., about 34 to 36 degrees Centigrade), the starting temperature for the waveform is typically body temperature (the temperature of the inner ear), or about 37 degrees Centigrade. In some embodiments, however, the temperature of the treatment device may not have equilibrated with the ear canal prior to the start of the treatment session, and in such case the start point for at least the first waveform may be at a value closer to room temperature (normally bout 23 to 26 degrees Centigrade).

A treatment session may have a total duration of five or ten minutes, up to 20 or 40 minutes or more, depending on factors such as the specific waveform or waveforms delivered, the patient, the condition being treated, the benefit being sought, etc. In some embodiments, a treatment session may comprise one or more breaks (i.e., periods wherein no CVS is given). For example, a treatment session may comprise multiple stimulation periods with a break between each stimulation period and may have a total duration of 60 minutes or more.

Treatment sessions are preferably once a day, though in some embodiments more frequent treatment sessions (e.g., two or three times a day or more) may be employed. Day-to-day treatments may be by any suitable schedule: every day, every other day, twice a week, as needed by the patient, etc. The overall pattern of treatment is thus typically chronic (in contrast to "acute," as used in one-time experimental studies).

Vestibular Stimulation Device

As noted above, the present invention provides a vestibular stimulation device for delivering one or more thermal waveforms to the vestibular system and/or the nervous system of a patient. The vestibular stimulation device may be configured to deliver any suitable thermal waveform or combination of thermal waveforms, including, but not limited to, those described in U.S. Provisional Patent Application Nos. 61/424,132, 61/498,096, 61/424,326, 61/498,080, 61/498,911 and 61/498,943, the disclosure of each of which is incorporated herein by reference in its entirety. In some embodiments, the vestibular stimulation device is configured to deliver one or more actively controlled, time-varying thermal waveforms to the vestibular system and/or the nervous system of a patient.

In some embodiments, the vestibular stimulation device is configured to generate a prescription comprising a set of instructions for delivering one or more thermal waveforms to the vestibular system and/or the nervous system of a patient and to deliver the prescribed thermal waveform(s) to the vestibular system and/or the nervous system of said patient.

In some embodiments, the vestibular stimulation device comprises, consists essentially of or consists of an earpiece, a TED and a controller, wherein said TED is thermally coupled to said earpiece and wherein said controller is operatively connected to said TED. The controller may be configured to activate said TED to deliver one or more thermal waveforms to the vestibular system and/or the nervous system of a patient (i.e., to activate the TED such that the earpiece is warmed and/or cooled so as to deliver the thermal waveform(s) to the vestibular system and/or the nervous system of the patient). In some embodiments, the controller is configured to generate a prescription comprising a set of instructions for delivering one or more thermal waveforms to the vestibular system and/or the nervous system of a patient and to activate the TED to deliver the prescribed thermal waveform(s).

In some embodiments, the vestibular stimulation device comprises, consists essentially of or consists of an earpiece, a plurality of TEDs and a controller, wherein each of said plurality of TEDs is thermally coupled to said earpiece and wherein said controller is operatively connected to each of said plurality of TEDs. The controller may be configured to selectively and separately activate each of said plurality of TEDs to deliver one or more thermal waveforms to the vestibular system and/or the nervous system of a patient (i.e., to activate one or more of the TEDs such that the earpiece is warmed and/or cooled so as to deliver the thermal waveform(s) to the vestibular system and/or the nervous system of the patient). In some embodiments, the controller is configured to generate a prescription comprising a set of instructions for delivering one or more thermal waveforms to the vestibular system and/or the nervous system of a patient and to activate the TEDs to deliver the prescribed thermal waveform(s).

In some embodiments, the vestibular stimulation device comprises, consists essentially of or consists of a pair of earpieces, a pair of TEDs and a controller, wherein one earpiece is configured so as to be insertable into the left ear canal of a patient and the other earpiece is configured so as to be insertable into the right canal of the patient, wherein one TED is thermally coupled to each earpiece and wherein said controller is operatively connected to each TED. The controller may be configured to selectively and separately activate each of said TEDs to deliver one or more thermal waveforms to the vestibular system and/or the nervous system of the patient. In some embodiments, the controller is configured to generate a prescription comprising a set of instructions for delivering one or more thermal waveforms to the vestibular system and/or the nervous system of the patient and to activate the TEDs to deliver the prescribed thermal waveform(s).

In some embodiments, the vestibular stimulation device comprises, consists essentially of or consists of a pair of earpieces, a plurality of TEDs and a controller, wherein one earpiece is configured so as to be insertable into the left ear canal of a patient and the other earpiece is configured so as to be insertable into the right canal of the patient, wherein at least one of said plurality of TEDs is thermally coupled to each earpiece and wherein said controller is operatively connected to each TED. The controller may be configured to selectively and separately activate each of said TEDs to deliver one or more thermal waveforms to the vestibular system and/or the nervous system of the patient. In some embodiments, the controller is configured to generate a prescription comprising a set of instructions for delivering one or more thermal waveforms to the vestibular system and/or the nervous system of the patient and to activate the TEDs to deliver the prescribed thermal waveform(s).

The vestibular stimulation device may comprise one or more heat sinks. In some embodiments, at least one heat sink is thermally coupled to each earpiece. In some embodiments, each TED thermally coupled to an earpiece is thermally coupled between the earpiece and at least one heat sink.

The vestibular stimulation device may comprise one or more sensors. In some embodiments, the sensor(s) is/are configured to provide feedback data to the controller. In some such embodiments, the controller is configured (e.g., with computer instructions (i.e., software)) to adjust one or more attributes of TED activation (e.g., magnitude, duration, wave pattern, etc.) in response to feedback data received from the sensor(s) with which it is associated. For example, the vestibular stimulation device may be configured such that, during delivery of a thermal waveform, the controller activates the TED(s) in a continuous or substantially continuous manner and repeatedly, continuously or substantially continuously adjusts one or more attributes of TED activation in response to feedback data received from one or more sensors (e.g., a temperature sensor configured to provide feedback data associated with the temperature of the ear canal of a patient).

The vestibular stimulation device may comprise a headband. In some embodiments, the headband is configured to position the earpiece(s) in the ear canal(s) of a patient.

As shown in FIG. 1, in some embodiments, the vestibular stimulation device 1 comprises a controller 11, a pair of earpieces 12a, 12b, a pair of TEDs 13a, 13b and a pair of heat sinks 15a, 15b, wherein one TED 13a is thermally connected between one heat sink 15a and an earpiece 12a that is configured so as to be insertable into the left ear canal of a patient, wherein the other TED 13b is thermally connected between the a heat sink 15b and an earpiece 12b that is configured so as to be insertable into the right ear canal of a patient and wherein the controller 11 is operatively connected to each of the TEDs 13a, 13b by a thermal stimulation conductive line 16a, 16b. In some such embodiments, each earpiece 12a, 12b is operatively connected to a sensor 14a, 14b (e.g., each earpiece may be thermally connected to a temperature sensor that is configured to detect the temperature of the earpiece), and each of the sensors 14a, 14b is operatively connected to the controller 11 by a wireless connection 17a, 17b (using a radiofrequency transceiver or a Bluetooth connection, for example).

Controller

Any suitable controller can be used to carry out the present invention, including, but not limited to, those described in U.S. Patent Publication Nos. 2010/0198204 and 2010/0198282; in U.S. patent application Ser. No. 12/970,312 and Ser. No. 12/970,347 and in U.S. Provisional Application Nos. 61/497,761, the disclosure of each of which is incorporated herein by reference in its entirety.

The controller may be configured to activate at least one TED. In some embodiments, the controller is configured to activate at least one TED to deliver one or more thermal waveforms to the vestibular system and/or the nervous system of a patient (e.g., by heating and/or cooling the earpiece(s) that is/are thermally coupled to the TED. For example, the controller may be configured to activate the TED(s) based upon a prescription comprising a set of instructions for delivering one or more thermal waveforms to the vestibular system and/or the nervous system of a patient (i.e., the controller may be configured to activate the TED(s) so as to deliver the prescribed thermal waveform(s) to the vestibular system and/or the nervous system of the patient).

The controller may be configured to selectively and separately activate a plurality of TEDs. For example, the controller may be configured to selectively and separately activate the TED(s) thermally coupled to an earpiece inserted into the left ear canal of a patient and the TED(s) thermally coupled to an earpiece inserted into the right ear canal of a patient (e.g., to deliver a thermal waveform only to the left ear canal of the patient, to deliver a thermal waveform only to right ear canal of the patient or to simultaneously deliver different thermal waveforms to the left and right ear canals of the patient). Likewise, the controller may be configured to separately activate a plurality of TEDs thermally coupled to a single earpiece.

The controller may be configured to activate the TED(s) in any suitable manner, including, but not limited to, activation with direct current and/or electrical pulses. In some embodiments, the controller is configured to activate the TED(s) in a continuous or substantially continuous manner, adjusting one or more parameters of TED activation (e.g., magnitude, duration, pulse width, etc.) to deliver the desired thermal stimulus. For example, the controller may be configured such that it continuously or substantially continuously activates each of the TEDs with which it is operatively connected and delivers different thermal stimuli by modulating the type and/or level of activation applied to each TED.

The controller may be configured to activate the TED(s) to deliver any suitable thermal waveform or combination of thermal waveforms, including, but not limited to, those described in U.S. Provisional Patent Application Nos. 61/424,132, 61/498,096, 61/424,326, 61/498,080, 61/498,911 and 61/498,943, the disclosure of each of which is incorporated herein by reference in its entirety. In some embodiments, the controller is configured to activate the TED(s) to deliver one or more actively controlled, time-varying thermal waveforms to the vestibular system and/or the nervous system of a patient.

The controller may also be configured to activate the TED(s) to deliver a constant thermal stimulus to the ear canal(s) of a patient. For example, the controller may be configured to activate the TED(s) so as to maintain the temperature of a patient's ear canal at a target temperature (e.g., to hold a patient's right canal at 20 degrees Centigrade while a thermal waveform is delivered to the patient's left canal).

The controller may likewise be configured to deliver one or more placebo waveforms (i.e., to fool a patient into believing one or more thermal waveforms has been delivered even though no such delivery has occurred).

In some embodiments, the controller is operatively connected to at least one TED via a thermal stimulation conductive line. In those embodiments wherein the controller is operatively connected to a plurality of TEDs, the controller may be operatively connected to each TED via a separate thermal stimulation conductive line. In some such embodiments, each of the plurality of separate thermal stimulation conductive lines is bundled together into one or more thermal stimulation leads (e.g., the thermal stimulation conductive lines connected to the TED(s) thermally coupled to the right earpiece may be bundled separately from the thermal stimulation conductive lines connected to the TED(s) thermally coupled to the left earpiece). In some such embodiments, each thermal stimulation lead is connected to the controller via a lead interface (e.g., one or more thermal stimulation leads may be connected to the controller using an 18-pin connector).

In some embodiments, the controller is operatively connected to at least one TED via a wireless connection (using a radiofrequency transceiver or a Bluetooth connection, for example).

The controller may be configured to receive and/or transmit any suitable data, including, but not limited to, data associated with the parameters, indications and/or approvals of one or more thermal waveforms, data associated with one or more prescriptions, controller feedback data, data associated with the delivery of one or more thermal waveforms, data associated with the fit of one or more earpieces, physician feedback data and/or patient information.

The controller may be configured to receive and/or transmit data from/to various devices, including, but not limited to, a patient control device, a physician control device, a physician support device, a registry, a TED, a sensor and/or a portable memory device (e.g., an SD memory card). In some embodiments, the controller is configured to receive data associated with the parameters, indications and/or approvals of one or more thermal waveforms (e.g., idealized thermal waveforms) from a patient control device, a physician control device, a physician support device, a registry and/or a portable memory device (e.g., an SD memory card); to receive one or more prescriptions from a patient control device, a physician control device, a physician support device, a registry and/or a portable memory device (e.g., an SD memory card); to receive controller feedback data from one or more TEDs and/or one or more sensors; to receive data associated with the delivery of one or more thermal waveforms (e.g., idealized thermal waveforms) from one or more TEDs and/or one or more sensors; to transmit data associated with the delivery of one or more thermal waveforms (e.g., idealized thermal waveforms) to a patient control device, a physician control device, a physician support device, a registry and/or a portable memory device (e.g., an SD memory card); to transmit patient feedback data to a physician support device, a registry and/or a portable memory device (e.g., an SD memory card) and/or to transmit patient information to a physician control device, a physician support device, a registry and/or a portable memory device (e.g., an SD memory card).

The controller may be configured to receive and/or transmit data over any suitable wired or wireless communications channel, including, but not limited to, a LAN, the Internet, a public telephone switching network, Bluetooth, WLAN and the like.

In some embodiments, the controller comprises memory, a processor and a power supply. As will be appreciated by one of skill in the art, the processor may be any commercially available or custom microprocessor. Memory can include, but is not limited to, the following types of devices: cache, ROM, PROM, EPROM, EEPROM, flash memory, SRAM and DRAM. The power supply may be an internal power supply (e.g., one or more rechargeable batteries that may be recharged without first being removed from the controller).

The controller's memory may comprise any suitable software and/or data, including, but not limited to, an operating system, applications, data and input/output (I/O) drivers.

As will be appreciated by one of skill in the art, the controller may use any suitable operating system, including, but not limited to, OS/2, AIX, OS/390 or System390 from International Business Machines Corp. (Armonk, N.Y.), Window CE, Windows NT, Windows95, Windows98, Windows2000, Windows 7 or Windows Vista from Microsoft Corp. (Redmond, Wash.), Mac OS from Apple, Inc. (Cupertino, Calif.), Unix, Linux or Android.

As will be appreciated by one of skill in the art, the controller may comprise any suitable application, including, but not limited to, one or more programs configured to implement one or more of the various features of the present invention. For example, the controller may comprise a waveform module that enables a user to generate and/or modify the parameters, indications and/or approvals of one or more thermal waveforms; a treatment module that enables a user to generate, modify, update and/or extend a prescription comprising a set of instructions for delivering one or more thermal waveforms to the vestibular system and/or the nervous system of a patient; a control module configured to activate one or more TEDs; a network module configured to receive and/or transmit data; a GUI module configured to display information and/or accept user input; a feedback module configured to receive, transmit, and/or analyze controller feedback data, data associated with the delivery of one or more thermal waveforms, data associated with the fit of one or more earpieces, physician feedback data and/or patient information; an alert generation module configured to generate one or more alert messages; a tone generation module configured to produce one or more audible tones; a visual indicator module configured to produce one or more visual indicators; an impedance module configured to detect and/or monitor the impedance between an earpiece inserted into the ear canal of a patient and an electrode affixed to a second location on/in said patient's body, a security module configured to prevent unauthorized use of the controller and/or a safety module configured to deactivate the controller in the event of a system malfunction and/or failure. In some embodiments, two or more of the aforementioned modules are combined to form a single module configured to carry out the function(s) of each of the individual modules (e.g., the controller may comprise a waveform-treatment module that enables a user to generate and/or modify one or more thermal waveforms and to generate, modify, update and/or extend a prescription). In some embodiments, one of the aforementioned modules is split into two or more distinct modules (e.g., the controller may comprise a waveform generation module that enables a user to generate the parameters, indications and/or approvals of one or more thermal waveforms and a waveform update module that enables a user to modify the parameters, indications and/or approvals of one or more thermal waveforms). In some embodiments, one or more of the functions described below with respect to one of the modules described below is performed by one of the other modules described below (e.g., the control module, rather than the feedback module, may be configured to receive/analyze controller feedback data).

Waveform Module

In some embodiments, the controller comprises a waveform module whereby a user may generate and/or modify the parameters, indications and/or approvals of one or more thermal waveforms.

In some embodiments, the waveform module comprises software that enables a user to generate and/or modify the parameters of one or more thermal waveforms by point-to-point design and/or by utilizing mathematical functions. For example, the waveform module may comprise software that enables a user to generate and/or modify the parameters, indications and/or approvals of a thermal waveform by selecting/altering one or more parameters, including, but not limited to, shape, frequency, amplitude and duration. In some embodiments, the waveform module enables a user to retrieve/select a thermal waveform from a database and then modify the parameters of that thermal waveform to generate a new thermal waveform.

Figure 3:
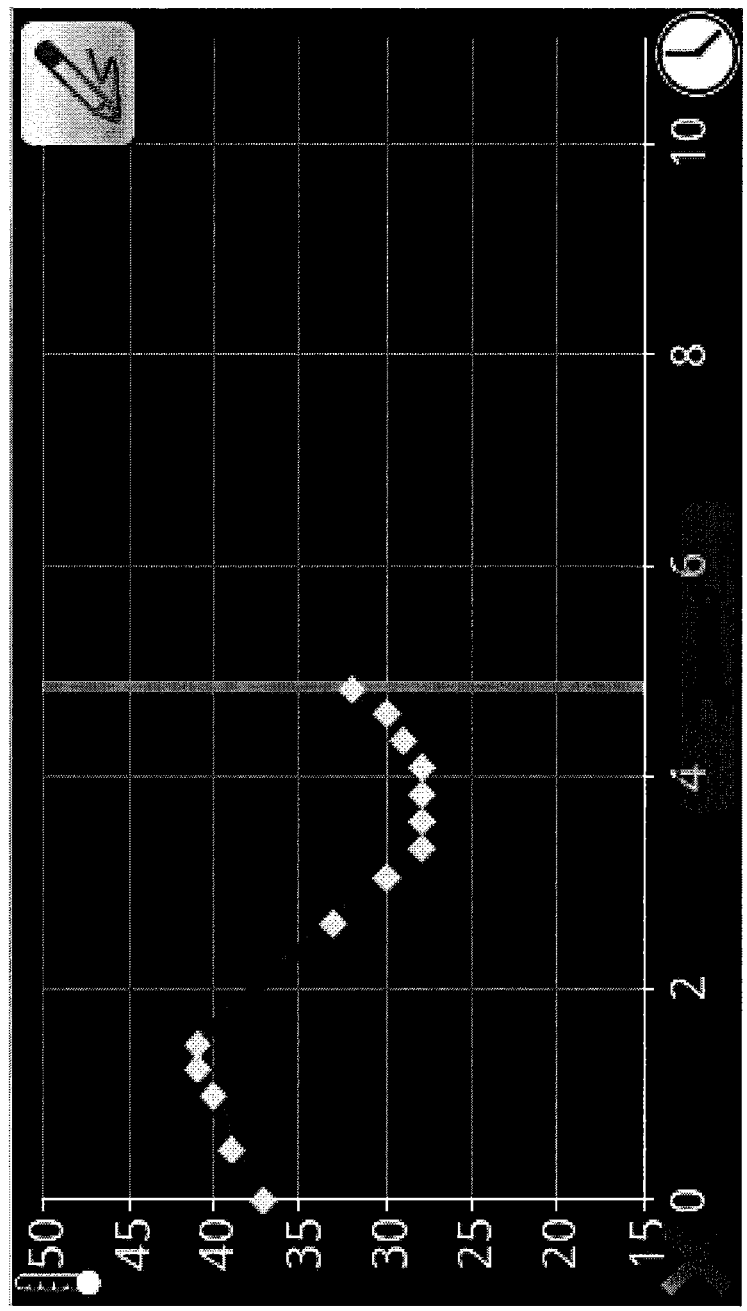
Figure 4:
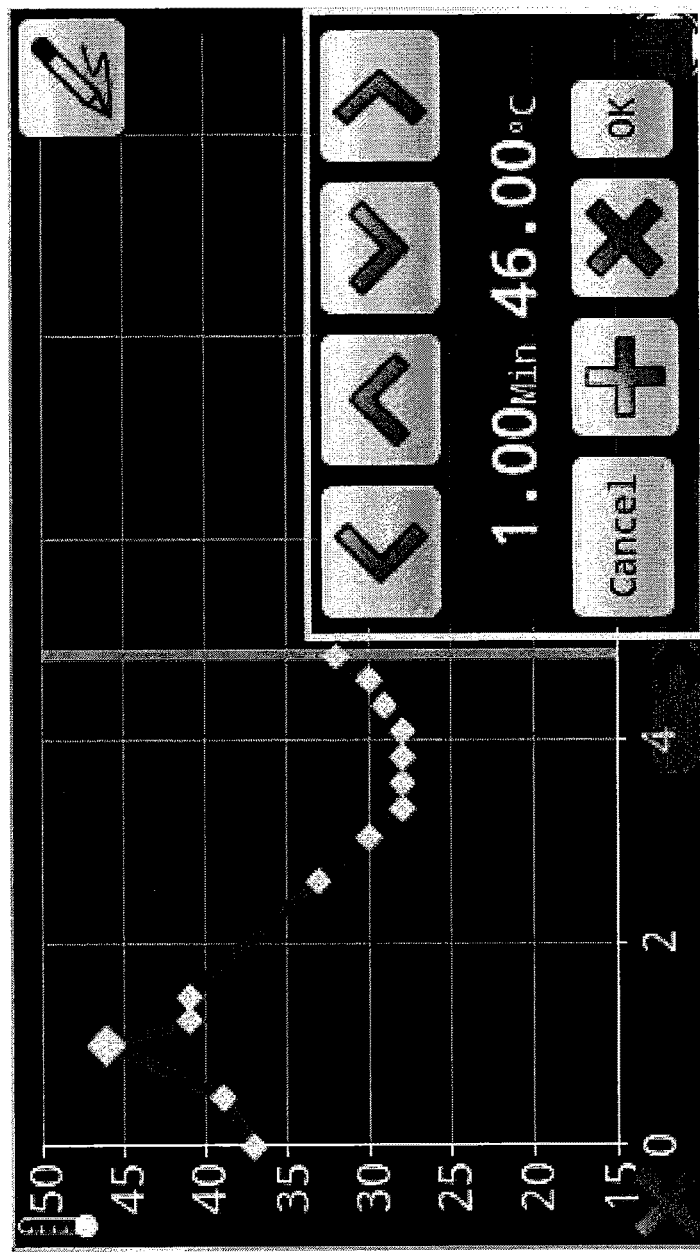

In some embodiments, the waveform module comprises software that enables a user to generate and/or modify the parameters, indications and/or approvals of one or more thermal waveforms using an interactive touch screen. For example, the waveform module may comprise software that enables a user to generate the parameters of a thermal waveform by drawing the desired waveform on an interactive touch screen (FIG. 3). Similarly, the waveform module may enable a user to modify the parameters of a thermal waveform by highlighting one or more points on the waveform and moving the point(s) to a new location (e.g., a higher/lower temperature) (FIG. 4).

In some embodiments, the waveform module comprises software that automatically adjusts the parameters of the thermal waveform(s) created by a user to account for system limitations. For example, the waveform module may comprise software that automatically adjusts the slope of a thermal waveform in accordance with the minimum/maximum temperature and/or the rate of temperature change that is achievable using a particular combination of earpiece(s), TED(s), etc. That is, the waveform module may comprise software that prevents a user from generating parameters for a thermal waveform that cannot be delivered because of system limitations.

In some embodiments, the waveform module comprises software that enables a user to protect one or more thermal waveforms (i.e., to prevent one or more users from modifying the parameters, indications and/or approvals of the thermal waveform(s) and/or from deleting the thermal waveform(s) from a waveform database). For example, the waveform module may comprise software that enables a user to protect one or more idealized thermal waveforms (e.g., by requiring users to enter a specified password prior to modifying and/or deleting the idealized thermal waveform(s)).

In some embodiments, the waveform module comprises software that enables a user to remove the protected status from one or more thermal waveforms. For example, the waveform module may comprise software that enables a user to remove the protected status from one or more idealized thermal waveforms (e.g., by entering the appropriate password).

In some embodiments, the waveform module is configured to automatically generate and/or modify the parameters, indications and/or approvals of one or more thermal waveforms (e.g., idealized thermal waveforms) in response to data received from one or more devices/modules. For example, the waveform module may be configured to automatically update one or more thermal waveforms responsive to data received from one or more TEDs and/or one or more sensors.

The waveform module may be configured to retrieve the parameters, indications and/or approvals of one or more thermal waveforms from any suitable database, including, but not limited to, a waveform database residing in the controller, a waveform database residing in a patient control device, a waveform database residing in a physician control device, a waveform database residing in a physician support device, a waveform database residing in a registry and/or a waveform database residing in a portable memory device (e.g., an SD memory card).

Waveform parameters, indications and/or approvals generated and/or modified by the waveform module may be stored in a database. In some embodiments, the generated/modified parameters, indications and/or approvals are stored in a waveform database comprising data associated with the parameters, indications and/or approvals of one or more thermal waveforms (e.g., idealized thermal waveforms). For example, the generated/modified waveform parameters, indications and/or approvals may be stored in a waveform database residing in the controller, a waveform database residing in a patient control device, a waveform database residing in a physician control device, a waveform database residing in a physician support device, a waveform database residing in a registry and/or a waveform database residing in a portable memory device (e.g., an SD memory card).

B. Treatment Module

In some embodiments, the controller comprises a treatment module whereby a user (e.g., a physician) may generate, modify, update and/or extend a prescription. For example, the treatment module may enable a user to generate, modify, update and/or extend a prescription comprising a set of instructions for delivering one or more thermal waveforms to the vestibular system and/or the nervous system of a patient.

Figure 5:
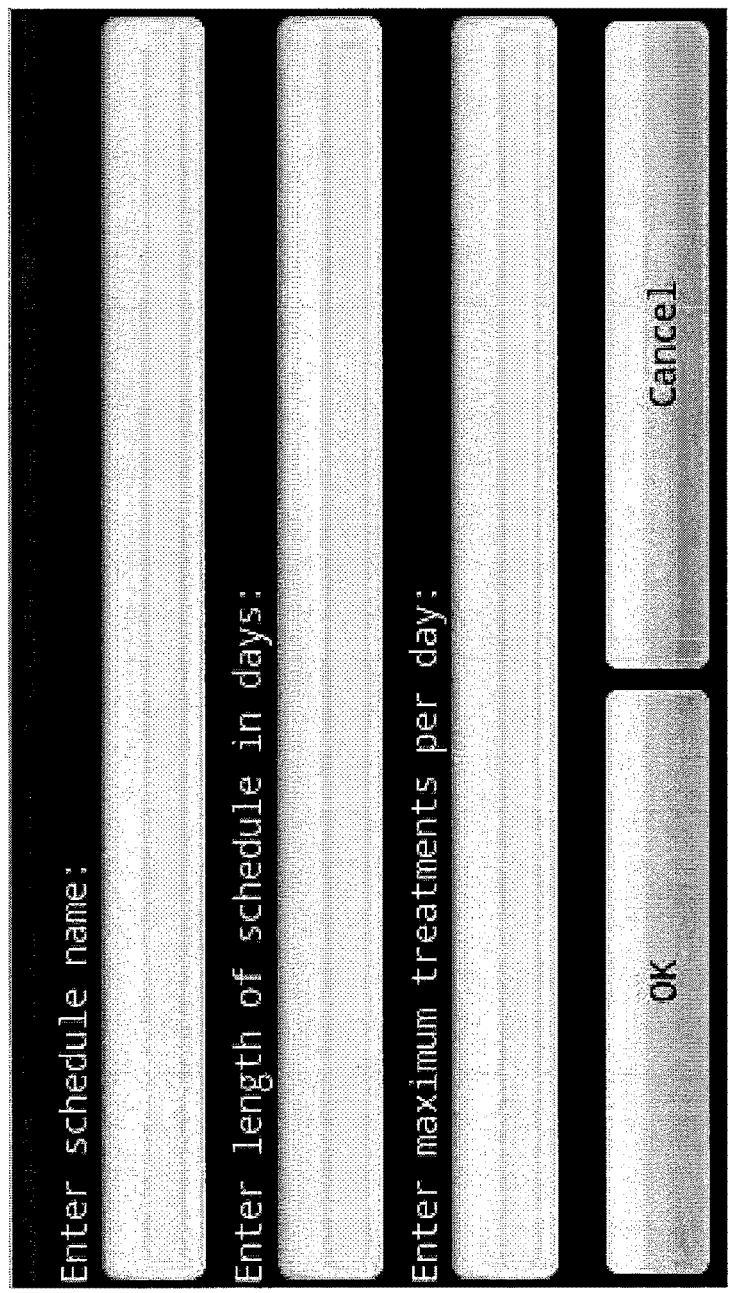
Figure 6:
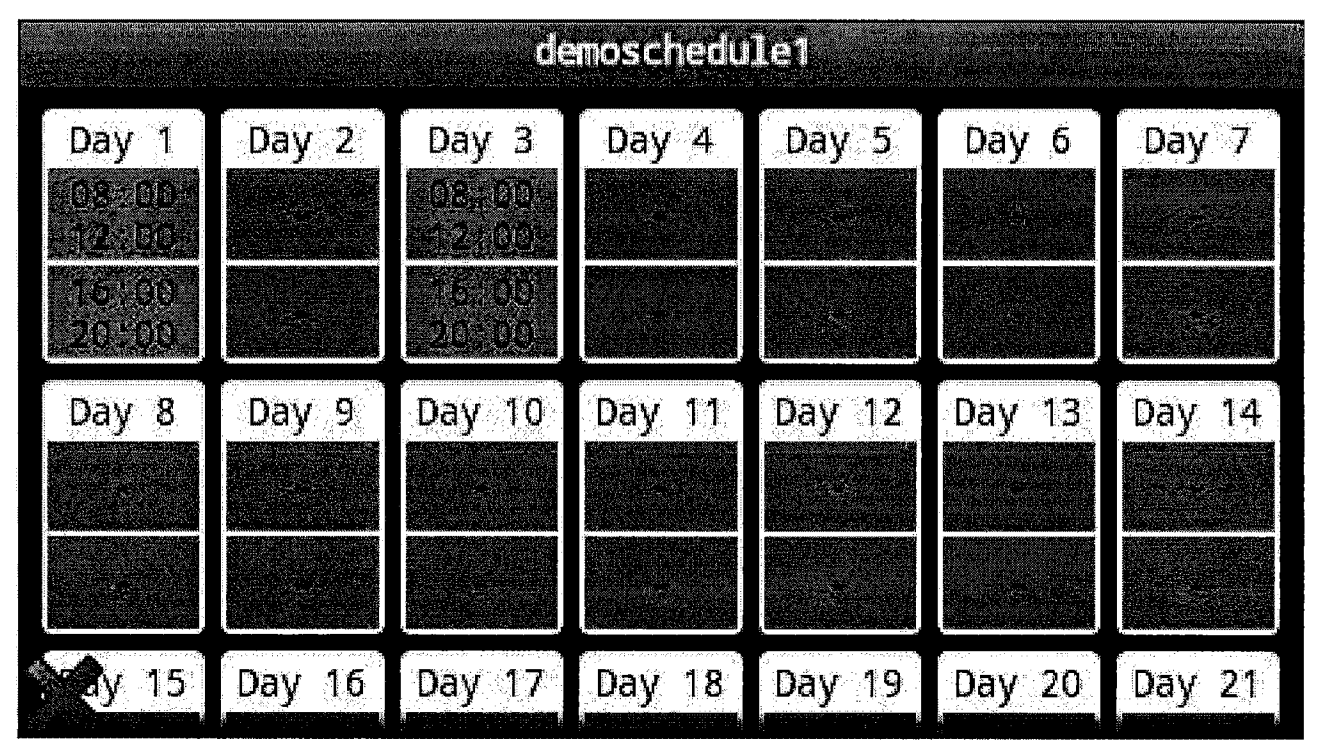
Figure 7:
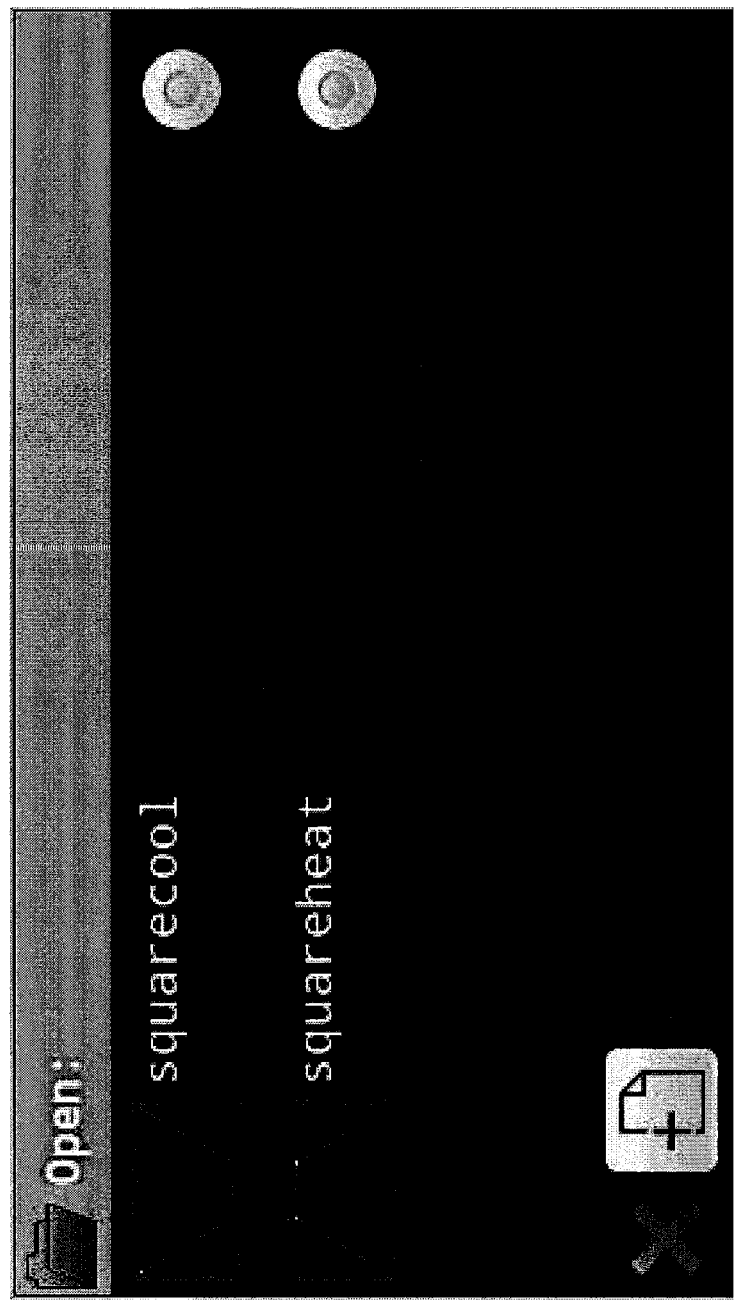
Figure 8:
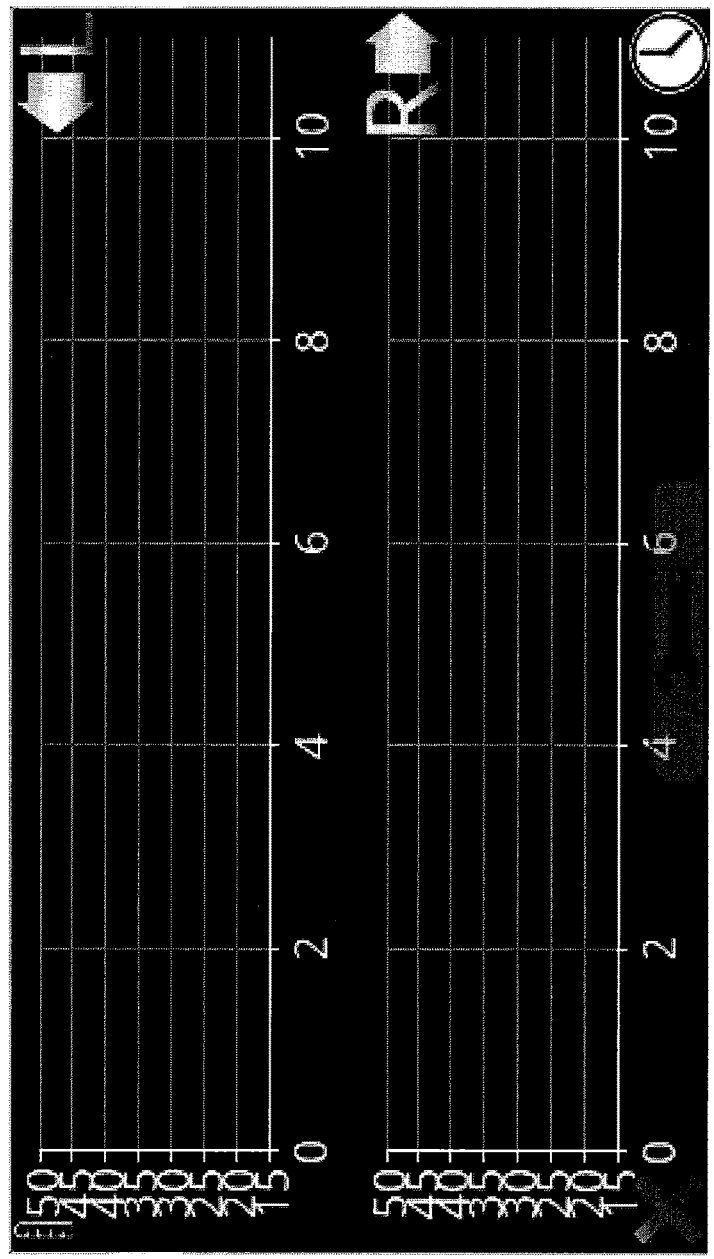
Figure 9:
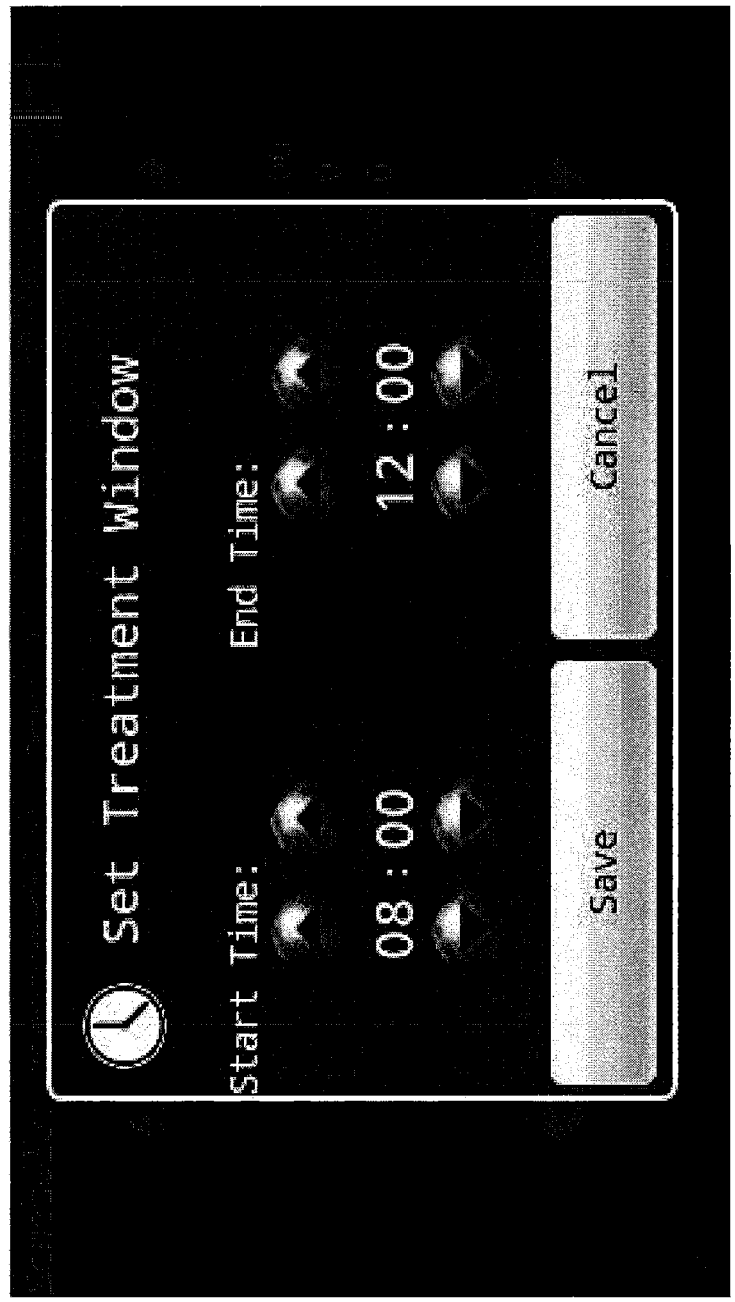

In some embodiments, the treatment module comprises software that enables a user to select one or more thermal waveforms from a database (e.g., an idealized thermal waveform from an idealized waveform database) and to provide instructions as to when/how each of those waveforms should be administered. For example, a treatment module may comprise software that enables a user to provide instructions as to how long a treatment schedule is to last (FIG. 5), to provide instructions as to how many treatments may be administered each day (FIG. 5), to provide instructions as to how often each thermal waveform is to be administered (FIG. 6), to provide instructions as to what time(s) of day each thermal waveform is to be administered (FIGS. 6 and 9), to select one or more idealized thermal waveforms from a database (FIG. 7), to provide instructions regarding whether each of the selected thermal waveforms is to be delivered to the right and/or left ear canal of a patient (FIG. 8), etc.

Figure 10:
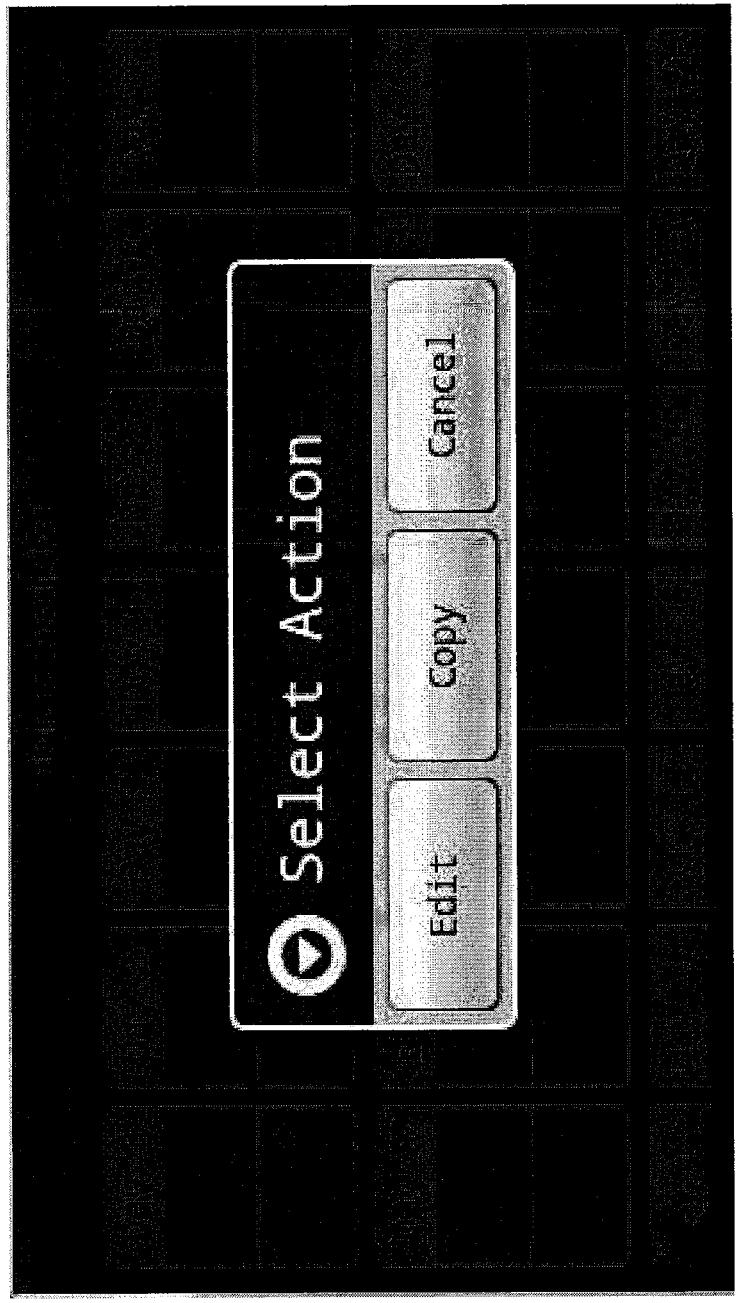

In some embodiments, the treatment module comprises software that enables a user to modify, update and/or extend a prescription by changing one or more parameters of the prescription (FIG. 10), including, but not limited to, which thermal waveform(s) are delivered, frequency with which the thermal waveform(s) is/are delivered, and the expiration date of the prescription. Any suitable prescription may be modified, updated and/or extended, including, but not limited to, prescriptions stored in a prescription database (e.g., a prescription database residing in the controller, in a patient control device, in a physician control device, in a physician support device, in a registry or in a portable memory device, such as a portable SD memory card).

The treatment module may be configured to retrieve/select thermal waveforms from any suitable database, including, but not limited to, a waveform database residing in the controller, a waveform database residing in a patient control device, a waveform database residing in a physician control device, a waveform database residing in a physician support device, a waveform database residing in a registry and/or a waveform database residing in a portable memory device (e.g., an SD memory card).

The treatment module may be configured to retrieve prescriptions from any suitable database, including, but not limited to, a prescription database residing in the controller, a prescription database residing in a patient control device, a prescription database residing in a physician control device, a prescription database residing in a physician support device, a prescription database residing in a registry and/or a prescription database residing in a portable memory device (e.g., an SD memory card).

Prescriptions generated, modified, updated and/or extended by the treatment module may be added to a database comprising one or more prescriptions. For example, the prescriptions may be stored in a prescription database residing in the controller, a prescription database residing in a patient control device, a prescription database residing in a physician control device, a prescription database residing in a physician support device, a prescription database residing in a registry and/or a prescription database residing in a portable memory device.

C. Control Module

In some embodiments, the controller comprises a control module configured to activate at least one TED (i.e., to control the magnitude, duration, waveform and other attributes of stimulation delivered by the at least one TED). The control module may be configured to activate the TED(s) to deliver any suitable thermal waveform or combination of thermal waveforms, including, but not limited to, those described in U.S. Provisional Patent Application Nos. 61/424,132, 61/498,096, 61/424,326, 61/498,080, 61/498,911 and 61/498,943, the disclosure of each of which is incorporated herein by reference in its entirety.

In some embodiments, the control module is configured to selectively and separately activate a plurality of TEDs (e.g., by activating only one of said plurality of TEDs, by heating one TED and cooling another, by sequentially activating the TEDs, by activating different TEDs using different temperature/timing parameters, combinations of some or all of the foregoing, etc.).

In some embodiments, the control module is configured to activate the TED(s) based upon a prescription. For example, the control module may be configured to activate one or more TEDs based upon a prescription comprising a set of instructions for delivering one or more thermal waveforms to the vestibular system and/or the nervous system of a patient.

In some embodiments, the control module is configured to receive and/or retrieve instructions for delivering a thermal waveform from a database. For example, the control may be configured to receive and/or retrieve a prescription comprising a set of instructions for delivering one or more thermal waveforms to the vestibular system and/or the nervous system of a patient from a prescription database residing in the controller, from a prescription database residing in a patient control device, from a prescription database residing in a physician control device, from a prescription database residing in a physician support device, from a prescription database residing in a registry and/or from a prescription database residing in a portable memory device (e.g., an SD memory card).

In some embodiments, the control module is configured to adjust one or more attributes of TED activation (e.g., magnitude, duration, wave pattern, etc.) in response to controller feedback data received from one or more TEDs and/or one or more sensors. For example, the control module may be configured to increase/decrease the magnitude of TED activation in response to controller feedback data indicating that an earpiece that is thermally coupled to the TED has not yet reached a target temperature (e.g., the control module may be configured to increase the current flowing through the TED in response to controller feedback data indicating that the temperature of the earpiece has not yet dropped to the target temperature in response to a cooling waveform).

D. Network Module

In some embodiments, the controller comprises a network module configured to receive, retrieve and/or transmit data.

The network module may be configured to receive, retrieve and/or transmit data from/to any suitable device/module/database, including, but not limited to, other modules residing in the controller, databases residing in the controller, a patient control device, a physician control device, a physician support device, a registry, a TED, a sensor and a portable memory device (e.g., an SD memory card).

The network module may be configured to receive, retrieve and/or transmit data over any suitable wired or wireless communications channel, including, but not limited to, a LAN, the Internet, a public telephone switching network, Bluetooth, WLAN and the like.

The network module may be configured to receive, retrieve and/or transmit any suitable data, including, but not limited to, data associated with the parameters, indications and/or approvals of one or more thermal waveforms, one or more prescriptions, controller feedback data, data associated with the delivery of one or more thermal waveforms, data associated with the fit of one or more earpieces, patient feedback data, physician feedback data and/or patient information.

In some embodiments, the network module is configured to receive and/or retrieve data associated with the parameters, indications and/or approvals of one or more thermal waveforms from a waveform module/database residing in the controller, from a patient control device, from a physician control device, from a physician support device, from a registry and/or from a portable memory device.

In some embodiments, the network module is configured to receive and/or retrieve one or more prescriptions from a treatment module residing in the controller, from a prescription database residing in the controller, from a patient control device, from a physician control device, from a physician support device, from a registry and/or from a portable memory device.

In some embodiments, the network module is configured to receive and/or retrieve controller feedback data, data associated with the delivery of one or more thermal waveforms and/or data associated with the fit of one or more earpieces from a control module residing in the controller, from an impedance module residing in the controller, from a feedback module/database residing in the controller, from one or more TEDs and/or from one or more sensors.

In some embodiments, the network module is configured to receive and/or retrieve patient feedback data, physician feedback data and/or patient information from a feedback module/database residing in the controller, from a GUI module residing in the controller, from a patient information database residing in the controller, from a patient control device, from a physician control device, from a physician support device, from a registry and/or from a portable memory device.

In some embodiments, the network module is configured to transmit data associated with the parameters, indications and/or approvals of one or more thermal waveforms to a waveform module/database residing in the controller, to a treatment module residing in the controller, to a patient control device, to a physician control device, to a physician support device, to a registry and/or a to portable memory device.

In some embodiments, the network module is configured to transmit one or more prescriptions to a treatment module residing in the controller, to a prescription database residing in the controller, to a patient control device, to a physician control device, to a physician support device, to a registry and/or to a portable memory device.

In some embodiments, the network module is configured to transmit controller feedback data, data associated with the delivery of one or more thermal waveforms and/or data associated with the fit of one or more earpieces to a control module residing in the controller, to a feedback module/database residing in the controller, to a patient control device, to a physician control device, to a physician support device, to a registry and/or to a portable memory device.

In some embodiments, the network module is configured to transmit patient feedback data, physician feedback data and/or patient information to a feedback module/database residing in the controller, to a patient information database residing in the controller, to a patient control device, to a physician control device, to a physician support device, to a registry and/or to a portable memory device.

In some embodiments, the network module is configured to access a database comprising data associated with the parameters, indications and/or approvals of one or more thermal waveforms (e.g., idealized thermal waveforms). For example, the network module maybe configured to access a waveform database residing in the controller, a waveform database residing in a patient control device, a waveform database residing in a physician control device, a waveform database residing in a physician support device, a waveform database residing in a registry and/or a waveform database residing in a portable memory device.

In some embodiments, the network module is configured to access a database comprising one or more prescriptions. For example, the network module maybe configured to access a prescription database residing in the controller, a prescription database residing in a patient control device, a prescription database residing in a physician control device, a prescription database residing in a physician support device, a prescription database residing in a registry and/or a prescription database residing in a portable memory device.

In some embodiments, the network module is configured to access a database comprising controller feedback data, data associated with the delivery of one or more thermal waveforms, data associated with the fit of one or more earpieces, patient feedback data and/or physician feedback data. For example, the network module maybe configured to access a feedback database residing in the controller, a feedback database residing in a patient control device, a feedback database residing in a physician control device, a feedback database residing in a physician support device, a feedback database residing in a registry and/or a feedback database residing in a portable memory device.

In some embodiments, the network module is configured to access a database comprising patient information. For example, the network module maybe configured to access a patient information database residing in the controller, a patient information database residing in a patient control device, a patient information database residing in a physician control device, a patient information database residing in a physician support device, a patient information database residing in a registry and/or a patient information database residing in a portable memory device.

E. Graphical User Interface Module

In some embodiments, the controller comprises a GUI module configured to display information and/or to accept user input. Any suitable GUI may be used, including, but not limited to, a keyboard, a mouse, an LCD display with one or more associated entry keys and an interactive touch screen. For example, the GUI may comprise a static pressure touch-sensitive display, a capacitive touch-sensitive display, a resistive touch-sensitive display, an electrostatic capacity proximity sensor, a magnetic proximity sensor and/or an infrared proximity sensor. See, e.g., U.S. Patent Publication Nos. 2011/0271222, 2011/0273575, 2011/0275414 and 2011/0275416.

The GUI module may be configured to display any suitable information, including, but not limited to, data associated with the delivery of one or more thermal waveforms. For example, the GUI module may be configured to display the current date and/or time (FIG. 10); the current temperature(s) of the earpiece(s) associated with the controller; the current temperature(s) of a patient's ear canal(s); the current temperature(s) of a patient's inner ear(s); the current temperature(s) of the heat sink(s) associated with the controller; one or more target temperatures (FIG. 11); the amount of time that has elapsed since the onset of delivery of one or more thermal waveforms (FIG. 11); the amount of time remaining in the delivery of one or more thermal waveforms (FIG. 11); the amount of time that has elapsed since the onset of a treatment session; the amount of time remaining in a treatment session; a graphical representation of the thermal waveform being applied (FIG. 11); the number of treatment sessions that have been administered for a prescription; the number of treatment sessions remaining in a prescription; the amount of time remaining until a prescription must be renewed/updated; the amount of remaining battery life, an alert message (e.g., a reminder to a patient that he/she is due for a treatment session); the target time/temperature parameters of one or more prescribed thermal waveform(s) (FIG. 11); the precise time/temperature parameters of the thermal waveform(s) delivered to a patient; the date/time of delivery of the thermal waveform(s) delivered to a patient; the temperature(s) of a patient's ear canal(s) at various time points before, during and/or after delivery of the thermal waveform(s); the temperature(s) of a patient's inner ear(s) at various time points before, during and/or after delivery of the thermal waveform(s); the fit of the earpiece(s) at various time points before, during and/or after delivery of the thermal waveform(s); an estimate of the thermal contact between the earpiece(s) and the patient's ear canal(s) at various time points before, during and/or after delivery of the thermal waveform(s); patient-specific time constants (e.g., a time constant associated with the transduction of heat from a patient's ear canal to the inner ear); reaction time (i.e., how long it took for a patient to react to one or more thermal waveforms); the effectiveness of one or more thermal waveforms (i.e., whether and to what extent symptoms were relieved, whether the thermal waveform(s) enhanced the effectiveness of another agent/therapy, etc.); the stability of a treatment (i.e., how long the effects of the treatment lasted); the instability of a treatment (i.e., which symptom(s) returned and when did it/they return); the presence or absence of comorbid disorders, injuries and/or diseases; disorder, injury and/or disease modulation(s) and/or modification(s) that occurred as a result of treatment; the cognitive effect(s) of one or more thermal waveforms; patient compliance (e.g., whether a patient initiated delivery at the prescribed time, whether a patient completed the prescribed treatment session, whether the earpiece(s) remained properly fitted in a patient's ear canal(s) for the duration of the treatment session, etc.); the mood of a patient at various time points before, during and/or after delivery of one or more thermal waveforms (e.g., videos/images of a patient that may be used to assess mood); objectives measures of efficacy (e.g., nystamography data, EEG data, MRI data, heart rate data, blood pressure data); subjective measures of efficacy (e.g., a patient-reported pain score); blood chemistry data (e.g., blood A1c levels, blood glucose levels and blood cortisol levels); saliva chemistry data (e.g., saliva cortisol levels); urine chemistry data (e.g., urine cortisol levels)), comments a patient made about his/her treatment session(s) (e.g., comments made to a physician, submitted in response to an automated survey and/or recorded in a treatment diary); the impedance between an earpiece inserted into the ear canal of a patient and an electrode affixed to a second location on/in said patient's body (e.g., an electrode placed in or adjacent to the patient's other ear canal); the rate at which a patient's inner ear cools in response to a cooling stimulus (e.g., data from a temperature sensor, such as thermistor, that monitors how quickly the inner ear cools in response to a cooling waveform); the rate at which a patient's inner ear warms in response to a warming stimulus (e.g., data from a temperature sensor, such as thermistor, that monitors how quickly the inner ear warms in response to a warming waveform) and/or patient comments regarding the subjective fit of his/her earpiece(s).

The GUI module may be configured to accept any suitable user input, including, but not limited to, instructions for generating and/or modifying the parameters, indications and/or approvals of a thermal waveforms; instructions for generating, modifying, updating and/or extending a prescription; patient feedback, physician feedback and/or patient information. For example, the GUI module may be configured to accept a pain score and/or patient comments regarding the effectiveness of a treatment session.

Figure 11:
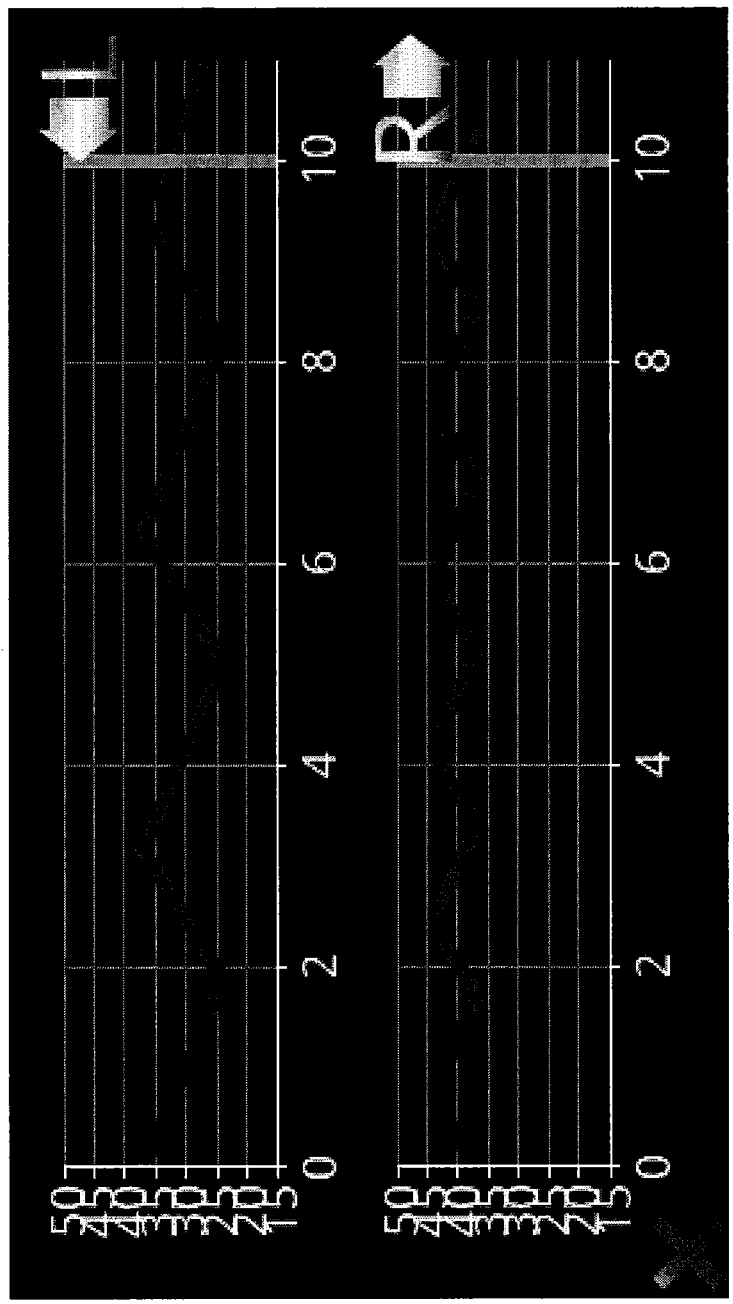

In some embodiments, the GUI module is configured to allow a user to initiate/stop a treatment session (e.g., by pushing/selecting an emergency shutoff button/icon) (FIG. 11).

F. Feedback Module

In some embodiments, the controller comprises a feedback module configured to receive, transmit and/or analyze data.

The feedback module may be configured to receive and/or transmit data from/to any suitable device/module/database, including, but not limited to, other modules residing in the controller, databases residing in the controller, a patient control device, a physician control device, a physician support device, a registry, a TED, a sensor and a portable memory device (e.g., an SD memory card).

The feedback module may be configured to receive and/or transmit data over any suitable wired or wireless communications channel, including, but not limited to, a LAN, the Internet, a public telephone switching network, Bluetooth, WLAN and the like.

The feedback module may be configured to receive, transmit and/or analyze any suitable data, including, but not limited to, controller feedback data, data associated with the delivery of one or more thermal waveforms, data associated with the fit of one or more earpieces, patient feedback data, physician feedback data and/or patient information.

In some embodiments, the feedback module is configured to receive and/or analyze controller feedback data, data associated with the delivery of one or more thermal waveforms and/or data associated with the fit of one or more earpieces from an impedance module residing in the controller, from a feedback database residing in the controller, from one or more TEDs and/or from one or more sensors. For example, the feedback module may be configured to analyze the accuracy with which one or more prescribed waveforms was delivered to a patient, the fit of an earpiece based upon the rate at which the temperature of the earpiece changes in response to a cooling/warming waveform, the slew rate associated with one or more TEDs, the impedance between an earpiece positioned in the left ear canal of a patient and an earpiece positioned in the right ear canal of a patient, the impedance between an earpiece positioned in the ear canal of a patient and an electrode affixed to a second location on/in the patient's body, etc.

In some embodiments, the feedback module is configured to receive and/or analyze patient feedback data, physician feedback data and/or patient information from a GUI module residing in the controller, from a feedback database residing in the controller, from a patient information database residing in the controller, from a patient control device, from a physician control device, from a physician support device, from a registry and/or from a portable memory device. For example, the feedback module may be configured to analyze the effectiveness of a given thermal waveform or combination of thermal waveforms (e.g., by analyzing pain scores entered before, during and after a treatment session), the effect(s) of one or more waveform modifications (e.g., by analyzing whether/how much a given waveform modification changed the effectiveness of a thermal waveform in treating a disease/disorder), etc.

In some embodiments, the feedback module is configured to transmit controller feedback data, data associated with the delivery of one or more thermal waveforms, data associated with the fit of one or more earpieces, patient feedback data, physician feedback data, patient information and/or data associated with its analysis to a control module residing in the controller, to a feedback database residing in the controller, to a patient information database residing in the controller, to a patient control device, to a physician control device, to a physician support device, to a registry and/or to a portable memory device (e.g., an SD memory card).

G. Alert Generation Module

In some embodiments, the controller comprises an alert generation module configured to generate one or more alert messages.

The alert generation module may be configured to generate any suitable alert message, including, but not limited to, a reminder that a patient is due for a treatment session; a reminder that a patient must enter patient feedback data (e.g., a pain score) following a treatment session; an indication of the number of treatment sessions remaining in a prescription; an error message indicating that a treatment session has been interrupted due to a system error; an alert indicating that one or more idealized thermal waveforms has been modified; an alert indicating that a given modification is likely to increase/decrease the effectiveness of a given thermal waveform and/or an alert indicating that a given thermal waveform, class of thermal waveforms or combination of thermal waveforms has been identified as being indicated and/or approved for use in the treatment of a disease/disorder; a reminder that a patient must contact his/her physician to update/extend his/her prescription and a warning that the controller's internal power supply is low.

In some embodiments, the alert generation module is configured to communicate with various devices/modules, including, but not limited to, a patient control device, a physician control device, a physician support device, a TED, a sensor, a portable memory device (e.g., an SD memory card) and other modules of the controller. For example, the alert generation module may be configured to provide instructions to the GUI module and/or the tone generation module for displaying one or more alert messages and/or for generation an audible tone to alert a user of the presence of the one or more alert messages. The graphical user interface module may be configured to display the one or more alert messages immediately upon generation or upon interaction with a user (e.g., an alert notification icon may be generated, with the alert message being displayed only after the user indicates that he/she wishes to view the message).

H. Tone Generation Module

In some embodiments, the controller comprises a tone generation module configured to produce audible tones. In some such embodiments, the tone generation module comprises a piezo buzzer. Audible tones may be produced to alert a user to various circumstances/events, including, but not limited to, the start of a treatment session, the end of a treatment session, interruption of a treatment session, low battery power and the existence of an unread/unviewed alert message. Audible tones may be generated repeatedly in response to a single circumstance/event (e.g., an audible tone may be generated repeatedly until the user views/reads the message) and may become progressively louder and/or more frequent with time.

Visual Indicator Module

In some embodiments, the controller comprises a visual indicator module configured to notify a user of the existence of an unread/unviewed alert message and/or to notify the user that a treatment session is in progress. In some such embodiments, the visual indicator module comprises an LED indicator light. The visual indicator module may be activated repeatedly in response to a single alert message (e.g., an LED light may be illuminated repeatedly until the user views/reads the message) or may remain activated until the user views/reads the message. In some preferred embodiments, an LED indicator light may be illuminated throughout a treatment session and deactivated upon completion of the treatment session, and may change color to signal various events within a treatment session (e.g., the light may appear blue during cooling periods and appear red during heating periods).

J. Impedance Module

In some embodiments, the controller comprises an impedance module configured to detect and/or monitor the impedance and/or capacitance between an earpiece inserted into the ear canal of a patient and an electrode affixed to a second location on/in said patient's body. For example, the impedance module may be configured to deliver an electrical current to the earpiece and to measure and/or record the impedance and/or capacitance between the earpiece and the electrode.

In some embodiments, the impedance module may be configured to detect and/or monitor the impedance and/or capacitance between an earpiece inserted into the right ear canal of a patient and an earpiece inserted into the left ear canal of said patient. For example, the impedance module may be configured to deliver an electrical current to the earpiece inserted into the right ear canal of the patient and to measure and/or record the impedance and/or capacitance between the two earpieces.

Without wishing to be bound by theory, it is believed that if each of the earpieces is in substantially good thermal contact with the patient's ear canal, then the earpieces will also be in substantially good electrical contact with the patient's ear canals, and the patient's head will substantially complete an electrical circuit between the earpieces. However, if either of the earpieces is not in substantially good thermal contact with the patient's ear canal, then there will generally be poor electrical contact with the patient's ear canal, and the patient's head will not complete the electrical circuit between the earpieces and an open circuit will be detected by the impedance module.

The impedance value between an earpiece inserted into the ear canal of the patient and the electrode affixed to a second location (e.g., an earpiece inserted into the patient's other ear canal) may be used to estimate the thermal contact between the earpiece(s) and the patient's ear canal(s). In some embodiments, impedance values may be detected for a range of patients to determine a range of impedance values in which it may be assumed that the earpiece(s) is/are in substantially good thermal contact with the patient's ear canal(s). When a vestibular stimulation device is being fitted to a new patient, the impedance value may be detected, and if the impedance value is within the acceptable range, it may be assumed that there is substantially good thermal contact between the earpiece(s) and the patient's ear canal(s). In some embodiments, when a vestibular stimulation device is being fitted to a new patient, the impedance value between the earpiece inserted into the right ear canal of the patient and the earpiece inserted into the left canal of the patient may be detected and used as a patient-specific baseline to later determine whether the patient is using the vestibular stimulation device in the proper configuration (i.e., whether the earpieces are properly fitted into the patient's ear canals during a given treatment session).

The impedance module may be configured to monitor the impedance value between an earpiece inserted into the ear canal of a patient and an electrode affixed to a second location on/in said patient's body (e.g., between two earpieces), and the impedance values may be analyzed (e.g., by a medical health professional or the impedance module) to determine whether the earpiece(s) is/was properly fitted at various times before, during and/or after delivery of the thermal waveform(s). In some embodiments, the impedance module may be configured to provide feedback to the user if/when the impedance value indicates that the earpiece(s) are not in substantially good thermal contact with the patient's ear canal(s). In this configuration, the impedance module may provide an estimation of a degree of thermal contact between the earpiece(s) and the patient's ear canal(s) in real-time or in data recorded and analyzed at a later time.

The impedance module may be configured to provide controller feedback data to the control module so that the control module may modulate the amplitude of the waveform(s) delivered by the TED(s) responsive to the degree of thermal contact between the earpiece(s) and the patient's ear canal(s). For example, if the impedance module determines that there is a poor fit and poor thermal contact between the earpiece(s) and the ear canal(s), then the control module may increase the thermal output of the TED(s) to compensate for the poor thermal contact.

K. Security Module

In some embodiments, the controller comprises a security module configured to prevent unauthorized use of the controller (i.e., to prevent unauthorized persons from using the vestibular stimulation device, to prevent authorized persons from using the vestibular stimulation device in an unauthorized manner, etc.).

Figure 12:
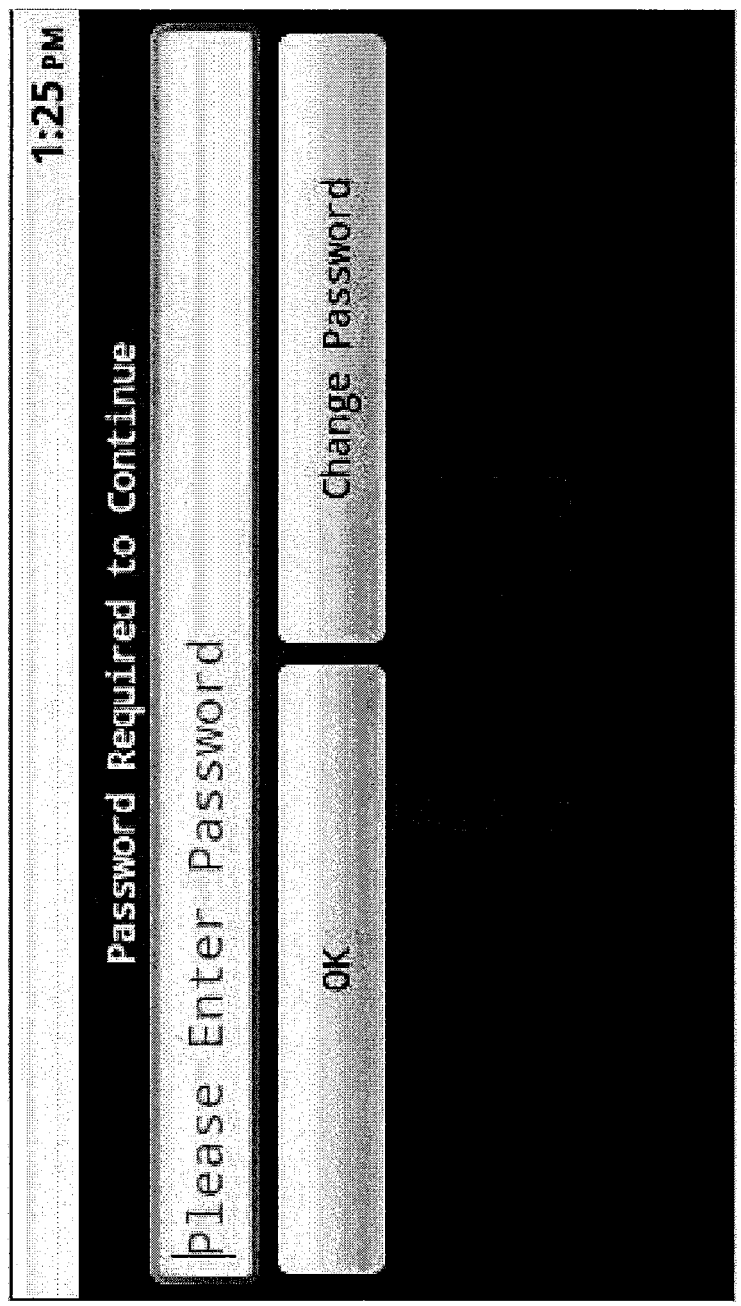

The security module may be configured to prevent unauthorized use of the controller using any suitable means of security, including, but not limited to, password protection and data encryption. For example, the security module may be configured such that a user is required to input a designated password prior to initializing treatment; generating and/or modifying a thermal waveform; generating, modifying, updating and/or extending a prescription; entering/viewing patient feedback data; entering/viewing physician feedback data and/or entering/viewing patient information (FIG. 12). In some embodiments, prescriptions are provided in an encrypted format, and the security module is configured such that the prescriptions can only be decrypted by the vestibular stimulation device assigned to or belonging to the patient for whom the prescription was generated. In some embodiments, prescriptions are provided in an encrypted format, and the security module is configured such that the prescriptions can only be decrypted by inputting a designated decryption key. In some embodiments, a patient may be required to purchase a decryption key and/or password for each treatment session, prescription, refill, etc.

L. Safety Module

In some embodiments, the controller comprises a safety module configured to deactivate the controller in the event of a system malfunction and/or failure.

The safety module may be configured to deactivate the controller for any suitable reason, including, but not limited to, excessive heating and/or cooling of an earpiece, excessive heating and/or cooling of a heat sink; a loss of thermal coupling between an earpiece and the TED(s) with which it is associated, a loss of thermal coupling between a heat sink and the TED(s) with which it is associated, patient noncompliance (e.g., if the patient has removed the earpiece(s) during a treatment session) and faulty signaling from the controller to the associated TED(s).

In some embodiments, the safety module is configured to deactivate the controller if/when the temperature of an earpiece surpasses a specified safety threshold. For example, the safety module may be configured to deactivate the controller if/when the temperature of the earpiece drops below about 10 degrees Centigrade and/or rises above about 50 degrees Centigrade.

In some embodiments, the safety module is configured to deactivate the controller if/when the temperature of a heat sink that is thermally coupled to an earpiece surpasses a specified safety threshold. For example, the safety module may be configured to deactivate the controller if/when the temperature of the heat sink drops below about 5 degrees Centigrade and/or rises above about 50 degrees Centigrade.

In some embodiments, the safety module is configured to deactivate the controller if/when one or more of the activation signals sent from the controller to the associated TED(s) indicates that the system is may be operating outside of a predefined safety range. For example, the safety module may be configured to deactivate the controller if/when an activation signal sent from the controller to an associated TED exceeds the level of activation that would normally be required to deliver the prescribed thermal waveform in a properly functioning system.

As will be appreciated by one of skill in the art, the controller may comprise any suitable data, including, but not limited to, static and/or dynamic data used by the operating system, applications, I/O device drivers and other software components, controller feedback data, data associated with the parameters, indications and/or approvals of one or more thermal waveforms (e.g., idealized thermal waveforms), data associated with one or more prescriptions, data associated with the delivery of one or more thermal waveforms, data associated with the fit of one or more earpieces, patient feedback data, physician feedback data and patient information. For example, the controller may comprise a waveform database comprising data associated with the parameters, indications and/or approvals of one or more idealized thermal waveforms; a prescription database comprising data associated with one or more prescriptions; a feedback database comprising controller feedback data, data associated with the delivery of one or more thermal waveforms to the vestibular system and/or the nervous system of a patient, patient feedback data and physician feedback data and/or a patient history database comprising data associated with one or more patients. In some embodiments, two or more of the aforementioned databases are combined to form a single database comprising data from each of the individual databases (e.g., the controller may comprise a feedback-history database comprising data associated with the delivery of one or more thermal waveforms and patient information). In some embodiments, one of the aforementioned databases is split into two or more distinct databases (e.g., the controller may comprise a controller feedback database comprising controller feedback data, a delivery feedback database comprising data associated with the specific parameters of the thermal waveform(s) delivered to a patient, a patient feedback database comprising patient feedback data and a physician feedback database comprising physician feedback data). In some embodiments, one or more of the data types described below with respect to one of the databases described below is stored in one of the other databases described below (e.g., the patient information database, rather than the feedback database, may be configured to receive/store patient feedback data). In some embodiments, data is transmitted, received and/or stored in a controlled format (e.g., in a standardized format using forms/programs supplied by a physician support device or a registry). The controller may be configured to transmit, receive and store data in a manner that ensures compliance with any and all applicable laws and/or regulations (e.g., the Health Insurance Portability and Accountability Act of 1996 (P.L. 104-191; "HIPAA")).

Waveform Database

In some embodiments, the controller comprises a waveform database configured to receive, store and/or transmit data associated with the parameters, indications and/or approvals of one or more thermal waveforms (e.g, one or more idealized thermal waveforms). In some such embodiments, the waveform database is configured such that one or more of the thermal waveforms stored therein is/are protected (e.g., users may be prevented from modifying and/or deleting the idealized thermal waveform(s) stored in the waveform database).

The waveform database may comprise any suitable type of memory including, but not limited to, cache, ROM, PROM, EPROM, EEPROM, flash memory, SRAM and DRAM. In some embodiments, the waveform database comprises a portable memory device, such as an SD memory card or a USB memory stick. For example, the waveform database may comprise an SD memory card interface and one or more prescriptions may be stored on a portable SD memory card.

The waveform database may be configured to receive and/or transmit data from/to any suitable device/module/database, including, but not limited to, modules residing in the controller, a patient control device, a physician control device, a physician support device, a registry, a TED, a sensor and a portable memory device (e.g., an SD memory card).

The waveform database may be configured to receive and/or transmit data over any suitable wired or wireless communications channel, including, but not limited to, a LAN, the Internet, a public telephone switching network, Bluetooth, WLAN and the like.

B. Prescription Database

In some embodiments, the controller comprises a prescription database configured to receive, transmit and/or store one or more prescriptions, wherein each prescription comprising a set of instructions for delivering one or more thermal waveforms to the vestibular system and/or the nervous system of a patient.

The prescription database may comprise any suitable type of memory including, but not limited to, cache, ROM, PROM, EPROM, EEPROM, flash memory, SRAM and DRAM. In some embodiments, the prescription database comprises a portable memory device, such as an SD memory card or a USB memory stick. For example, the prescription database may comprise an SD memory card interface and one or more prescriptions may be stored on a portable SD memory card.

The prescription database may be configured to receive and/or transmit data from/to any suitable device/module/database, including, but not limited to, modules residing in the controller, a patient control device, a physician control device, a physician support device, a registry, a TED, a sensor and a portable memory device (e.g., an SD memory card)

The prescription database may be configured to receive and/or transmit data over any suitable wired or wireless communications channel, including, but not limited to, a LAN, the Internet, a public telephone switching network, Bluetooth, WLAN and the like.

C. Feedback Database

In some embodiments, the controller comprises a feedback database configured to receive, transmit and/or store feedback data.

The feedback database may comprise any suitable type of memory including, but not limited to, cache, ROM, PROM, EPROM, EEPROM, flash memory, SRAM and DRAM. In some embodiments, the feedback database comprises a portable memory device, such as an SD memory card or a USB memory stick. For example, the feedback database may comprise an SD memory card interface and one or more prescriptions may be stored on a portable SD memory card.

The feedback database may be configured to receive and/or transmit feedback data from/to any suitable device/module/database, including, but not limited to, modules residing in the controller, a patient control device, a physician control device, a physician support device, a registry, a TED, a sensor and a portable memory device (e.g., an SD memory card).

The feedback database may be configured to receive and/or transmit data over any suitable wired or wireless communications channel, including, but not limited to, a LAN, the Internet, a public telephone switching network, Bluetooth, WLAN and the like.

Feedback data may comprise any suitable data, including, but not limited to, controller feedback data, data associated with the delivery of one or more thermal waveforms, data associated with the fit of one or more earpieces, patient feedback data, physician feedback data and/or patient information. For example, the feedback database may comprise a log file detailing the target time/temperature parameters of one or more prescribed thermal waveform(s); the time/temperature parameters of the thermal waveform(s) delivered to a patient; the date/time of delivery of the thermal waveform(s) delivered to a patient; the temperature(s) of a patient's ear canal(s) at various time points before, during and/or after delivery of one or more thermal waveforms; the temperature(s) of a patient's inner ear(s) at various time points before, during and/or after delivery of one or more thermal waveforms; the fit of one or more earpieces at various time points before, during and/or after delivery of one or more thermal waveforms; an estimate of the thermal contact between one or more earpieces and a patient's ear canal(s) at various time points before, during and/or after delivery of one or more thermal waveforms; patient-specific time constants (e.g., a time constant associated with the transduction of heat from a patient's ear canal to the inner ear); a patient's reaction time (i.e., how long it took for a patient to react to one or more thermal waveforms); effectiveness of one or more thermal waveforms (i.e., whether and to what extent symptoms were relieved, whether the thermal waveform(s) enhanced the effectiveness of another agent/therapy, etc.); stability of a treatment (i.e., how long the effects of a treatment lasted); instability of a treatment (i.e., which symptom(s) returned and when did it/they return); the presence or absence of comorbid disorders, injuries and/or diseases; disorder, injury and/or disease modulation(s) and/or modification(s) that occurred as a result of treatment; the cognitive effect(s) of one or more thermal waveforms; patient compliance (e.g., whether a patient initiated delivery at the prescribed time, whether a patient completed the prescribed treatment session, whether the earpiece(s) remained properly fitted in a patient's ear canal(s) for the duration of the treatment session, etc.); the mood of a patient at various time points before, during and/or after delivery of one or more thermal waveforms (e.g., videos/images of a patient that may be used to assess mood); objectives measures of efficacy (e.g., nystamography data, EEG data, MRI data, heart rate data, blood pressure data); subjective measures of efficacy (e.g., a patient-reported pain score); blood chemistry data (e.g., blood A1c levels, blood glucose levels and blood cortisol levels); saliva chemistry data (e.g., saliva cortisol levels); urine chemistry data (e.g., urine cortisol levels)); comments a patient made about his/her treatment session(s) (e.g., comments made to a physician, submitted in response to an automated survey and/or recorded in a treatment diary); the impedance between an earpiece inserted into the ear canal of a patient and an electrode affixed to a second location on/in said patient's body (e.g., an electrode placed in or adjacent to the patient's other ear canal); the rate at which an earpiece is cooled in response to a cooling stimulus (e.g., data from a temperature sensor, such as thermistor, that monitors how quickly the earpiece cools in response to a cooling waveform); the rate at which an earpiece is warmed in response to a warming stimulus (e.g., data from a temperature sensor, such as a thermistor, that monitors how quickly the earpiece warms in response to a warming waveform); the rate at which a patient's ear canal and/or inner ear cooled in response to a cooling stimulus (e.g., data from a temperature sensor, such as thermistor, that monitors how quickly the ear canal and/or the inner ear cools in response to a cooling waveform); the rate at which a patient's ear canal and/or inner ear warmed in response to a warming stimulus (e.g., data from a temperature sensor, such as a thermistor, that monitors how quickly the ear canal and/or the inner ear warms in response to a warming waveform); patient comments regarding the subjective fit of one or more earpieces; physician comments regarding the effectiveness of one or more thermal waveforms and/or physician comments regarding the effect(s) of one or more waveform modifications.

D. Patient History Database

In some embodiments, the controller comprises a patient history database configured to receive, transmit and/or store patient information.

The patient history database may comprise any suitable type of memory including, but not limited to, cache, ROM, PROM, EPROM, EEPROM, flash memory, SRAM and DRAM. In some embodiments, the patient history database comprises a portable memory device, such as an SD memory card or a USB memory stick. For example, the patient history database may comprise an SD memory card interface and one or more prescriptions may be stored on a portable SD memory card.

The patient history database may be configured to receive and/or transmit data from/to any suitable device/module/database, including, but not limited to, modules residing in the controller, a patient control device, a physician control device, a physician support device, a registry, a TED, a sensor and a portable memory device (e.g., an SD memory card).

The patient history database may be configured to receive and/or transmit data over any suitable wired or wireless communications channel, including, but not limited to, a LAN, the Internet, a public telephone switching network, Bluetooth, WLAN and the like.

Patient information may comprise any suitable information that is associated with a patient, including, but not limited to, the patient's medical history, the patient's current symptoms (if any), the patient's present diagnosis (if any), the patient's current prescriptions (if any) and data associated with the delivery of one or more thermal waveforms to the vestibular system and/or the nervous system of the patient.

As will be appreciated by one of skill in the art, the controller may comprise any I/O device drivers, including, but not limited to, software routines accessed through the operating system by the applications to communicate with devices such as I/O ports, memory components, TEDs and/or sensors.

As will be appreciated by one of skill in the art, the controller may be configured (e.g., with computer instructions (i.e., software)) to operate in a plurality of distinct modes. In each mode, the controller may be configured to permit access to some modules, databases and/or functionalities and to prevent access to other modules, database and/or functionalities. For example, the controller may be configured to operate in a patient mode, wherein the user is allowed to perform patient-oriented tasks, such as starting/stopping a treatment session and/or providing feedback regarding the effectiveness of a treatment session, but is prevented from accessing other modules/databases/functionalities (e.g., the user may be prevented generating, modifying, updating and/or extending prescriptions). Similarly, the controller may be configured to operate in a physician mode, wherein the user is allowed to perform physician-oriented tasks, such as generating, modifying, updating and/or extending a prescription comprising a set of instructions for delivering one or more thermal waveforms to the vestibular system and/or the nervous system of a patient, but is prevented from accessing other modules/databases/functionalities (e.g., the user may be prevented from generating and/or modifying one or more thermal waveforms). Likewise, the controller may be configured to operate in a researcher mode, wherein the user is allowed to perform researcher-oriented tasks, such as generating and/or modifying one or more idealized thermal waveforms, but is prevented from accessing other modules/databases/functionalities (e.g., the user may be prevented from modifying the underlying operational parameters of the controller). In addition, the controller may be configured to operate in an engineer mode, wherein the user is allowed to access all of the controller's modules/databases/functionalities. Each mode may be protected via a unique security measure (e.g., the controller may be configured such that each mode is protected by a unique password).

Figure 13:
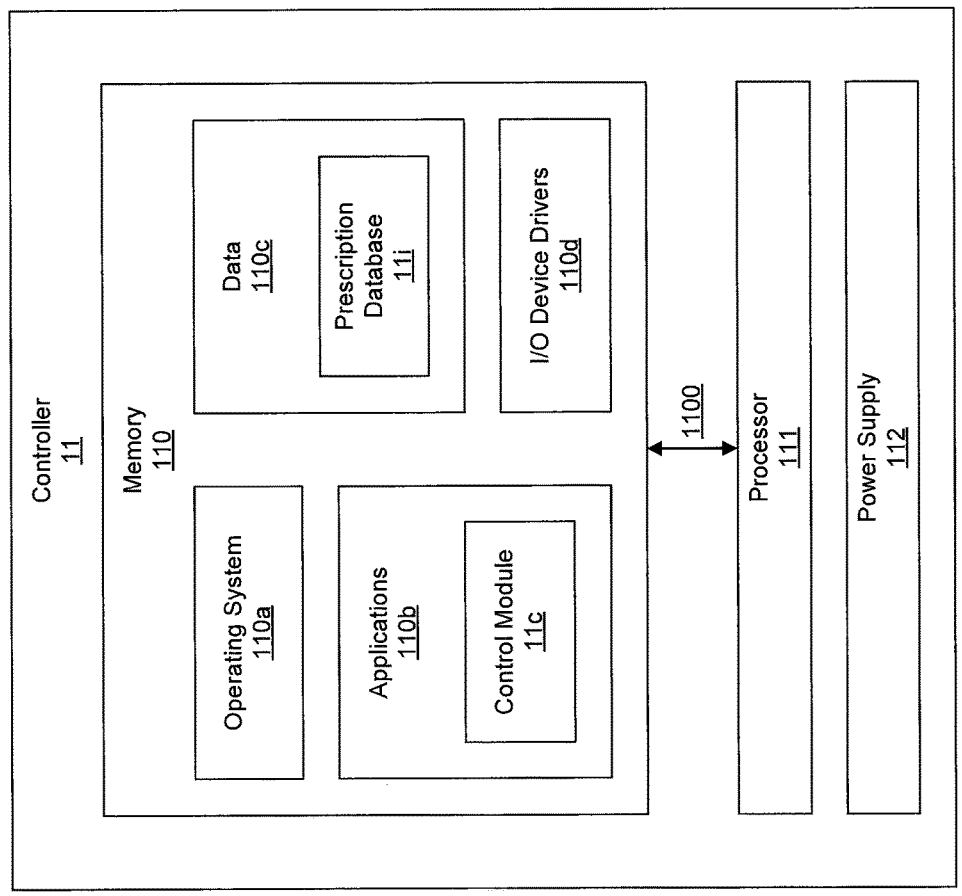
FIG. 13 is a block diagram of a controller according to some embodiments of the present invention.
Figure 14:
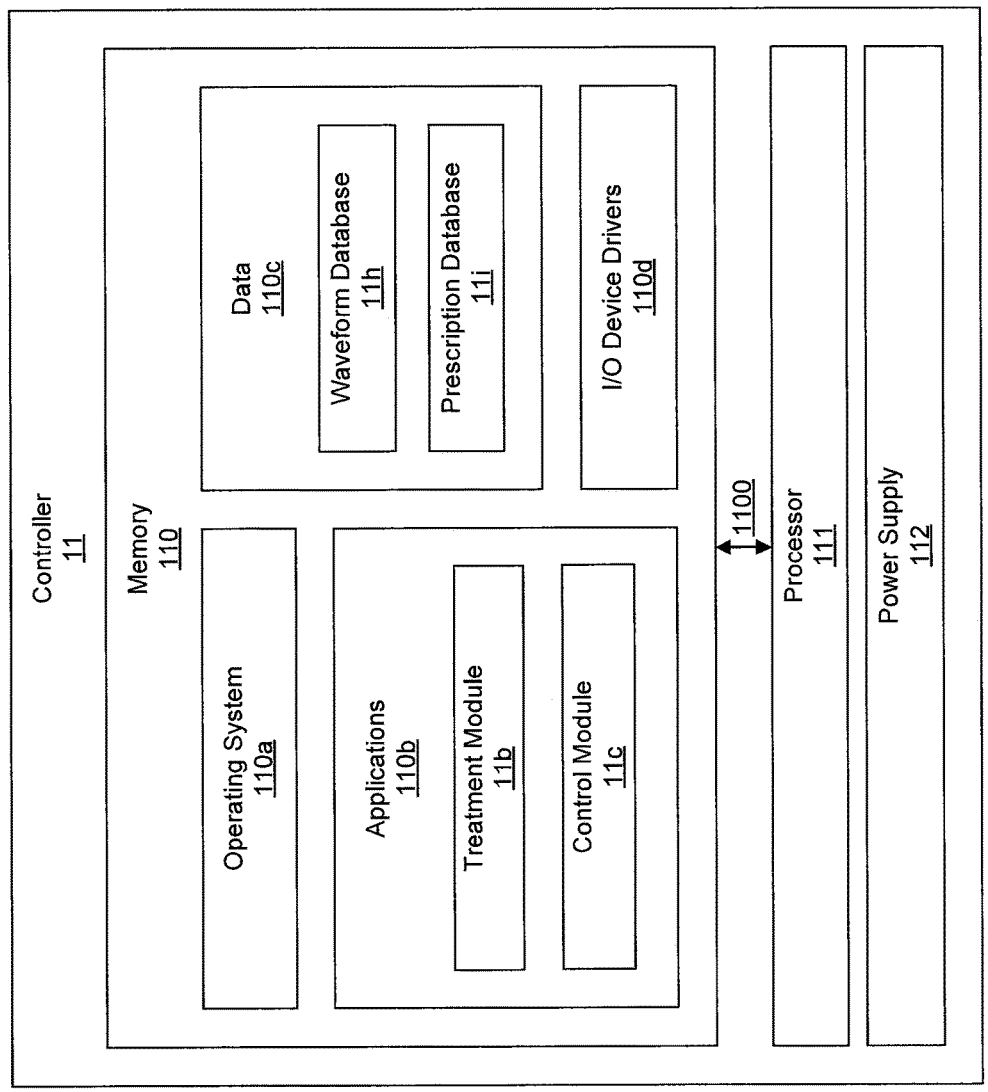
FIG. 14 is a block diagram of a controller according to some embodiments of the present invention.
Figure 15:
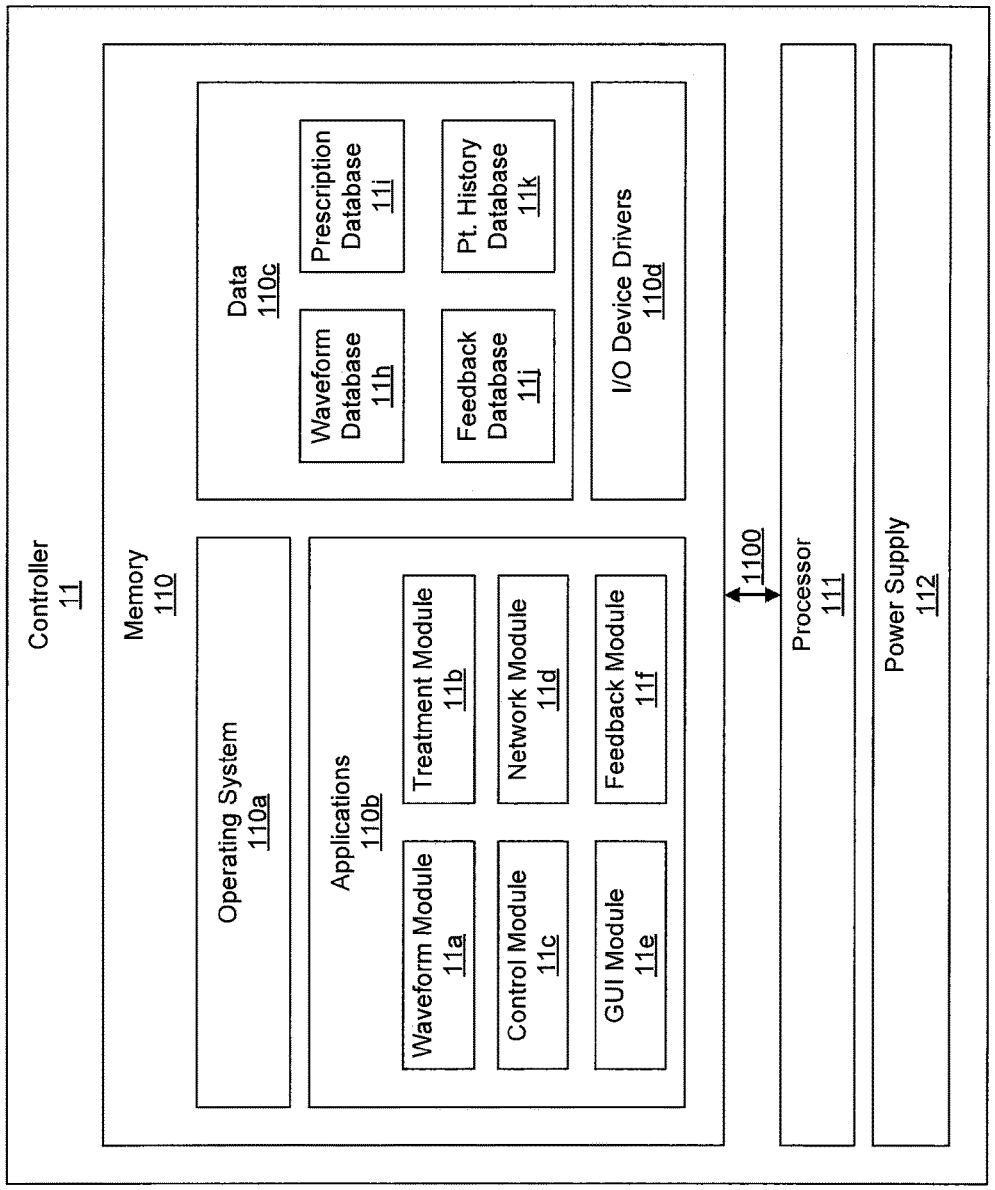
FIG. 15 is a block diagram of a controller according to some embodiments of the present invention.

As shown in FIGS. 13-15, in some embodiments of the present invention, the controller 11 comprises memory 110, a processor 111 and a power supply 112 (e.g., an internal power supply), wherein memory 110 is representative of the overall hierarchy of memory devices containing software and data used to implement the functionality of the controller 11 and wherein the processor 111 communicates with the memory 110 via an address/data bus 1100. In particular embodiments, memory 110 comprises an operating system 110a, applications 110b (e.g., a waveform module 11a configured to generate and/or modify the parameters, indications and/or approvals of one or more thermal waveforms; a treatment module 11b configured to generate, modify, update and/or extend a prescription comprising a set of instructions for delivering one or more thermal waveforms to the vestibular system and/or the nervous system of a patient; a control module 11c configured to activate at least one TED to deliver one or more thermal waveforms to the vestibular system and/or the nervous system of a patient; a network module 11d configured to receive and/or transmit data, a GUI module 11e configured to display information and/or accept user input and/or a feedback module 11f configured to receive, transmit, and/or analyze data), data 110c (e.g., a waveform database 11h comprising data associated with the parameters, indications and/or approvals of one or more thermal waveforms; a prescription database 11i comprising at least one prescription comprising a set of instructions for delivering one or more thermal waveforms to the vestibular system and/or the nervous system of a patient; a feedback database 11j comprising data associated with the delivery of one or more thermal waveforms and/or a patient history database 11k comprising patient information) and I/O drivers 110d. In some such embodiments, data 110c comprises one or more databases stored on a portable memory device. For example, data 110c may comprise an SD memory card interface and a portable SD memory card comprising a waveform database 11h, a prescription database 11i, a feedback database 11j and/or a patient history database 11k.

In some embodiments, the control module 11c is configured to activate one or more TEDs to delivery of one or more thermal waveforms to the vestibular system and/or the nervous system of a patient. For example, the control module 11c may be configured to activate the TED(s) based upon a prescription stored in the prescription database 11i. In some such embodiments, the prescription is stored on an SD memory card inserted into an SD memory card interface.

In some embodiments, the network module 11d is configured to receive data associated with the parameters, indications and/or approvals of one or more thermal waveforms from the waveform module 11a, a patient control device, a physician control device, a physician support device, a registry and/or a portable memory device (e.g., an SD memory card) and to transmit the data to the waveform database 11h for storage. In some such embodiments, the data is stored on an SD memory card inserted into an SD memory card interface.

In some embodiments, the network module 11d is configured to retrieve data associated with the parameters, indications and/or approvals of one or more thermal waveforms from the waveform database 11h, a patient control device, a physician control device, a physician support device, a registry and/or a portable memory device (e.g., an SD memory card) and to transmit the data to the waveform module 11a and/or the treatment module 11b.

In some embodiments, the network module 11d is configured to receive one or more prescriptions from the treatment module 11b, a patient control device, a physician control device, a physician support device, a registry and/or a portable memory device (e.g., an SD memory card) and to transmit the prescription(s) to the prescription database 11i for storage. In some such embodiments, the prescription(s) is/are stored on an SD memory card inserted into an SD memory card interface.

In some embodiments, the network module 11d is configured to retrieve one or more prescriptions from the prescription database 11i, a patient control device, a physician control device, a physician support device, a registry and/or a portable memory device (e.g., an SD memory card) and to transmit the prescription(s) to the treatment module 11b and/or the control module 11c.

In some embodiments, the network module 11d is configured to receive controller feedback data, data associated with the delivery of one or more thermal waveforms and/or data associated with the fit of one or more earpieces from the control module 11c, one or more TEDs 13a, 13b, one or more sensors 14a, 14b, a patient control device, a physician control device, a physician support device, a registry and/or a portable memory device (e.g., an SD memory card) and to transmit that data to the feedback database 11j for storage. In some such embodiments, the data is stored on an SD memory card inserted into an SD memory card interface.

In some embodiments, the network module 11d is configured to receive patient feedback data from the GUI module 11e and to transmit that data to the feedback database 11j for storage. In some such embodiments, the patient information is stored on an SD memory card inserted into an SD memory card interface.

In some embodiments, the network module 11d is configured to retrieve controller feedback data, data associated with the delivery of one or more thermal waveforms, data associated with the fit of one or more earpieces and/or patient feedback data from the feedback database 11j and to transmit the data to the control module 11c, the feedback module 11f, a patient control device, a physician control device, a physician support device, a registry and/or a portable memory device (e.g., an SD memory card).

In some embodiments, the network module 11d is configured to receive patient feedback data from the GUI module 11e and to transmit that data to the feedback database 11j for storage. In some such embodiments, the patient information is stored on an SD memory card inserted into an SD memory card interface.

In some embodiments, the network module 11d is configured to retrieve patient feedback data from the feedback database 11j and to transmit the data to the feedback module 11f, a patient control device, a physician control device, a physician support device, a registry and/or a portable memory device (e.g., an SD memory card).

In some embodiments, the network module 11d is configured to receive patient information from the GUI module 11e, a patient control device, a physician control device, a physician support device, a registry and/or a portable memory device (e.g., an SD memory card) and to transmit that data to the patient history database 11k for storage. In some such embodiments, the patient information is stored on an SD memory card inserted into an SD memory card interface.

In some embodiments, the network module 11d is configured to retrieve patient information from the patient history database 11k and to transmit the patient information to a patient control device, a physician control device, a physician support device, a registry and/or a portable memory device (e.g., an SD memory card).

Figure 16:
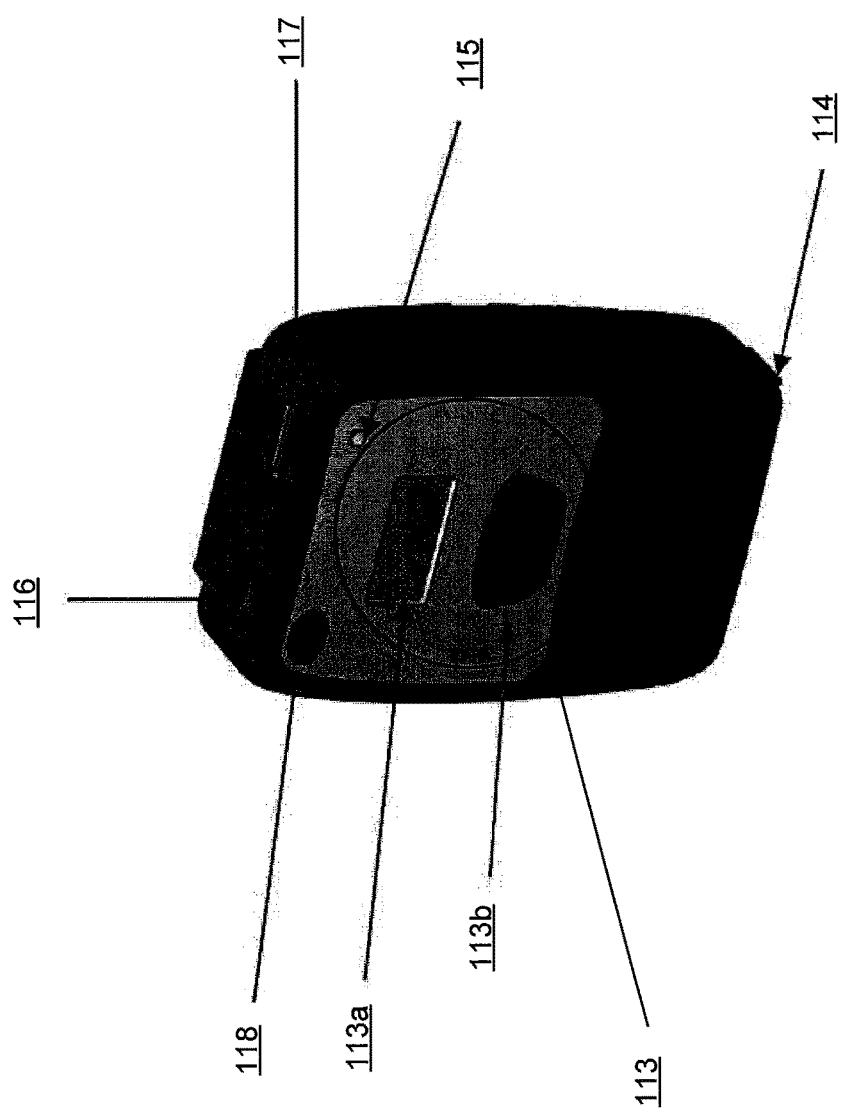
FIG. 16 is an illustration of a controller according to some embodiments of the present invention.

FIG. 16 is an illustration of a controller of the present invention. As shown therein, in some embodiments, the controller may comprise a graphical user interface 113 comprising an LCD display 113a configured to display data associated with the delivery of one or more thermal waveforms and a treatment start/stop button 113b whereby a patient may initiate and/or terminate a treatment session, an SD memory card interface 114 into which an SD memory card comprising a prescription may be inserted, an LED indicator light 115 configured to notify a patient of the occurrence of various events (e.g., the start of a treatment session or the generation of an alert message), a USB interface 116 configured to transmit/receive data and/or to recharge an internal power supply, a lead interface 117 whereby a patient may operatively connect one or more thermal stimulation leads and an on/off button 118.

Figure 17:
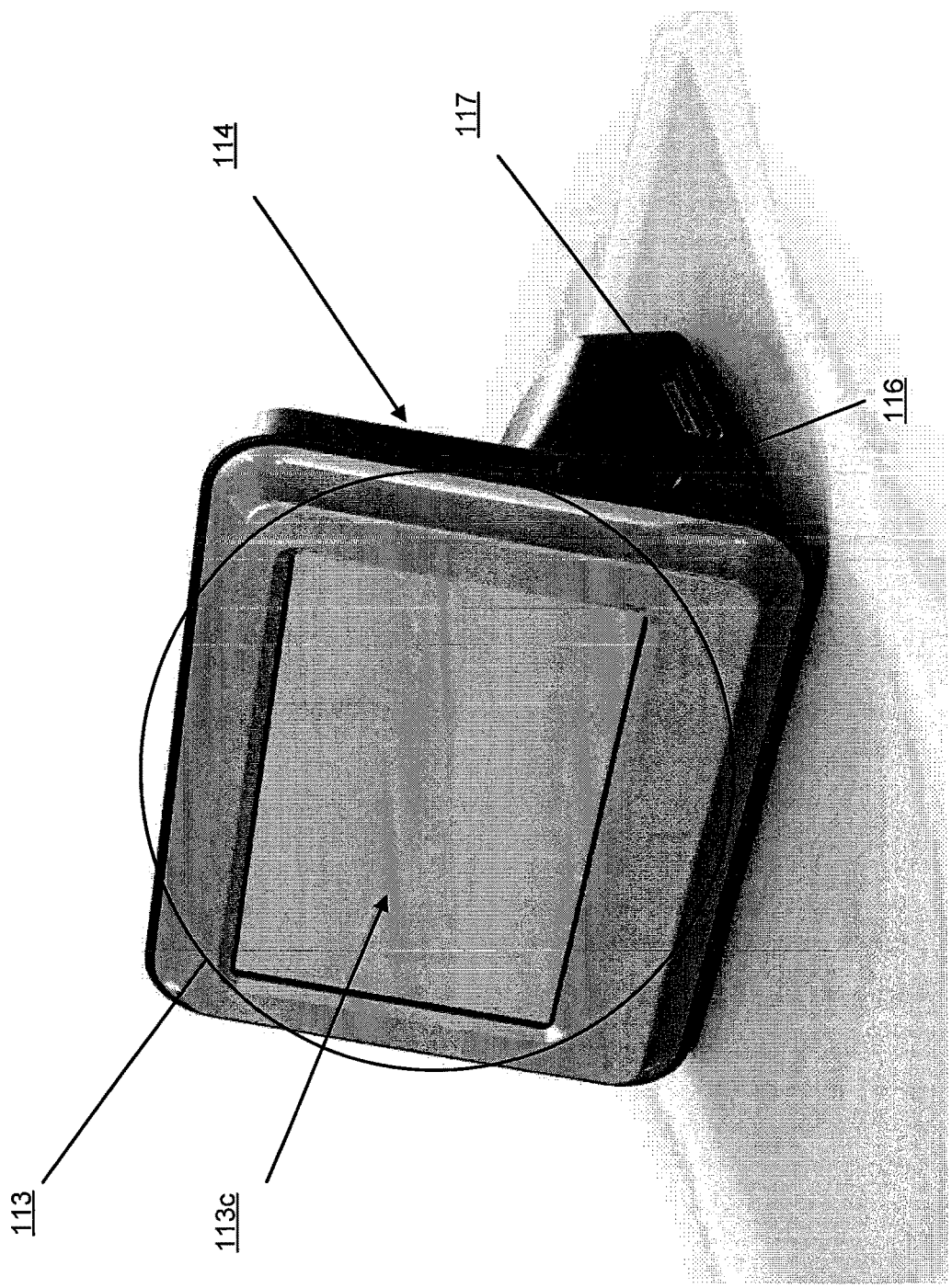
FIG. 17 is an illustration of a controller according to some embodiments of the present invention.

FIG. 17 is an illustration of another controller of the present invention. As shown therein, in some embodiments, the controller may comprise a graphical user interface comprising an interactive touchscreen 113c, an SD memory card interface 114 into which an SD memory card may be inserted, a USB interface 116 configured to transmit/receive data and/or to recharge an internal batter supply and a lead interface 117 whereby a user may operatively connect one or more thermal stimulation leads.

II. Earpiece

The vestibular stimulation device may comprise one or more earpieces. Earpieces of the present invention may be configured so as to be insertable into the left ear canal and/or the right ear canal of a patient.

Any suitable earpiece can be used to carry out the present invention, including, but not limited to, those described in U.S. Patent Publication Nos. 2010/0198204 and 2010/0198282; in U.S. patent application Ser. No. 12/970,312 and Ser. No. 12/970,347; in U.S. Provisional Application Nos. 61/497,761 and in U.S. Design Pat. No. D645,455, the disclosure of each of which is incorporated herein by reference in its entirety.

Earpieces of the present invention may comprise any suitable material, including, but not limited to, a rigid, thermally conductive material (e.g., a metal or a metal alloy). For example, the earpiece(s) may comprise aluminum or an aluminum alloy (e.g., 6061 aluminum).

Earpieces of the present invention may be of any suitable size/shape. In some embodiments, the earpiece(s) comprise(s) a distal end configured so as to be insertable into the left ear canal and/or the right ear canal of a patient and a proximal end configured so as to be thermally connected to one or more TEDs. In some embodiments, each earpiece weighs between about 1 and about 10 grams (e.g., about 9 grams or less or about 4 grams or less).

Earpieces of the present invention may possess any suitable heat transfer properties. In some embodiments, the earpiece(s) is/are more efficiently heated than cooled. For example, the earpiece(s) may have a slew rate of about 15 degrees Centigrade per minute or greater during delivery of a cooling stimulus and a slew rate of about 20 degrees Centigrade per minute or greater during delivery of a warming stimulus.

Earpieces of the present invention may comprise a thermally conductive covering. For example, a thermally conductive cushion may cover one or more portions of the earpiece(s) (e.g., the portion of an earpiece that is inserted into the ear canal of a patient during use may be covered in a thermally conductive cushioning material to increase thermal contact between the earpiece and the ear canal (i.e., by conforming to the shape of the ear canal)). The thermally conductive covering may comprise any suitable material, including, but not limited to, coating materials that must be reapplied to the earpiece(s) before each use (e.g., water, water-based lubricants, thermal grease, gels and the like) and reusable coating materials (e.g., a thermally conductive plastic sheath or sleeve).

Earpieces of the present invention may comprise a thermally insulating covering. For example, an insulating sleeve may cover one or more portions of the earpiece(s) (e.g., the portion of an earpiece that remains outside the ear canal of a patient during use may be covered in an insulating sleeve to reduce heat transfer between the earpiece and the outer ear of the patient). The insulating covering may comprise any suitable material, including, but not limited to, coating materials that must be reapplied to the earpiece(s) before each use (e.g., mineral oil, polypropylene, gels and the like) and reusable coating materials (e.g., a thermally insulative sheath or sleeve). In some embodiments, the thermally insulating covering comprises a silicone sleeve.

Earpieces of the present invention may comprise an electrically insulating covering. For example, an electrically insulating coating may cover one or more portions of the earpiece(s) (e.g., the portion of an earpiece that is inserted into the ear canal of a patient during use may be coated with an electrically insulating coating to prevent electrical conductance between the earpiece and the ear canal). The electrically insulating covering may comprises any suitable material, including, but not limited to, metal oxides (e.g., aluminum oxide), glass, porcelain and composite polymer materials. In some embodiments, the surface of an earpiece comprising aluminum is anodized to produce an aluminum oxide coating that electrically insulates the surface of the earpiece.

Earpieces of the present invention may comprise a protective coating. For example, a protective coating may cover one or more portions of the earpiece(s) (e.g., the portion of an earpiece that is inserted into the ear canal of a patient during use may be coated with a protective coating to prevent the underlying surface of the earpiece from coming into contact with the surface of the ear canal during use). The protective coating may comprise any suitable material, including, but not limited to, metals and metal alloys (gold, silver, copper and alloys thereof).

As will be appreciated by one of skill in the art, earpieces of the present invention may comprise a single covering/coating that fulfills multiple purposes. For example, the a thermally conductive coating applied to the portion of an earpiece that is inserted into the ear canal of a patient during use may also prevent the underlying surface of the earpiece from coming into contact with the surface of the ear canal during use.

As will be appreciated by one of skill in the art, earpieces of the present invention may comprise multiple coatings. For example, the earpiece(s) may comprise both a thermally conductive covering and a thermally insulative covering (e.g., a thermally conductive cushion may cover the portion of an earpiece that is inserted into the ear canal of a patient during use and an insulating sleeve may cover the portion of an earpiece that remains outside the ear canal of a patient during use).

Figure 18A:
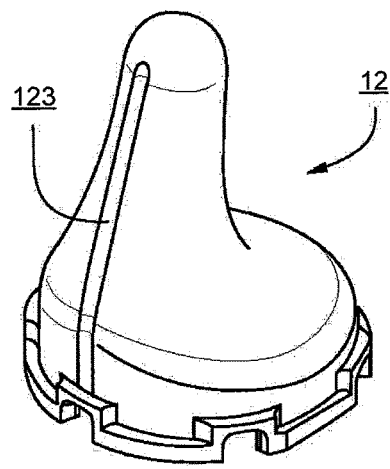
FIG. 18A is a perspective view of an earpiece according to some embodiments of the present invention.
Figure 18B:
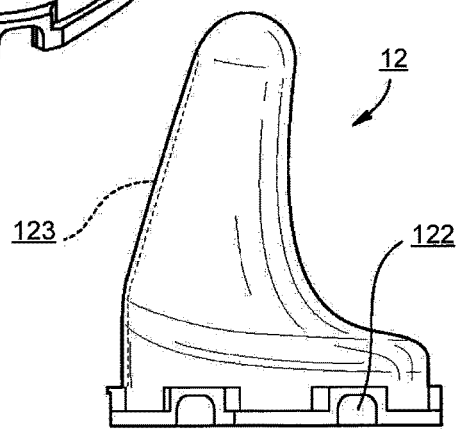
FIG. 18B is a side view of an earpiece according to some embodiments of the present invention.
Figure 18C:
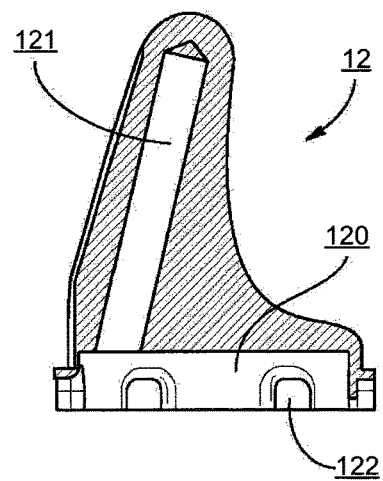
FIG. 18C is a cross-sectional view of an earpiece according to some embodiments of the present invention.

As shown in FIGS. 18A-18C, an earpiece 12 of the present invention may comprise a base cavity 120, a tip cavity 121, one or more base apertures 122, and a pressure-relief channel 123.

The base cavity 120 may be configured to receive a TED such that the TED may be thermally coupled to the earpiece 12 by mounting the TED on an interior cavity surface of the base cavity 120.

The tip cavity 121 may be configured to receive a sensor (e.g., a sensor configured to detect the temperature of the earpiece).

The base apertures 122 may be configured to provide a passageway for one or more wires and/or cables (e.g., a thermal stimulation lead connected to a TED, a wire connected to the sensor 14, etc.).

The pressure-relief channel 123 may be configured to provide a pathway through which air and/or moisture may flow during and/or after insertion of the earpiece 12 into the ear canal of a patient (e.g., to reduce the pressure in the ear canal during and/or after insertion of the earpiece 12 and/or to allow moisture to escape the ear canal during and/or after insertion of the earpiece 12). The pressure-relief channel 123 may be of any suitable length and depth (i.e., any length/depth that is sufficient to provide air flow from the interior of the ear canal at the distal tip of the earpiece to the external air outside of the ear canal during and/or after insertion of the earpiece 12). For example, the pressure-relief channel 123 may be generally as long as a side of the earpiece 12 and may be about 0.5 mm to about 2.0 mm deep. The pressure-relief channel 123 may be located in any suitable location in/on the earpiece (e.g., embedded in an outer surface of earpiece 12 or passing through the interior of the earpiece 12 so as to provide a conduit between the interior of the ear canal and the exterior environment).

III. Thermoelectric Device

The vestibular stimulation device may comprise one or more TEDs. TEDs of the present invention may be operatively connected to one or more controllers and may be used deliver one or more thermal waveforms to the vestibular system and/or the nervous system of a patient (e.g., by warming and/or cooling an earpiece inserted into the ear canal of said patient).

Any suitable thermoelectric device can be used to carry out the present invention, including, but not limited to, those described U.S. Pat. Nos. 5,974,806, 6,229,123, 6,977,360, 7,024,865, 7,098,393, 7,202,443 and 7,205,675; in U.S. Patent Publication Nos. 2004/0199266 and 2010/0198204 and 2010/0198282; in U.S. patent application Ser. No. 12/970,312 and Ser. No. 12/970,347 and in U.S. Provisional Application No. 61/497,761, the disclosure of each of which is incorporated herein by reference in its entirety. For example, the vestibular stimulation device comprises one or more thin film TEDs (including, but not limited to, those described in U.S. Pat. No. 6,300,150 and U.S. Patent Publication Nos. 2006/0086118 and 2007/0028956).

TEDs of the present invention may comprise any suitable material. For example, the TED(s) may comprise a thermoelectric material such as bismuth telluride. In some embodiments, the TED(s) comprise a P-type thermoelectric element and an N-type thermoelectric element that are electrically coupled in series and thermally coupled in parallel.

TEDs of the present invention may be of any suitable size/shape. In some embodiments, the TED(s) is/are of a generally rectangular shape, with typical rectangular areas being about 2×1 mm or about 5×2 mm or more and with a typical height profile of about 1.0 mm, about 0.65 mm or about 0.5 mm or less.

TEDs of the present invention may be configured to sense the temperature of the earpiece(s) and/or the heat sink(s) with which it is associated.

As will be appreciated by one of skill in the art, in those embodiments comprising a plurality of TEDs, the TEDs may be arranged in any suitable manner. For example, the TEDs may be positioned adjacent one another in a linear array, a two-dimensional array or a three-dimensional array (e.g., at a density of about 5, 10 or 20 per square centimeter to about 100, 200 or 400 per square centimeter or more).

As will be appreciated by one of skill in the art, in those embodiments comprising a plurality of TEDs, the TEDs may be thermally coupled to one another. For example, the TEDs may be thermally coupled to one another (e.g., through a common heat sink) such that thermal energy displaced by one TED can be at least partially offset by thermal energy displaced by another TED (e.g., by heating tissue with one TED while cooling adjacent tissue with an adjacent TED).

IV. Heat Sink

The vestibular stimulation device may comprise one or more heat sinks. In some embodiments, at least one heat sink is thermally coupled to each earpiece. In some embodiments, each TED thermally coupled to an earpiece is thermally coupled between the earpiece and at least one heat sink. In some embodiments, the heat sink(s) may be thermally isolated from the earpiece(s) except insofar as they are thermally coupled to opposite sides of the TED(s). In those embodiments comprising a pair of earpieces, each earpiece may be thermally coupled to a separate heat sink and/or to a common heat sink.

Any suitable heat sink can be used to carry out the present invention, including, but not limited to, those described in U.S. Patent Publication Nos. 2010/0198204 and 2010/0198282; in U.S. patent application Ser. No. 12/970,312 and Ser. No. 12/970,347 and in U.S. Provisional Application No. 61/497,761, the disclosure of each of which is incorporated herein by reference in its entirety.

Heat sinks of the present invention may comprise any suitable material, including, but not limited to, metal alloys. For example, the heat sink(s) may comprise aluminum or an aluminum alloy (e.g., 6061 aluminum).

Heat sinks of the present invention may be of any suitable size/shape. In some embodiments, the heat sink(s) comprise(s) a plurality of fins. Such fins may be from about 1 to about 500 mm in height, preferably about 1 to about 100 mm. In some embodiments, each heat sink weighs between about 30 grams and about 70 grams.

Heat sinks of the present invention may be passively and/or actively cooled. For example, each heat sink may be associated with one of more fans configured to increase air flow over the heat sink, thereby facilitating heat dissipation from the heat sink.

V. Sensors

The vestibular stimulation device may comprise one or more sensors. In some embodiments, the sensor(s) is/are configured to transmit controller feedback data, data associated with the delivery of one or more thermal waveforms to the vestibular system and/or the nervous system of a patient and/or data associated with the fit of one or more earpieces to the controller. In some such embodiments, the controller is configured (e.g., with computer instructions (i.e., software)) to adjust one or more attributes of TED activation (e.g., magnitude, duration, wave pattern, etc.) in response to feedback data received from the sensor(s) with which it is associated. The sensor(s) may be configured to transmit data to the controller over any suitable wired or wireless communications channel, including, but not limited to, a LAN, the Internet, a public telephone switching network, Bluetooth, WLAN and the like.

Any suitable sensor can be used to carry out the present invention, including, but not limited to, those described in U.S. Pat. Nos. 7,578,793, 7,558,622, 7,396,330, 7,215,994, 7,197,357, 7,087,075 and 6,467,905; in U.S. Patent Publication No. 2010/0198282; in U.S. patent application Ser. No. 12/970,312 and Ser. No. 12/970,347 and in U.S. Provisional Application No. 61/497,761, the disclosure of each of which is incorporated herein by reference in its entirety. For example, the vestibular stimulation device may comprise one or more of a galvanic skin resistance sensor, a position sensor, a motion detector, a blood pressure sensor, a heart rate sensor, a blood gas level sensor, an electrocardiogram sensor, an electroencephalogram sensor, an electrooculogram sensor, an electronystragmography sensor, a breathing rate sensor, a nystagmus sensor and a temperature sensor. Numerous such sensors are known and can be operatively associated with the systems described herein in accordance with known techniques or variations thereof that will be apparent to those skilled in the art given the present disclosure.

In some embodiments, the vestibular stimulation device comprises one or more temperature sensors. In some such embodiments, the vestibular stimulation device comprises a temperature sensor configured to provide controller feedback data associated with the temperature of the heat sink, a temperature sensor configured to provide controller feedback data associated with the temperature of the earpiece, a temperature sensor configured to provide controller feedback data associated with the temperature of the ear canal of the patient and/or a temperature sensor configured to provide controller feedback data associated with the temperature of the inner ear of the patient. In some embodiments, each earpiece comprises a sensor (e.g., an infrared sensor) configured to detect the temperature of the inner ear.

VI. Headband

The vestibular stimulation device may comprise a headband. In some embodiments, the headband is configured to position the earpiece(s) in the ear canal(s) of a patient. In some embodiments the headband is adjustable. It should be appreciated that, while the headband may be worn over the head, it may also be positioned under the chin, behind the head and/or over the ear(s).

Any suitable headband can be used to carry out the present invention, including, but not limited to, those described in U.S. patent application Ser. Nos. 12/704,872; 12/970,312 and Ser. No. 12/970,347 and in U.S. Provisional Application Nos. 61/287,873; 61/303,984; 61/304,059 and 61/497,761, the disclosure of each of which is incorporated herein by reference in its entirety.

As noted above with respect to FIG. 1, the vestibular stimulation device 1 may comprise a controller 11 that is operatively connected to a TED 13a that is thermally connected to an earpiece 12a that is configured so as to be insertable into the left ear canal of a patient and to a TED 13b that is thermally connected to an earpiece 12b that is configured so as to be insertable into the right ear canal of a patient. In some such embodiments, the controller 11 (e.g., a controller 11 as described above with respect to FIG. 14) is configured to enable a user to deliver one or more thermal waveforms to the vestibular system and/or the nervous system of a patient by:

generating and/or modifying the parameters, indications and/or approvals of one or more thermal waveforms using the waveform module 11a;

transmitting the generated/modified parameters, indications and/or approvals to the treatment module 11b and/or storing the generated/modified parameters, indications and/or approvals in the waveform database 11h;

generating a prescription comprising a set of instructions for delivering one or more thermal waveforms to the vestibular system and/or the nervous system of the patient by:

receiving one or more thermal waveforms from the waveform module 11a and providing instructions as to how each thermal waveform is to be administered to the patient using the treatment module 11b; or selecting one or more thermal waveforms from the waveform database 11h and providing instructions as to how each thermal waveform is to be administered to the patient using the treatment module 11b;

transmitting the generated prescription to the control module 11c and/or storing the generated prescription in the prescription database 11i; and/or delivering one or more thermal waveform(s) to the vestibular system and/or the nervous system of the patient by:

receiving a prescription comprising a set of instructions for delivering one or more thermal waveforms to the vestibular system and/or the nervous system of the patient from the treatment module 11b and activating the TEDs 13a, 13b in accordance with the instructions; or retrieving a prescription comprising a set of instructions for delivering one or more thermal waveforms to the vestibular system and/or the nervous system of the patient from the prescription database 11i and activating the TEDs 13a, 13b in accordance with the instructions.

In some such embodiments, the controller 11 (e.g., a controller 11 as described above with respect to FIG. 15) is configured to enable a user to deliver one or more thermal waveforms to the vestibular system and/or the nervous system of a patient by:

receiving and/or retrieving the parameters, indications and/or approvals of one or more thermal waveforms from a patient control device, a physician control device, a physician support device, a registry and/or a portable memory device using the network module 11d;

storing the received/retrieved parameters, indications and/or approvals in the waveform database 11h and/or transmitting the received/retrieved parameters, indications and/or approvals to the waveform module 11a and/or the treatment module 11b;

generating and/or modifying the parameters, indications and/or approvals of one or more thermal waveforms using the waveform module 11a;

transmitting the generated/modified parameters, indications and/or approvals to the treatment module 11b and/or storing the generated/modified parameters, indications and/or approvals in the waveform database 11h;

receiving and/or retrieving a prescription from a patient control device, a physician control device, a physician support device, a registry and/or a portable memory device using the network module 11d;

storing the received/retrieved prescription in the prescription database 11i and/or transmitting the received/retrieved prescription to the treatment module 11b and/or the control module 11c;

generating a prescription comprising a set of instructions for delivering one or more thermal waveforms to the vestibular system and/or the nervous system of the patient by:

receiving one or more thermal waveforms from the network module 11d and/or the waveform module 11a and providing instructions as to how each thermal waveform is to be administered to the patient using the treatment module 11b;

selecting one or more thermal waveforms from the waveform database 11h and providing instructions as to how each thermal waveform is to be administered to the patient using the treatment module 11b;

receiving a prescription from the network module 11d and modifying the instructions as to how each thermal waveform is to be administered to the patient using the treatment module 11b;

retrieving a prescription from the prescription database 11i and modifying the instructions as to how each thermal waveform is to be administered to the patient using the treatment module 11b;

transmitting the generated prescription to the control module 11c and/or storing the generated prescription in the prescription database 11i; and/or delivering one or more thermal waveform(s) to the vestibular system and/or the nervous system of the patient by:

receiving a prescription comprising a set of instructions for delivering one or more thermal waveforms to the vestibular system and/or the nervous system of the patient from the treatment module 11b and activating the TEDs 13a, 13b in accordance with the instructions; or retrieving a prescription comprising a set of instructions for delivering one or more thermal waveforms to the vestibular system and/or the nervous system of the patient from the prescription database 11i and activating the TEDs 13a, 13b in accordance with the instructions.

Also as noted above with respect to FIG. 1, the vestibular stimulation device 1 may further comprise a pair of sensors 14a, 14b, wherein one of the sensors 14a is operatively connected to the earpiece 12a that is configured so as to be insertable into the left ear canal of the patient, wherein the other sensor 14b is operatively connected to the earpiece 12b that is configured so as to be insertable into the right ear canal of the patient and wherein the controller 11 is operatively connected to each of the sensors 14a, 14b via a wireless connection 17a, 17b. In some such embodiments, controller 11 (e.g., a controller 11 as described above with respect to FIG. 15) is configured such that controller feedback data received from the sensors (e.g., data associated with the temperature of the earpiece(s), data associated with the temperature of the patient's ear canal(s), data associated with the rate at which an earpiece is warmed/cooled in response to a warming/cooling stimulus, etc.) is used by the control module 11c to ensure that the appropriate thermal waveform(s) is delivered to the vestibular system and/or the nervous system of the patient (e.g., the control module 11c may be configured to increase/decrease the magnitude of TED 13a activation if/when controller feedback data from the sensor 14b associated with the left earpiece 12a indicates that the temperature of the earpiece 12a is not at the appropriate temperature given the parameters of the prescribed thermal waveform).

Figure 19:
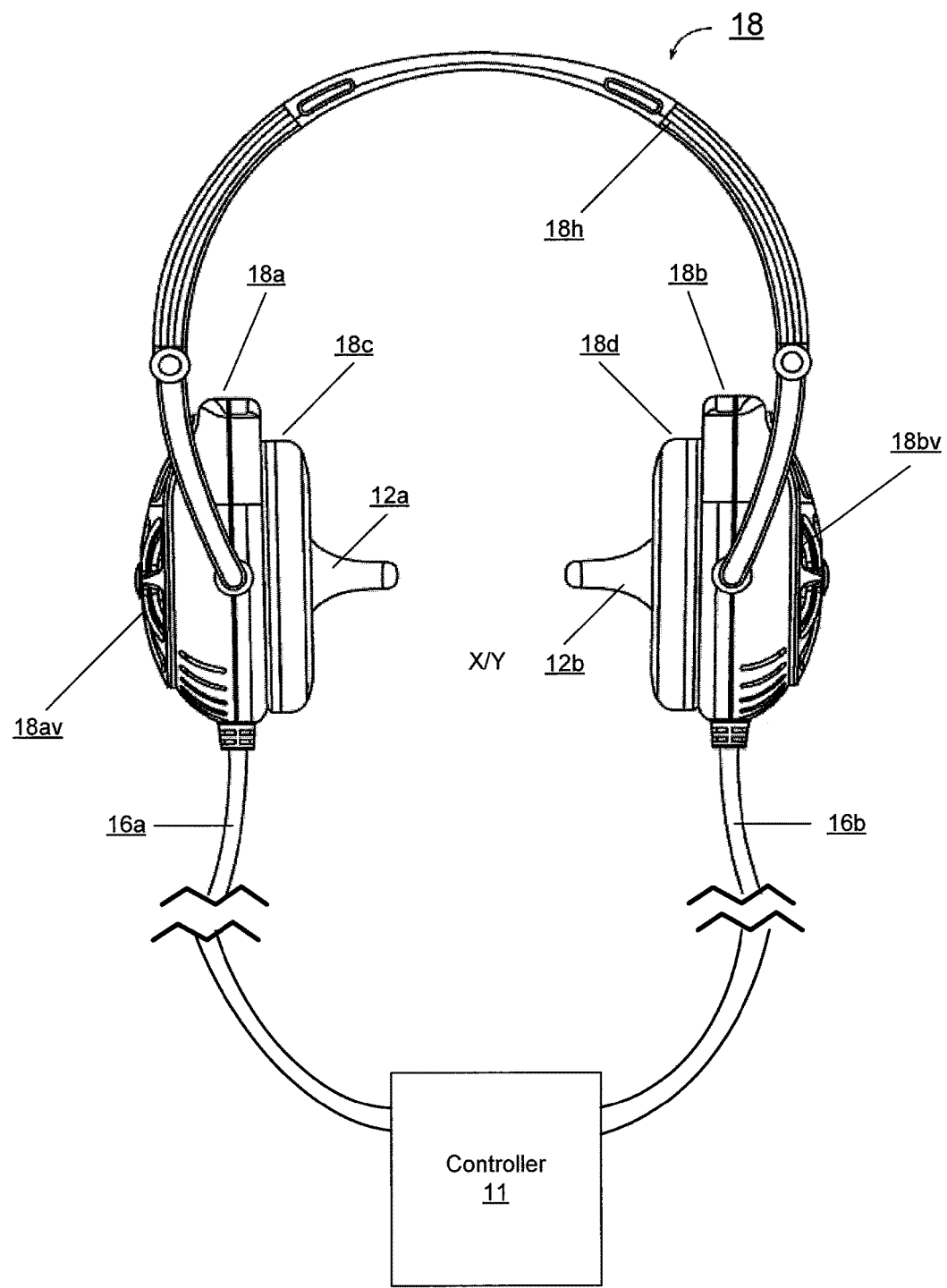
FIG. 19 is a perspective view of a vestibular stimulation device according to some embodiments of the present invention.

As shown in FIG. 19, in some embodiments, the vestibular stimulation device comprises a controller 11 and a headset 18. As shown therein, the headset may comprise a headband 18h configured to position a first earpiece 12a in the left ear canal of a patient and to position a second earpiece 12b in the right ear canal of the subject; a first heat sink thermally coupled to the first earpiece 12a (as shown, the first heat sink is concealed within a first housing 18a, the ventilation apertures 18av of which allow for heat exchange between the first heat sink and the ambient environment), a second heat sink thermally coupled to the second earpiece 12b (as shown, the first heat sink is concealed within a second housing 18b, the ventilation apertures 18bv of which allow for heat exchange between the second heat sink and the ambient environment); a first TED thermally coupled between the first earpiece 12a and the first heat sink (as shown, the first TED is concealed within the first housing 18a); a second TED 13b thermally coupled between the second earpiece 12b and the second heat sink (as shown, the second TED 13b is concealed within the second housing 18b); a first sensor operatively connected to the first TED and the controller 11 (as shown, the first sensor is concealed within the first earpiece 12a; a second sensor operatively connected to the second TED and the controller 11 (as shown, the second sensor is concealed within the second earpiece 12a; a first cushion 18c connected to the first housing 18a and a second cushion 18d connected to the second housing 18b. In some such embodiments, the controller is operatively connected to the first and second TEDs by a pair of thermal stimulation leads 16a, 16b. In some such embodiments, the controller 11 is operatively connected to the first and second sensors via a wireless connection (e.g., via a radiofrequency transceiver or a Bluetooth connection). In some such embodiments, one or both of the first and second cushions 18c, 18d is configured to be adjustable (e.g., the first cushion 18c and/or the second cushion 18d may comprise an inner chamber that may be inflated/deflated to adjust the firmness and/or the size of the cushion, thereby allowing a user to adjust the fit of the vestibular stimulation device (i.e., to adjust how far the first and/or second earpiece 12a, 12b inserts into the patient's ear canal by increasing/decreasing the amount of gas/liquid in the inner chamber)).

Figure 20:
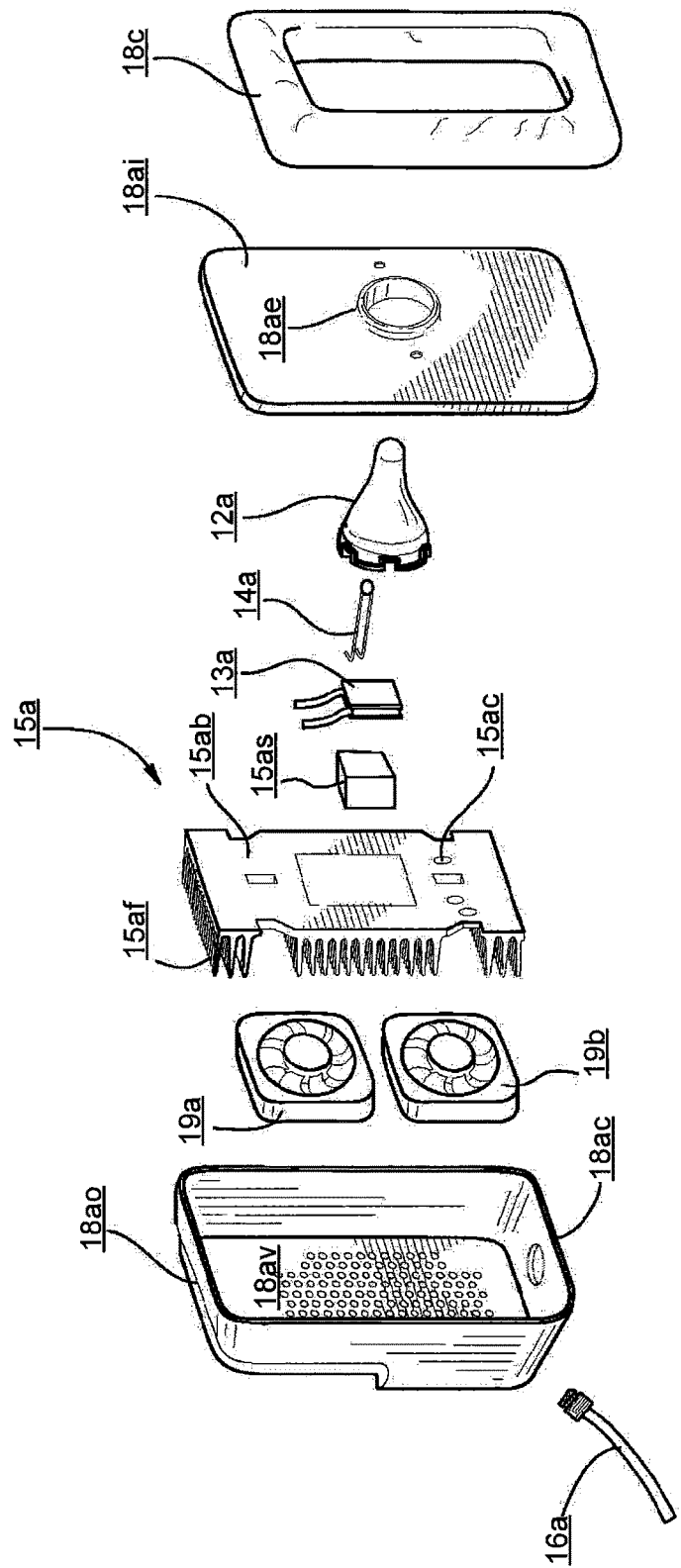
FIG. 20 is an exploded view of a vestibular stimulation device headset housing according to some embodiments of the present invention.
Figure 21:
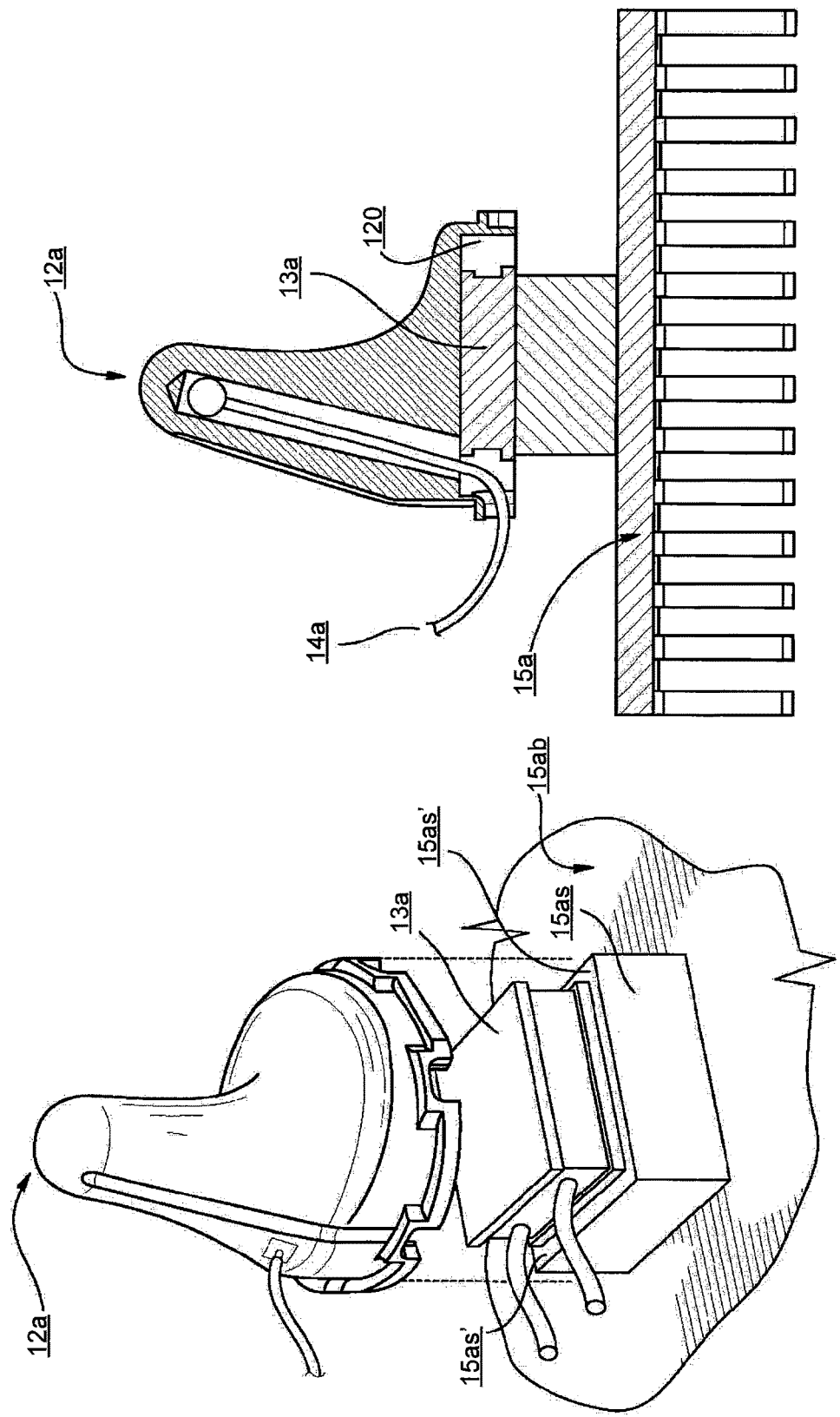
FIG. 21A is an exploded, perspective view of an earpiece, a TED and a heat sink according to some embodiments of the present invention.
FIG. 21B is an exploded, cross-sectional view of an earpiece, a TED, a spacer and a heat sink according to some embodiments of the present invention.

As discussed above with respect to FIG. 19, in some embodiments of the present invention, various components of the vestibular stimulation device 1 are concealed within the first and/or second housings 18a, 18b. FIG. 20 provides an exploded view of a first housing 18a according to some embodiments of the present invention. As shown therein, the first housing 18a may conceal a first TED 13a; a first sensor 14a; a first heat sink 15a, said first heat sink 15a comprising a first heat sink base 15ab, a first heat sink spacer 18as, a plurality of fins 15af and a plurality of cable apertures 15ac to provide passageways for one or more wires and/or cables (e.g., one or wires connected to the first TED 13a and/or one or wires connected to the first sensor 14a), and two heat dissipating fans 19a, 19b. The first earpiece 12a may be thermally connected to the first TED 13a and the first heat sink 15a as shown in FIGS. 21A-21B. The first TED 13a may be positioned on the top surface 15as' of the heat sink spacer 15as and inside the base cavity 120a of the first earpiece 12a and may be adhered to the heat sink 15a and/or the first earpiece 12a using a thermally conductive adhesive (e.g., silver paste). The first sensor 14a may be positioned inside the tip cavity 121 of the first earpiece 12a and may be configured to provide controller feedback data associated with the temperature of the first earpiece 12a to the controller (as discussed above). Upon activation, the heat dissipating fans 19a, 19b may facilitate the transfer of heat between the first heat sink 15a and the ambient environment by increasing air flow across the first heat sink 15a. The outer member 18ao of the first housing 18a comprises ventilation apertures 18av to further facilitate the transfer of heat between the first heat sink 15a and the ambient environment (by increasing the flow of air across the first heat sink 15a) and a cable aperture 18ac to provide a passageway for one or more wires and/or cables (e.g., the thermal stimulation lead 16a and/or one or wires connected to the first sensor 14a). The inner member 18ai of the first housing 18a comprises an earpiece aperture 18ae through which the distal portion of the first earpiece 12a protrudes. As will be appreciated by one skilled in the art, the second housing 18b may be similarly configured.

Physician Control Device

As noted above, the present invention provides a physician control device for generating and/or modifying the parameters, indications and/or approvals of one of more thermal waveforms; for generating, modifying, updating and/or extending one or more prescriptions and/or for receiving, analyzing and/or transmitting data.

In some embodiments, the physician control device is configured to generate a prescription comprising instructions for delivering one or more thermal waveforms to the vestibular system and/or the nervous system of a patient and to transmit the prescription to a vestibular stimulation device (e.g., a vestibular stimulation device of the present invention) and/or a patient control device (e.g., a patient control device of the present invention).

In some such embodiments, the physician control device comprises, consists essentially of or consists of a treatment module configured to generate a prescription and a network module configured to transmit the prescription to a vestibular stimulation device and/or a patient control device.

A physician control device of the present invention may be any suitable computing device/system, including, but not limited to, a desktop computer, a laptop computer, a handheld computer, a personal digital assistant (PDA), and a smart phone.

Any conventional security means may be provided to prevent unauthorized activation of the physician control device. For example, the physician control device may be password protected.

The physician control support device may be configured to receive and/or transmit and suitable data, including, but not limited to, data associated with the parameters, indications and/or approvals of one or more thermal waveforms, data associated with one or more prescriptions, controller feedback data, data associated with the delivery of one or more thermal waveforms, data associated with the fit of one or more earpieces, patient feedback data, physician feedback data and/or patient information.

The physician control device may be configured to receive and/or transmit data from/to various devices, including, but not limited to, a vestibular stimulation device, a patient control device, a physician support device, a registry, a TED, a sensor and/or a portable memory device (e.g., an SD memory card). In some embodiments, the physician control device is configured to receive data associated with the parameters, indications and/or approvals of one or more thermal waveforms (e.g., idealized thermal waveforms) from a physician support device, a registry and/or a portable memory device (e.g., an SD memory card); to transmit data associated with the parameters, indications and/or approvals of one or more thermal waveforms (e.g., idealized thermal waveforms) to a vestibular stimulation device, a patient control device, a registry and/or a portable memory device (e.g., an SD memory card); to receive one or more prescriptions from a physician support device, a registry and/or a portable memory device (e.g., an SD memory card); to transmit one or more prescriptions to a vestibular stimulation device, a patient control device, a registry and/or a portable memory device (e.g., an SD memory card); to receive one or more prescription modifications, updates and/or extensions from a physician support device, a registry and/or a portable memory device (e.g., an SD memory card); to transmit one or more prescription modifications, updates and/or extensions to a vestibular stimulation device, a patient control device, a registry and/or a portable memory device (e.g., an SD memory card); to receive data associated with the delivery of one or more thermal waveforms (e.g., idealized thermal waveforms) from a vestibular stimulation device, a patient control device and/or a portable memory device (e.g., an SD memory card); to transmit data associated with the delivery of one or more thermal waveforms (e.g., idealized thermal waveforms) to a physician support device, a registry and/or a portable memory device (e.g., an SD memory card); to receive patient feedback data from a vestibular stimulation device, a patient control device and/or a portable memory device (e.g., an SD memory card); to transmit patient feedback data to a physician support device, a registry and/or a portable memory device (e.g., an SD memory card); to transmit physician feedback data to a physician support device, a registry and/or a portable memory device (e.g., an SD memory card); to receive patient information from a vestibular stimulation device, a patient control device and/or a portable memory device (e.g., an SD memory card) and/or to transmit patient information to a physician support device, a registry and/or a portable memory device (e.g., an SD memory card).

The physician control device may be configured to receive and/or transmit data over any suitable wired or wireless communications channel, including, but not limited to, a LAN, the Internet, a public telephone switching network, Bluetooth, WLAN and the like.

In some embodiments, the physician control device comprises memory, a processor and a power supply. As will be appreciated by one of skill in the art, the processor may be any commercially available or custom microprocessor. Memory can include, but is not limited to, the following types of devices: cache, ROM, PROM, EPROM, EEPROM, flash memory, SRAM and DRAM. The power supply may be an internal power supply (e.g., one or more rechargeable batteries that may be recharged without first being removed from the physician control device).

The physician control device's memory may comprise any suitable software and/or data, including, but not limited to, an operating system, applications, data and input/output (I/O) drivers.

As will be appreciated by one of skill in the art, the physician control device may use any suitable operating system, including, but not limited to, OS/2, AIX, OS/390 or System390 from International Business Machines Corp. (Armonk, N.Y.), Window CE, Windows NT, Windows95, Windows98, Windows2000, Windows 7 or Windows Vista from Microsoft Corp. (Redmond, Wash.), Mac OS from Apple, Inc. (Cupertino, Calif.), Unix, Linux or Android.

As will be appreciated by one of skill in the art, the physician control device may comprise any suitable application, including, but not limited to, one or more programs configured to implement one or more of the various features of the present invention. For example, the physician control device may comprise a waveform module that enables a user to generate and/or modify the parameters, indications and/or approvals of one or more thermal waveforms; a treatment module that enables a user to generate, modify, update and/or extend a prescription comprising a set of instructions for delivering one or more thermal waveforms to the vestibular system and/or the nervous system of a patient; a network module configured to receive and/or transmit data; a GUI module configured to display information and/or accept user input; a feedback module configured to receive, transmit, and/or analyze data associated with the delivery of one or more thermal waveforms, data associated with the fit of one or more earpieces, patient feedback data, physician feedback data and/or patient information; an alert generation module configured to generate one or more alert messages; a tone generation module configured to produce one or more audible tones; a visual indicator module configured to produce one or more visual indicators and/or a security module configured to prevent unauthorized use of the physician control device. In some embodiments, two or more of the aforementioned modules are combined to form a single module configured to carry out the function(s) of each of the individual modules (e.g., the physician control device may comprise a waveform-treatment module that enables a user to generate and/or modify one or more thermal waveforms and to generate, modify, update and/or extend a prescription). In some embodiments, one of the aforementioned modules is split into two or more distinct modules (e.g., the physician control device may comprise a waveform generation module that enables a user to generate the parameters, indications and/or approvals of one or more thermal waveforms and a waveform update module that enables a user to modify the parameters, indications and/or approvals of one or more thermal waveforms). In some embodiments, one or more of the functions described below with respect to one of the modules described below is performed by one of the other modules described below (e.g., the treatment module, rather than the waveform module, may be configured to modify the parameters, indications and/or approvals of one or more thermal waveforms).

Waveform Module

In some embodiments, the physician control device comprises a waveform module whereby a user may generate and/or modify the parameters, indications and/or approvals of one or more thermal waveforms.

In some embodiments, the waveform module comprises software that enables a user to generate and/or modify the parameters of one or more thermal waveforms by point-to-point design and/or by utilizing mathematical functions. For example, the waveform module may comprise software that enables a user to generate and/or modify the parameters, indications and/or approvals of a thermal waveform by selecting/altering one or more parameters, including, but not limited to, shape, frequency, amplitude and duration. In some embodiments, the waveform module enables a user to retrieve/select a thermal waveform from a database and then modify the parameters of that thermal waveform to generate a new thermal waveform.

In some embodiments, the waveform module comprises software that enables a user to generate and/or modify the parameters, indications and/or approvals of one or more thermal waveforms using an interactive touch screen. For example, the waveform module may comprise software that enables a user to generate the parameters of a thermal waveform by drawing the desired waveform on an interactive touch screen (as discussed above with respect to FIG. 3). Similarly, the waveform module may enable a user to modify the parameters of a thermal waveform by highlighting one or more points on the waveform and moving the point(s) to a new location (e.g., a higher/lower temperature) (as discussed above with respect to FIG. 4).

In some embodiments, the waveform module comprises software that automatically adjusts the parameters of the thermal waveform(s) created by a user to account for system limitations. For example, the waveform module may comprise software that automatically adjusts the slope of a thermal waveform in accordance with the minimum/maximum temperature and/or the rate of temperature change that is achievable using a particular combination of earpiece(s), TED(s), etc. That is, the waveform module may comprise software that prevents a user from generating parameters for a thermal waveform that cannot be delivered because of system limitations.

In some embodiments, the waveform module comprises software that enables a user to protect one or more thermal waveforms (i.e., to prevent one or more users from modifying the parameters, indications and/or approvals of the thermal waveform(s) and/or from deleting the thermal waveform(s) from a waveform database). For example, the waveform module may comprise software that enables a user to protect one or more idealized thermal waveforms (e.g., by requiring users to enter a specified password prior to modifying and/or deleting the idealized thermal waveform(s)).

In some embodiments, the waveform module comprises software that enables a user to remove the protected status from one or more thermal waveforms. For example, the waveform module may comprise software that enables a user to remove the protected status from one or more idealized thermal waveforms (e.g., by entering the appropriate password).

In some embodiments, the waveform module is configured to automatically generate and/or modify the parameters, indications and/or approvals of one or more thermal waveforms (e.g., idealized thermal waveforms) in response to data received from one or more devices/modules. For example, the waveform module may be configured to automatically update one or more thermal waveforms responsive to data received from one or more TEDs and/or one or more sensors.

The waveform module may be configured to retrieve the parameters, indications and/or approvals of one or more thermal waveforms from any suitable database, including, but not limited to, a waveform database residing in a vestibular stimulation device, a waveform database residing in a patient control device, a waveform database residing in the physician control device, a waveform database residing in a physician support device, a waveform database residing in a registry and/or a waveform database residing in a portable memory device (e.g., an SD memory card).

Waveform parameters, indications and/or approvals generated and/or modified by the waveform module may be stored in a database. In some embodiments, the generated/modified parameters, indications and/or approvals are stored in a waveform database comprising data associated with the parameters, indications and/or approvals of one or more thermal waveforms (e.g., idealized thermal waveforms). For example, the generated/modified waveform parameters, indications and/or approvals may be stored in a waveform database residing in a vestibular stimulation device, a waveform database residing in a patient control device, a waveform database residing in the physician control device, a waveform database residing in a physician support device, a waveform database residing in a registry and/or a waveform database residing in a portable memory device (e.g., an SD memory card).

B. Treatment Module

In some embodiments, the physician control device comprises a treatment module whereby a user (e.g., a physician) may generate, modify, update and/or extend a prescription. For example, the treatment module may enable a user to generate, modify, update and/or extend a prescription comprising a set of instructions for delivering one or more thermal waveforms to the vestibular system and/or the nervous system of a patient.

In some embodiments, the treatment module comprises software that enables a user to select one or more thermal waveforms from a database (e.g., an idealized thermal waveform from an idealized waveform database) and to provide instructions as to when/how each of those waveforms should be administered. For example, a treatment module may comprise software that enables a user to provide instructions as to how long a treatment schedule is to last (as discussed above with respect to FIG. 5), to provide instructions as to how many treatments may be administered each day (as discussed above with respect to FIG. 5), to provide instructions as to how often each thermal waveform is to be administered (as discussed above with respect to FIG. 6), to provide instructions as to what time(s) of day each thermal waveform is to be administered (as discussed above with respect to FIGS. 6 and 9), to select one or more idealized thermal waveforms from a database (as discussed above with respect to FIG. 7), to provide instructions regarding whether each of the selected thermal waveforms is to be delivered to the right and/or left ear canal of a patient (as discussed above with respect to FIG. 8), etc.

In some embodiments, the treatment module comprises software that enables a user to modify, update and/or extend a prescription by changing one or more parameters of the prescription (as discussed above with respect to FIG. 10), including, but not limited to, which thermal waveform(s) are delivered, frequency with which the thermal waveform(s) is/are delivered, and the expiration date of the prescription. Any suitable prescription may be modified, updated and/or extended, including, but not limited to, prescriptions stored in a prescription database (e.g., a prescription database residing in a vestibular stimulation device, in a patient control device, in the physician control device, in a physician support device or in a portable memory device, such as a portable SD memory card).

The treatment module may be configured to retrieve/select thermal waveforms from any suitable database, including, but not limited to, a waveform database residing in a vestibular stimulation device, a waveform database residing in a patient control device, a waveform database residing in the physician control device, a waveform database residing in a physician support device, a waveform database residing in a registry and/or a waveform database residing in a portable memory device (e.g., an SD memory card).

The treatment module may be configured to retrieve prescriptions from any suitable database, including, but not limited to, a prescription database residing in a vestibular stimulation device, a prescription database residing in a patient control device, a prescription database residing in the physician control device, a prescription database residing in a physician support device, a prescription database residing in a registry and/or a prescription database residing in a portable memory device (e.g., an SD memory card).

Prescriptions generated, modified, updated and/or extended by the treatment module may be added to a database comprising one or more prescriptions. For example, the prescriptions may be stored in a prescription database residing in a vestibular stimulation device, a prescription database residing in a patient control device, a prescription database residing in the physician control device, a prescription database residing in a physician support device, a prescription database residing in a registry and/or a prescription database residing in a portable memory device.

C. Network Module

In some embodiments, the physician control device comprises a network module configured to receive, retrieve and/or transmit data.

The network module may be configured to receive, retrieve and/or transmit data from/to any suitable device/module/database, including, but not limited to, other modules residing in the physician control device, databases residing in the physician control device, a vestibular stimulation device, a patient control device, a physician support device, a registry, a TED, a sensor and a portable memory device (e.g., an SD memory card).

The network module may be configured to receive, retrieve and/or transmit data over any suitable wired or wireless communications channel, including, but not limited to, a LAN, the Internet, a public telephone switching network, Bluetooth, WLAN and the like.

The network module may be configured to receive, retrieve and/or transmit any suitable data, including, but not limited to, data associated with the parameters, indications and/or approvals of one or more thermal waveforms, one or more prescriptions, controller feedback data, data associated with the delivery of one or more thermal waveforms, data associated with the fit of one or more earpieces, patient feedback data, physician feedback data and/or patient information.

In some embodiments, the network module is configured to receive and/or retrieve data associated with the parameters, indications and/or approvals of one or more thermal waveforms from a waveform module/database residing in the physician control device, from a vestibular stimulation device, from a patient control device, from a physician support device, from a registry and/or from a portable memory device.

In some embodiments, the network module is configured to receive and/or retrieve one or more prescriptions from a treatment module residing in the physician control device, from a prescription database residing in the physician control device, from a vestibular stimulation device, from a patient control device, from a physician support device, from a registry and/or from a portable memory device.

In some embodiments, the network module is configured to receive and/or retrieve controller feedback data, data associated with the delivery of one or more thermal waveforms and/or data associated with the fit of one or more earpieces from a feedback module/database residing in the physician control device, from a vestibular stimulation device and/or from a patient control device.

In some embodiments, the network module is configured to receive and/or retrieve patient feedback data, physician feedback data and/or patient information from a feedback module/database residing in the physician control device, from a GUI module residing in the physician control device, from a patient information database residing in the physician control device, from a vestibular stimulation device, from a patient control device, from a physician support device, from a registry and/or from a portable memory device.

In some embodiments, the network module is configured to transmit data associated with the parameters, indications and/or approvals of one or more thermal waveforms to a waveform module/database residing in the physician control device, to a treatment module residing in the physician control device, to a vestibular stimulation device, to a patient control device, to a physician support device, to a registry and/or to a portable memory device.

In some embodiments, the network module is configured to transmit one or more prescriptions to a treatment module residing in the physician control device, to a prescription database residing in the physician control device, to a vestibular stimulation device, to a patient control device, to a physician support device, to a registry and/or to a portable memory device.

In some embodiments, the network module is configured to transmit controller feedback data, data associated with the delivery of one or more thermal waveforms and/or data associated with the fit of one or more earpieces to a feedback module/database residing in the physician control device, to a vestibular stimulation device, to a patient control device, to a physician support device, to a registry and/or to a portable memory device.

In some embodiments, the network module is configured to transmit patient feedback data, physician feedback data and/or patient information to a feedback module/database residing in the physician control device, to a patient information database residing in the physician control device, to a vestibular stimulation device, to a patient control device, to a physician support device, to a registry and/or to a portable memory device.

In some embodiments, the network module is configured to access a database comprising data associated with the parameters, indications and/or approvals of one or more thermal waveforms (e.g., idealized thermal waveforms). For example, the network module maybe configured to access a waveform database residing in a vestibular stimulation device, a waveform database residing in a patient control device, a waveform database residing in the physician control device, a waveform database residing in a physician support device, a waveform database residing in a registry and/or a waveform database residing in a portable memory device.

In some embodiments, the network module is configured to access a database comprising one or more prescriptions. For example, the network module maybe configured to access a prescription database residing in a vestibular stimulation device, a prescription database residing in a patient control device, a prescription database residing in the physician control device, a prescription database residing in a physician support device, a prescription database residing in a registry and/or a prescription database residing in a portable memory device.

In some embodiments, the network module is configured to access a database comprising controller feedback data, data associated with the delivery of one or more thermal waveforms, data associated with the fit of one or more earpieces, patient feedback data and/or physician feedback data. For example, the network module maybe configured to access a feedback database residing in a vestibular stimulation device, a feedback database residing in a patient control device, a feedback database residing in the physician control device, a feedback database residing in a physician support device, a feedback database residing in a registry and/or a feedback database residing in a portable memory device.

In some embodiments, the network module is configured to access a database comprising patient information. For example, the network module maybe configured to access a patient information database residing in a vestibular stimulation device, a patient information database residing in a patient control device, a patient information database residing in the physician control device, a patient information database residing in a physician support device, a patient information database residing in a registry and/or a patient information database residing in a portable memory device.

E. Graphical User Interface Module

In some embodiments, the physician control device comprises a GUI module configured to display information and/or to accept user input. Any suitable GUI may be used, including, but not limited to, a keyboard, a mouse, an LCD display with one or more associated entry keys and an interactive touch screen. For example, the GUI may comprise a static pressure touch-sensitive display, a capacitive touch-sensitive display, a resistive touch-sensitive display, an electrostatic capacity proximity sensor, a magnetic proximity sensor and/or an infrared proximity sensor. See, e.g., U.S. Patent Publication Nos. 2011/0271222, 2011/0273575, 2011/0275414 and 2011/0275416.

The GUI module may be configured to display any suitable information, including, but not limited to, data associated with the delivery of one or more thermal waveforms. For example, the GUI module may be configured to display the current date and/or time (as discussed above with respect to FIG. 10); one or more target temperatures (as discussed above with respect to FIG. 11); the number of treatment sessions that have been administered for a prescription; the number of treatment sessions remaining in a prescription; the amount of time remaining until a prescription must be renewed/updated; the amount of remaining battery life, an alert message (e.g., a reminder to a physician that he/she needs to modify, update and/or extend a prescription); the target time/temperature parameters of one or more prescribed thermal waveform(s) (as discussed above with respect to FIG. 11); the precise time/temperature parameters of the thermal waveform(s) delivered to a patient; the date/time of delivery of the thermal waveform(s) delivered to a patient; the temperature(s) of a patient's ear canal(s) at various time points before, during and/or after delivery of the thermal waveform(s); the temperature(s) of a patient's inner ear(s) at various time points before, during and/or after delivery of the thermal waveform(s); the fit of the earpiece(s) at various time points before, during and/or after delivery of the thermal waveform(s); an estimate of the thermal contact between the earpiece(s) and the patient's ear canal(s) at various time points before, during and/or after delivery of the thermal waveform(s); patient-specific time constants (e.g., a time constant associated with the transduction of heat from a patient's ear canal to the inner ear); reaction time (i.e., how long it took for a patient to react to one or more thermal waveforms); the effectiveness of one or more thermal waveforms (i.e., whether and to what extent symptoms were relieved, whether the thermal waveform(s) enhanced the effectiveness of another agent/therapy, etc.); the stability of a treatment (i.e., how long the effects of the treatment lasted); the instability of a treatment (i.e., which symptom(s) returned and when did it/they return); the presence or absence of comorbid disorders, injuries and/or diseases; disorder, injury and/or disease modulation(s) and/or modification(s) that occurred as a result of treatment; the cognitive effect(s) of one or more thermal waveforms; patient compliance (e.g., whether a patient initiated delivery at the prescribed time, whether a patient completed the prescribed treatment session, whether the earpiece(s) remained properly fitted in a patient's ear canal(s) for the duration of the treatment session, etc.); the mood of a patient at various time points before, during and/or after delivery of one or more thermal waveforms (e.g., videos/images of a patient that may be used to assess mood); objectives measures of efficacy (e.g., nystamography data, EEG data, MRI data, heart rate data, blood pressure data); subjective measures of efficacy (e.g., a patient-reported pain score); blood chemistry data (e.g., blood A1c levels, blood glucose levels and blood cortisol levels); saliva chemistry data (e.g., saliva cortisol levels); urine chemistry data (e.g., urine cortisol levels)), comments a patient made about his/her treatment session(s) (e.g., comments made to a physician, submitted in response to an automated survey and/or recorded in a treatment diary); the impedance between an earpiece inserted into the ear canal of a patient and an electrode affixed to a second location on/in said patient's body (e.g., an electrode placed in or adjacent to the patient's other ear canal); the rate at which a patient's inner ear cools in response to a cooling stimulus (e.g., data from a temperature sensor, such as thermistor, that monitors how quickly the inner ear cools in response to a cooling waveform); the rate at which a patient's inner ear warms in response to a warming stimulus (e.g., data from a temperature sensor, such as thermistor, that monitors how quickly the inner ear warms in response to a warming waveform) and/or patient comments regarding the subjective fit of his/her earpiece(s).

The GUI module may be configured to accept any suitable user input, including, but not limited to, instructions for generating and/or modifying the parameters, indications and/or approvals of a thermal waveforms; instructions for generating, modifying, updating and/or extending a prescription; physician feedback and/or patient information. For example, the GUI module may be configured to accept a physician comments regarding the effectiveness of a particular combination of thermal waveforms.

F. Feedback Module

In some embodiments, the physician control device comprises a feedback module configured to receive, transmit and/or analyze data.

The feedback module may be configured to receive and/or transmit data from/to any suitable device/module/database, including, but not limited to, other modules residing in the physician control device, databases residing in the physician control device, a vestibular stimulation device, a patient control device, a physician support device, a registry, a TED, a sensor and a portable memory device (e.g., an SD memory card).

The feedback module may be configured to receive and/or transmit data over any suitable wired or wireless communications channel, including, but not limited to, a LAN, the Internet, a public telephone switching network, Bluetooth, WLAN and the like.

The feedback module may be configured to receive, transmit and/or analyze any suitable data, including, but not limited to, controller feedback data, data associated with the delivery of one or more thermal waveforms, data associated with the fit of one or more earpieces, patient feedback data, physician feedback data and/or patient information.

In some embodiments, the feedback module is configured to receive and/or analyze data associated with the delivery of one or more thermal waveforms and/or data associated with the fit of one or more earpieces from a feedback database residing in the physician control device, from one or more vestibular stimulation devices and/or from one or more patient control devices. For example, the feedback module may be configured to analyze the accuracy with which one or more prescribed waveforms was delivered to a patient, the fit of an earpiece based upon the rate at which the temperature of the earpiece changes in response to a cooling/warming waveform, the slew rate associated with one or more TEDs, the impedance between an earpiece positioned in the left ear canal of a patient and an earpiece positioned in the right ear canal of a patient, the impedance between an earpiece positioned in the ear canal of a patient and an electrode affixed to a second location on/in the patient's body, etc.

In some embodiments, the feedback module is configured to receive and/or analyze patient feedback data, physician feedback data and/or patient information from a GUI module residing in the physician control device, from a feedback database residing in the physician control device, from a patient information database residing in the physician control device, from a vestibular stimulation device, from a patient control device, from a physician support device and/or from a portable memory device. For example, the feedback module may be configured to analyze the effectiveness of a given thermal waveform or combination of thermal waveforms (e.g., by analyzing pain scores entered before, during and after a treatment session), the effect(s) of one or more waveform modifications (e.g., by analyzing whether/how much a given waveform modification changed the effectiveness of a thermal waveform in treating a disease/disorder), etc.

In some embodiments, the feedback module is configured to transmit data associated with the delivery of one or more thermal waveforms, data associated with the fit of one or more earpieces, patient feedback data, physician feedback data, patient information and/or data associated with its analysis to a feedback database residing in the physician control device, to a patient information database residing in the physician control device, to a physician support device, to a registry and/or to a portable memory device (e.g., an SD memory card).

G. Alert Generation Module

In some embodiments, the physician control device comprises an alert generation module configured to generate one or more alert messages.

The alert generation module may be configured to generate any suitable alert message, including, but not limited to, a reminder that a patient is due for a prescription refill; an alert indicating that one or more idealized thermal waveforms has been modified; an alert indicating that a given modification is likely to increase/decrease the effectiveness of a given thermal waveform and/or an alert indicating that a given thermal waveform, class of thermal waveforms or combination of thermal waveforms has been identified as being indicated and/or approved for use in the treatment of a disease/disorder and a warning that the physician control device's internal power supply is low.

In some embodiments, the alert generation module is configured to communicate with various devices/modules, including, but not limited to, a vestibular stimulation device, a patient control device, a physician support device, a registry, a TED, a sensor, a portable memory device (e.g., an SD memory card) and other modules of the physician control device. For example, the alert generation module may be configured to provide instructions to the GUI module and/or the tone generation module for displaying one or more alert messages and/or for generation an audible tone to alert a user of the presence of the one or more alert messages. The graphical user interface module may be configured to display the one or more alert messages immediately upon generation or upon interaction with a user (e.g., an alert notification icon may be generated, with the alert message being displayed only after the user indicates that he/she wishes to view the message).

H. Tone Generation Module

In some embodiments, the physician control device comprises a tone generation module configured to produce audible tones. In some such embodiments, the tone generation module comprises a piezo buzzer. Audible tones may be produced to alert a user to various circumstances/events, including, but not limited to, the existence of an unread/unviewed alert message. Audible tones may be generated repeatedly in response to a single circumstance/event (e.g., an audible tone may be generated repeatedly until the user views/reads the message) and may become progressively louder and/or more frequent with time.

Visual Indicator Module

In some embodiments, the physician control device comprises a visual indicator module configured to notify a user of the existence of an unread/unviewed alert message. In some such embodiments, the visual indicator module comprises an LED indicator light. The visual indicator module may be activated repeatedly in response to a single alert message (e.g., an LED light may be illuminated repeatedly until the user views/reads the message) or may remain activated until the user views/reads the message.

J. Security Module

In some embodiments, the physician control device comprises a security module configured to prevent unauthorized use of the physician control device (i.e., to prevent unauthorized persons from using the physician control device, to prevent authorized persons from using the physician control device in an unauthorized manner, etc.).

The security module may be configured to prevent unauthorized use of the physician control device using any suitable means of security, including, but not limited to, password protection and data encryption. For example, the security module may be configured such that a user is required to input a designated password prior to generating and/or modifying a thermal waveform; generating, modifying, updating and/or extending a prescription; entering/viewing patient feedback data; entering/viewing physician feedback data and/or entering/viewing patient information (as discussed above with respect to FIG. 12).

As will be appreciated by one of skill in the art, the physician control device may comprise any suitable data, including, but not limited to, static and/or dynamic data used by the operating system, applications, I/O device drivers and other software components, controller feedback data, data associated with the parameters, indications and/or approvals of one or more thermal waveforms (e.g., idealized thermal waveforms), data associated with one or more prescriptions, data associated with the delivery of one or more thermal waveforms, data associated with the fit of one or more earpieces, patient feedback data, physician feedback data and patient information. For example, the physician control device may comprise a waveform database comprising data associated with one or more idealized thermal waveforms; a prescription database comprising data associated with one or more prescriptions; a feedback database comprising controller feedback data, data associated with the delivery of one or more thermal waveforms to the vestibular system and/or the nervous system of a patient, patient feedback data and physician feedback data and/or a patient history database comprising data associated with one or more patients. In some embodiments, two or more of the aforementioned databases are combined to form a single database comprising data from each of the individual databases (e.g., the physician control device may comprise a feedback-history database comprising data associated with the delivery of one or more thermal waveforms and patient information). In some embodiments, one of the aforementioned databases is split into two or more distinct databases (e.g., the physician control device may comprise a delivery feedback database comprising data associated with the specific parameters of the thermal waveform(s) delivered to a patient, a patient feedback database comprising patient feedback data and a physician feedback database comprising physician feedback data). In some embodiments, one or more of the data types described below with respect to one of the databases described below is stored in one of the other databases described below (e.g., the patient information database, rather than the feedback database, may be configured to receive/store patient feedback data). In some embodiments, data is transmitted, received and/or stored in a controlled format (e.g., in a standardized format using forms/programs supplied by a physician support device or a registry). The physician control device may be configured to transmit, receive and store data in a manner that ensures compliance with any and all applicable laws and/or regulations (e.g., the Health Insurance Portability and Accountability Act of 1996 (P.L. 104-191; "HIPAA")).

Waveform Database

In some embodiments, the physician control device comprises a waveform database configured to receive, store and/or transmit data associated with the parameters, indications and/or approvals of one or more thermal waveforms (e.g, one or more idealized thermal waveforms). In some such embodiments, the waveform database is configured such that one or more of the thermal waveforms stored therein is/are protected (e.g., users may be prevented from modifying and/or deleting the idealized thermal waveform(s) stored in the waveform database).

The waveform database may comprise any suitable type of memory including, but not limited to, cache, ROM, PROM, EPROM, EEPROM, flash memory, SRAM and DRAM. In some embodiments, the waveform database comprises a portable memory device, such as an SD memory card or a USB memory stick. For example, the waveform database may comprise an SD memory card interface and one or more prescriptions may be stored on a portable SD memory card.

The waveform database may be configured to receive and/or transmit data from/to any suitable device/module/database, including, but not limited to, modules residing in the physician control device, a vestibular stimulation device, a patient control device, a physician support device, a registry, a TED, a sensor and a portable memory device (e.g., an SD memory card).

The waveform database may be configured to receive and/or transmit data over any suitable wired or wireless communications channel, including, but not limited to, a LAN, the Internet, a public telephone switching network, Bluetooth, WLAN and the like.

B. Prescription Database

In some embodiments, the physician control device comprises a prescription database configured to receive, transmit and/or store one or more prescriptions, wherein each prescription comprising a set of instructions for delivering one or more thermal waveforms to the vestibular system and/or the nervous system of a patient.

The prescription database may comprise any suitable type of memory including, but not limited to, cache, ROM, PROM, EPROM, EEPROM, flash memory, SRAM and DRAM. In some embodiments, the prescription database comprises a portable memory device, such as an SD memory card or a USB memory stick. For example, the prescription database may comprise an SD memory card interface and one or more prescriptions may be stored on a portable SD memory card.

The prescription database may be configured to receive and/or transmit data from/to any suitable device/module/database, including, but not limited to, modules residing in the physician control device, a vestibular stimulation device, a patient control device, a physician support device, a registry, a TED, a sensor and a portable memory device (e.g., an SD memory card).

The prescription database may be configured to receive and/or transmit data over any suitable wired or wireless communications channel, including, but not limited to, a LAN, the Internet, a public telephone switching network, Bluetooth, WLAN and the like.

C. Feedback Database

In some embodiments, the physician control device comprises a feedback database configured to receive, transmit and/or store feedback data.

The feedback database may comprise any suitable type of memory including, but not limited to, cache, ROM, PROM, EPROM, EEPROM, flash memory, SRAM and DRAM. In some embodiments, the feedback database comprises a portable memory device, such as an SD memory card or a USB memory stick. For example, the feedback database may comprise an SD memory card interface and one or more prescriptions may be stored on a portable SD memory card.

The feedback database may be configured to receive and/or transmit feedback data from/to any suitable device/module/database, including, but not limited to, modules residing in the physician control device, a vestibular stimulation device, a patient control device, a physician support device, a registry, a TED, a sensor and a portable memory device (e.g., an SD memory card).

The feedback database may be configured to receive and/or transmit data over any suitable wired or wireless communications channel, including, but not limited to, a LAN, the Internet, a public telephone switching network, Bluetooth, WLAN and the like.

Feedback data may comprise any suitable data, including, but not limited to, controller feedback data, data associated with the delivery of one or more thermal waveforms, data associated with the fit of one or more earpieces, patient feedback data, physician feedback data and/or patient information. For example, the feedback database may comprise a log file detailing the target time/temperature parameters of one or more prescribed thermal waveform(s); the time/temperature parameters of the thermal waveform(s) delivered to a patient; the date/time of delivery of the thermal waveform(s) delivered to a patient; the temperature(s) of a patient's ear canal(s) at various time points before, during and/or after delivery of one or more thermal waveforms; the temperature(s) of a patient's inner ear(s) at various time points before, during and/or after delivery of one or more thermal waveforms; the fit of one or more earpieces at various time points before, during and/or after delivery of one or more thermal waveforms; an estimate of the thermal contact between one or more earpieces and a patient's ear canal(s) at various time points before, during and/or after delivery of one or more thermal waveforms; patient-specific time constants (e.g., a time constant associated with the transduction of heat from a patient's ear canal to the inner ear); a patient's reaction time (i.e., how long it took for a patient to react to one or more thermal waveforms); effectiveness of one or more thermal waveforms (i.e., whether and to what extent symptoms were relieved, whether the thermal waveform(s) enhanced the effectiveness of another agent/therapy, etc.); stability of a treatment (i.e., how long the effects of a treatment lasted); instability of a treatment (i.e., which symptom(s) returned and when did it/they return); the presence or absence of comorbid disorders, injuries and/or diseases; disorder, injury and/or disease modulation(s) and/or modification(s) that occurred as a result of treatment; the cognitive effect(s) of one or more thermal waveforms; patient compliance (e.g., whether a patient initiated delivery at the prescribed time, whether a patient completed the prescribed treatment session, whether the earpiece(s) remained properly fitted in a patient's ear canal(s) for the duration of the treatment session, etc.); the mood of a patient at various time points before, during and/or after delivery of one or more thermal waveforms (e.g., videos/images of a patient that may be used to assess mood); objectives measures of efficacy (e.g., nystamography data, EEG data, MRI data, heart rate data, blood pressure data); subjective measures of efficacy (e.g., a patient-reported pain score); blood chemistry data (e.g., blood A1c levels, blood glucose levels and blood cortisol levels); saliva chemistry data (e.g., saliva cortisol levels); urine chemistry data (e.g., urine cortisol levels)); comments a patient made about his/her treatment session(s) (e.g., comments made to a physician, submitted in response to an automated survey and/or recorded in a treatment diary); the impedance between an earpiece inserted into the ear canal of a patient and an electrode affixed to a second location on/in said patient's body (e.g., an electrode placed in or adjacent to the patient's other ear canal); the rate at which an earpiece is cooled in response to a cooling stimulus (e.g., data from a temperature sensor, such as thermistor, that monitors how quickly the earpiece cools in response to a cooling waveform); the rate at which an earpiece is warmed in response to a warming stimulus (e.g., data from a temperature sensor, such as a thermistor, that monitors how quickly the earpiece warms in response to a warming waveform); the rate at which a patient's ear canal and/or inner ear cooled in response to a cooling stimulus (e.g., data from a temperature sensor, such as thermistor, that monitors how quickly the ear canal and/or the inner ear cools in response to a cooling waveform); the rate at which a patient's ear canal and/or inner ear warmed in response to a warming stimulus (e.g., data from a temperature sensor, such as a thermistor, that monitors how quickly the ear canal and/or the inner ear warms in response to a warming waveform); patient comments regarding the subjective fit of one or more earpieces; physician comments regarding the effectiveness of one or more thermal waveforms and/or physician comments regarding the effect(s) of one or more waveform modifications.

D. Patient History Database

In some embodiments, the physician control device comprises a patient history database configured to receive, transmit and/or store patient information.

The patient history database may comprise any suitable type of memory including, but not limited to, cache, ROM, PROM, EPROM, EEPROM, flash memory, SRAM and DRAM. In some embodiments, the patient history database comprises a portable memory device, such as an SD memory card or a USB memory stick. For example, the patient history database may comprise an SD memory card interface and one or more prescriptions may be stored on a portable SD memory card.

The patient history database may be configured to receive and/or transmit data from/to any suitable device/module/database, including, but not limited to, modules residing in the physician control device, a vestibular stimulation device, a patient control device, a physician support device, a registry, a TED, a sensor and a portable memory device (e.g., an SD memory card).

The patient history database may be configured to receive and/or transmit data over any suitable wired or wireless communications channel, including, but not limited to, a LAN, the Internet, a public telephone switching network, Bluetooth, WLAN and the like.

Patient information may comprise any suitable information that is associated with a patient, including, but not limited to, the patient's medical history, the patient's current symptoms (if any), the patient's present diagnosis (if any), the patient's current prescriptions (if any) and data associated with the delivery of one or more thermal waveforms to the vestibular system and/or the nervous system of the patient.

As will be appreciated by one of skill in the art, the physician control device may comprise any I/O device drivers, including, but not limited to, software routines accessed through the operating system by the applications to communicate with devices such as I/O ports, memory components, vestibular stimulation devices, patient control devices and/or physician support devices.

As will be appreciated by one of skill in the art, the physician control device may be configured (e.g., with computer instructions (i.e., software)) to operate in a plurality of distinct modes. In each mode, the physician control device may be configured to permit access to some functionalities/modules and to prevent access to other functionalities/modules. For example, the physician control device may be configured to operate in a physician mode, wherein the user is allowed to perform physician-oriented tasks, such as generating, modifying, updating and/or extending a prescription comprising a set of instructions for delivering one or more thermal waveforms to the vestibular system and/or the nervous system of a patient, but is prevented from accessing other functionalities/modules (e.g., the user may be prevented from generating and/or modifying one or more thermal waveforms). Likewise, the physician control device may be configured to operate in a researcher mode, wherein the user is allowed to perform researcher-oriented tasks, such as generating and/or modifying one or more idealized thermal waveforms, but is prevented, from accessing other functionalities/modules (e.g., the user may be prevented from modifying the underlying operational parameters of the physician control device). Similarly, the physician control device may be configured to operate in an engineer mode, wherein the user is allowed to access all of the physician control device's functionalities/modules. Each mode may be protected via a unique security measure (e.g., the physician control device may be configured such that each mode is protected by a unique password).

Figure 22:
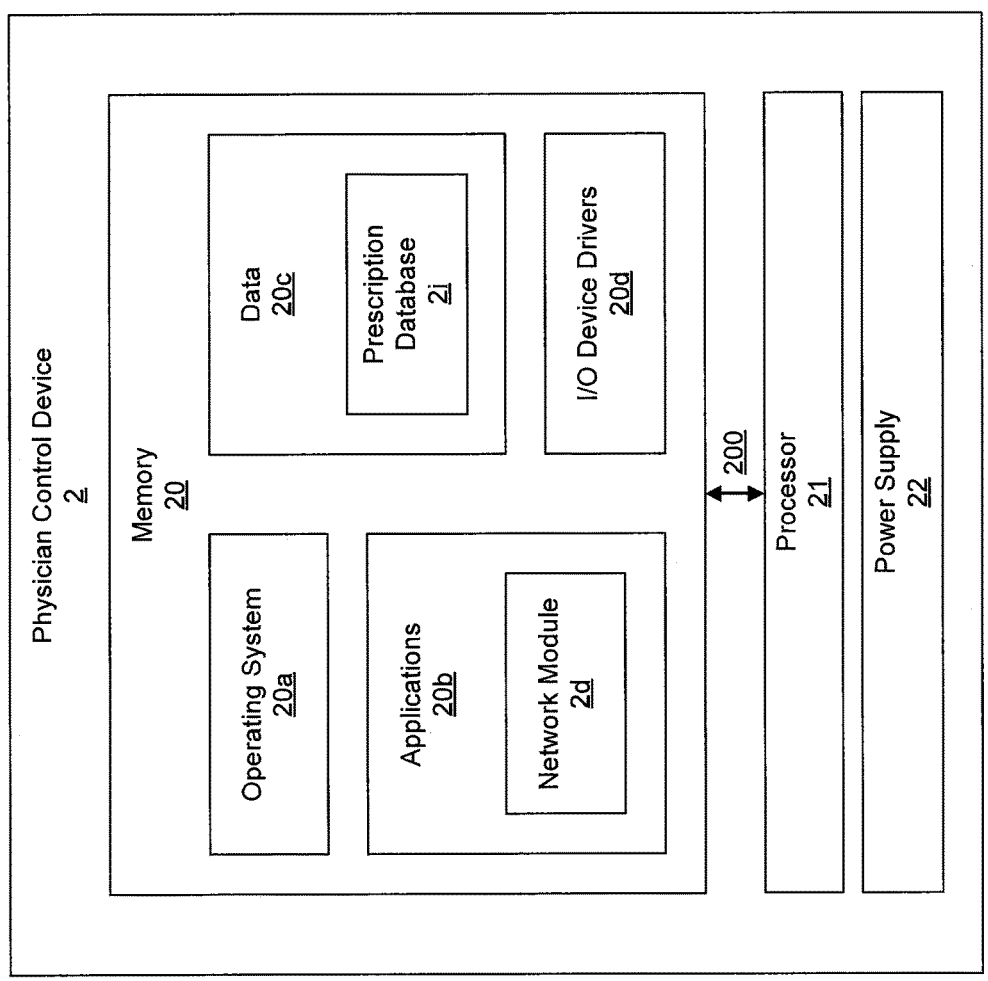
FIG. 22 is a block diagram of a physician control device according to some embodiments of the present invention.
Figure 23:
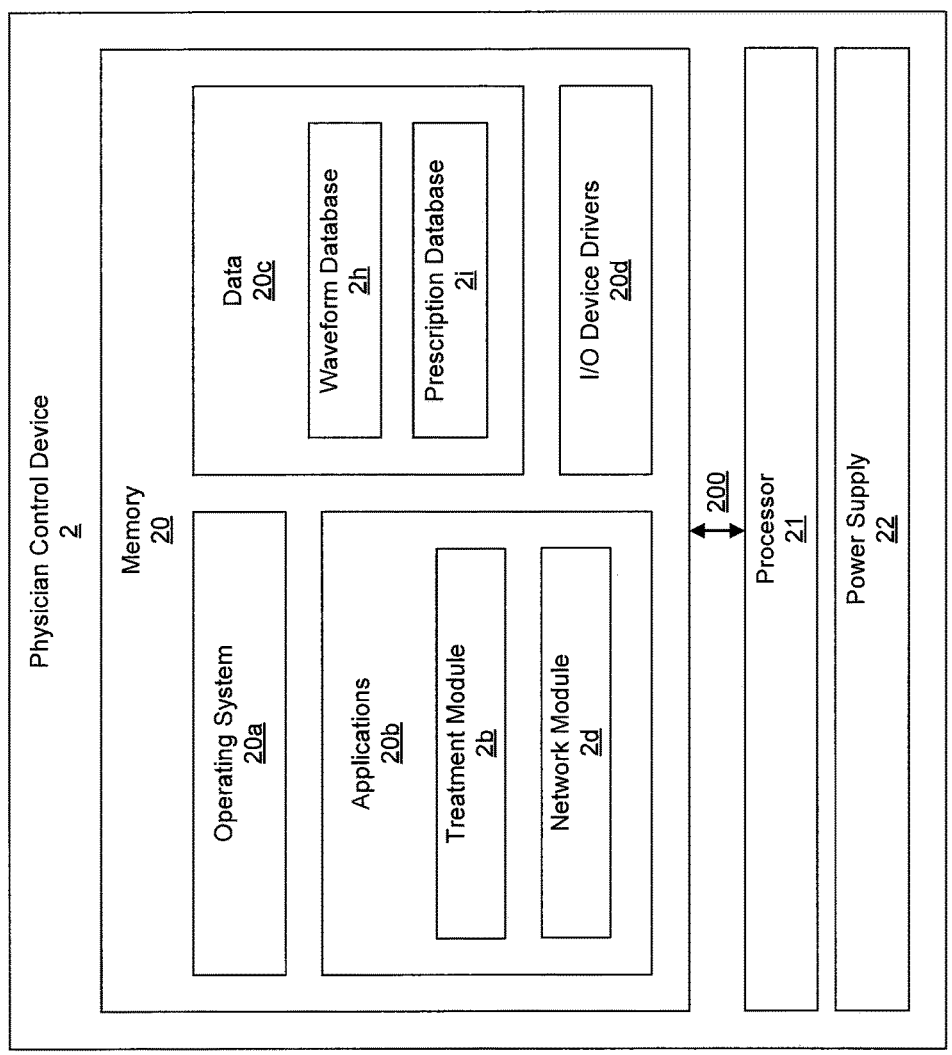
FIG. 23 is a block diagram of a physician control device according to some embodiments of the present invention.
Figure 24:
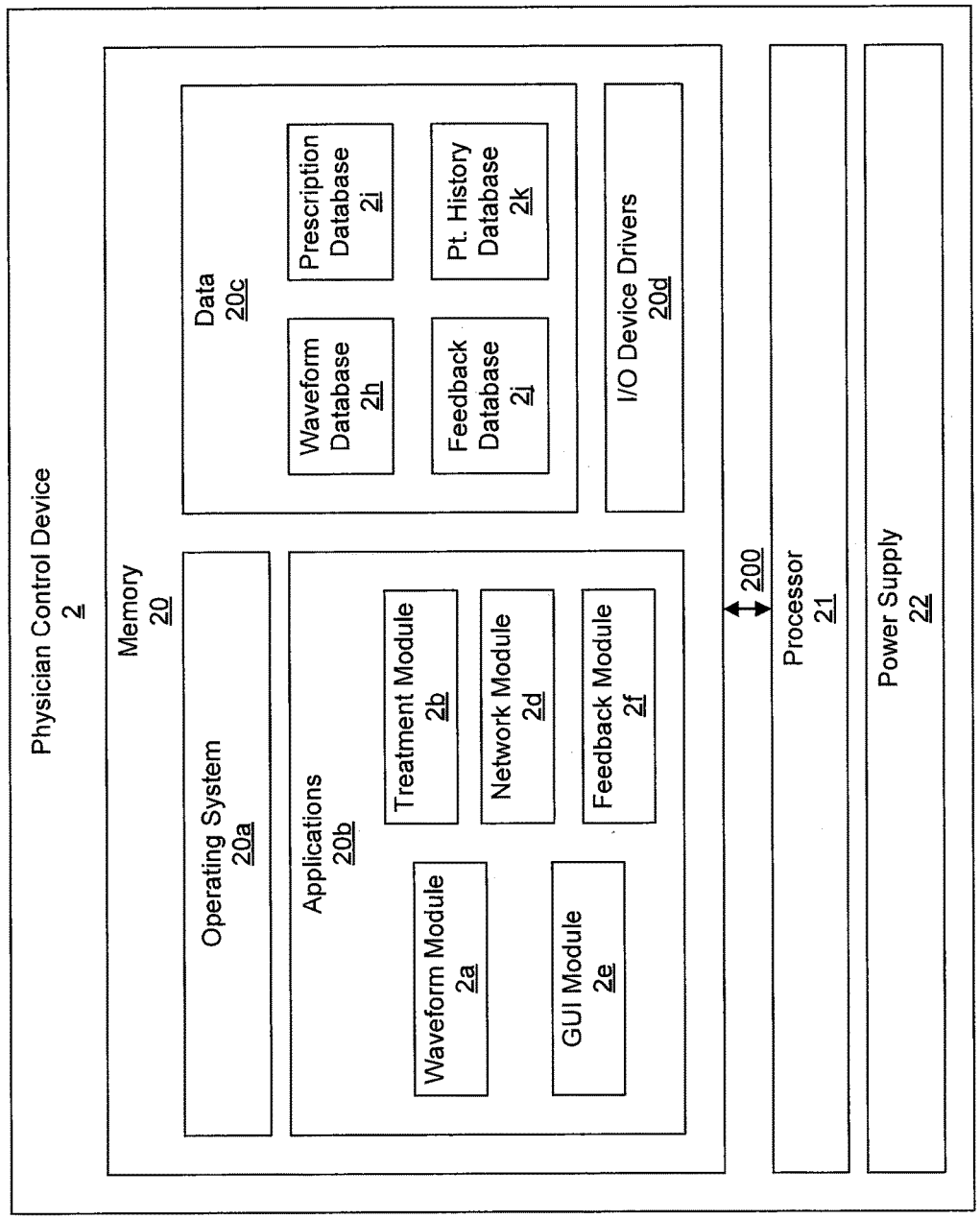
FIG. 24 is a block diagram of a physician control device according to some embodiments of the present invention.

As shown in FIGS. 22-24, in some embodiments of the present invention, the physician control device 2 comprises memory 20, a processor 21 and a power supply 22 (e.g., an internal power supply), wherein memory 20 is representative of the overall hierarchy of memory devices containing software and data used to implement the functionality of the physician control device 2 and wherein the processor 21 communicates with the memory 20 via an address/data bus 200. In particular embodiments, memory 20 comprises an operating system 20a, applications 20b (e.g., a waveform module 2a configured to generate and/or modify the parameters, indications and/or approvals of one or more thermal waveforms; a treatment module 2b configured to generate, modify, update and/or extend a prescription comprising a set of instructions for delivering one or more thermal waveforms to the vestibular system and/or the nervous system of a patient; a network module 2d configured to receive and/or transmit data, a GUI module 2e configured to display information and/or accept user input and/or a feedback module 2f configured to receive, transmit, and/or analyze data), data 20c (e.g., a waveform database 2h comprising data associated with the parameters, indications and/or approvals of one or more thermal waveforms; a prescription database 2i comprising at least one prescription comprising a set of instructions for delivering one or more thermal waveforms to the vestibular system and/or the nervous system of a patient; a feedback database 2j comprising data associated with the delivery of one or more thermal waveforms and/or a patient history database 2k comprising patient information) and I/O drivers 20d. In some such embodiments, data 20c comprises one or more databases stored on a portable memory device. For example, data 20c may comprise an SD memory card interface and a portable SD memory card comprising a waveform database 2h, a prescription database 2i, a feedback database 2j and/or a patient history database 2k.

In some embodiments, the network module 2d is configured to receive data associated with the parameters, indications and/or approvals of one or more thermal waveforms from the waveform module 2a, a patient control device, a physician support device, a registry and/or a portable memory device (e.g., an SD memory card) and to transmit the data to the waveform database 2h for storage. In some such embodiments, the data is stored on an SD memory card inserted into an SD memory card interface.

In some embodiments, the network module 2d is configured to retrieve data associated with the parameters, indications and/or approvals of one or more thermal waveforms from the waveform database 2h, a physician support device, a registry and/or a portable memory device (e.g., an SD memory card) and to transmit the data to the waveform module 2a, the treatment module 2b, a vestibular stimulation device, a patient control device and/or a physician support device.

In some embodiments, the network module 2d is configured to receive one or more prescriptions from the treatment module 2b, a patient control device, a physician support device, a registry and/or a portable memory device (e.g., an SD memory card) and to transmit the prescription(s) to the prescription database 2i for storage. In some such embodiments, the prescription(s) is/are stored on an SD memory card inserted into an SD memory card interface.

In some embodiments, the network module 2d is configured to retrieve one or more prescriptions from the prescription database 2i, a physician support device, a registry and/or a portable memory device (e.g., an SD memory card) and to transmit the prescription(s) to the treatment module 2b, a vestibular stimulation device, a patient control device and/or a physician support device.

In some embodiments, the network module 2d is configured to receive controller feedback data, data associated with the delivery of one or more thermal waveforms, data associated with the fit of one or more earpieces, patient feedback data and/or physician feedback data from a vestibular stimulation device, a patient control device and/or a portable memory device (e.g., an SD memory card) and to transmit that data to the feedback database 2j for storage. In some such embodiments, the data is stored on an SD memory card inserted into an SD memory card interface.

In some embodiments, the network module 2d is configured to receive physician feedback data from the GUI module 2e and to transmit that data to the feedback database 2j for storage. In some such embodiments, the patient information is stored on an SD memory card inserted into an SD memory card interface.

In some embodiments, the network module 2d is configured to retrieve controller feedback data, data associated with the delivery of one or more thermal waveforms, data associated with the fit of one or more earpieces and/or physician feedback data from the feedback database 2j and to transmit the data to the feedback module 2f, a physician support device, a registry and/or a portable memory device (e.g., an SD memory card).

In some embodiments, the network module 2d is configured to receive patient information from the GUI module 2e, a vestibular stimulation device, a patient control device, a physician support device, a registry and/or a portable memory device (e.g., an SD memory card) and to transmit that data to the patient history database 2k for storage. In some such embodiments, the patient information is stored on an SD memory card inserted into an SD memory card interface.

In some embodiments, the network module 2d is configured to retrieve patient information from the patient history database 2k and to transmit the patient information to a physician support device, a registry and/or a portable memory device (e.g., an SD memory card).

Patient Control Device

As noted above, the present invention provides a patient control device for receiving, analyzing and/or transmitting data.

In some embodiments, the patient control device is configured to receive a prescription comprising instructions for delivering one or more thermal waveforms to the vestibular system and/or the nervous system of a patient from a physician control device and to transmit the prescription to a vestibular stimulation device (e.g., a vestibular stimulation device of the present invention).

In some embodiments, the patient control device comprises, consists essentially of or consists of a network module, a feedback module, a prescription database and a feedback database. In some such embodiments, the network module is configured to receive one or more prescriptions from a physician control device, to transmit the prescription(s) to a vestibular stimulation device, to receive feedback data from the vestibular stimulation device and to transmit the feedback data to the physician control device. In some such embodiments, the prescription database comprises one or more prescriptions (e.g., one or more prescriptions received from a physician control device), and the feedback database comprises data associated with the delivery of one or more thermal waveforms, data associated with the fit or one or more earpieces and/or patient feedback data.

A patient control device of the present invention may be any suitable computing device/system, including, but not limited to, a desktop computer, a laptop computer, a hand-held computer, a personal digital assistant (PDA), and a smart phone.

Any conventional security means may be provided to prevent unauthorized activation of the patient control device. For example, the patient control device may be password protected.

The patient control support device may be configured to receive and/or transmit and suitable data, including, but not limited to, data associated with the parameters, indications and/or approvals of one or more thermal waveforms, data associated with one or more prescriptions, controller feedback data, data associated with the delivery of one or more thermal waveforms, data associated with the fit of one or more earpieces, patient feedback data and/or patient information.

The patient control device may be configured to receive and/or transmit data from/to various devices, including, but not limited to, a vestibular stimulation device, a physician control device, a physician support device, a TED, a sensor and/or a portable memory device (e.g., an SD memory card). In some embodiments, the patient control device is configured to receive data associated with the parameters, indications and/or approvals of one or more thermal waveforms (e.g., idealized thermal waveforms) from a physician control device, a physician support device, a registry and/or a portable memory device (e.g., an SD memory card); to transmit data associated with the parameters, indications and/or approvals of one or more thermal waveforms (e.g., idealized thermal waveforms) to a vestibular stimulation device and/or a portable memory device (e.g., an SD memory card); to receive one or more prescriptions from a physician control device, a physician support device, a registry and/or a portable memory device (e.g., an SD memory card); to transmit one or more prescriptions to a vestibular stimulation device and/or a portable memory device (e.g., an SD memory card); to receive one or more prescription modifications, updates and/or extensions from a physician control device, a physician support device, a registry and/or a portable memory device (e.g., an SD memory card); to transmit one or more prescription modifications, updates and/or extensions to a vestibular stimulation device and/or a portable memory device (e.g., an SD memory card); to receive data associated with the delivery of one or more thermal waveforms (e.g., idealized thermal waveforms) from a vestibular stimulation device and/or a portable memory device (e.g., an SD memory card); to transmit data associated with the delivery of one or more thermal waveforms (e.g., idealized thermal waveforms) to a physician control device, a physician support device, a registry and/or a portable memory device (e.g., an SD memory card); to transmit patient feedback data to a physician control device, a physician support device, a registry and/or a portable memory device (e.g., an SD memory card); to receive patient information from a vestibular stimulation device and/or a portable memory device (e.g., an SD memory card) and/or to transmit patient information to a physician control device, a physician support device, a registry and/or a portable memory device (e.g., an SD memory card).

The patient control device may be configured to receive and/or transmit data over any suitable wired or wireless communications channel, including, but not limited to, a LAN, the Internet, a public telephone switching network, Bluetooth, WLAN and the like.

In some embodiments, the patient control device comprises memory, a processor and a power supply. As will be appreciated by one of skill in the art, the processor may be any commercially available or custom microprocessor. Memory can include, but is not limited to, the following types of devices: cache, ROM, PROM, EPROM, EEPROM, flash memory, SRAM and DRAM. The power supply may be an internal power supply (e.g., one or more rechargeable batteries that may be recharged without first being removed from the physician control device).

The patient control device's memory may comprise any suitable software and/or data, including, but not limited to, an operating system, applications, data and input/output (I/O) drivers.

As will be appreciated by one of skill in the art, the patient control device may use any suitable operating system, including, but not limited to, OS/2, AIX, OS/390 or System390 from International Business Machines Corp. (Armonk, N.Y.), Window CE, Windows NT, Windows95, Windows98, Windows2000, Windows 7 or Windows Vista from Microsoft Corp. (Redmond, Wash.), Mac OS from Apple, Inc. (Cupertino, Calif.), Unix, Linux or Android.

As will be appreciated by one of skill in the art, the patient control device may comprise any suitable application, including, but not limited to, one or more programs configured to implement one or more of the various features of the present invention. For example, the patient control device may comprise a network module configured to receive and/or transmit data; a GUI module configured to display information and/or accept user input; a feedback module configured to receive, transmit, and/or analyze data associated with the delivery of one or more thermal waveforms, data associated with the fit of one or more earpieces, patient feedback data and/or patient information; an alert generation module configured to generate one or more alert messages; a tone generation module configured to produce one or more audible tones; a visual indicator module configured to produce one or more visual indicators and/or a security module configured to prevent unauthorized use of the patient control device. In some embodiments, two or more of the aforementioned modules are combined to form a single module configured to carry out the function(s) of each of the individual modules (e.g., the patient control device may comprise a network-feedback module that receives feedback data from a vestibular stimulation device, analyzes the data and transmits the data and the results of its analysis to a physician control device). In some embodiments, one of the aforementioned modules is split into two or more distinct modules (e.g., the patient control device may comprise a delivery feedback module that receives data associated with the delivery of one or more thermal waveforms from a vestibular stimulation device and a patient feedback module that receives patient feedback data from the a GUI module residing in the patient control device). In some embodiments, one or more of the functions described below with respect to one of the modules described below is performed by one of the other modules described below (e.g., the network module, rather than the feedback module may be configured to receive feedback data from a vestibular stimulation device, while the feedback module is tasked only with analyzing the data).

Network Module

In some embodiments, the patient control device comprises a network module configured to receive, retrieve and/or transmit data.

The network module may be configured to receive, retrieve and/or transmit data from/to any suitable device/module/database, including, but not limited to, other modules residing in the patient control device, databases residing in the patient control device, a vestibular stimulation device, a physician control device, a physician support device, a registry, a TED, a sensor and a portable memory device (e.g., an SD memory card).

The network module may be configured to receive, retrieve and/or transmit data over any suitable wired or wireless communications channel, including, but not limited to, a LAN, the Internet, a public telephone switching network, Bluetooth, WLAN and the like.

The network module may be configured to receive, retrieve and/or transmit any suitable data, including, but not limited to, data associated with the parameters, indications and/or approvals of one or more thermal waveforms, one or more prescriptions, controller feedback data, data associated with the delivery of one or more thermal waveforms, data associated with the fit of one or more earpieces, patient feedback data and/or patient information.

In some embodiments, the network module is configured to receive and/or retrieve data associated with the parameters, indications and/or approvals of one or more thermal waveforms from a waveform database residing in the patient control device, from a vestibular stimulation device, from a physician control device, from a physician support device, from a registry and/or from a portable memory device.

In some embodiments, the network module is configured to receive and/or retrieve one or more prescriptions from a prescription database residing in the patient control device, from a vestibular stimulation device, from a physician control device, from a physician support device, from a registry and/or from a portable memory device.

In some embodiments, the network module is configured to receive and/or retrieve controller feedback data, data associated with the delivery of one or more thermal waveforms and/or data associated with the fit of one or more earpieces from a feedback module/database residing in the patient control device and/or a vestibular stimulation device.

In some embodiments, the network module is configured to receive and/or retrieve patient feedback data and/or patient information from a feedback module/database residing in the patient control device, from a GUI module residing in the patient control device, from a patient information database residing in the patient control device, from a vestibular stimulation device, from a physician control device, from a physician support device, from a registry and/or from a portable memory device.

In some embodiments, the network module is configured to transmit data associated with the parameters, indications and/or approvals of one or more thermal waveforms to a waveform database residing in the patient control device, to a vestibular stimulation device, to a physician control device, to a physician support device, to a registry and/or to a portable memory device.

In some embodiments, the network module is configured to transmit one or more prescriptions to a prescription database residing in the patient control device, to a vestibular stimulation device, to a physician control device, to a physician support device, to a registry and/or to a portable memory device.

In some embodiments, the network module is configured to transmit controller feedback data, data associated with the delivery of one or more thermal waveforms and/or data associated with the fit of one or more earpieces to a feedback module/database residing in the patient control device, to a vestibular stimulation device, to a physician control device, to a physician support device, to a registry and/or to a portable memory device.

In some embodiments, the network module is configured to transmit patient feedback data and/or patient information to a feedback module/database residing in the patient control device, to a patient information database residing in the patient control device, to a vestibular stimulation device, to a physician control device, to a physician support device, to a registry and/or to a portable memory device.

In some embodiments, the network module is configured to access a database comprising data associated with the parameters, indications and/or approvals of one or more thermal waveforms (e.g., idealized thermal waveforms). For example, the network module maybe configured to access a waveform database residing in a vestibular stimulation device, a waveform database residing in the patient control device, a waveform database residing in a physician control device, a waveform database residing in a physician support device, a waveform database residing in a registry and/or a waveform database residing in a portable memory device.

In some embodiments, the network module is configured to access a database comprising one or more prescriptions. For example, the network module maybe configured to access a prescription database residing in a vestibular stimulation device, a prescription database residing in the patient control device, a prescription database residing in a physician control device, a prescription database residing in a physician support device, a prescription database residing in a registry and/or a prescription database residing in a portable memory device.

In some embodiments, the network module is configured to access a database comprising controller feedback data, data associated with the delivery of one or more thermal waveforms, data associated with the fit of one or more earpieces, patient feedback data and/or physician feedback data. For example, the network module maybe configured to access a feedback database residing in a vestibular stimulation device, a feedback database residing in the patient control device, a feedback database residing in a physician control device, a feedback database residing in a physician support device, a feedback database residing in a registry and/or a feedback database residing in a portable memory device.

In some embodiments, the network module is configured to access a database comprising patient information. For example, the network module maybe configured to access a patient information database residing in a vestibular stimulation device, a patient information database residing in the patient control device, a patient information database residing in a physician control device, a patient information database residing in a physician support device, a patient information database residing in a registry and/or a patient information database residing in a portable memory device.

B. Graphical User Interface Module

In some embodiments, the patient control device comprises a GUI module configured to display information and/or to accept user input. Any suitable GUI may be used, including, but not limited to, a keyboard, a mouse, an LCD display with one or more associated entry keys and an interactive touch screen. For example, the GUI may comprise a static pressure touch-sensitive display, a capacitive touch-sensitive display, a resistive touch-sensitive display, an electrostatic capacity proximity sensor, a magnetic proximity sensor and/or an infrared proximity sensor. See, e.g., U.S. Patent Publication Nos. 2011/0271222, 2011/0273575, 2011/0275414 and 2011/0275416.

The GUI module may be configured to display any suitable information, including, but not limited to, data associated with the delivery of one or more thermal waveforms. For example, the GUI module may be configured to display the current date and/or time (as discussed above with respect to FIG. 10); delivery of one or more the current temperature(s) of the earpiece(s) associated with the controller; the current temperature(s) of a patient's ear canal(s); the current temperature(s) of a patient's inner ear(s); the current temperature(s) of the heat sindelivery of one or more the current temperature(s) of the earpiece(s) associated with the controller; the current temperature(s) of a patient's ear canal(s); the current temperature(s) of a patient's inner ear(s); the current temperature(s) of the heat sine controller; one or more target temperatures (as discussed above with respect to FIG. 11); the amount of time that has elapsed since the onset of delivery of one or more thermal waveforms (as discussed above with respect to FIG. 11); the amount of time remaining in the delivery of one or more thermal waveforms (as discussed above with respect to FIG. 11); the amount of time that has elapsed since the onset of a treatment session; the amount of time remaining in a treatment session; a graphical representation of the thermal waveform being applied (as discussed above with respect to FIG. 11); the number of treatment sessions that have been administered for a prescription; the number of treatment sessions remaining in a prescription; the amount of time remaining until a prescription must be renewed/updated; the amount of remaining battery life, an alert message (e.g., a reminder to a patient that he/she is due for a treatment session); the target time/temperature parameters of one or more prescribed thermal waveform(s) (as discussed above with respect to FIG. 11); the precise time/temperature parameters of the thermal waveform(s) delivered to a patient; the date/time of delivery of the thermal waveform(s) delivered to a patient; the temperature(s) of a patient's ear canal(s) at various time points before, during and/or after delivery of the thermal waveform(s); the temperature(s) of a patient's inner ear(s) at various time points before, during and/or after delivery of the thermal waveform(s); the fit of the earpiece(s) at various time points before, during and/or after delivery of the thermal waveform(s); an estimate of the thermal contact between the earpiece(s) and the patient's ear canal(s) at various time points before, during and/or after delivery of the thermal waveform(s); patient-specific time constants (e.g., a time constant associated with the transduction of heat from a patient's ear canal to the inner ear); reaction time (i.e., how long it took for a patient to react to one or more thermal waveforms); the effectiveness of one or more thermal waveforms (i.e., whether and to what extent symptoms were relieved, whether the thermal waveform(s) enhanced the effectiveness of another agent/therapy, etc.); the stability of a treatment (i.e., how long the effects of the treatment lasted); the instability of a treatment (i.e., which symptom(s) returned and when did it/they return); the presence or absence of comorbid disorders, injuries and/or diseases; disorder, injury and/or disease modulation(s) and/or modification(s) that occurred as a result of treatment; the cognitive effect(s) of one or more thermal waveforms; patient compliance (e.g., whether a patient initiated delivery at the prescribed time, whether a patient completed the prescribed treatment session, whether the earpiece(s) remained properly fitted in a patient's ear canal(s) for the duration of the treatment session, etc.); the mood of a patient at various time points before, during and/or after delivery of one or more thermal waveforms (e.g., videos/images of a patient that may be used to assess mood); objectives measures of efficacy (e.g., nystamography data, EEG data, MRI data, heart rate data, blood pressure data); subjective measures of efficacy (e.g., a patient-reported pain score); blood chemistry data (e.g., blood A1c levels, blood glucose levels and blood cortisol levels); saliva chemistry data (e.g., saliva cortisol levels); urine chemistry data (e.g., urine cortisol levels)), comments a patient made about his/her treatment session(s) (e.g., comments made to a physician, submitted in response to an automated survey and/or recorded in a treatment diary); the impedance between an earpiece inserted into the ear canal of a patient and an electrode affixed to a second location on/in said patient's body (e.g., an electrode placed in or adjacent to the patient's other ear canal); the rate at which a patient's inner ear cools in response to a cooling stimulus (e.g., data from a temperature sensor, such as thermistor, that monitors how quickly the inner ear cools in response to a cooling waveform); the rate at which a patient's inner ear warms in response to a warming stimulus (e.g., data from a temperature sensor, such as thermistor, that monitors how quickly the inner ear warms in response to a warming waveform) and/or patient comments regarding the subjective fit of his/her earpiece(s).

The GUI module may be configured to accept any suitable user input, including, but not limited to, patient feedback data and/or patient information. For example, the GUI module may be configured to accept a pain score and/or patient comments regarding the effectiveness of a treatment session.

In some embodiments, the GUI module is configured to allow a user to initiate/stop a treatment session (e.g., by pushing/selecting an emergency shutoff button/icon) (as discussed above with respect to FIG. 11).

C. Feedback Module

In some embodiments, the patient control device comprises a feedback module configured to receive, transmit and/or analyze data.

The feedback module may be configured to receive and/or transmit data from/to any suitable device/module/database, including, but not limited to, other modules residing in the patient control device, databases residing in the patient control device, a vestibular stimulation device, a physician control device, a physician support device, a registry, a TED, a sensor and a portable memory device (e.g., an SD memory card).

The feedback module may be configured to receive and/or transmit data over any suitable wired or wireless communications channel, including, but not limited to, a LAN, the Internet, a public telephone switching network, Bluetooth, WLAN and the like.

The feedback module may be configured to receive, transmit and/or analyze any suitable data, including, but not limited to, controller feedback data, data associated with the delivery of one or more thermal waveforms, data associated with the fit of one or more earpieces, patient feedback data and/or patient information.

In some embodiments, the feedback module is configured to receive and/or analyze data associated with the delivery of one or more thermal waveforms and/or data associated with the fit of one or more earpieces from a feedback database residing in the physician control device, from one or more vestibular stimulation devices. For example, the feedback module may be configured to analyze the accuracy with which one or more prescribed waveforms was delivered to a patient, the fit of an earpiece based upon the rate at which the temperature of the earpiece changes in response to a cooling/warming waveform, the slew rate associated with one or more TEDs, the impedance between an earpiece positioned in the left ear canal of a patient and an earpiece positioned in the right ear canal of a patient, the impedance between an earpiece positioned in the ear canal of a patient and an electrode affixed to a second location on/in the patient's body, etc.

In some embodiments, the feedback module is configured to receive and/or analyze patient feedback data and/or patient information from a GUI module residing in the patient control device, from a feedback database residing in the patient control device, from a patient information database residing in the patient, from a vestibular stimulation device, from a physician control device, from a physician support device and/or from a portable memory device. For example, the feedback module may be configured to analyze the effectiveness of a given thermal waveform or combination of thermal waveforms (e.g., by analyzing pain scores entered before, during and after a treatment session), the effect(s) of one or more waveform modifications (e.g., by analyzing whether/how much a given waveform modification changed the effectiveness of a thermal waveform in treating a disease/disorder), etc.

In some embodiments, the feedback module is configured to transmit data associated with the delivery of one or more thermal waveforms, data associated with the fit of one or more earpieces, patient feedback data, physician feedback data, patient information and/or data associated with its analysis to a feedback database residing in the patient control device, to a patient information database residing in the patient control device, to a physician control device, to a physician support device, to a registry and/or to a portable memory device (e.g., an SD memory card).

D. Alert Generation Module

In some embodiments, the patient control device comprises an alert generation module configured to generate one or more alert messages.

The alert generation module may be configured to generate any suitable alert message, including, but not limited to, a reminder that a patient is due for a treatment session; a reminder that a patient must enter patient feedback data (e.g., a pain score) following a treatment session; an indication of the number of treatment sessions remaining in a prescription; an error message indicating that a treatment session has been interrupted due to a system error; a reminder that a patient must contact his/her physician to update/extend his/her prescription; a warning that the patient control device's internal power supply is low and a warning that the internal power supply of an associated vestibular stimulation device is low.

In some embodiments, the alert generation module is configured to communicate with various devices/modules, including, but not limited to, a vestibular stimulation device, a physician control device, a physician support device, a TED, a sensor, a portable memory device (e.g., an SD memory card) and other modules of the patient control device. For example, the alert generation module may be configured to provide instructions to the GUI module and/or the tone generation module for displaying one or more alert messages and/or for generation an audible tone to alert a user of the presence of the one or more alert messages. The graphical user interface module may be configured to display the one or more alert messages immediately upon generation or upon interaction with a user (e.g., an alert notification icon may be generated, with the alert message being displayed only after the user indicates that he/she wishes to view the message).

E. Tone Generation Module

In some embodiments, the patient control device comprises a tone generation module configured to produce audible tones. In some such embodiments, the tone generation module comprises a piezo buzzer. Audible tones may be produced to alert a user to various circumstances/events, including, but not limited to, the existence of an unread/ unviewed alert message. Audible tones may be generated repeatedly in response to a single circumstance/event (e.g., an audible tone may be generated repeatedly until the user views/reads the message) and may become progressively louder and/or more frequent with time.

F. Visual Indicator Module

In some embodiments, the patient control device comprises a visual indicator module configured to notify a user of the existence of an unread/unviewed alert message. In some such embodiments, the visual indicator module comprises an LED indicator light. The visual indicator module may be activated repeatedly in response to a single alert message (e.g., an LED light may be illuminated repeatedly until the user views/reads the message) or may remain activated until the user views/reads the message.

G. Security Module

In some embodiments, the patient control device comprises a security module configured to prevent unauthorized use of the physician control device (i.e., to prevent unauthorized persons from using the patient control device, to prevent authorized persons from using the patient control device in an unauthorized manner, etc.).

The security module may be configured to prevent unauthorized use of the patient control device using any suitable means of security, including, but not limited to, password protection and data encryption. For example, the security module may be configured such that a user is required to input a designated password prior to entering/viewing patient feedback data; and/or entering/viewing patient information (as discussed above with respect to FIG. 12).

As will be appreciated by one of skill in the art, the patient control device may comprise any suitable data, including, but not limited to, static and/or dynamic data used by the operating system, applications, I/O device drivers and other software components, controller feedback data, data associated with the parameters, indications and/or approvals of one or more thermal waveforms (e.g., idealized thermal waveforms), data associated with one or more prescriptions, data associated with the delivery of one or more thermal waveforms, data associated with the fit of one or more earpieces, patient feedback data and patient information. For example, the patient control device may comprise a waveform database comprising data associated with one or more idealized thermal waveforms; a prescription database comprising data associated with one or more prescriptions; a feedback database comprising controller feedback data, data associated with the delivery of one or more thermal waveforms to the vestibular system and/or the nervous system of a patient and patient feedback data and/or a patient history database comprising data associated with one or more patients. In some embodiments, two or more of the aforementioned databases are combined to form a single database comprising data from each of the individual databases (e.g., the patient control device may comprise a feedback-history database comprising data associated with the delivery of one or more thermal waveforms and patient information). In some embodiments, one of the aforementioned databases is split into two or more distinct databases (e.g., the patient control device may comprise a delivery feedback database comprising data associated with the specific parameters of the thermal waveform(s) delivered to a patient and a patient feedback database comprising patient feedback data). In some embodiments, one or more of the data types described below with respect to one of the databases described below is stored in one of the other databases described below (e.g., the patient information database, rather than the feedback database, may be configured to receive/store patient feedback data). In some embodiments, data is transmitted, received and/or stored in a controlled format (e.g., in a standardized format using forms/programs supplied by a physician support device or a registry). The patient control device may be configured to transmit, receive and store data in a manner that ensures compliance with any and all applicable laws and/or regulations (e.g., the Health Insurance Portability and Accountability Act of 1996 (P.L. 104-191; "HIPAA")).

Waveform Database

In some embodiments, the patient control device comprises a waveform database configured to receive, store and/or transmit data associated with the parameters, indications and/or approvals of one or more thermal waveforms (e.g, one or more idealized thermal waveforms). In some such embodiments, the waveform database is configured such that one or more of the thermal waveforms stored therein is/are protected (e.g., users may be prevented from modifying and/or deleting the idealized thermal waveform(s) stored in the waveform database).

The waveform database may comprise any suitable type of memory including, but not limited to, cache, ROM, PROM, EPROM, EEPROM, flash memory, SRAM and DRAM. In some embodiments, the waveform database comprises a portable memory device, such as an SD memory card or a USB memory stick. For example, the waveform database may comprise an SD memory card interface and one or more prescriptions may be stored on a portable SD memory card.

The waveform database may be configured to receive and/or transmit data from/to any suitable device/module/database, including, but not limited to, modules residing in the patient control device, a vestibular stimulation device, a physician control device, a physician support device, a registry, a TED, a sensor and a portable memory device (e.g., an SD memory card).

The waveform database may be configured to receive and/or transmit data over any suitable wired or wireless communications channel, including, but not limited to, a LAN, the Internet, a public telephone switching network, Bluetooth, WLAN and the like.

B. Prescription Database

In some embodiments, the patient control device comprises a prescription database configured to receive, transmit and/or store one or more prescriptions, wherein each prescription comprising a set of instructions for delivering one or more thermal waveforms to the vestibular system and/or the nervous system of a patient.

The prescription database may comprise any suitable type of memory including, but not limited to, cache, ROM, PROM, EPROM, EEPROM, flash memory, SRAM and DRAM. In some embodiments, the prescription database comprises a portable memory device, such as an SD memory card or a USB memory stick. For example, the prescription database may comprise an SD memory card interface and one or more prescriptions may be stored on a portable SD memory card.

The prescription database may be configured to receive and/or transmit data from/to any suitable device/module/database, including, but not limited to, modules residing in the patient control device, a vestibular stimulation device, a physician control device, a physician support device, a registry, a TED, a sensor and a portable memory device (e.g., an SD memory card).

The prescription database may be configured to receive and/or transmit data over any suitable wired or wireless communications channel, including, but not limited to, a LAN, the Internet, a public telephone switching network, Bluetooth, WLAN and the like.

C. Feedback Database

In some embodiments, the patient control device comprises a feedback database configured to receive, transmit and/or store feedback data.

The feedback database may comprise any suitable type of memory including, but not limited to, cache, ROM, PROM, EPROM, EEPROM, flash memory, SRAM and DRAM. In some embodiments, the feedback database comprises a portable memory device, such as an SD memory card or a USB memory stick. For example, the feedback database may comprise an SD memory card interface and one or more prescriptions may be stored on a portable SD memory card.

The feedback database may be configured to receive and/or transmit feedback data from/to any suitable device/module/database, including, but not limited to, modules residing in the patient control device, a vestibular stimulation device, a physician control device, a physician support device, a registry, a TED, a sensor and a portable memory device (e.g., an SD memory card).

The feedback database may be configured to receive and/or transmit data over any suitable wired or wireless communications channel, including, but not limited to, a LAN, the Internet, a public telephone switching network, Bluetooth, WLAN and the like.

Feedback data may comprise any suitable data, including, but not limited to, controller feedback data, data associated with the delivery of one or more thermal waveforms, data associated with the fit of one or more earpieces, patient feedback data and/or patient information. For example, the feedback database may comprise a log file detailing the target time/temperature parameters of one or more prescribed thermal waveform(s); the time/temperature parameters of the thermal waveform(s) delivered to a patient; the date/time of delivery of the thermal waveform(s) delivered to a patient; the temperature(s) of a patient's ear canal(s) at various time points before, during and/or after delivery of one or more thermal waveforms; the temperature(s) of a patient's inner ear(s) at various time points before, during and/or after delivery of one or more thermal waveforms; the fit of one or more earpieces at various time points before, during and/or after delivery of one or more thermal waveforms; an estimate of the thermal contact between one or more earpieces and a patient's ear canal(s) at various time points before, during and/or after delivery of one or more thermal waveforms; patient-specific time constants (e.g., a time constant associated with the transduction of heat from a patient's ear canal to the inner ear); a patient's reaction time (i.e., how long it took for a patient to react to one or more thermal waveforms); effectiveness of one or more thermal waveforms (i.e., whether and to what extent symptoms were relieved, whether the thermal waveform(s) enhanced the effectiveness of another agent/therapy, etc.); stability of a treatment (i.e., how long the effects of a treatment lasted); instability of a treatment (i.e., which symptom(s) returned and when did it/they return); the presence or absence of comorbid disorders, injuries and/or diseases; disorder, injury and/or disease modulation(s) and/or modification(s) that occurred as a result of treatment; the cognitive effect(s) of one or more thermal waveforms; patient compliance (e.g., whether a patient initiated delivery at the prescribed time, whether a patient completed the prescribed treatment session, whether the earpiece(s) remained properly fitted in a patient's ear canal(s) for the duration of the treatment session, etc.); the mood of a patient at various time points before, during and/or after delivery of one or more thermal waveforms (e.g., videos/images of a patient that may be used to assess mood); objectives measures of efficacy (e.g., nystamography data, EEG data, MRI data, heart rate data, blood pressure data); subjective measures of efficacy (e.g., a patient-reported pain score); blood chemistry data (e.g., blood A1c levels, blood glucose levels and blood cortisol levels); saliva chemistry data (e.g., saliva cortisol levels); urine chemistry data (e.g., urine cortisol levels)); comments a patient made about his/her treatment session(s) (e.g., comments made to a physician, submitted in response to an automated survey and/or recorded in a treatment diary); the impedance between an earpiece inserted into the ear canal of a patient and an electrode affixed to a second location on/in said patient's body (e.g., an electrode placed in or adjacent to the patient's other ear canal); the rate at which an earpiece is cooled in response to a cooling stimulus (e.g., data from a temperature sensor, such as thermistor, that monitors how quickly the earpiece cools in response to a cooling waveform); the rate at which an earpiece is warmed in response to a warming stimulus (e.g., data from a temperature sensor, such as a thermistor, that monitors how quickly the earpiece warms in response to a warming waveform); the rate at which a patient's ear canal and/or inner ear cooled in response to a cooling stimulus (e.g., data from a temperature sensor, such as thermistor, that monitors how quickly the ear canal and/or the inner ear cools in response to a cooling waveform); the rate at which a patient's ear canal and/or inner ear warmed in response to a warming stimulus (e.g., data from a temperature sensor, such as a thermistor, that monitors how quickly the ear canal and/or the inner ear warms in response to a warming waveform) and/or patient comments regarding the subjective fit of one or more earpieces.

D. Patient History Database

In some embodiments, the patient control device comprises a patient history database configured to receive, transmit and/or store patient information.

The patient history database may comprise any suitable type of memory including, but not limited to, cache, ROM, PROM, EPROM, EEPROM, flash memory, SRAM and DRAM. In some embodiments, the patient history database comprises a portable memory device, such as an SD memory card or a USB memory stick. For example, the patient history database may comprise an SD memory card interface and one or more prescriptions may be stored on a portable SD memory card.

The patient history database may be configured to receive and/or transmit data from/to any suitable device/module/database, including, but not limited to, modules residing in the patient control device, a vestibular stimulation device, a physician control device, a physician support device, a registry, a TED, a sensor and a portable memory device (e.g., an SD memory card).

The patient history database may be configured to receive and/or transmit data over any suitable wired or wireless communications channel, including, but not limited to, a LAN, the Internet, a public telephone switching network, Bluetooth, WLAN and the like.

Patient information may comprise any suitable information that is associated with a patient, including, but not limited to, the patient's medical history, the patient's current symptoms (if any), the patient's present diagnosis (if any), the patient's current prescriptions (if any) and data associated with the delivery of one or more thermal waveforms to the vestibular system and/or the nervous system of the patient.

As will be appreciated by one of skill in the art, the patient control device may comprise any I/O device drivers, including, but not limited to, software routines accessed through the operating system by the applications to communicate with devices such as I/O ports, memory components, vestibular stimulation devices, physician control devices and/or physician support devices.

As will be appreciated by one of skill in the art, the patient control device may be configured (e.g., with computer instructions (i.e., software)) to operate in a plurality of distinct modes. In each mode, the patient control device may be configured to permit access to some functionalities/modules and to prevent access to other functionalities/modules. For example, the patient control device may be configured to operate in a patient mode, wherein the user is allowed to perform patient-oriented tasks, such as starting/stopping a treatment session and/or providing feedback regarding the effectiveness of a treatment session, but is prevented from accessing other modules/databases/functionalities (e.g., the user may be prevented generating, modifying, updating and/or extending prescriptions). Likewise, the patient control device may be configured to operate in an engineer mode, wherein the user is allowed to access all of the patient control device's functionalities/modules. Each mode may be protected via a unique security measure (e.g., the patient control device may be configured such that each mode is protected by a unique password).

Figure 25:
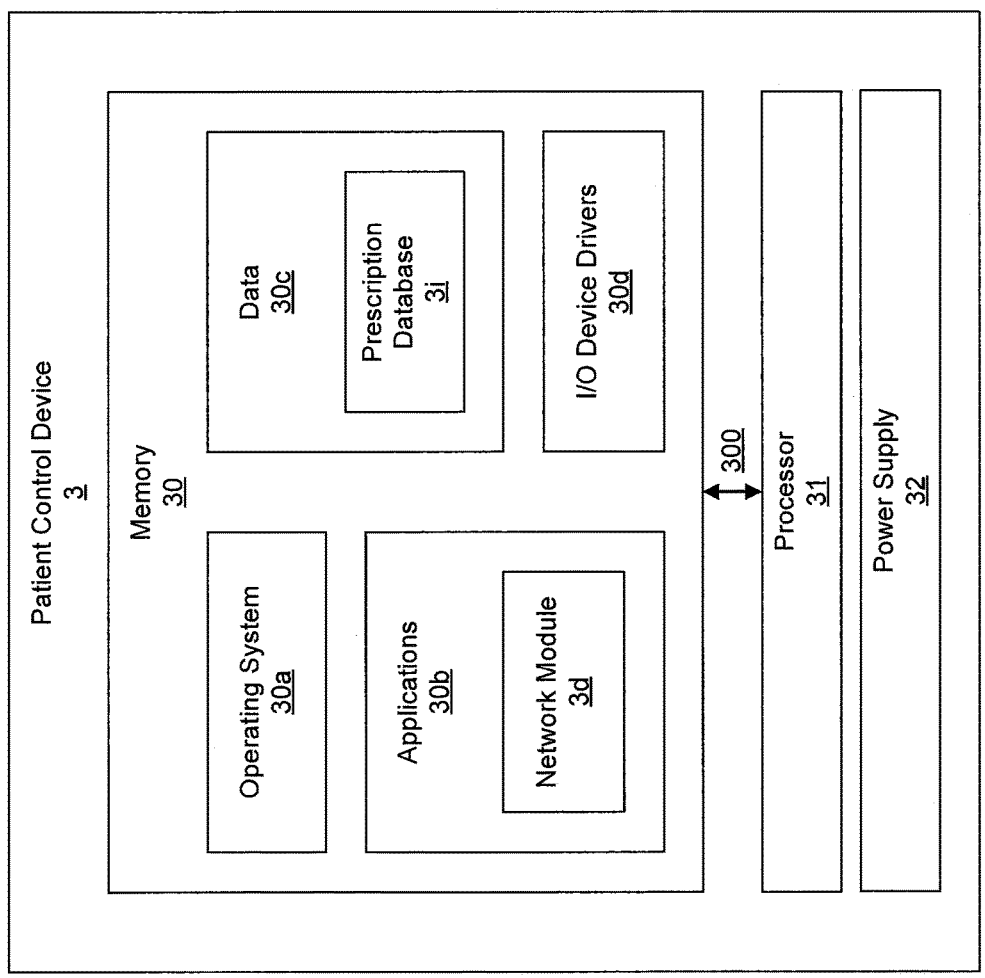
FIG. 25 is a block diagram of a patient control device according to some embodiments of the present invention.
Figure 26:
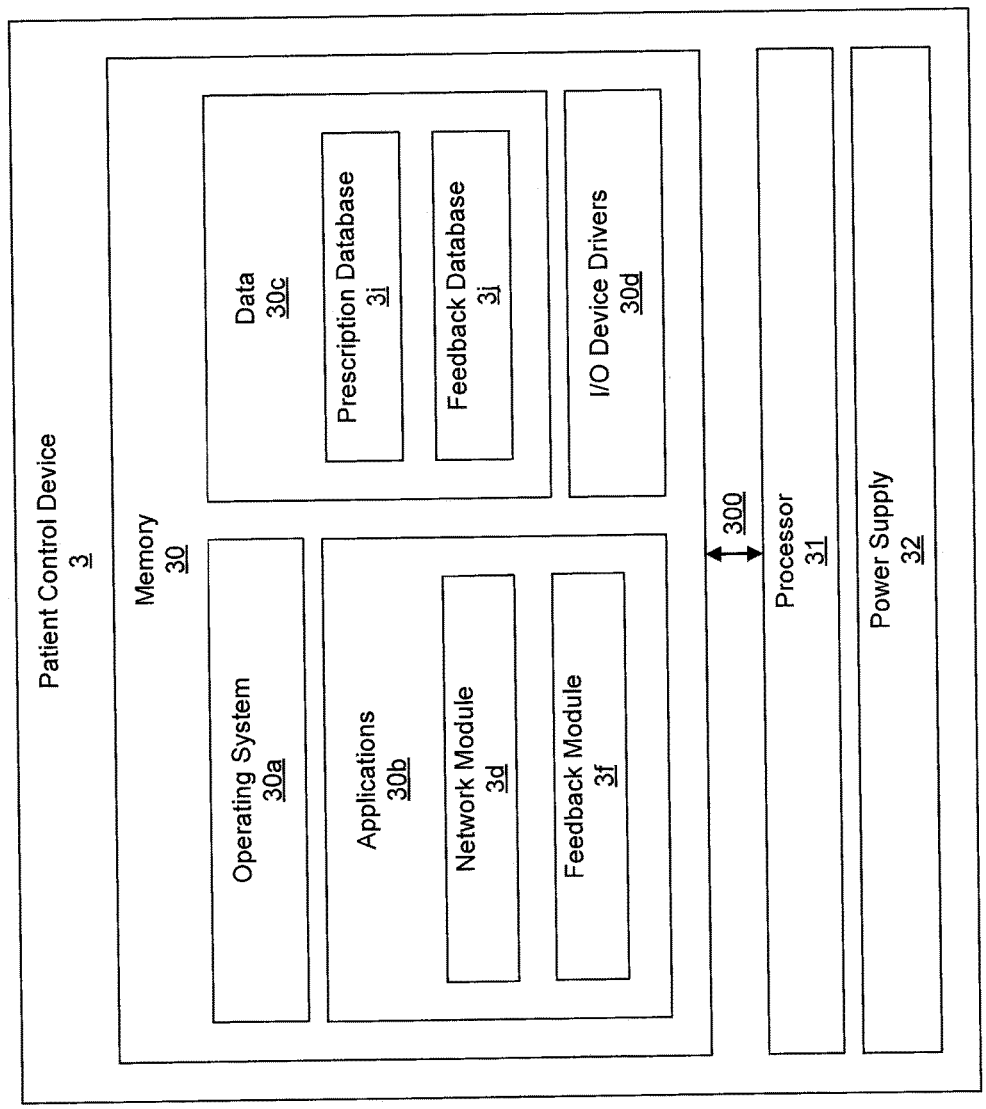
FIG. 26 is a block diagram of a patient control device according to some embodiments of the present invention.
Figure 27:
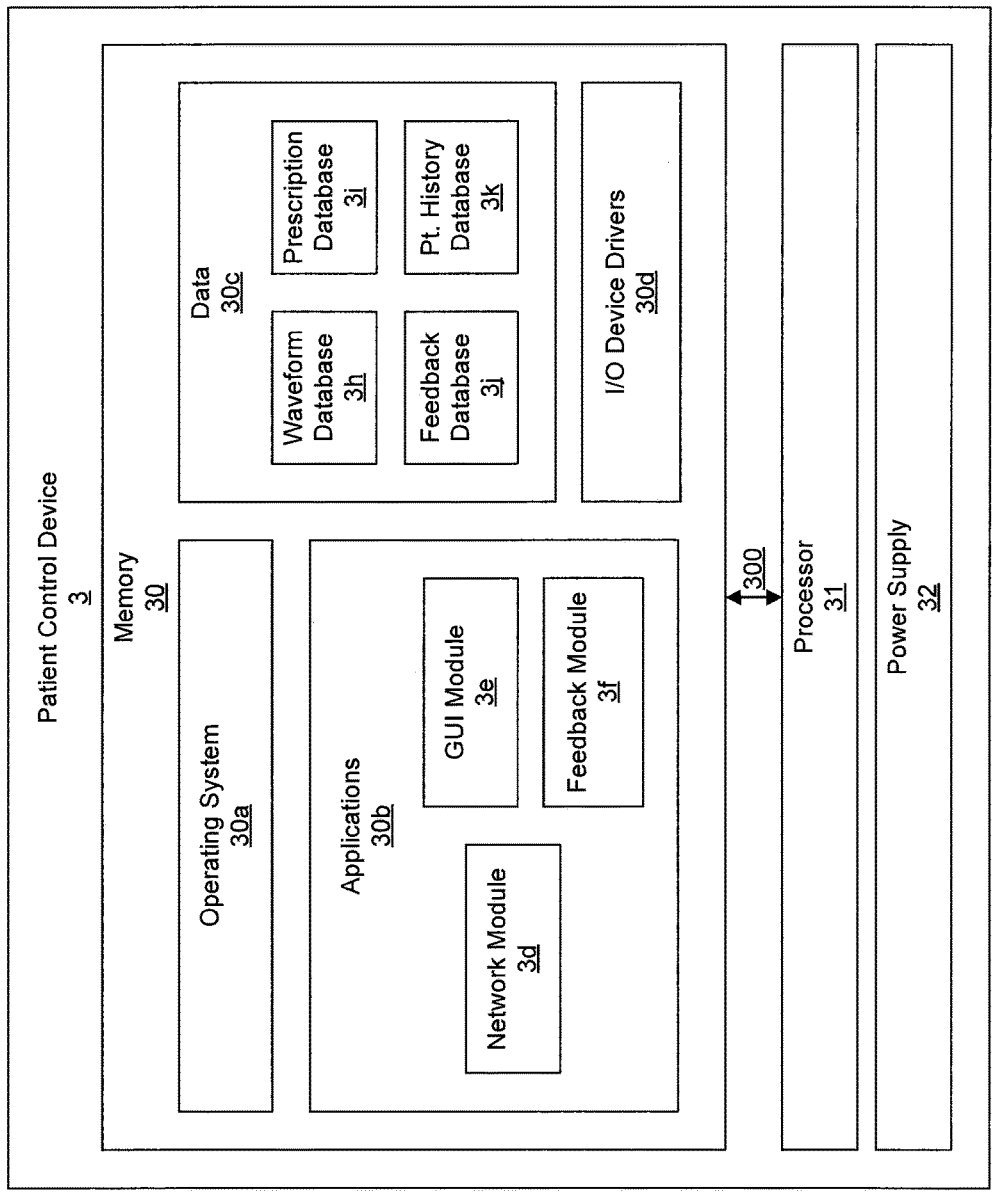
FIG. 27 is a block diagram of a patient control device according to some embodiments of the present invention.

As shown in FIGS. 25-27, in some embodiments of the present invention, the patient control device 3 comprises memory 30, a processor 31 and a power supply 32 (e.g., an internal power supply), wherein memory 30 is representative of the overall hierarchy of memory devices containing software and data used to implement the functionality of the patient control device 3 and wherein the processor 31 communicates with the memory 30 via an address/data bus 300. In particular embodiments, memory 30 comprises an operating system 30*a*, applications 30*b* (e.g., a network module 3*d* configured to receive and/or transmit data, a GUI module 3*e* configured to display information and/or accept user input and/or a feedback module 3*f* configured to receive, transmit, and/or analyze data associated with the delivery of one or more thermal waveforms), data 30*c* (e.g., a waveform database 3*h* comprising data associated with the parameters, indications and/or approvals of one or more thermal waveforms; a prescription database 3*i* comprising at least one prescription comprising a set of instructions for delivering one or more thermal waveforms to the vestibular system and/or the nervous system of a patient; a feedback database 3*j* comprising data associated with the delivery of one or more thermal waveforms and/or a patient history database 3*k* comprising patient information) and I/O drivers 30*d*. In some such embodiments, data 30*c* comprises one or more databases stored on a portable memory device. For example, data 30*c* may comprise an SD memory card interface and a portable SD memory card comprising a waveform database 3*h*, a prescription database 3*i*, a feedback database 3*j* and/or a patient history database 3*k*.

In some embodiments, the network module 3*d* is configured to receive data associated with the parameters, indications and/or approvals of one or more thermal waveforms from a physician control device, a physician support device, a registry and/or a portable memory device (e.g., an SD memory card) and to transmit the data to the waveform database 3*h* for storage. In some such embodiments, the data is stored on an SD memory card inserted into an SD memory card interface.

In some embodiments, the network module 3*d* is configured to retrieve data associated with the parameters, indications and/or approvals of one or more thermal waveforms from the waveform database 3*h*, a physician control device, a physician support device, a registry and/or a portable memory device (e.g., an SD memory card) and to transmit the data to a vestibular stimulation device.

In some embodiments, the network module 3*d* is configured to receive one or more prescriptions from a physician control device, a physician support device, a registry and/or a portable memory device (e.g., an SD memory card) and to transmit the prescription(s) to the prescription database 3*i* for storage. In some such embodiments, the prescription(s) is/are stored on an SD memory card inserted into an SD memory card interface.

In some embodiments, the network module 3*d* is configured to retrieve one or more prescriptions from the prescription database 3*i*, a physician control device, a physician support device, a registry and/or a portable memory device (e.g., an SD memory card) and to transmit the prescription(s) to a vestibular stimulation device.

In some embodiments, the network module 3*d* is configured to receive controller feedback data, data associated with the delivery of one or more thermal waveforms and/or data associated with the fit of one or more earpieces from a vestibular stimulation device and/or a portable memory device (e.g., an SD memory card) and to transmit that data to the feedback database 3*j* for storage. In some such embodiments, the data is stored on an SD memory card inserted into an SD memory card interface.

In some embodiments, the network module 3*d* is configured to retrieve controller feedback data, data associated with the delivery of one or more thermal waveforms and/or data associated with the fit of one or more earpieces from the feedback database 3*j* and to transmit the data to the feedback module 3*f*, a physician control device, a physician support device, a registry and/or a portable memory device (e.g., an SD memory card).

In some embodiments, the network module 3*d* is configured to receive patient feedback data from the GUI module 3*e*, a vestibular stimulation device and/or a portable memory device (e.g., an SD memory card) and to transmit that data to the feedback database 3*j* for storage. In some such embodiments, the patient information is stored on an SD memory card inserted into an SD memory card interface.

In some embodiments, the network module 3*d* is configured to retrieve patient feedback data from the feedback database 3*j* and to transmit the data to the feedback module 3*f*, a physician control device, a physician support device, a registry and/or a portable memory device (e.g., an SD memory card).

In some embodiments, the network module 3*d* is configured to receive patient information from the GUI module 3*e*, a vestibular stimulation device, a physician control device, a physician support device, a registry and/or a portable memory device (e.g., an SD memory card) and to transmit that data to the patient history database 3*k* for storage. In some such embodiments, the patient information is stored on an SD memory card inserted into an SD memory card interface.

In some embodiments, the network module 3*d* is configured to retrieve patient information from the patient history database 3*k* and to transmit the patient information to a physician control device, a physician support device, a registry and/or a portable memory device (e.g., an SD memory card).

Physician Support Device

As noted above, the present invention provides a physician support device for generating and/or modifying the parameters, indications and/or approvals of one of more thermal waveforms; for generating, modifying, updating and/or extending one or more prescriptions and/or for receiving, analyzing and/or transmitting data.

In some embodiments, the physician support device is configured to generate and/or modify the parameters, indications and/or approvals of one or more idealized thermal waveforms and to transmit the parameters, indications and/or approvals of the idealized thermal waveform(s) to a physician control device (e.g., a physician control device of the present invention).

In some embodiments, the physician support device comprises, consists essentially of or consists of a waveform module configured to generate and/or modify the parameters, indications and/or approvals of one or more idealized thermal waveforms and a network module configured to transmit the parameters, indications and/or approvals of the idealized thermal waveform(s) to one or more physician control devices.

A physician support device of the present invention may be any suitable computing device/system, including, but not limited to, a desktop computer, a laptop computer, a handheld computer, a personal digital assistant (PDA), and a smart phone.

Any conventional security means may be provided to prevent unauthorized activation of the physician support device. For example, the physician support device may be password protected.

The physician support device may be configured to receive and/or transmit and suitable data, including, but not limited to, data associated with the parameters, indications and/or approvals of one or more thermal waveforms, one or more prescriptions, controller feedback data, data associated with the delivery of one or more thermal waveforms, data associated with the fit of one or more earpieces, patient feedback data, physician feedback data and patient information.

The physician support device may be configured to receive and/or transmit data from/to various devices, including, but not limited to, a vestibular stimulation device, a patient control device, a physician control device, a registry, a TED, a sensor and a portable memory device (e.g., an SD memory card). In some embodiments, the physician support device is configured to receive data associated with the parameters, indications and/or approvals of one or more thermal waveforms (e.g., idealized thermal waveforms) from a registry and/or a portable memory device (e.g., an SD memory card); to transmit data associated with the parameters, indications and/or approvals of one or more thermal waveforms (e.g., idealized thermal waveforms) to a vestibular stimulation device, a patient control device, a physician control device, a registry and/or a portable memory device (e.g., an SD memory card); to receive one or more prescriptions from a registry and/or a portable memory device (e.g., an SD memory card); to transmit one or more prescriptions to a vestibular stimulation device, a patient control device, a physician control device, a registry and/or a portable memory device (e.g., an SD memory card); to transmit one or more prescription modifications, updates and/or extensions to a vestibular stimulation device, a patient control device, a physician control device, a registry and/or a portable memory device (e.g., an SD memory card); to receive data associated with the delivery of one or more thermal waveforms (e.g., idealized thermal waveforms) from a vestibular stimulation device, a patient control device, a physician control device and/or a portable memory device (e.g., an SD memory card); to transmit data associated with the delivery of one or more thermal waveforms (e.g., idealized thermal waveforms) to a registry and/or a portable memory device (e.g., an SD memory card); to receive patient feedback data from a vestibular stimulation device, a patient control device, a physician control device and/or a portable memory device (e.g., an SD memory card); to transmit patient feedback to a registry and/or a portable memory device (e.g., an SD memory card); to receive physician feedback data from a physician control device and/or a portable memory device (e.g., an SD memory card); to transmit physician feedback to a registry and/or a portable memory device (e.g., an SD memory card); to receive patient information from a vestibular stimulation device, a patient control device, a physician control device, a registry and/or a portable memory device (e.g., an SD memory card) and/or to transmit patient information to a vestibular stimulation device, a patient control device, a physician control device, a registry and/or a portable memory device (e.g., an SD memory card).

The physician support device may be configured to receive and/or transmit data over any suitable wired or wireless communications channel, including, but not limited to, a LAN, the Internet, a public telephone switching network, Bluetooth, WLAN and the like.

In some embodiments, the physician support device comprises memory, a processor and a power supply. As will be appreciated by one of skill in the art, the processor may be any commercially available or custom microprocessor. Memory can include, but is not limited to, the following types of devices: cache, ROM, PROM, EPROM, EEPROM, flash memory, SRAM and DRAM. The power supply may be an internal power supply (e.g., one or more rechargeable batteries that may be recharged without first being removed from the physician control device).

The physician support device's memory may comprise any suitable software and/or data, including, but not limited to, an operating system, applications, data and input/output (I/O) drivers.

As will be appreciated by one of skill in the art, the physician support device may use any suitable operating system, including, but not limited to, OS/2, AIX, OS/390 or System390 from International Business Machines Corp. (Armonk, N.Y.), Window CE, Windows NT, Windows95, Windows98, Windows2000, Windows 7 or Windows Vista from Microsoft Corp. (Redmond, Wash.), Mac OS from Apple, Inc. (Cupertino, Calif.), Unix, Linux or Android.

As will be appreciated by one of skill in the art, the physician support device may comprise any suitable application, including, but not limited to, one or more programs configured to implement one or more of the various features of the present invention. For example, the physician control device may comprise a waveform module that enables a user to generate and/or modify the parameters, indications and/or approvals of one or more thermal waveforms; a treatment module that enables a user to generate, modify, update and/or extend a prescription comprising a set of instructions for delivering one or more thermal waveforms to the vestibular system and/or the nervous system of a patient; a network module configured to receive and/or transmit data;

a GUI module configured to display information and/or accept user input; a feedback module configured to receive, transmit, and/or analyze data associated with the delivery of one or more thermal waveforms, data associated with the fit of one or more earpieces, patient feedback data, physician feedback data and/or patient information; an alert generation module configured to generate one or more alert messages; a tone generation module configured to produce one or more audible tones; a visual indicator module configured to produce one or more visual indicators and/or a security module configured to prevent unauthorized use of the physician support device. In some embodiments, two or more of the aforementioned modules are combined to form a single module configured to carry out the function(s) of each of the individual modules (e.g., the physician support device may comprise a waveform-treatment module that enables a user to generate and/or modify one or more thermal waveforms and to generate, modify, update and/or extend a prescription). In some embodiments, one of the aforementioned modules is split into two or more distinct modules (e.g., the physician support device may comprise a waveform generation module that enables a user to generate the parameters, indications and/or approvals of one or more thermal waveforms and a waveform update module that enables a user to modify the parameters, indications and/or approvals of one or more thermal waveforms). In some embodiments, one or more of the functions described below with respect to one of the modules described below is performed by one of the other modules described below (e.g., the treatment module, rather than the waveform module, may be configured to modify the parameters, indications and/or approvals of one or more thermal waveforms).

Waveform Module

In some embodiments, the physician support device comprises a waveform module whereby a user may generate and/or modify the parameters, indications and/or approvals of one or more thermal waveforms.

In some embodiments, the waveform module comprises software that enables a user to generate and/or modify the parameters of one or more thermal waveforms by point-to-point design and/or by utilizing mathematical functions. For example, the waveform module may comprise software that enables a user to generate and/or modify the parameters of a thermal waveform by selecting/altering one or more parameters, including, but not limited to, shape, frequency, amplitude and duration. In some embodiments, the waveform module enables a user to retrieve/select a thermal waveform from a database and then modify the parameters of that thermal waveform to generate a new thermal waveform.

In some embodiments, the waveform module comprises software that enables a user to generate and/or modify the parameters, indications and/or approvals of one or more thermal waveforms using an interactive touch screen. For example, the waveform module may comprise software that enables a user to generate the parameters of a thermal waveform by drawing the desired waveform on an interactive touch screen (as discussed above with respect to FIG. 3). Similarly, the waveform module may enable a user to modify the parameters of a thermal waveform by highlighting one or more points on the waveform and moving the point(s) to a new location (e.g., a higher/lower temperature) (as discussed above with respect to FIG. 4).

In some embodiments, the waveform module comprises software that automatically adjusts the parameters of the thermal waveform(s) created by a user to account for system limitations. For example, the waveform module may comprise software that automatically adjusts the slope of a thermal waveform in accordance with the minimum/maximum temperature and/or the rate of temperature change that is achievable using a particular combination of earpiece(s), TED(s), etc. That is, the waveform module may comprise software that prevents a user from generating parameters for a thermal waveform that cannot be delivered because of system limitations.

In some embodiments, the waveform module comprises software that enables a user to protect one or more thermal waveforms (i.e., to prevent one or more users from modifying the parameters, indications and/or approvals of the thermal waveform(s) and/or from deleting the thermal waveform(s) from a waveform database). For example, the waveform module may comprise software that enables a user to protect one or more idealized thermal waveforms (e.g., by requiring users to enter a specified password prior to modifying and/or deleting the idealized thermal waveform(s)).

In some embodiments, the waveform module comprises software that enables a user to remove the protected status from one or more thermal waveforms. For example, the waveform module may comprise software that enables a user to remove the protected status from one or more idealized thermal waveforms (e.g., by entering the appropriate password).

In some embodiments, the waveform module is configured to automatically generate and/or modify the parameters, indications and/or approvals of one or more thermal waveforms (e.g., idealized thermal waveforms) in response to data received from one or more devices/modules. For example, the waveform module may be configured to automatically update one or more thermal waveforms responsive to data received from one or more TEDs and/or one or more sensors.

The waveform module may be configured to retrieve the parameters, indications and/or approvals of one or more thermal waveforms from any suitable database, including, but not limited to, a waveform database residing in a vestibular stimulation device, a waveform database residing in a patient control device, a waveform database residing in a physician control device, a waveform database residing in the physician support device, a waveform database residing in a registry and/or a waveform database residing in a portable memory device (e.g., an SD memory card).

Waveform parameters, indications and/or approvals generated and/or modified by the waveform module may be stored in a database. In some embodiments, the generated/modified parameters, indications and/or approvals are stored in a waveform database comprising data associated with the parameters, indications and/or approvals of one or more thermal waveforms (e.g., idealized thermal waveforms). For example, the generated/modified waveform parameters, indications and/or approvals may be stored in a waveform database residing in a vestibular stimulation device, a waveform database residing in a patient control device, a waveform database residing in a physician control device, a waveform database residing in the physician support device, a waveform database residing in a registry and/or a waveform database residing in a portable memory device (e.g., an SD memory card).

B. Treatment Module

In some embodiments, the physician support device comprises a treatment module whereby a user (e.g., a physician) may generate, modify, update and/or extend a prescription. For example, the treatment module may enable a user to generate, modify, update and/or extend a prescription comprising a set of instructions for delivering one or more thermal waveforms to the vestibular system and/or the nervous system of a patient.

In some embodiments, the treatment module comprises software that enables a user to select one or more thermal waveforms from a database (e.g., an idealized thermal waveform from an idealized waveform database) and to provide instructions as to when/how each of those waveforms should be administered. For example, a treatment module may comprise software that enables a user to provide instructions as to how long a treatment schedule is to last (as discussed above with respect to FIG. 5), to provide instructions as to how many treatments may be administered each day (as discussed above with respect to FIG. 5), to provide instructions as to how often each thermal waveform is to be administered (as discussed above with respect to FIG. 6), to provide instructions as to what time(s) of day each thermal waveform is to be administered (as discussed above with respect to FIGS. 6 and 9), to select one or more idealized thermal waveforms from a database (as discussed above with respect to FIG. 7), to provide instructions regarding whether each of the selected thermal waveforms is to be delivered to the right and/or left ear canal of a patient (as discussed above with respect to FIG. 8), etc.

In some embodiments, the treatment module comprises software that enables a user to modify, update and/or extend a prescription by changing one or more parameters of the prescription (as discussed above with respect to FIG. 10), including, but not limited to, which thermal waveform(s) are delivered, frequency with which the thermal waveform(s) is/are delivered, and the expiration date of the prescription. Any suitable prescription may be modified, updated and/or extended, including, but not limited to, prescriptions stored in a prescription database (e.g., a prescription database residing in a vestibular stimulation device, in a patient control device, in a physician control device, in the physician support device or in a portable memory device, such as a portable SD memory card).

The treatment module may be configured to retrieve/select thermal waveforms from any suitable database, including, but not limited to, a waveform database residing in a vestibular stimulation device, a waveform database residing in a patient control device, a waveform database residing in a physician control device, a waveform database residing in the physician support device, a waveform database residing in a registry and/or a waveform database residing in a portable memory device (e.g., an SD memory card).

The treatment module may be configured to retrieve prescriptions from any suitable database, including, but not limited to, a prescription database residing in a vestibular stimulation device, a prescription database residing in a patient control device, a prescription database residing in a physician control device, a prescription database residing in the physician support device, a prescription database residing in a registry and/or a prescription database residing in a portable memory device (e.g., an SD memory card).

Prescriptions generated, modified, updated and/or extended by the treatment module may be added to a database comprising one or more prescriptions. For example, the prescriptions may be stored in a prescription database residing in a vestibular stimulation device, a prescription database residing in a patient control device, a prescription database residing in a physician control device, a prescription database residing in the physician support device, a prescription database residing in a registry and/or a prescription database residing in a portable memory device.

C. Network Module

In some embodiments, the physician support device comprises a network module configured to receive, retrieve and/or transmit data.

The network module may be configured to receive, retrieve and/or transmit data from/to any suitable device/module/database, including, but not limited to, other modules residing in the physician support device, databases residing in the physician support device, a vestibular stimulation device, a patient control device, a physician control device, a registry, a TED, a sensor and a portable memory device (e.g., an SD memory card).

The network module may be configured to receive, retrieve and/or transmit data over any suitable wired or wireless communications channel, including, but not limited to, a LAN, the Internet, a public telephone switching network, Bluetooth, WLAN and the like.

The network module may be configured to receive, retrieve and/or transmit any suitable data, including, but not limited to, data associated with the parameters, indications and/or approvals of one or more thermal waveforms, one or more prescriptions, controller feedback data, data associated with the delivery of one or more thermal waveforms, data associated with the fit of one or more earpieces, patient feedback data, physician feedback data and/or patient information.

In some embodiments, the network module is configured to receive and/or retrieve data associated with the parameters, indications and/or approvals of one or more thermal waveforms from a waveform module/database residing in the physician support device, from a vestibular stimulation device, from a patient control device, from a physician control device, from a registry and/or from a portable memory device.

In some embodiments, the network module is configured to receive and/or retrieve one or more prescriptions from a treatment module residing in the physician support device, from a prescription database residing in the physician support device, from a vestibular stimulation device, from a patient control device, from a physician control device, from a registry and/or from a portable memory device.

In some embodiments, the network module is configured to receive and/or retrieve controller feedback data, data associated with the delivery of one or more thermal waveforms and/or data associated with the fit of one or more earpieces from a feedback module/database residing in the physician support device, from a vestibular stimulation device and/or from a patient control device.

In some embodiments, the network module is configured to receive and/or retrieve patient feedback data, physician feedback data and/or patient information from a feedback module/database residing in the physician support device, from a GUI module residing in the physician support device, from a patient information database residing in the physician support device, from a vestibular stimulation device, from a patient control device, from a physician control device, from a registry and/or from a portable memory device.

In some embodiments, the network module is configured to transmit data associated with the parameters, indications and/or approvals of one or more thermal waveforms to a waveform module/database residing in the physician support device, to a treatment module residing in the physician support device, to a vestibular stimulation device, to a patient control device, to a physician control device, to a registry and/or to a portable memory device.

In some embodiments, the network module is configured to transmit one or more prescriptions to a treatment module residing in the physician support device, to a prescription database residing in the physician support device, to a vestibular stimulation device, to a patient control device, to a physician control device, to a registry and/or to a portable memory device.

In some embodiments, the network module is configured to transmit controller feedback data, data associated with the delivery of one or more thermal waveforms and/or data associated with the fit of one or more earpieces to a feedback module/database residing in the physician support device, to a vestibular stimulation device, to a patient control device, to a physician control device, to a registry and/or to a portable memory device.

In some embodiments, the network module is configured to transmit patient feedback data, physician feedback data and/or patient information to a feedback module/database residing in the physician support device, to a patient information database residing in the physician support device, to a vestibular stimulation device, to a patient control device, to a physician control device, to a registry and/or to a portable memory device.

In some embodiments, the network module is configured to access a database comprising data associated with the parameters, indications and/or approvals of one or more thermal waveforms (e.g., idealized thermal waveforms). For example, the network module maybe configured to access a waveform database residing in a vestibular stimulation device, a waveform database residing in a patient control device, a waveform database residing in a physician control device, a waveform database residing in the physician support device, a waveform database residing in a registry and/or a waveform database residing in a portable memory device.

In some embodiments, the network module is configured to access a database comprising one or more prescriptions. For example, the network module maybe configured to access a prescription database residing in a vestibular stimulation device, a prescription database residing in a patient control device, a prescription database residing in a physician control device, a prescription database residing in the physician support device, a prescription database residing in a registry and/or a prescription database residing in a portable memory device.

In some embodiments, the network module is configured to access a database comprising controller feedback data, data associated with the delivery of one or more thermal waveforms, data associated with the fit of one or more earpieces, patient feedback data and/or physician feedback data. For example, the network module maybe configured to access a feedback database residing in a vestibular stimulation device, a feedback database residing in a patient control device, a feedback database residing in a physician control device, a feedback database residing in the physician support device, a feedback database residing in a registry and/or a feedback database residing in a portable memory device.

In some embodiments, the network module is configured to access a database comprising patient information. For example, the network module maybe configured to access a patient information database residing in a vestibular stimulation device, a patient information database residing in a patient control device, a patient information database residing in a physician control device, a patient information database residing in the physician support device, a patient information database residing in a registry and/or a patient information database residing in a portable memory device.

D. Graphical User Interface Module

In some embodiments, the physician support device comprises a GUI module configured to display information and/or to accept user input. Any suitable GUI may be used, including, but not limited to, a keyboard, a mouse, an LCD display with one or more associated entry keys and an interactive touch screen. For example, the GUI may comprise a static pressure touch-sensitive display, a capacitive touch-sensitive display, a resistive touch-sensitive display, an electrostatic capacity proximity sensor, a magnetic proximity sensor and/or an infrared proximity sensor. See, e.g., U.S. Patent Publication Nos. 2011/0271222, 2011/0273575, 2011/0275414 and 2011/0275416.

The GUI module may be configured to display any suitable information, including, but not limited to, data associated with the delivery of one or more thermal waveforms. For example, the GUI module may be configured to display the current date and/or time (as discussed above with respect to FIG. 10); one or more target temperatures (as discussed above with respect to FIG. 11); the number of treatment sessions that have been administered for a prescription; the number of treatment sessions remaining in a prescription; the amount of time remaining until a prescription must be renewed/updated; the amount of remaining battery life, an alert message (e.g., a reminder to a physician that he/she needs to modify, update and/or extend a prescription); the target time/temperature parameters of one or more prescribed thermal waveform(s) (as discussed above with respect to FIG. 11); the precise time/temperature parameters of the thermal waveform(s) delivered to a patient; the date/time of delivery of the thermal waveform(s) delivered to a patient; the temperature(s) of a patient's ear canal(s) at various time points before, during and/or after delivery of the thermal waveform(s); the temperature(s) of a patient's inner ear(s) at various time points before, during and/or after delivery of the thermal waveform(s); the fit of the earpiece(s) at various time points before, during and/or after delivery of the thermal waveform(s); an estimate of the thermal contact between the earpiece(s) and the patient's ear canal(s) at various time points before, during and/or after delivery of the thermal waveform(s); patient-specific time constants (e.g., a time constant associated with the transduction of heat from a patient's ear canal to the inner ear); reaction time (i.e., how long it took for a patient to react to one or more thermal waveforms); the effectiveness of one or more thermal waveforms (i.e., whether and to what extent symptoms were relieved, whether the thermal waveform(s) enhanced the effectiveness of another agent/therapy, etc.); the stability of a treatment (i.e., how long the effects of the treatment lasted); the instability of a treatment (i.e., which symptom(s) returned and when did it/they return); the presence or absence of comorbid disorders, injuries and/or diseases; disorder, injury and/or disease modulation(s) and/or modification(s) that occurred as a result of treatment; the cognitive effect(s) of one or more thermal waveforms; patient compliance (e.g., whether a patient initiated delivery at the prescribed time, whether a patient completed the prescribed treatment session, whether the earpiece(s) remained properly fitted in a patient's ear canal(s) for the duration of the treatment session, etc.); the mood of a patient at various time points before, during and/or after delivery of one or more thermal waveforms (e.g., videos/images of a patient that may be used to assess mood); objectives measures of efficacy (e.g., nystamography data, EEG data, MRI data, heart rate data, blood pressure data); subjective measures of efficacy (e.g., a patient-reported pain score); blood chemistry data (e.g., blood A1c levels, blood glucose levels and blood cortisol levels); saliva chemistry data (e.g., saliva cortisol levels); urine chemistry data (e.g., urine cortisol levels)), comments a patient made about his/her treatment session(s) (e.g., comments made to a physician, submitted in response to an automated survey and/or recorded in a treatment diary); the impedance between an earpiece inserted into the ear canal of a patient and an electrode affixed to a second location on/in said patient's body (e.g., an electrode placed in or adjacent to the patient's other ear canal); the rate at which a patient's inner ear cools in response to a cooling stimulus (e.g., data from a temperature sensor, such as thermistor, that monitors how quickly the inner ear cools in response to a cooling waveform); the rate at which a patient's inner ear warms in response to a warming stimulus (e.g., data from a temperature sensor, such as thermistor, that monitors how quickly the inner ear warms in response to a warming waveform); patient comments regarding the subjective fit of his/her earpiece(s); physician comments regarding the effectiveness of one or more thermal waveforms and/or physician comments regarding the effect(s) of one or more waveform modifications.

The GUI module may be configured to accept any suitable user input, including, but not limited to, instructions for generating and/or modifying the parameters, indications and/or approvals of a thermal waveforms and/or instructions for generating, modifying, updating and/or extending a prescription.

E. Feedback Module

In some embodiments, the physician support device comprises a feedback module configured to receive, transmit and/or analyze data.

The feedback module may be configured to receive and/or transmit data from/to any suitable device/module/database, including, but not limited to, other modules residing in the physician support device, databases residing in the physician support device, a vestibular stimulation device, a patient control device, a physician control device, a registry, a TED, a sensor and a portable memory device (e.g., an SD memory card).

The feedback module may be configured to receive and/or transmit data over any suitable wired or wireless communications channel, including, but not limited to, a LAN, the Internet, a public telephone switching network, Bluetooth, WLAN and the like.

The feedback module may be configured to receive, transmit and/or analyze any suitable data, including, but not limited to, controller feedback data, data associated with the delivery of one or more thermal waveforms, data associated with the fit of one or more earpieces, patient feedback data, physician feedback data and/or patient information.

In some embodiments, the feedback module is configured to receive and/or analyze controller feedback data, data associated with the delivery of one or more thermal waveforms, data associated with the fit of one or more earpieces, patient feedback data, physician feedback data and/or patient information from a GUI module residing in the physician support device, from a feedback database residing in the physician support device, from a patient information database residing in the physician support device, from a vestibular stimulation device, from a patient control device, from a physician control device and/or from a portable memory device (e.g., an SD memory card). For example, the feedback module may be configured to analyze the accuracy with which one or more prescribed waveforms was delivered to a patient, the fit of an earpiece based upon the rate at which the temperature of the earpiece changes in response to a cooling/warming waveform, the slew rate associated with one or more TEDs, the impedance between an earpiece positioned in the left ear canal of a patient and an earpiece positioned in the right ear canal of a patient, the impedance between an earpiece positioned in the ear canal of a patient and an electrode affixed to a second location on/in the patient's body; the effectiveness of a given thermal waveform or combination of thermal waveforms (e.g., by analyzing pain scores entered before, during and after a treatment session); the effect(s) of one or more waveform modifications (e.g., by analyzing whether/how much a given waveform modification changed the effectiveness of a thermal waveform in treating a disease/disorder), etc.

In some embodiments, the feedback module is configured to analyze data (e.g., patient feedback data, physician feedback data and/or patient information) to identify modifications that are likely to increase the effectiveness of a given thermal waveform, class of thermal waveforms or combination of thermal waveforms; to identify new diseases/disorders/injuries for which a given thermal waveform, class of thermal waveforms, combination of thermal waveforms and/or treatment regimen may provide an effective treatment; to predict which thermal waveform(s) or combination(s) of thermal waveforms may be most effective in treating a given disease/disorder/injury; to identify thermal waveforms, classes of thermal waveforms and/or combinations of thermal waveforms that are not likely to be effective in the treatment of a given disease/disorder/injury and/or to identify waveform characteristics that may be linked to increased/decreased efficacy with regard to the treatment of a given disease/disorder/injury. For example, the feedback module may be configured to identify new idealized thermal waveforms by identifying one or more diseases/disorders/injuries for which a thermal waveform or class of waveforms is likely to be an effective treatment (e.g., by identifying a new thermal waveform that belongs to a class of waveforms known to be effective in treating one or more diseases/disorders/injuries). Likewise, the feedback module may be configured to identify one or more additional diseases/disorders/injuries for which a previously identified idealized thermal waveform is likely to be an effective treatment (e.g., by identifying, in a population of patients receiving treatment with an idealized thermal waveform for treatment of a first disease/disorder/injury, one or more co-morbid diseases/disorders/injuries that also appear to be effectively treated by the idealized thermal waveform). Conversely, the feedback module may be configured to identify one or more diseases/disorders/injuries for which a previously identified idealized thermal waveform is not likely to be an effective treatment (e.g., one or more of the diseases/disorders/injuries for which an idealized thermal waveform had previously been indicated and/or approved may be removed from the list of indications for that thermal waveform or for the class of thermal waveforms to which it belongs).

In some embodiments, the feedback module is configured to transmit data associated with its analysis to a feedback database residing in the physician support device, to a patient information database residing in the physician support device, to a vestibular stimulation device, to a patient control device, to a physician control device and/or to a portable memory device (e.g., an SD memory card).

F. Alert Generation Module

In some embodiments, the physician support device comprises an alert generation module configured to generate one or more alert messages.

The alert generation module may be configured to generate any suitable alert message, including, but not limited to, an alert indicating that physician feedback data has been received from a physician control device; a reminder to analyze previously received physician feedback data; an alert indicating that one or more idealized thermal waveforms has been modified and an alert indicating that a given modification is likely to increase/decrease the effectiveness of a given thermal waveform and/or an alert indicating that a given thermal waveform, class of thermal waveforms or combination of thermal waveforms has been identified as being indicated and/or approved for use in the treatment of a disease/disorder.

In some embodiments, the alert generation module is configured to communicate with various devices/modules, including, but not limited to, a vestibular stimulation device, a patient control device, a physician control device, a registry, a portable memory device (e.g., an SD memory card) and other modules of the physician support device. For example, the alert generation module may be configured to provide instructions to the GUI module and/or the tone generation module for displaying one or more alert messages and/or for generation an audible tone to alert a user of the presence of the one or more alert messages. The graphical user interface module may be configured to display the one or more alert messages immediately upon generation or upon interaction with a user (e.g., an alert notification icon may be generated, with the alert message being displayed only after the user indicates that he/she wishes to view the message).

G. Tone Generation Module

In some embodiments, the physician support device comprises a tone generation module configured to produce audible tones. In some such embodiments, the tone generation module comprises a piezo buzzer. Audible tones may be produced to alert a user to various circumstances/events, including, but not limited to, the existence of an unread/unviewed alert message. Audible tones may be generated repeatedly in response to a single circumstance/event (e.g., an audible tone may be generated repeatedly until the user views/reads the message) and may become progressively louder and/or more frequent with time.

H. Visual Indicator Module

In some embodiments, the physician support device comprises a visual indicator module configured to notify a user of the existence of an unread/unviewed alert message. In some such embodiments, the visual indicator module comprises an LED indicator light. The visual indicator module may be activated repeatedly in response to a single alert message (e.g., an LED light may be illuminated repeatedly until the user views/reads the message) or may remain activated until the user views/reads the message.

Security Module

In some embodiments, the physician support device comprises a security module configured to prevent unauthorized use of the physician support device (i.e., to prevent unauthorized persons from using the physician support device, to prevent authorized persons from using the physician support device in an unauthorized manner, etc.).

The security module may be configured to prevent unauthorized use of the physician support device using any suitable means of security, including, but not limited to, password protection and data encryption. For example, the security module may be configured such that a user is required to input a designated password prior to generating and/or modifying a thermal waveform; generating, modifying, updating and/or extending a prescription; entering/viewing patient feedback data; viewing/analyzing physician feedback data and/or entering/viewing patient information (as discussed above with respect to FIG. 12).

As will be appreciated by one of skill in the art, the physician support device may comprise any suitable data, including, but not limited to, static and/or dynamic data used by the operating system, applications, I/O device drivers and other software components, controller feedback data, data associated with the parameters, indications and/or approvals of one or more thermal waveforms (e.g., idealized thermal waveforms), data associated with one or more prescriptions, data associated with the delivery of one or more thermal waveforms, data associated with the fit of one or more earpieces, patient feedback data, physician feedback data and patient information. For example, the physician support device may comprise a waveform database comprising data associated with one or more idealized thermal waveforms; a prescription database comprising data associated with one or more prescriptions; a feedback database comprising controller feedback data, data associated with the delivery of one or more thermal waveforms to the vestibular system and/or the nervous system of a patient, patient feedback data and physician feedback data and/or a patient history database comprising data associated with one or more patients. In some embodiments, two or more of the aforementioned databases are combined to form a single database comprising data from each of the individual databases (e.g., the physician support device may comprise a feedback-history database comprising data associated with the delivery of one or more thermal waveforms and patient information). In some embodiments, one of the aforementioned databases is split into two or more distinct databases (e.g., the physician support device may comprise a delivery feedback database comprising data associated with the specific parameters of the thermal waveform(s) delivered to a patient, a patient feedback database comprising patient feedback data and a physician feedback database comprising physician feedback data). In some embodiments, one or more of the data types described below with respect to one of the databases described below is stored in one of the other databases described below (e.g., the patient information database, rather than the feedback database, may be configured to receive/store patient feedback data). In some embodiments, data is transmitted, received and/or stored in a controlled format (e.g., in a standardized format using forms/programs supplied by the physician support device or a registry). The physician support device may be configured to transmit, receive and store data in a manner that ensures compliance with any and all applicable laws and/or regulations (e.g., the Health Insurance Portability and Accountability Act of 1996 (P.L. 104-191; "HIPAA")).

Waveform Database

In some embodiments, the physician support device comprises a waveform database configured to receive, store and/or transmit data associated with the parameters, indications and/or approvals of one or more thermal waveforms (e.g, one or more idealized thermal waveforms). In some such embodiments, the waveform database is configured such that one or more of the thermal waveforms stored therein is/are protected (e.g., users may be prevented from modifying and/or deleting the idealized thermal waveform(s) stored in the waveform database).

The waveform database may comprise any suitable type of memory including, but not limited to, cache, ROM, PROM, EPROM, EEPROM, flash memory, SRAM and DRAM. In some embodiments, the waveform database comprises a portable memory device, such as an SD memory card or a USB memory stick. For example, the waveform database may comprise an SD memory card interface and one or more prescriptions may be stored on a portable SD memory card.

The waveform database may be configured to receive and/or transmit data from/to any suitable device/module/database, including, but not limited to, modules residing in the physician support device, a vestibular stimulation device, a patient control device, a physician control device, a registry, a TED, a sensor and a portable memory device (e.g., an SD memory card).

The waveform database may be configured to receive and/or transmit data over any suitable wired or wireless communications channel, including, but not limited to, a LAN, the Internet, a public telephone switching network, Bluetooth, WLAN and the like.

B. Prescription Database

In some embodiments, the physician support device comprises a prescription database configured to receive, transmit and/or store one or more prescriptions, wherein each prescription comprising a set of instructions for delivering one or more thermal waveforms to the vestibular system and/or the nervous system of a patient.

The prescription database may comprise any suitable type of memory including, but not limited to, cache, ROM, PROM, EPROM, EEPROM, flash memory, SRAM and DRAM. In some embodiments, the prescription database comprises a portable memory device, such as an SD memory card or a USB memory stick. For example, the prescription database may comprise an SD memory card interface and one or more prescriptions may be stored on a portable SD memory card.

The prescription database may be configured to receive and/or transmit data from/to any suitable device/module/database, including, but not limited to, modules residing in the physician support device, a vestibular stimulation device, a patient control device, a physician control device, a registry, a TED, a sensor and a portable memory device (e.g., an SD memory card).

The prescription database may be configured to receive and/or transmit data over any suitable wired or wireless communications channel, including, but not limited to, a LAN, the Internet, a public telephone switching network, Bluetooth, WLAN and the like.

C. Feedback Database

In some embodiments, the physician support device comprises a feedback database configured to receive, transmit and/or store feedback data.

The feedback database may comprise any suitable type of memory including, but not limited to, cache, ROM, PROM, EPROM, EEPROM, flash memory, SRAM and DRAM. In some embodiments, the feedback database comprises a portable memory device, such as an SD memory card or a USB memory stick. For example, the feedback database may comprise an SD memory card interface and one or more prescriptions may be stored on a portable SD memory card.

The feedback database may be configured to receive and/or transmit feedback data from/to any suitable device/module/database, including, but not limited to, modules residing in the physician support device, a vestibular stimulation device, a patient control device, a physician control device, a registry, a TED, a sensor and a portable memory device (e.g., an SD memory card).

The feedback database may be configured to receive and/or transmit data over any suitable wired or wireless communications channel, including, but not limited to, a LAN, the Internet, a public telephone switching network, Bluetooth, WLAN and the like.

Feedback data may comprise any suitable data, including, but not limited to, controller feedback data, data associated with the delivery of one or more thermal waveforms, data associated with the fit of one or more earpieces, patient feedback data, physician feedback data and/or patient information. For example, the feedback database may comprise a log file detailing the target time/temperature parameters of one or more prescribed thermal waveform(s); the time/temperature parameters of the thermal waveform(s) delivered to a patient; the date/time of delivery of the thermal waveform(s) delivered to a patient; the temperature(s) of a patient's ear canal(s) at various time points before, during and/or after delivery of one or more thermal waveforms; the temperature(s) of a patient's inner ear(s) at various time points before, during and/or after delivery of one or more thermal waveforms; the fit of one or more earpieces at various time points before, during and/or after delivery of one or more thermal waveforms; an estimate of the thermal contact between one or more earpieces and a patient's ear canal(s) at various time points before, during and/or after delivery of one or more thermal waveforms; patient-specific time constants (e.g., a time constant associated with the transduction of heat from a patient's ear canal to the inner ear); a patient's reaction time (i.e., how long it took for a patient to react to one or more thermal waveforms); effectiveness of one or more thermal waveforms (i.e., whether and to what extent symptoms were relieved, whether the thermal waveform(s) enhanced the effectiveness of another agent/therapy, etc.); stability of a treatment (i.e., how long the effects of a treatment lasted); instability of a treatment (i.e., which symptom(s) returned and when did it/they return); the presence or absence of comorbid disorders, injuries and/or diseases; disorder, injury and/or disease modulation(s) and/or modification(s) that occurred as a result of treatment; the cognitive effect(s) of one or more thermal waveforms; patient compliance (e.g., whether a patient initiated delivery at the prescribed time, whether a patient completed the prescribed treatment session, whether the earpiece(s) remained properly fitted in a patient's ear canal(s) for the duration of the treatment session, etc.); the mood of a patient at various time points before, during and/or after delivery of one or more thermal waveforms (e.g., videos/images of a patient that may be used to assess mood); objectives measures of efficacy (e.g., nystamography data, EEG data, MRI data, heart rate data, blood pressure data); subjective measures of efficacy (e.g., a patient-reported pain score); blood chemistry data (e.g., blood A1c levels, blood glucose levels and blood cortisol levels); saliva chemistry data (e.g., saliva cortisol levels); urine chemistry data (e.g., urine cortisol levels)); comments a patient made about his/her treatment session(s) (e.g., comments made to a physician, submitted in response to an automated survey and/or recorded in a treatment diary); the impedance between an earpiece inserted into the ear canal of a patient and an electrode affixed to a second location on/in said patient's body (e.g., an electrode placed in or adjacent to the patient's other ear canal); the rate at which an earpiece is cooled in response to a cooling stimulus (e.g., data from a temperature sensor, such as thermistor, that monitors how quickly the earpiece cools in response to a cooling waveform); the rate at which an earpiece is warmed in response to a warming stimulus (e.g., data from a temperature sensor, such as a thermistor, that monitors how quickly the earpiece warms in response to a warming waveform); the rate at which a patient's ear canal and/or inner ear cooled in response to a cooling stimulus (e.g., data from a temperature sensor, such as thermistor, that monitors how quickly the ear canal and/or the inner ear cools in response to a cooling waveform); the rate at which a patient's ear canal and/or inner ear warmed in response to a warming stimulus (e.g., data from a temperature sensor, such as a thermistor, that monitors how quickly the ear canal and/or the inner ear warms in response to a warming waveform); patient comments regarding the subjective fit of one or more earpieces; physician comments regarding the effectiveness of one or more thermal waveforms and/or physician comments regarding the effect(s) of one or more waveform modifications.

D. Patient History Database

In some embodiments, the physician support device comprises a patient history database configured to receive, transmit and/or store patient information.

The patient history database may comprise any suitable type of memory including, but not limited to, cache, ROM, PROM, EPROM, EEPROM, flash memory, SRAM and DRAM. In some embodiments, the patient history database comprises a portable memory device, such as an SD memory card or a USB memory stick. For example, the patient history database may comprise an SD memory card interface and one or more prescriptions may be stored on a portable SD memory card.

The patient history database may be configured to receive and/or transmit data from/to any suitable device/module/database, including, but not limited to, modules residing in the physician support device, a vestibular stimulation device, a patient control device, a physician control device, a registry, a TED, a sensor and a portable memory device (e.g., an SD memory card).

The patient history database may be configured to receive and/or transmit data over any suitable wired or wireless communications channel, including, but not limited to, a LAN, the Internet, a public telephone switching network, Bluetooth, WLAN and the like.

Patient information may comprise any suitable information that is associated with a patient, including, but not limited to, the patient's medical history, the patient's current symptoms (if any), the patient's present diagnosis (if any), the patient's current prescriptions (if any) and data associated with the delivery of one or more thermal waveforms to the vestibular system and/or the nervous system of the patient.

As will be appreciated by one of skill in the art, the physician support device may comprise any I/O device drivers, including, but not limited to, software routines accessed through the operating system by the applications to communicate with devices such as I/O ports, memory components, vestibular stimulation devices, patient control devices and/or physician control devices.

As will be appreciated by one of skill in the art, the physician support device may be configured (e.g., with computer instructions (i.e., software)) to operate in a plurality of distinct modes. In each mode, the physician support device may be configured to permit access to some functionalities/modules and to prevent access to other functionalities/modules. For example, the physician support device may be configured to operate in a researcher mode, wherein the user is allowed to perform researcher-oriented tasks, such as generating and/or modifying the parameters, indications and/or approvals of one or more idealized thermal waveforms, but is prevented from accessing other functionalities/modules (e.g., the user may be prevented from modifying the underlying operational parameters of the physician control device). Similarly, the physician support device may be configured to operate in an engineer mode, wherein the user is allowed to access all of the physician support device's functionalities/modules. Each mode may be protected via a unique security measure (e.g., the physician support device may be configured such that each mode is protected by a unique password).

Figure 28:
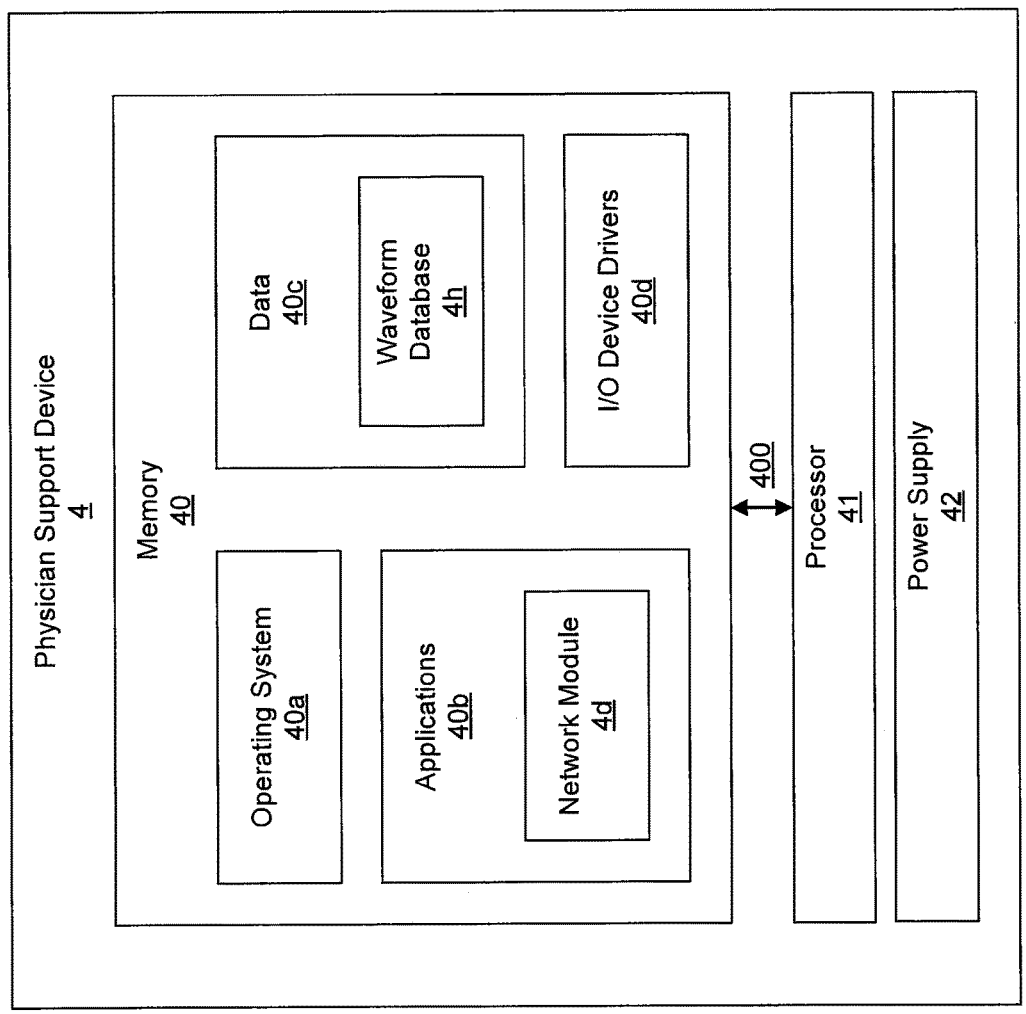
FIG. 28 is a block diagram of a physician support device according to some embodiments of the present invention.
Figure 29:
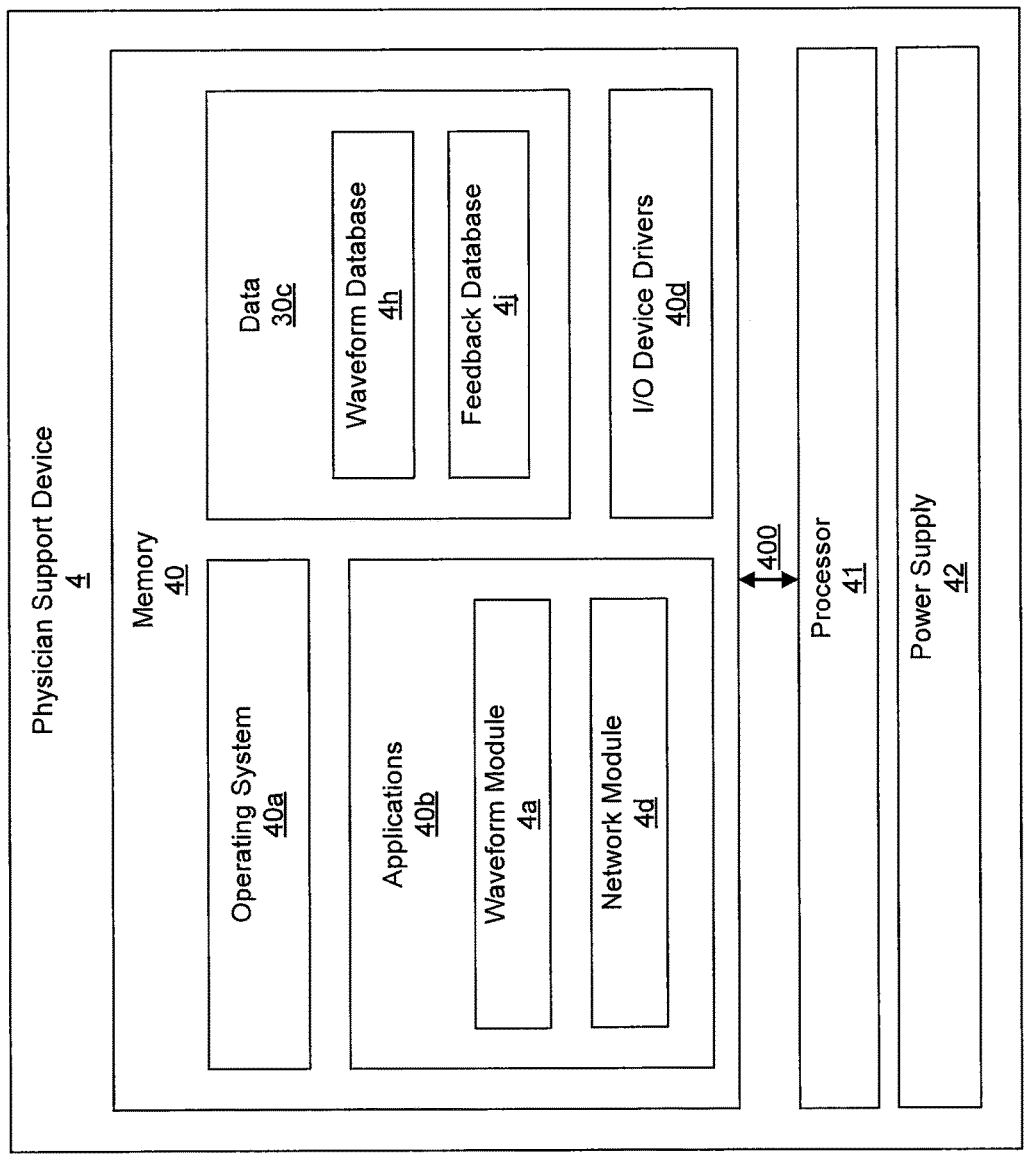
FIG. 29 is a block diagram of a physician support device according to some embodiments of the present invention.
Figure 30:
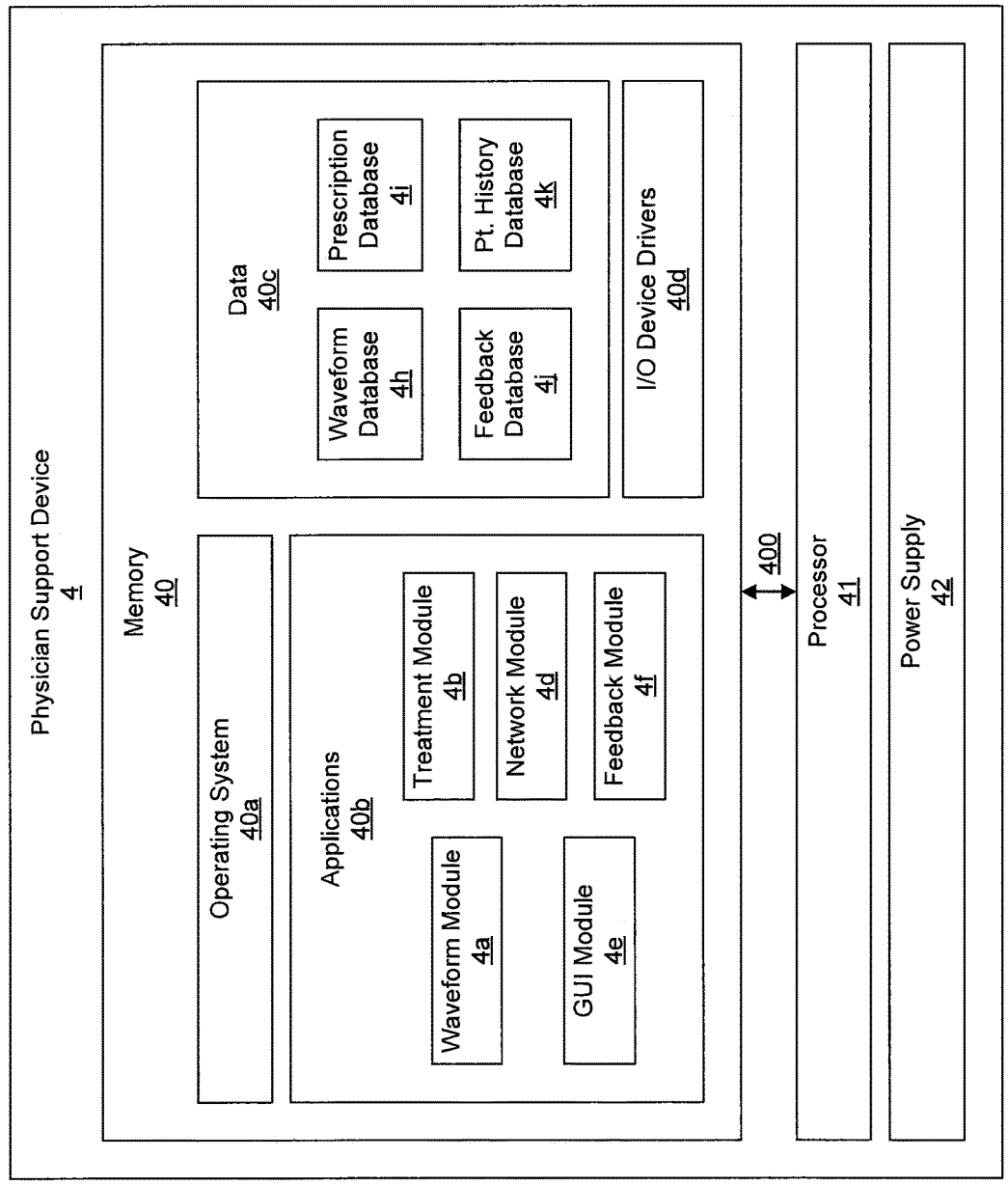
FIG. 30 is a block diagram of a physician support device according to some embodiments of the present invention.

As shown in FIGS. 28-30, in some embodiments of the present invention, the physician support device 4 comprises memory 40, a processor 41 and a power supply 42 (e.g., an internal power supply), wherein memory 40 is representative of the overall hierarchy of memory devices containing software and data used to implement the functionality of the physician support device 4 and wherein the processor 41 communicates with the memory 40 via an address/data bus 400. In particular embodiments, memory 40 comprises an operating system 40*a*, applications 40*b* (e.g., a waveform module 4*a* configured to generate and/or modify the parameters, indications and/or approvals of one or more thermal waveforms; a treatment module 4*b* configured to generate, modify, update and/or extend a prescription comprising a set of instructions for delivering one or more thermal waveforms to the vestibular system and/or the nervous system of a patient; a network module 4*d* configured to receive and/or transmit data, a GUI module 4*e* configured to display information and/or accept user input and/or a feedback module 4*f* configured to receive, transmit, and/or analyze data associated with the delivery of one or more thermal waveforms), data 40*c* (e.g., a waveform database 4*h* comprising data associated with the parameters, indications and/or approvals of one or more thermal waveforms; a prescription database 4*i* comprising at least one prescription comprising a set of instructions for delivering one or more thermal waveforms to the vestibular system and/or the nervous system of a patient; a feedback database 4*j* comprising data associated with the delivery of one or more thermal waveforms and/or a patient history database 4*k* comprising patient information) and I/O drivers 40*d*. In some such embodiments, data 40*c* comprises one or more databases stored on a portable memory device. For example, data 40*c* may comprise an SD memory card interface and a portable SD memory card comprising a waveform database 4*h*, a prescription database 4*i*, a feedback database 4*j* and/or a patient history database 4*k*.

In some embodiments, the waveform module 4*a* is configured to update the waveform database 4*h* by adding a newly generated idealized thermal waveform, by modifying one or more of the idealized thermal waveforms stored therein, by deleting one or more of the idealized thermal waveforms stored therein and/or by modifying the indication/approvals associated with one or more of the idealized thermal waveforms stored therein in response to the analysis of data (e.g., physician feedback data) by the feedback module 4*f*.

In some embodiments, the network module 4*d* is configured to receive data associated with the parameters, indications and/or approvals of one or more thermal waveforms from the waveform module 4*a*, a patient control device, a physician control device, a registry and/or a portable memory device (e.g., an SD memory card) and to transmit the data to the waveform database 4*h* for storage. In some such embodiments, the data is stored on an SD memory card inserted into an SD memory card interface.

In some embodiments, the network module 4d is configured to retrieve data associated with the parameters, indications and/or approvals of one or more thermal waveforms from the waveform database 4h, a registry and/or a portable memory device (e.g., an SD memory card) and to transmit the data to the waveform module 4a, the treatment module 4b, a vestibular stimulation device, a patient control device, a physician control device, a registry and/or a portable memory device (e.g., an SD memory card). In some such embodiments, the physician support device is configured to transmit all of the idealized thermal waveforms in the waveform database or a subset thereof (e.g., waveforms indicated for use in the treatment of migraines) to one or more physician control devices upon request (e.g., after receiving an update request from a physician control device) or at a specified interval (e.g., every two weeks). In some preferred embodiments, the physician support device is configured to replace the idealized thermal waveforms in a physician control device's waveform database with the idealized thermal waveforms from the physician support device's waveform database.

In some embodiments, the network module 4d is configured to receive one or more prescriptions from the treatment module 4b, a patient control device, a physician control device, a registry and/or a portable memory device (e.g., an SD memory card) and to transmit the prescription(s) to the prescription database 4i for storage. In some such embodiments, the prescription(s) is/are stored on an SD memory card inserted into an SD memory card interface.

In some embodiments, the network module 4d is configured to retrieve one or more prescriptions from the prescription database 4i, a registry and/or a portable memory device (e.g., an SD memory card) and to transmit the prescription(s) to the treatment module 4b, a vestibular stimulation device, a patient control device, a physician control device, a registry and/or a portable memory device (e.g., an SD memory card).

In some embodiments, the network module 4d is configured to receive data associated with the delivery of one or more thermal waveforms, data associated with the fit of one or more earpieces, patient feedback data and/or physician feedback data from a vestibular stimulation device, a patient control device, a physician control device, a registry and/or a portable memory device (e.g., an SD memory card) and to transmit that data to the feedback database 4j for storage. In some such embodiments, the data is stored on an SD memory card inserted into an SD memory card interface.

In some embodiments, the network module 4d is configured to retrieve data associated with the delivery of one or more thermal waveforms, data associated with the fit of one or more earpieces, patient feedback data and/or physician feedback data from the feedback database 4j and to transmit the data to the feedback module 4f, a physician control device, a registry and/or a portable memory device (e.g., an SD memory card).

In some embodiments, the network module 4d is configured to receive patient information from the GUI module 4e, a vestibular stimulation device, a patient control device, a physician control device, a registry and/or a portable memory device (e.g., an SD memory card) and to transmit that data to the patient history database 4k for storage. In some such embodiments, the patient information is stored on an SD memory card inserted into an SD memory card interface.

In some embodiments, the network module 4d is configured to retrieve patient information from the patient history database 4k and to transmit the patient information to a physician control device, a registry and/or a portable memory device (e.g., an SD memory card).

In some embodiments, the feedback module 4f is configured to analyze data from the waveform database 4h, the prescription database 4i, the feedback database 4j and/or the patient history database 4k to identify diseases/disorders/injuries for which a given thermal waveform, class of thermal waveforms, combination of thermal waveforms and/or treatment regimen may be an effective treatment. In some such embodiments, the feedback module 4d is configured to automatically initiate such data analysis each time one of the aforementioned databases is modified or at a predetermined interval (e.g., every two weeks). In some such embodiments, the feedback module 4d is configured to communicate the results of its analysis to the waveform module 4a (e.g., by transmitting the results to the waveform module 4a via the network module 4d) and/or to a registry.

Registry

As noted above, the present invention provides a registry for receiving, storing and/or transmitting data.

In some embodiments, the registry comprises, consists essentially of or consists of a network module configured to receive/transmit data and one or more databases configured to store data.

A registry of the present invention may comprise any suitable computing device/system, including, but not limited to, a desktop computer, a laptop computer, a handheld computer, a personal digital assistant (PDA), and a smart phone.

Any conventional security means may be provided to prevent unauthorized activation of the registry. For example, the registry may be password protected.

The registry may be configured to receive and/or transmit any suitable data, including, but not limited to, data associated with the parameters, indications and/or approvals of one or more thermal waveforms, one or more prescriptions, controller feedback data, data associated with the delivery of one or more thermal waveforms, data associated with the fit of one or more earpieces, patient feedback data, physician feedback data and/or patient information.

The registry may be configured to receive and/or transmit data from/to various devices, including, but not limited to, a vestibular stimulation device, a patient control device, a physician control device, a physician support device and a portable memory device (e.g., an SD memory card). In some embodiments, the registry is configured to receive data associated with the parameters, indications and/or approvals of one or more thermal waveforms (e.g., idealized thermal waveforms) from a vestibular stimulation device, a patient control device, a physician control device, a physician support device, another registry and/or a portable memory device (e.g., an SD memory card); to transmit data associated with the parameters, indications and/or approvals of one or more thermal waveforms (e.g., idealized thermal waveforms) to a vestibular stimulation device, a patient control device, a physician control device, a physician support device, another registry and/or a portable memory device (e.g., an SD memory card); to receive feedback data and/or patient information from a vestibular stimulation device, a patient control device, a physician control device, a physician support device, another registry and/or a portable memory device (e.g., an SD memory card); and/or to transmit feedback data and/or patient information to a vestibular stimulation device, a patient control device, a physician control device, a physician support device, another registry and/or a portable memory device (e.g., an SD memory card). In some embodiments, the registry is configured to receive, store and/or transmit data from/to one or more devices located within a specified geographical region (e.g., one or more physician control devices located within the United States, one or more physician support devices located within North America, etc.).

The registry may be configured to receive and/or transmit data over any suitable wired or wireless communications channel, including, but not limited to, a LAN, the Internet, a public telephone switching network, Bluetooth, WLAN and the like.

In some embodiments, the registry comprises memory, a processor and a power supply. As will be appreciated by one of skill in the art, the processor may be any commercially available or custom microprocessor. Memory can include, but is not limited to, the following types of devices: cache, ROM, PROM, EPROM, EEPROM, flash memory, SRAM and DRAM. The power supply may be an internal power supply (e.g., one or more rechargeable batteries that may be recharged without first being removed from the registry).

The registry's memory may comprise any suitable software and/or data, including, but not limited to, an operating system, applications, data and input/output (I/O) drivers.

As will be appreciated by one of skill in the art, the registry may use any suitable operating system, including, but not limited to, OS/2, AIX, OS/390 or System390 from International Business Machines Corp. (Armonk, N.Y.), Window CE, Windows NT, Windows95, Windows98, Windows2000, Windows 7 or Windows Vista from Microsoft Corp. (Redmond, Wash.), Mac OS from Apple, Inc. (Cupertino, Calif.), Unix, Linux or Android.

As will be appreciated by one of skill in the art, the registry may comprise any suitable application, including, but not limited to, one or more programs configured to implement one or more of the various features of the present invention. For example, the registry may comprise a network module configured to receive and/or transmit data, a GUI module configured to display information and/or accept user input, an alert generation module configured to generate one or more alert messages; a tone generation module configured to produce one or more audible tones; a visual indicator module configured to produce one or more visual indicators and/or a security module configured to prevent unauthorized use of the registry.

Network Module

In some embodiments, the registry comprises a network module configured to receive, retrieve and/or transmit data.

The network module may be configured to receive, retrieve and/or transmit data from/to any suitable device/module/database, including, but not limited to, other modules residing in the registry, databases residing in the registry, a vestibular stimulation device, a patient control device, a physician control device, a physician support device, another registry and a portable memory device (e.g., an SD memory card).

The network module may be configured to receive, retrieve and/or transmit data over any suitable wired or wireless communications channel, including, but not limited to, a LAN, the Internet, a public telephone switching network, Bluetooth, WLAN and the like.

The network module may be configured to receive, retrieve and/or transmit any suitable data, including, but not limited to, data associated with the parameters, indications and/or approvals of one or more thermal waveforms, one or more prescriptions, controller feedback data, data associated with the delivery of one or more thermal waveforms, data associated with the fit of one or more earpieces, patient feedback data, physician feedback data and/or patient information.

In some embodiments, the network module is configured to receive and/or retrieve data associated with the parameters, indications and/or approvals of one or more thermal waveforms from a waveform database residing in the registry, from a vestibular stimulation device, from a patient control device, from a physician control device, from a physician support device, from another registry and/or from a portable memory device.

In some embodiments, the network module is configured to receive and/or retrieve one or more prescriptions from a prescription database residing in the registry, from a vestibular stimulation device, from a patient control device, from a physician control device, from a physician support device, from another registry and/or from a portable memory device.

In some embodiments, the network module is configured to receive and/or retrieve controller feedback data, data associated with the delivery of one or more thermal waveforms, data associated with the fit of one or more earpieces, patient feedback data, physician feedback data and/or patient information from a feedback database residing in the registry, from a vestibular stimulation device, from a patient control device, from a physician control device, from a physician support device, from another registry and/or from a portable memory device.

In some embodiments, the network module is configured to transmit data associated with the parameters, indications and/or approvals of one or more thermal waveforms to a waveform database residing in the registry, to a vestibular stimulation device, to a patient control device, to a physician control device, to a physician support device, to another registry and/or to a portable memory device.

In some embodiments, the network module is configured to transmit one or more prescriptions to a prescription database residing in the registry, to a vestibular stimulation device, to a patient control device, to a physician control device, to a physician support device, to another registry and/or to a portable memory device.

In some embodiments, the network module is configured to transmit controller feedback data, data associated with the delivery of one or more thermal waveforms, data associated with the fit of one or more earpieces, patient feedback data, physician feedback data and/or patient information to a feedback database residing in the registry, to a vestibular stimulation device, to a patient control device, to a physician control device, to a physician support device, to another registry and/or to a portable memory device.

In some embodiments, the network module is configured to access a database comprising data associated with the parameters, indications and/or approvals of one or more thermal waveforms (e.g., idealized thermal waveforms). For example, the network module maybe configured to access a waveform database residing in a vestibular stimulation device, a waveform database residing in a patient control device, a waveform database residing in a physician control device, a waveform database residing in a physician support device, a waveform database residing in the registry, a waveform database residing in another registry and/or a waveform database residing in a portable memory device.

In some embodiments, the network module is configured to access a database comprising one or more prescriptions.

For example, the network module maybe configured to access a prescription database residing in a vestibular stimulation device, a prescription database residing in a patient control device, a prescription database residing in a physician control device, a prescription database residing in a physician support device, a prescription database residing in the registry, a prescription database residing in another registry and/or a prescription database residing in a portable memory device.

In some embodiments, the network module is configured to access a database comprising controller feedback data, data associated with the delivery of one or more thermal waveforms, data associated with the fit of one or more earpieces, patient feedback data and/or physician feedback data. For example, the network module maybe configured to access a feedback database residing in a vestibular stimulation device, a feedback database residing in a patient control device, a feedback database residing in a physician control device, a feedback database residing in a physician support device, a feedback database residing in the registry, a feedback database residing in another registry and/or a feedback database residing in a portable memory device.

In some embodiments, the network module is configured to access a database comprising patient information. For example, the network module maybe configured to access a patient information database residing in a vestibular stimulation device, a patient information database residing in a patient control device, a patient information database residing in a physician control device, a patient information database residing in a physician support device, a patient information database residing in the registry, a patient information database residing in another registry and/or a patient information database residing in a portable memory device.

B. Graphical User Interface Module

In some embodiments, the registry comprises a GUI module configured to display information and/or to accept user input. Any suitable GUI may be used, including, but not limited to, a keyboard, a mouse, an LCD display with one or more associated entry keys and an interactive touch screen. For example, the GUI may comprise a static pressure touch-sensitive display, a capacitive touch-sensitive display, a resistive touch-sensitive display, an electrostatic capacity proximity sensor, a magnetic proximity sensor and/or an infrared proximity sensor. See, e.g., U.S. Patent Publication Nos. 2011/0271222, 2011/0273575, 2011/0275414 and 2011/0275416.

The GUI module may be configured to display any suitable information, including, but not limited to, data associated with the parameters, indications and/or approvals of one or more thermal waveforms. For example, the GUI module may be configured to display one or more prescribed thermal waveforms; the precise time/temperature parameters of the thermal waveform(s) delivered to a patient; the date/time of delivery of the thermal waveform(s) delivered to a patient; the temperature(s) of a patient's ear canal(s) at various time points before, during and/or after delivery of the thermal waveform(s); the temperature(s) of a patient's inner ear(s) at various time points before, during and/or after delivery of the thermal waveform(s); the fit of the earpiece(s) at various time points before, during and/or after delivery of the thermal waveform(s); an estimate of the thermal contact between the earpiece(s) and the patient's ear canal(s) at various time points before, during and/or after delivery of the thermal waveform(s); patient-specific time constants (e.g., a time constant associated with the transduction of heat from a patient's ear canal to the inner ear); reaction time (i.e., how long it took for a patient to react to one or more thermal waveforms); the effectiveness of one or more thermal waveforms (i.e., whether and to what extent symptoms were relieved, whether the thermal waveform(s) enhanced the effectiveness of another agent/therapy, etc.); the stability of a treatment (i.e., how long the effects of the treatment lasted); the instability of a treatment (i.e., which symptom(s) returned and when did it/they return); the presence or absence of comorbid disorders, injuries and/or diseases; disorder, injury and/or disease modulation(s) and/or modification(s) that occurred as a result of treatment; the cognitive effect(s) of one or more thermal waveforms; patient compliance (e.g., whether a patient initiated delivery at the prescribed time, whether a patient completed the prescribed treatment session, whether the earpiece(s) remained properly fitted in a patient's ear canal(s) for the duration of the treatment session, etc.); the mood of a patient at various time points before, during and/or after delivery of one or more thermal waveforms (e.g., videos/images of a patient that may be used to assess mood); objectives measures of efficacy (e.g., nystamography data, EEG data, MRI data, heart rate data, blood pressure data); subjective measures of efficacy (e.g., a patient-reported pain score); blood chemistry data (e.g., blood A1c levels, blood glucose levels and blood cortisol levels); saliva chemistry data (e.g., saliva cortisol levels); urine chemistry data (e.g., urine cortisol levels)), comments a patient made about his/her treatment session(s) (e.g., comments made to a physician, submitted in response to an automated survey and/or recorded in a treatment diary); the impedance between an earpiece inserted into the ear canal of a patient and an electrode affixed to a second location on/in said patient's body (e.g., an electrode placed in or adjacent to the patient's other ear canal); the rate at which a patient's inner ear cools in response to a cooling stimulus (e.g., data from a temperature sensor, such as thermistor, that monitors how quickly the inner ear cools in response to a cooling waveform); the rate at which a patient's inner ear warms in response to a warming stimulus (e.g., data from a temperature sensor, such as thermistor, that monitors how quickly the inner ear warms in response to a warming waveform); patient comments regarding the subjective fit of his/her earpiece(s); physician comments regarding the effectiveness of one or more thermal waveforms and/or physician comments regarding the effect(s) of one or more waveform modifications.

The GUI module may be configured to accept any suitable user input, including, but not limited to, instructions for transmitting the parameters, indications and/or approvals of a thermal waveforms to one or more vestibular stimulation devices, one or more patient control devices, one or more physician control devices and/or one or more physician support devices.

C. Alert Generation Module

In some embodiments, the registry comprises an alert generation module configured to generate one or more alert messages.

The alert generation module may be configured to generate any suitable alert message, including, but not limited to, an alert indicating that data has been received and an alert indicating that a request for data has been received.

In some embodiments, the alert generation module is configured to communicate with various devices/modules, including, but not limited to, a vestibular stimulation device, a patient control device, a physician control device, a physician support device, another registry, a portable memory device (e.g., an SD memory card) and other modules of the registry. For example, the alert generation module may be configured to provide instructions to the GUI module and/or the tone generation module for displaying one or more alert messages and/or for generation an audible tone to alert a user of the presence of the one or more alert messages. The graphical user interface module may be configured to display the one or more alert messages immediately upon generation or upon interaction with a user (e.g., an alert notification icon may be generated, with the alert message being displayed only after the user indicates that he/she wishes to view the message).

D. Tone Generation Module

In some embodiments, the registry comprises a tone generation module configured to produce audible tones. In some such embodiments, the tone generation module comprises a piezo buzzer. Audible tones may be produced to alert a user to various circumstances/events, including, but not limited to, the existence of an unread/unviewed alert message. Audible tones may be generated repeatedly in response to a single circumstance/event (e.g., an audible tone may be generated repeatedly until the user views/reads the message) and may become progressively louder and/or more frequent with time.

E. Visual Indicator Module

In some embodiments, the registry comprises a visual indicator module configured to notify a user of the existence of an unread/unviewed alert message. In some such embodiments, the visual indicator module comprises an LED indicator light. The visual indicator module may be activated repeatedly in response to a single alert message (e.g., an LED light may be illuminated repeatedly until the user views/reads the message) or may remain activated until the user views/reads the message.

F. Security Module

In some embodiments, the registry comprises a security module configured to prevent unauthorized use of the registry (i.e., to prevent unauthorized persons from using the registry, to prevent authorized persons from using the registry in an unauthorized manner, etc.).

The security module may be configured to prevent unauthorized use of the registry using any suitable means of security, including, but not limited to, password protection and data encryption. For example, the security module may be configured such that a user is required to input a designated password prior to accessing the waveform database; entering/viewing patient feedback data; entering/viewing physician feedback data and/or entering/viewing patient information (as discussed above with respect to FIG. 12).

As will be appreciated by one of skill in the art, the registry may comprise any suitable data, including, but not limited to, static and/or dynamic data used by the operating system, applications, I/O device drivers and other software components, controller feedback data, data associated with the parameters, indications and/or approvals of one or more thermal waveforms (e.g., idealized thermal waveforms), data associated with one or more prescriptions, data associated with the delivery of one or more thermal waveforms, data associated with the fit of one or more earpieces, patient feedback data, physician feedback data and patient information. For example, the registry may comprise a waveform database comprising data associated with one or more idealized thermal waveforms; a prescription database comprising data associated with one or more prescriptions; a feedback database comprising controller feedback data, data associated with the delivery of one or more thermal waveforms to the vestibular system and/or the nervous system of a patient, patient feedback data and physician feedback data and/or a patient history database comprising data associated with one or more patients. In some embodiments, two or more of the aforementioned databases are combined to form a single database comprising data from each of the individual databases (e.g., the registry may comprise a feedback-history database comprising data associated with the delivery of one or more thermal waveforms and patient information). In some embodiments, one of the aforementioned databases is split into two or more distinct databases (e.g., the registry may comprise a delivery feedback database comprising data associated with the specific parameters of the thermal waveform(s) delivered to a patient, a patient feedback database comprising patient feedback data and a physician feedback database comprising physician feedback data). In some embodiments, one or more of the data types described below with respect to one of the databases described below is stored in one of the other databases described below (e.g., the patient information database, rather than the feedback database, may be configured to receive/store patient feedback data). In some embodiments, data is transmitted, received and/or stored in a controlled format (e.g., in a standardized format using forms/programs supplied by a physician support device or a registry). The registry may be configured to transmit, receive and store data in a manner that ensures compliance with any and all applicable laws and/or regulations (e.g., the Health Insurance Portability and Accountability Act of 1996 (P.L. 104-191; "HIPAA")).

Waveform Database

In some embodiments, the registry comprises a waveform database configured to receive, store and/or transmit data associated with the parameters, indications and/or approvals of one or more thermal waveforms (e.g, one or more idealized thermal waveforms). In some such embodiments, the waveform database is configured such that one or more of the thermal waveforms stored therein is/are protected (e.g., users may be prevented from modifying and/or deleting the idealized thermal waveform(s) stored in the waveform database).

The waveform database may comprise any suitable type of memory including, but not limited to, cache, ROM, PROM, EPROM, EEPROM, flash memory, SRAM and DRAM. In some embodiments, the waveform database comprises a portable memory device, such as an SD memory card or a USB memory stick. For example, the waveform database may comprise an SD memory card interface and one or more prescriptions may be stored on a portable SD memory card.

The waveform database may be configured to receive and/or transmit data from/to any suitable device/module/database, including, but not limited to, modules residing in the registry, a vestibular stimulation device, a patient control device, a physician control device, a physician support device, another registry and a portable memory device (e.g., an SD memory card).

In some embodiments, the registry is configured to receive, store and/or transmit data associated with the parameters, indications and/or approvals of one or more thermal waveforms (e.g, one or more idealized thermal waveforms) from/to one or more devices located within a specified geographical region. For example, the waveform database may be configured to receive, store and/or transmit data associated with the parameters, indications and/or approvals of one or more idealized, actively controlled, time-varying thermal waveforms from/to one or more physician control devices and/or one or more physician support devices located within a specified geographical region (e.g., the northeastern United States, the southeastern United States, the United States, North America, Europe, Japan, China, etc.).

The waveform database may be configured to receive and/or transmit data over any suitable wired or wireless communications channel, including, but not limited to, a LAN, the Internet, a public telephone switching network, Bluetooth, WLAN and the like.

B. Prescription Database

In some embodiments, the registry comprises a prescription database configured to receive, transmit and/or store one or more prescriptions, wherein each prescription comprising a set of instructions for delivering one or more thermal waveforms to the vestibular system and/or the nervous system of a patient.

The prescription database may comprise any suitable type of memory including, but not limited to, cache, ROM, PROM, EPROM, EEPROM, flash memory, SRAM and DRAM. In some embodiments, the prescription database comprises a portable memory device, such as an SD memory card or a USB memory stick. For example, the prescription database may comprise an SD memory card interface and one or more prescriptions may be stored on a portable SD memory card.

The prescription database may be configured to receive and/or transmit data from/to any suitable device/module/database, including, but not limited to, modules residing in the registry, a vestibular stimulation device, a patient control device, a physician control device, a physician support device, another registry and a portable memory device (e.g., an SD memory card).

In some embodiments, the registry is configured to receive, store and/or transmit data associated with one or more prescriptions from/to one or more devices located within a specified geographical region. For example, the prescription database may be configured to receive, store and/or transmit data associated with one or more prescriptions from/to one or more physician control devices and/or one or more physician support devices located within a specified geographical region (e.g., the northeastern United States, the southeastern United States, the United States, North America, Europe, Japan, China, etc.).

The prescription database may be configured to receive and/or transmit data over any suitable wired or wireless communications channel, including, but not limited to, a LAN, the Internet, a public telephone switching network, Bluetooth, WLAN and the like.

C. Feedback Database

In some embodiments, the registry comprises a feedback database configured to receive, transmit and/or store feedback data.

The feedback database may comprise any suitable type of memory including, but not limited to, cache, ROM, PROM, EPROM, EEPROM, flash memory, SRAM and DRAM. In some embodiments, the feedback database comprises a portable memory device, such as an SD memory card or a USB memory stick. For example, the feedback database may comprise an SD memory card interface and one or more prescriptions may be stored on a portable SD memory card.

The feedback database may be configured to receive and/or transmit feedback data from/to any suitable device/module/database, including, but not limited to, modules residing in the physician support device, a vestibular stimulation device, a patient control device, a physician control device, a physician support device, another registry and a portable memory device (e.g., an SD memory card).

In some embodiments, the registry is configured to receive, store and/or transmit feedback data from/to one or more devices located within a specified geographical region. For example, the feedback database may be configured to receive, store and/or transmit feedback from/to one or more physician control devices and/or one or more physician support devices located within a specified geographical region (e.g., the northeastern United States, the southeastern United States, the United States, North America, Europe, Japan, China, etc.).

The feedback database may be configured to receive and/or transmit data over any suitable wired or wireless communications channel, including, but not limited to, a LAN, the Internet, a public telephone switching network, Bluetooth, WLAN and the like.

Feedback data may comprise any suitable data, including, but not limited to, controller feedback data, data associated with the delivery of one or more thermal waveforms, data associated with the fit of one or more earpieces, patient feedback data, physician feedback data and/or patient information. For example, the feedback database may comprise a log file detailing the target time/temperature parameters of one or more prescribed thermal waveform(s); the time/temperature parameters of the thermal waveform(s) delivered to a patient; the date/time of delivery of the thermal waveform(s) delivered to a patient; the temperature(s) of a patient's ear canal(s) at various time points before, during and/or after delivery of one or more thermal waveforms; the temperature(s) of a patient's inner ear(s) at various time points before, during and/or after delivery of one or more thermal waveforms; the fit of one or more earpieces at various time points before, during and/or after delivery of one or more thermal waveforms; an estimate of the thermal contact between one or more earpieces and a patient's ear canal(s) at various time points before, during and/or after delivery of one or more thermal waveforms; patient-specific time constants (e.g., a time constant associated with the transduction of heat from a patient's ear canal to the inner ear); a patient's reaction time (i.e., how long it took for a patient to react to one or more thermal waveforms); effectiveness of one or more thermal waveforms (i.e., whether and to what extent symptoms were relieved, whether the thermal waveform(s) enhanced the effectiveness of another agent/therapy, etc.); stability of a treatment (i.e., how long the effects of a treatment lasted); instability of a treatment (i.e., which symptom(s) returned and when did it/they return); the presence or absence of comorbid disorders, injuries and/or diseases; disorder, injury and/or disease modulation(s) and/or modification(s) that occurred as a result of treatment; the cognitive effect(s) of one or more thermal waveforms; patient compliance (e.g., whether a patient initiated delivery at the prescribed time, whether a patient completed the prescribed treatment session, whether the earpiece(s) remained properly fitted in a patient's ear canal(s) for the duration of the treatment session, etc.); the mood of a patient at various time points before, during and/or after delivery of one or more thermal waveforms (e.g., videos/images of a patient that may be used to assess mood); objectives measures of efficacy (e.g., nystamography data, EEG data, MRI data, heart rate data, blood pressure data); subjective measures of efficacy (e.g., a patient-reported pain score); blood chemistry data (e.g., blood A1c levels, blood glucose levels and blood cortisol levels); saliva chemistry data (e.g., saliva cortisol levels); urine chemistry data (e.g., urine cortisol levels)); comments a patient made about his/her treatment session(s) (e.g., comments made to a physician, submitted in response to an automated survey and/or recorded in a treatment diary); the impedance between an earpiece inserted into the ear canal of a patient and an electrode affixed to a second location on/in said patient's body (e.g., an electrode placed in or adjacent to the patient's other ear canal); the rate at which an earpiece is cooled in response to a cooling stimulus (e.g., data from a temperature sensor, such as thermistor, that monitors how quickly the earpiece cools in response to a cooling waveform); the rate at which an earpiece is warmed in response to a warming stimulus (e.g., data from a temperature sensor, such as a thermistor, that monitors how quickly the earpiece warms in response to a warming waveform); the rate at which a patient's ear canal and/or inner ear cooled in response to a cooling stimulus (e.g., data from a temperature sensor, such as thermistor, that monitors how quickly the ear canal and/or the inner ear cools in response to a cooling waveform); the rate at which a patient's ear canal and/or inner ear warmed in response to a warming stimulus (e.g., data from a temperature sensor, such as a thermistor, that monitors how quickly the ear canal and/or the inner ear warms in response to a warming waveform); patient comments regarding the subjective fit of one or more earpieces; physician comments regarding the effectiveness of one or more thermal waveforms and/or physician comments regarding the effect(s) of one or more waveform modifications.

D. Patient History Database

In some embodiments, the registry comprises a patient history database configured to receive, transmit and/or store patient information.

The patient history database may comprise any suitable type of memory including, but not limited to, cache, ROM, PROM, EPROM, EEPROM, flash memory, SRAM and DRAM. In some embodiments, the patient history database comprises a portable memory device, such as an SD memory card or a USB memory stick. For example, the patient history database may comprise an SD memory card interface and one or more prescriptions may be stored on a portable SD memory card.

The patient history database may be configured to receive and/or transmit data from/to any suitable device/module/database, including, but not limited to, modules residing in the registry, a vestibular stimulation device, a patient control device, a physician control device, a physician support device, another registry and a portable memory device (e.g., an SD memory card).

In some embodiments, the registry is configured to receive, store and/or transmit patient information from/to one or more devices located within a specified geographical region. For example, the patient history database may be configured to receive, store and/or transmit patient information from/to one or more physician control devices and/or one or more physician support devices located within a specified geographical region (e.g., the northeastern United States, the southeastern United States, the United States, North America, Europe, Japan, China, etc.).

The patient history database may be configured to receive and/or transmit data over any suitable wired or wireless communications channel, including, but not limited to, a LAN, the Internet, a public telephone switching network, Bluetooth, WLAN and the like.

Patient information may comprise any suitable information that is associated with a patient, including, but not limited to, the patient's medical history, the patient's current symptoms (if any), the patient's present diagnosis (if any), the patient's current prescriptions (if any) and data associated with the delivery of one or more thermal waveforms to the vestibular system and/or the nervous system of the patient.

As will be appreciated by one of skill in the art, the registry may comprise any I/O device drivers, including, but not limited to, software routines accessed through the operating system by the applications to communicate with devices such as I/O ports, memory components, vestibular stimulation devices, patient control devices, physician control devices and/or physician support devices.

As will be appreciated by one of skill in the art, the registry may be configured (e.g., with computer instructions (i.e., software)) to operate in a plurality of distinct modes. In each mode, the registry may be configured to permit access to some functionalities/modules and to prevent access to other functionalities/modules. For example, the registry may be configured to operate in a researcher mode, wherein the user is allowed to perform researcher-oriented tasks, such as uploading and/or downloading data associated with the parameters, indication and/or approvals of one or more idealized thermal waveforms, but is prevented from accessing other functionalities/modules (e.g., the user may be prevented from modifying the underlying operational parameters of the registry). Similarly, the registry may be configured to operate in an engineer mode, wherein the user is allowed to access all of the registry's functionalities/modules. Each mode may be protected via a unique security measure (e.g., the registry may be configured such that each mode is protected by a unique password).

Figure 31:
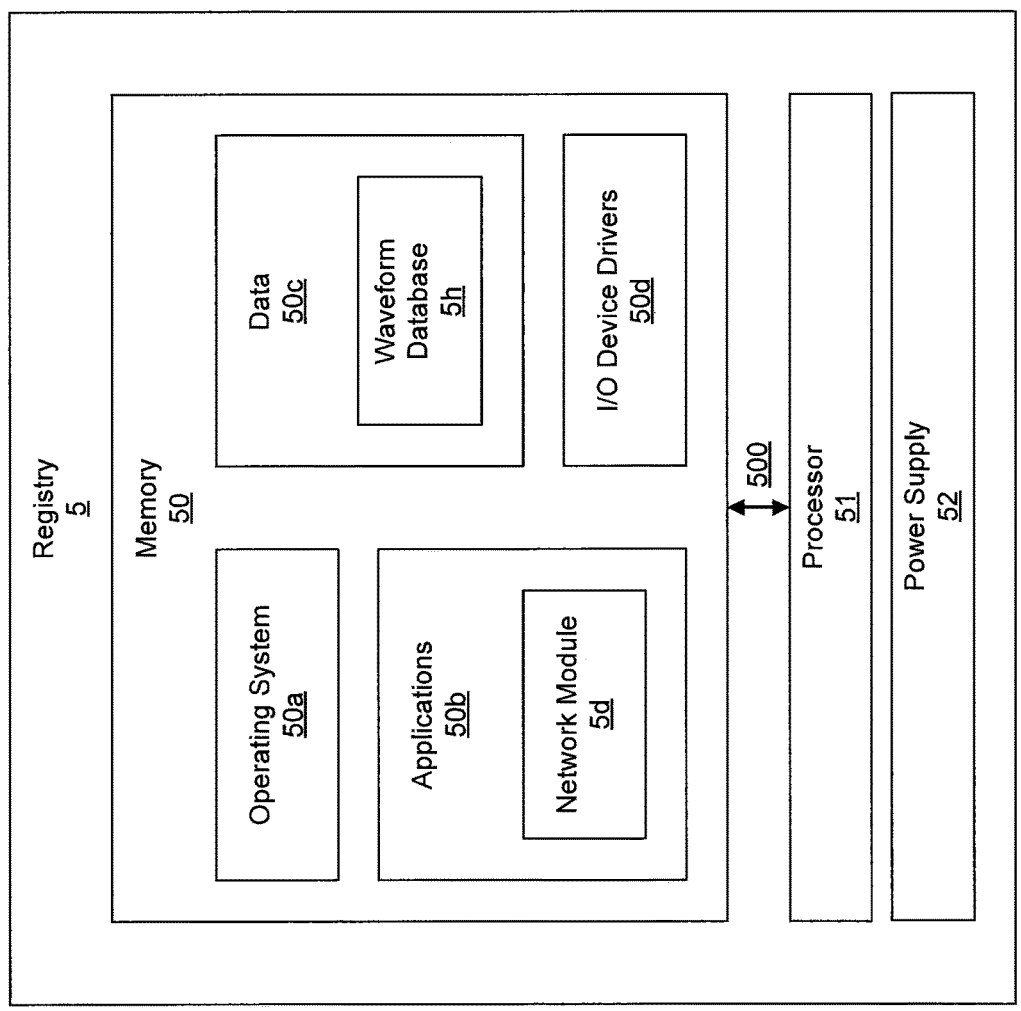
FIG. 31 is a block diagram of a registry according to some embodiments of the present invention.
Figure 32:
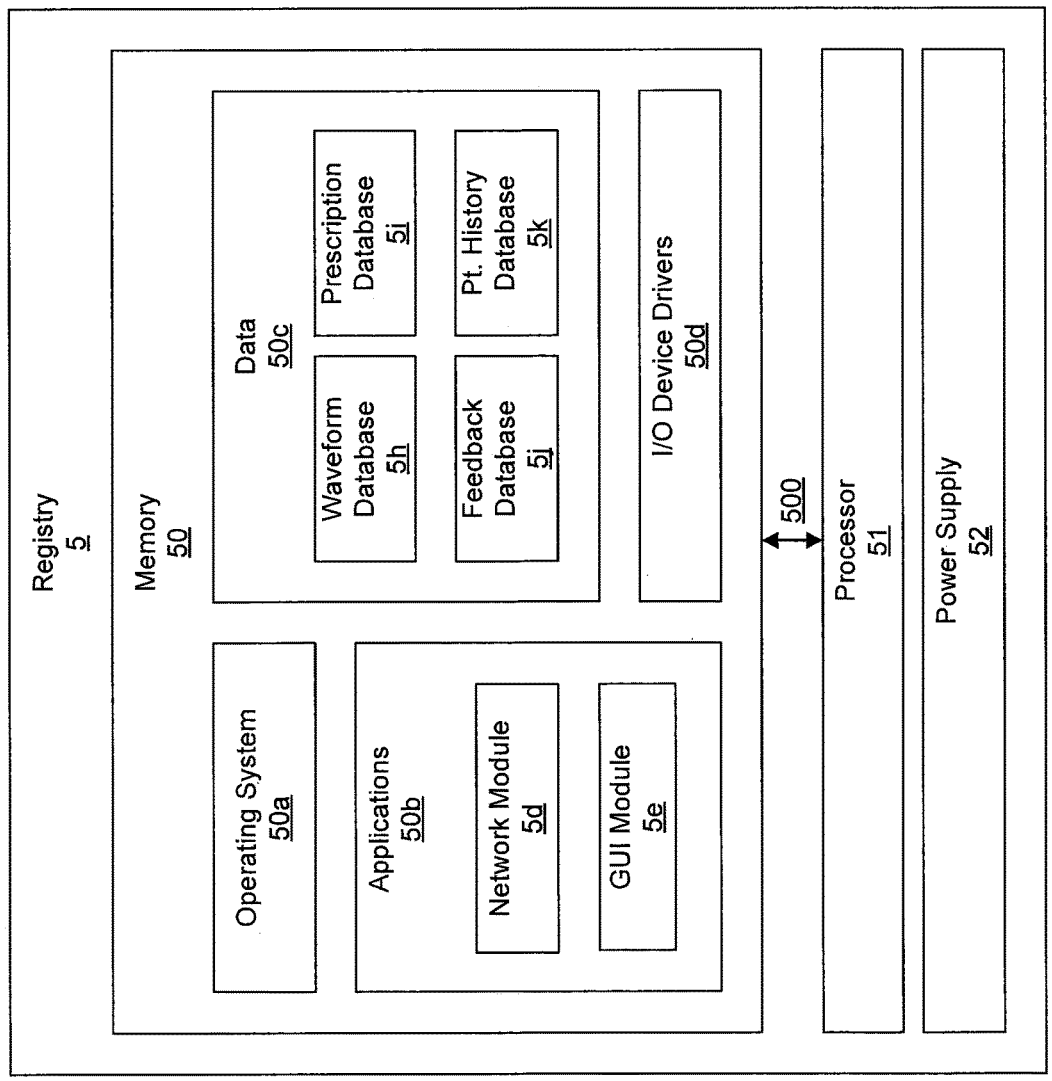
FIG. 32 is a block diagram of a registry according to some embodiments of the present invention.

As shown in FIGS. 31-32, in some embodiments of the present invention, the registry 5 comprises memory 50, a processor 51 and a power supply 52 (e.g., an internal power supply), wherein memory 50 is representative of the overall hierarchy of memory devices containing software and data used to implement the functionality of the registry 5 and wherein the processor 51 communicates with the memory 50 via an address/data bus 500. In particular embodiments, memory 50 comprises an operating system 50a, applications 50b (e.g., a network module 5d configured to receive and/or transmit data and/or a GUI module 5e configured to display information and/or accept user input), data 50c (e.g., a waveform database 5h comprising data associated with the parameters, indications and/or approvals of one or more thermal waveforms; a prescription database 5i comprising at least one prescription comprising a set of instructions for delivering one or more thermal waveforms to the vestibular system and/or the nervous system of a patient; a feedback database 5j comprising data associated with the delivery of one or more thermal waveforms and/or a patient history database 5k comprising patient information) and I/O drivers 50d. In some such embodiments, data 50c comprises one or more databases stored on a portable memory device. For example, data 50c may comprise an SD memory card interface and a portable SD memory card comprising a waveform database 5h, a prescription database 5i, a feedback database 5j and/or a patient history database 5k.

In some embodiments, the network module 5d is configured to receive data associated with the parameters, indications and/or approvals of one or more thermal waveforms from a vestibular stimulation device, a patient control device, a physician control device, a physician support device, another registry and/or a portable memory device (e.g., an SD memory card) and to transmit the data to the waveform database 5h for storage. For example, the network module 5d may be configured to receive data associated with the parameters, indications and/or approvals of one or more idealized, actively controlled, time-varying thermal waveforms from one or more physician control devices and/or one or more physician support devices located in a specified geographical region (e.g., the northeastern United States, the southeastern United States, the United States, North America, Europe, Japan, China, etc.).

In some embodiments, the network module 5d is configured to retrieve data associated with the parameters, indications and/or approvals of one or more thermal waveforms from the waveform database 5h and to transmit the data to a vestibular stimulation device, a patient control device, a physician control device, a physician support device, another registry and/or a portable memory device (e.g., an SD memory card). For example, the network module 5d may be configured to transmit data associated with the parameters, indications and/or approvals of one or more thermal waveforms from the waveform database 5h to one or more physician control devices and/or one or more physician support devices located in a specified geographical region (e.g., the northeastern United States, the southeastern United States, the United States, North America, Europe, Japan, China, etc.). In some such embodiments, the physician support device is configured to transmit all of the idealized thermal waveforms in the waveform database or a subset thereof (e.g., waveforms indicated for use in the treatment of migraines) to one or more physician control devices and/or one or more physician support devices upon request (e.g., after receiving an update request from a physician support device) or at a specified interval (e.g., every two weeks).

In some embodiments, the registry is configured to replace the idealized thermal waveforms in a physician support device's waveform database with the idealized thermal waveforms from the registry's waveform database. For example, the network module 5d may be configured to update the waveform database(s) of one or more physician control devices and/or one or more physician support devices located in a specified geographical region (e.g., the northeastern United States, the southeastern United States, the United States, North America, Europe, Japan, China, etc.) by replacing the idealized thermal waveforms located therein with idealized thermal waveforms from the registry's waveform database.

In some embodiments, the network module 5d is configured to receive one or more prescriptions from a vestibular stimulation device, a patient control device, a physician control device, a physician support device, another registry and/or a portable memory device (e.g., an SD memory card) and to transmit the prescription(s) to the prescription database 5i for storage. For example, the network module 5d may be configured to receive data associated with one or more prescriptions from one or more physician control devices and/or one or more physician support devices located in a specified geographical region (e.g., the northeastern United States, the southeastern United States, the United States, North America, Europe, Japan, China, etc.).

In some embodiments, the network module 5d is configured to retrieve one or more prescriptions from the prescription database 5i and to transmit the prescription(s) to a vestibular stimulation device, a patient control device, a physician control device, a physician support device, another registry and/or a portable memory device (e.g., an SD memory card). For example, the network module 5d may be configured to transmit data associated with one or more prescriptions from the prescription database 5i to one or more physician control devices and/or one or more physician support devices located in a specified geographical region (e.g., the northeastern United States, the southeastern United States, the United States, North America, Europe, Japan, China, etc.).

In some embodiments, the network module 5d is configured to receive data associated with the delivery of one or more thermal waveforms, data associated with the fit of one or more earpieces, patient feedback data and/or physician feedback data from a vestibular stimulation device, a patient control device, a physician control device, a physician support device, another registry and/or a portable memory device (e.g., an SD memory card) and to transmit that data to the feedback database 5j for storage. For example, the network module 5d may be configured to receive data associated with the delivery of one or more thermal waveforms, data associated with the fit of one or more earpieces, patient feedback data and/or physician feedback data from one or more physician control devices and/or one or more physician support devices located in a specified geographical region (e.g., the northeastern United States, the southeastern United States, the United States, North America, Europe, Japan, China, etc.).

In some embodiments, the network module 5d is configured to retrieve data associated with the delivery of one or more thermal waveforms, data associated with the fit of one or more earpieces, patient feedback data and/or physician feedback data from the feedback database 5j and to transmit the data to a vestibular stimulation device, a patient control device, a physician control device, a physician support device, another registry and/or a portable memory device (e.g., an SD memory card). For example, the network module 5d may be configured to transmit data associated with the delivery of one or more thermal waveforms, data associated with the fit of one or more earpieces, patient feedback data and/or physician feedback data from the feedback database 5j to one or more physician control devices and/or one or more physician support devices located in a specified geographical region (e.g., the northeastern United States, the southeastern United States, the United States, North America, Europe, Japan, China, etc.).

In some embodiments, the network module 5d is configured to receive patient information from a vestibular stimulation device, a patient control device, a physician control device, a physician support device, another registry and/or a portable memory device (e.g., an SD memory card) and to transmit that data to the patient history database 5k for storage. For example, the network module 5d may be configured to receive patient information from one or more physician control devices and/or one or more physician support devices located in a specified geographical region (e.g., the northeastern United States, the southeastern United States, the United States, North America, Europe, Japan, China, etc.).

In some embodiments, the network module 5d is configured to retrieve patient information from the patient history database 5k and to transmit the patient information to a vestibular stimulation device, a patient control device, a physician control device, a physician support device, another registry and/or a portable memory device (e.g., an SD memory card). For example, the network module 5d may be configured to transmit patient information from the patient history database 5k to one or more physician control devices and/or one or more physician support devices located in a specified geographical region (e.g., the northeastern United States, the southeastern United States, the United States, North America, Europe, Japan, China, etc.).

Telemedicine Module

As noted above, the present invention provides a telemedicine module for facilitating and/or controlling communications between vestibular stimulation devices, patient control devices, physician control devices, physician support devices and/or registries.

In some embodiments, the telemedicine module is configured to facilitate and/or control communications between a vestibular stimulation device, a patient control device, a physician control device, a physician support device and/or a registry by ensuring that data is transmitted between the devices in a manner that complies with any and all applicable laws and/or regulations (e.g., the Health Insurance Portability and Accountability Act of 1996 (P.L. 104-191; "HIPAA")).

The telemedicine module may facilitate and/or control communications sent over any suitable wired or wireless communications channel, including, but not limited to, a LAN, the Internet, a public telephone switching network, Bluetooth, WLAN and the like.

Vestibular Stimulation System

As noted above, the present invention provides a vestibular stimulation system for delivering one or more thermal waveforms (e.g., one or more actively controlled, time-varying thermal waveforms) to the vestibular system and/or the nervous system of a patient.

The vestibular stimulation system may comprise, consist essentially of or consist of a vestibular stimulation device and a physician control device (as shown in FIGS. 33, 35-36, 38-39, 41-42 and 44). In some embodiments, the vestibular stimulation system comprises, consists essentially of or consists of a physician control device and a plurality of vestibular stimulation devices (as shown in FIGS. 34, 37 and 40). In some embodiments, the vestibular stimulation system comprises a plurality of physician control devices and a plurality of vestibular stimulation devices 1 (as shown in FIGS. 40 and 43). Any suitable vestibular stimulation device(s) and physician control device(s) may be used, including, but not limited to, those described above.

Figure 36:
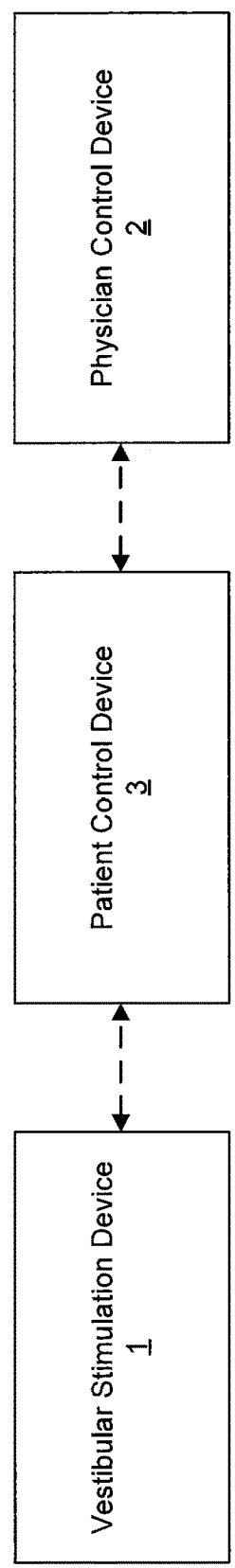
FIG. 36 is a block diagram of a vestibular stimulation system according to some embodiments of the present invention comprising a vestibular stimulation device, a patient control device and a physician control device.
Figure 37:
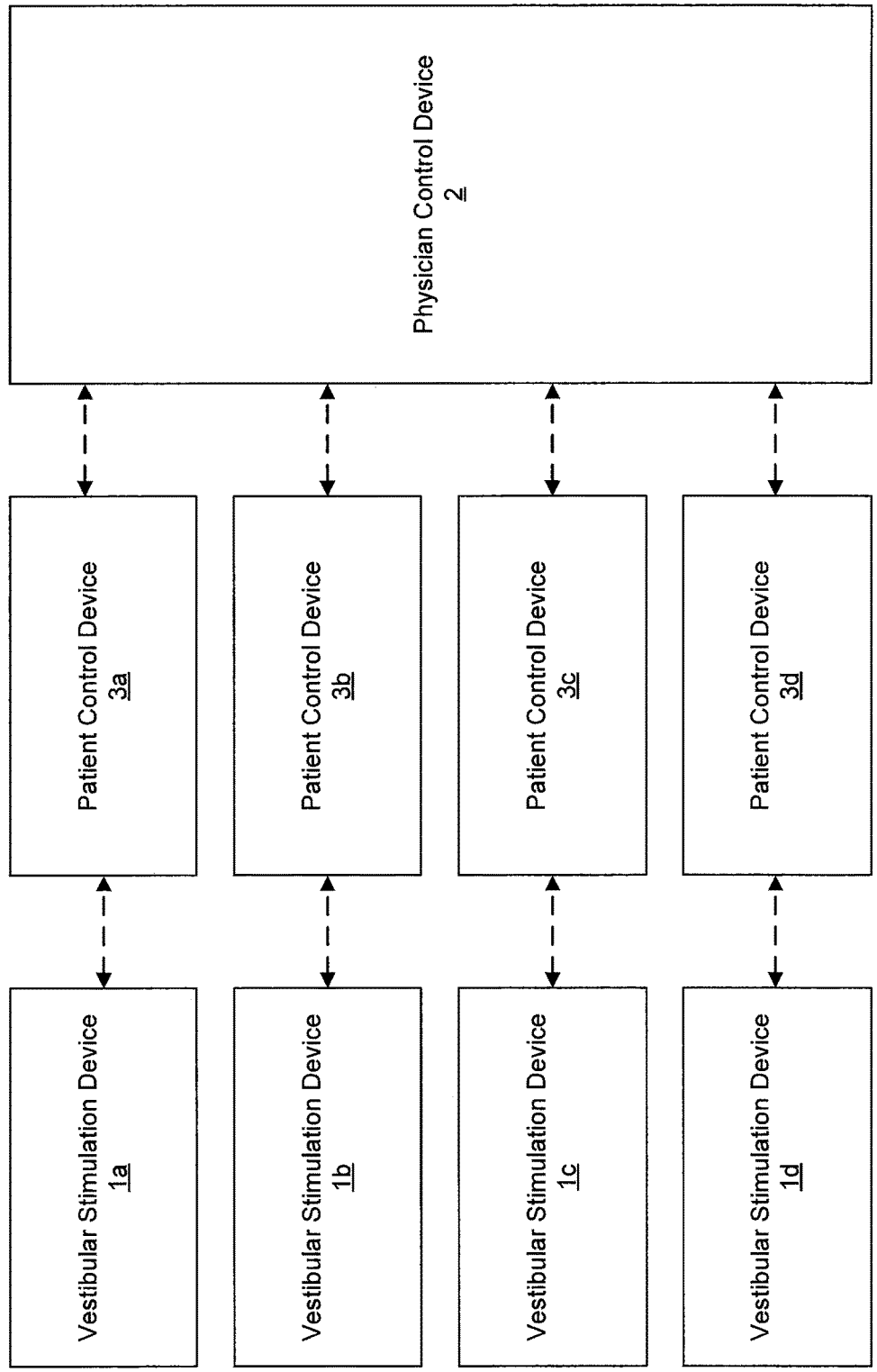
FIG. 37 is a block diagram of a vestibular stimulation system according to some embodiments of the present invention comprising a physician control device, a plurality of patient control devices and a plurality of vestibular stimulation devices.
Figure 38:
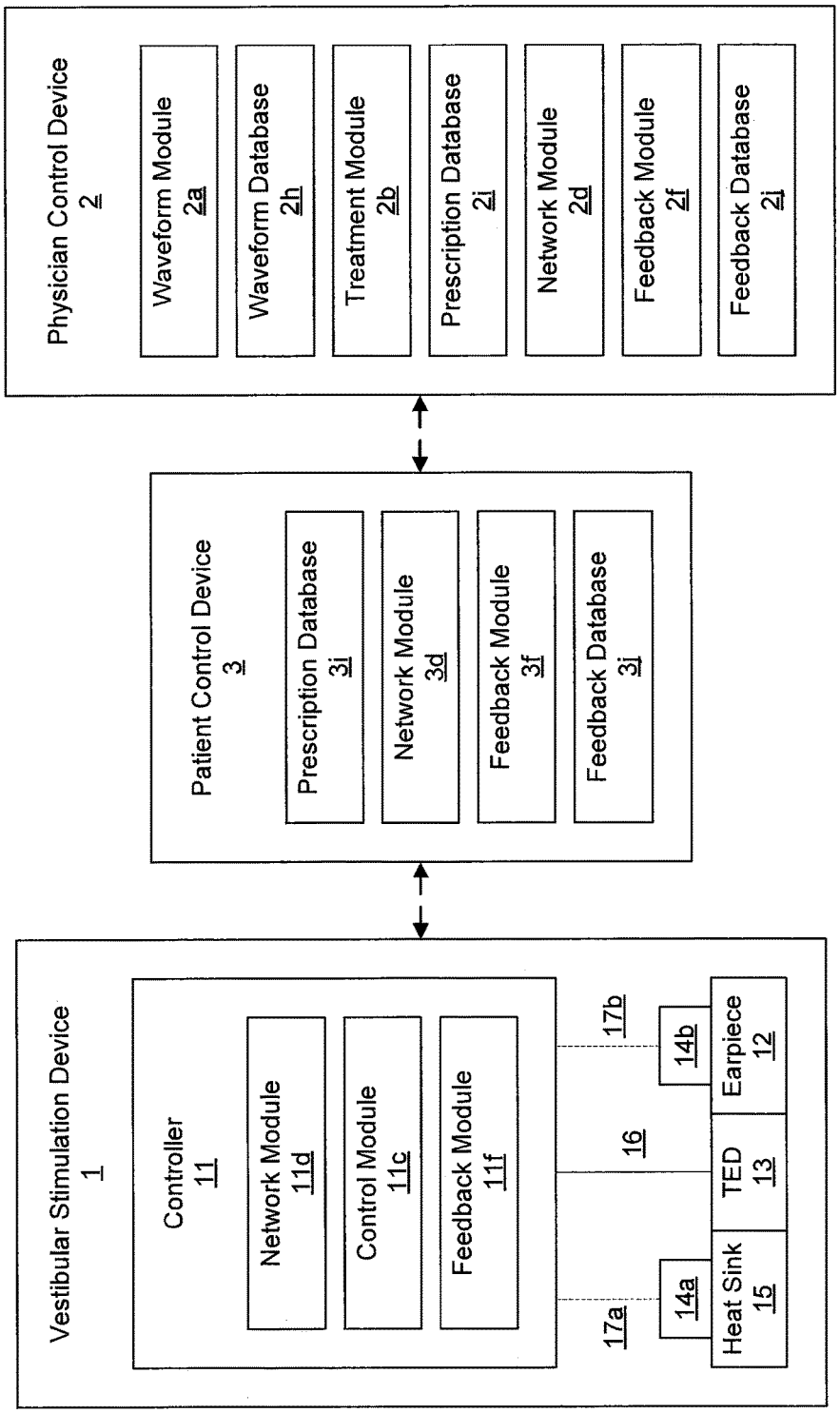
FIG. 38 is a block diagram of a vestibular stimulation system according to some embodiments of the present invention comprising a vestibular stimulation device, a patient control device and a physician control device.

The vestibular stimulation system may further comprise a patient control device (as shown in FIGS. 36 and 38). In some embodiments, the vestibular stimulation system comprises a plurality of patient control devices (as shown in FIG. 37). Any suitable patient control device(s) may be used, including, but not limited to, those described above.

The vestibular stimulation system may further comprise a physician support device (as shown in FIGS. 39-42). In some embodiments, the vestibular stimulation system comprises a plurality of physician support devices. Any suitable physician support device(s) may be used, including, but not limited to, those described above.

Figure 42:
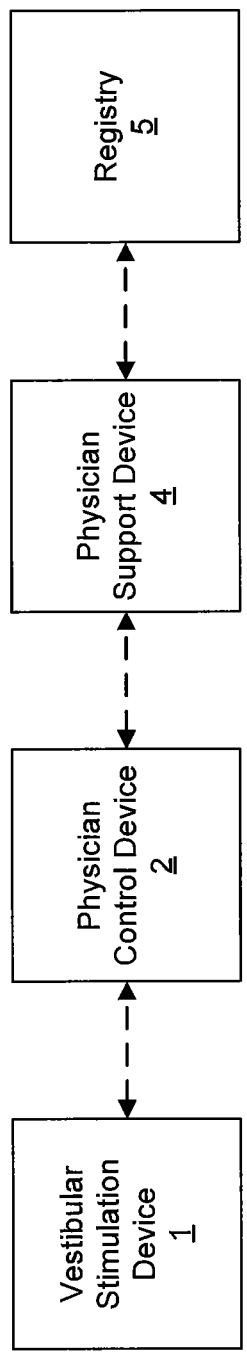
FIG. 42 is a block diagram of a vestibular stimulation system according to some embodiments of the present invention comprising a vestibular stimulation device, a physician control device, a physician support device and a registry.
Figure 43:
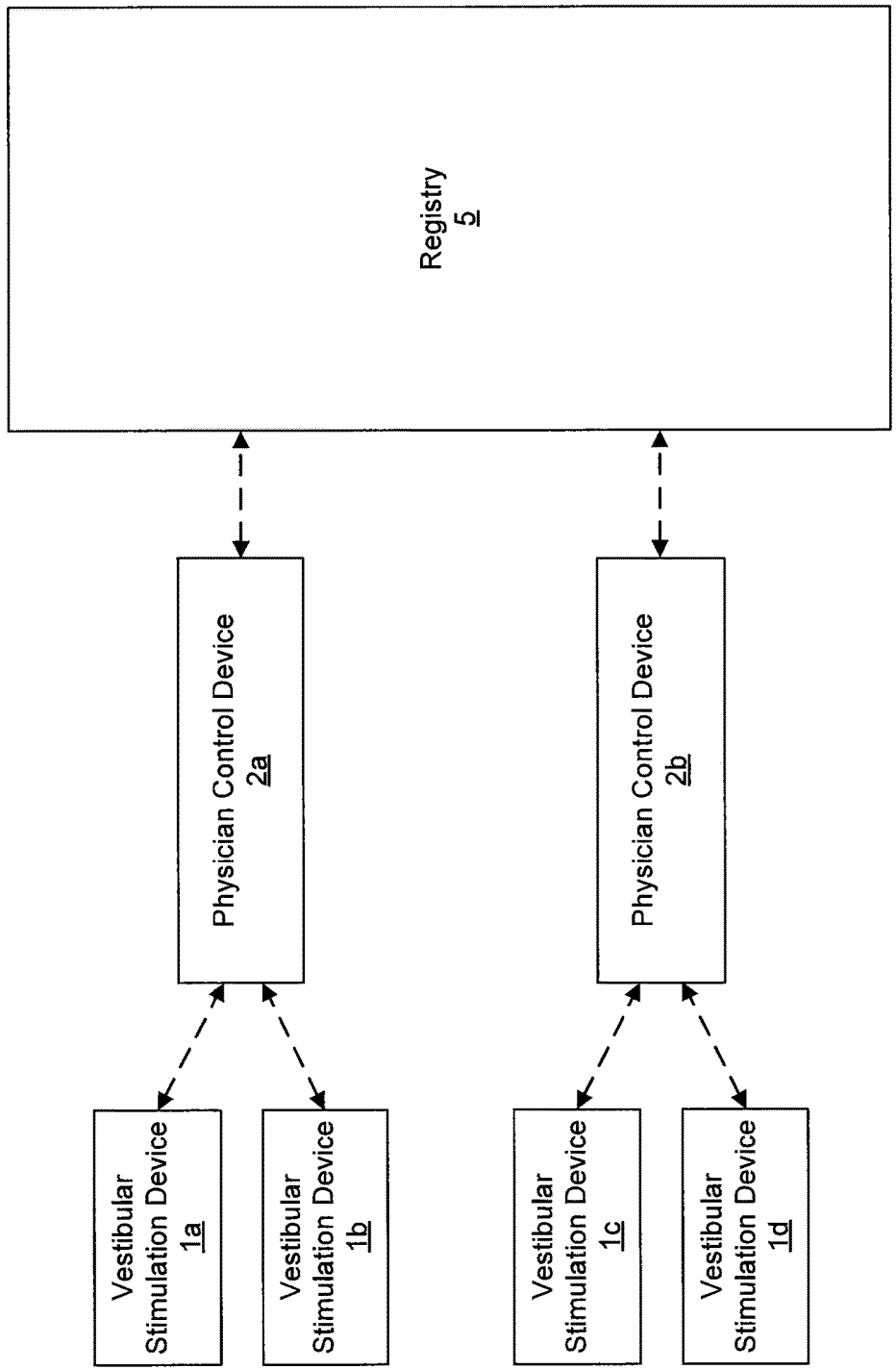
FIG. 43 is a block diagram of a vestibular stimulation system according to some embodiments of the present invention comprising a registry, a plurality of physician control devices and a plurality of vestibular stimulation devices.
Figure 44:
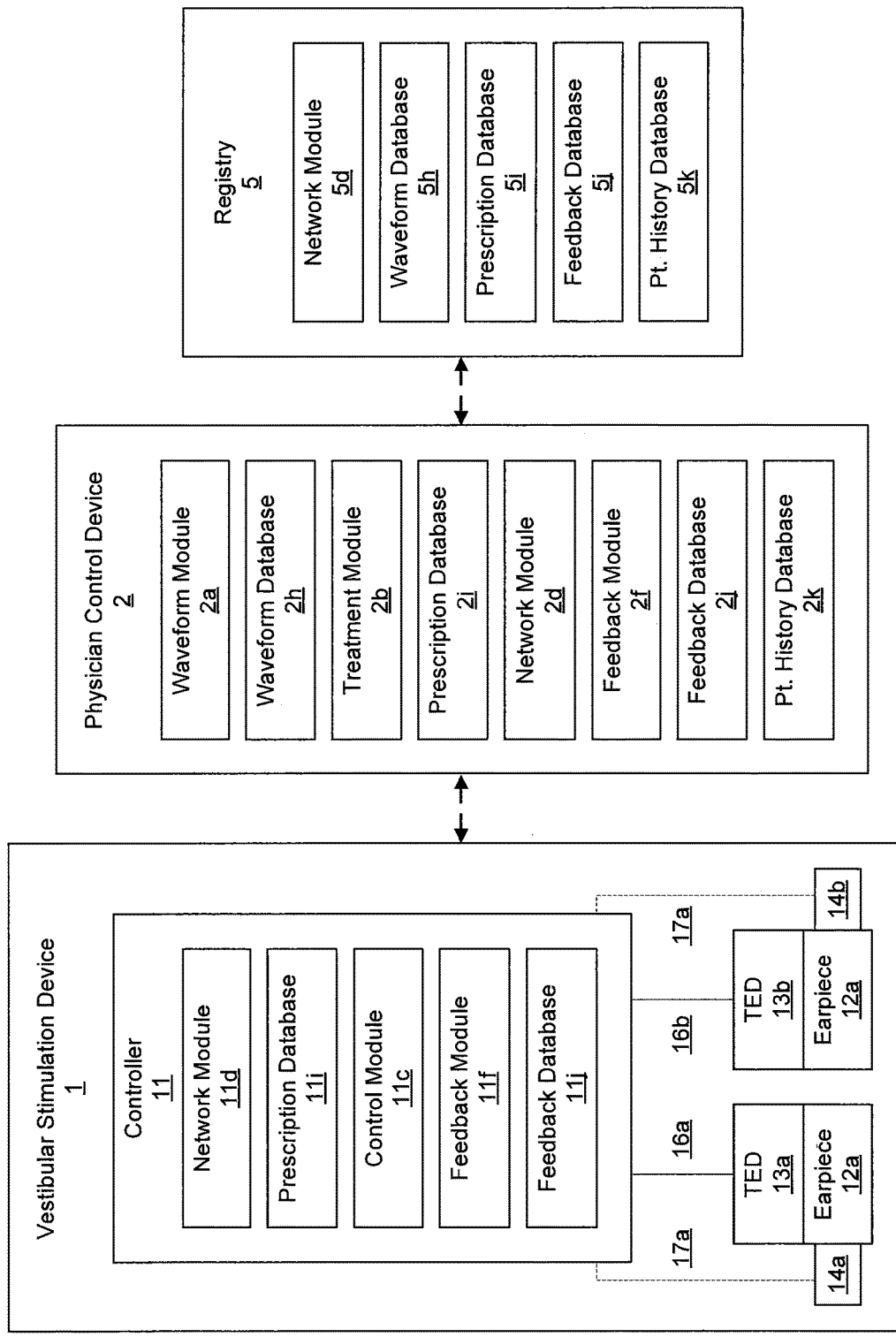
FIG. 44 is a block diagram of a vestibular stimulation system according to some embodiments of the present invention comprising a vestibular stimulation device, a physician control device and a registry.

The vestibular stimulation system may further comprise a registry (as shown in FIGS. 42-44). In some embodiments, the vestibular stimulation system comprises a plurality of registries. Any suitable registry (or registries) may be used, including, but not limited to, those described above.

Figure 33:
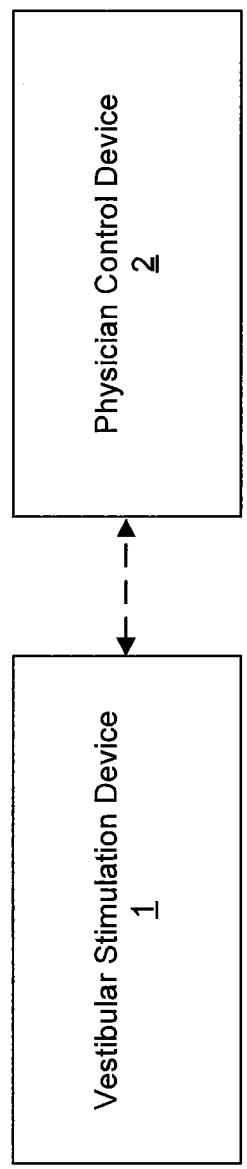
FIG. 33 is a block diagram of a vestibular stimulation system according to some embodiments of the present invention comprising a vestibular stimulation device and a physician control device.
Figure 34:
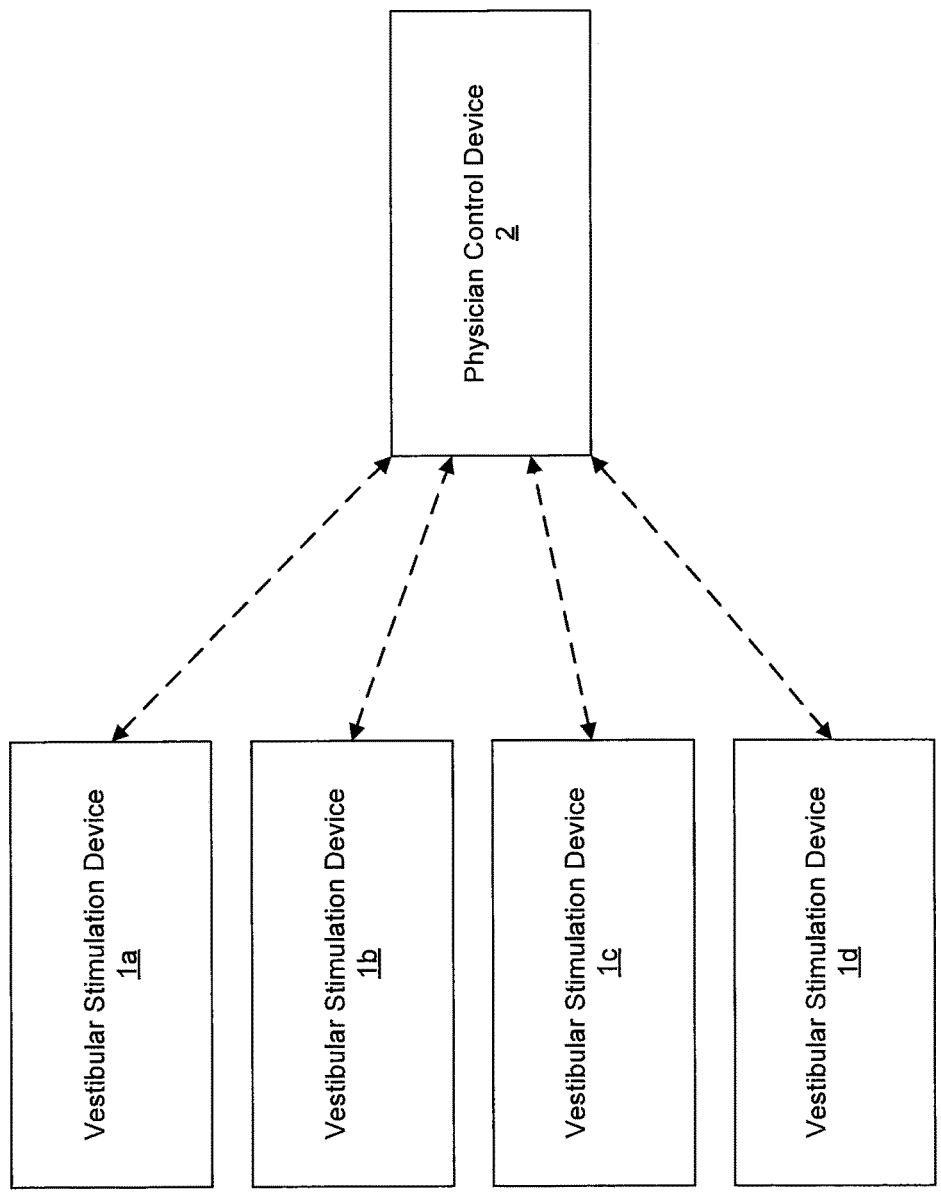
FIG. 34 is a block diagram of a vestibular stimulation system according to some embodiments of the present invention comprising a physician control device and a plurality of vestibular stimulation devices.

As shown in FIG. 33, the vestibular stimulation system may comprise, consist essentially of or consist of a vestibular stimulation device 1 operatively connected to a physician control device 2.

The physician control device 2 may be configured to generate one or more thermal waveforms (i.e., to generate the parameters, indications and/or approvals of one or more thermal waveforms) and/or to store the thermal waveform(s) in a database (e.g., to store the parameters, indications and/or approvals of the thermal waveform(s) in a waveform database as described above).

The physician control device 2 may be configured to generate one or more prescriptions. Each prescription may comprise, consist essentially of or consist of a set of instructions for delivering one or more thermal waveforms to the vestibular system and/or the nervous system of a patient. In such embodiments, the prescription may comprise a set of instructions for delivering one or more of the thermal waveforms generated by the physician control device 2 to the vestibular system and/or the nervous system of a patient.

The physician control device 2 may be configured to store one or more prescriptions in a database residing therein (e.g., a prescription database as described above) and/or to relay one or more prescriptions to the vestibular stimulation device 1. The physician control device 2 may be configured to transmit one or more prescriptions to the vestibular stimulation device 1 over any suitable wired or wireless communications channel, including, but not limited to, a LAN, the Internet, a public telephone switching network, Bluetooth, WLAN and the like. Likewise, the vestibular stimulation device 1 may be configured to access a prescription database residing in the physician control device 2 and to retrieve one or more prescriptions using any suitable wired or wireless communications channel, including, but not limited to, a LAN, the Internet, a public telephone switching network, Bluetooth, WLAN and the like. Alternatively, one or more prescriptions may be transferred to the vestibular stimulation device 1 using a portable memory device, such as an SD memory card or a USB memory stick.

The vestibular stimulation device 1 may be configured to deliver one or more prescribed thermal waveforms to the vestibular system and/or the nervous system of a patient. For example, as described above, the vestibular stimulation device 1 may be configured to deliver the prescribed thermal waveform(s) the vestibular system and/or the nervous system of the patient by activating one or more TEDs to warm and/or cool an earpiece inserted into an ear canal of the patient.

The vestibular stimulation device 1 may be configured to generate feedback data. For example, the vestibular stimulation device 1 may comprise one or more sensors as described above, which may generate feedback data responsive to delivering the prescribed thermal waveform(s) to the vestibular system and/or the nervous system of the patient. Similarly, the vestibular stimulation device 1 may comprise a GUI configured generate feedback data (e.g., patient feedback data) responsive to user input.

The vestibular stimulation device 1 may be configured to store feedback data in a database residing therein (e.g., a feedback database as described above) and/or to relay feedback data to the physician control device 2. The vestibular stimulation device 1 may be configured to transmit feedback data to the physician control device 2 over any suitable wired or wireless communications channel, including, but not limited to, a LAN, the Internet, a public telephone switching network, Bluetooth, WLAN and the like. Likewise, the physician control device 2 may be configured to access a feedback database residing in the vestibular stimulation device 1 and to retrieve feedback data using any suitable wired or wireless communications channel, including, but not limited to, a LAN, the Internet, a public telephone switching network, Bluetooth, WLAN and the like. Alternatively, feedback data may be transferred to the physician control device 2 using a portable memory device, such as an SD memory card or a USB memory stick.

The physician control device 2 may be configured to analyze feedback data received and/or retrieved from the vestibular stimulation device 1. For example, the physician control device 2 may be configured to use the feedback data to estimate the thermal contact between one or more earpiece and the patient's ear canal(s), to calculate patient-specific time constants, to evaluate the precision with the prescribed thermal waveform(s) was/were delivered, etc.

The physician control device 2 may be configured to modify one or more thermal waveforms responsive to analyzing feedback data received and/or retrieved from the vestibular stimulation device 1. For example, the physician control device 2 may be configured to modify one or more parameters of a thermal waveform generated by the physician control device 2 and/or stored in a waveform database residing therein. The physician control device 2 may be configured to modify the thermal waveform(s) automatically (e.g., the physician control device 2 may be configured to automatically modify one or more thermal waveforms if/when any of its analyses indicate that such modifications are likely to improve the efficacy of the thermal waveform(s)) or responsive to user input.

The physician control device 2 may be configured to store one or more modified thermal waveforms in a database residing therein (e.g., a waveform database as described above) and/or to relay the modified thermal waveform(s) to the vestibular stimulation device 1. The physician control device 2 may be configured to transmit one or more modified thermal waveforms to the vestibular stimulation device 1 over any suitable wired or wireless communications channel, including, but not limited to, a LAN, the Internet, a public telephone switching network, Bluetooth, WLAN and the like. Likewise, the vestibular stimulation device 1 may be configured to access a waveform database residing in the physician control device 2 and to retrieve the modified thermal waveform(s) using any suitable wired or wireless communications channel, including, but not limited to, a LAN, the Internet, a public telephone switching network, Bluetooth, WLAN and the like. Alternatively, the modified thermal waveform(s) may be transferred to the vestibular stimulation device 1 using a portable memory device, such as an SD memory card or a USB memory stick.

The physician control device 2 may be configured to modify one or more prescriptions responsive to analyzing feedback data received and/or retrieved from the vestibular stimulation device 1. For example, the physician control device 2 may be configured to modify one or more parameters of a prescription generated by the physician control device 2 and/or stored in a prescription database residing therein. The physician control device 2 may be configured to modify the prescription(s) automatically (e.g., the physician control device 2 may be configured to automatically modify one or more prescriptions if/when any of its analyses indicate that such modifications are likely to improve the efficacy of the prescription(s)) or responsive to user input.

The physician control device 2 may be configured to store one or more modified prescriptions in a database residing therein (e.g., a waveform database as described above) and/or to relay the modified thermal waveform(s) to the vestibular stimulation device 1. The physician control device 2 may be configured to transmit one or more modified prescriptions to the vestibular stimulation device 1 over any suitable wired or wireless communications channel, including, but not limited to, a LAN, the Internet, a public telephone switching network, Bluetooth, WLAN and the like. Likewise, the vestibular stimulation device 1 may be configured to access a prescription database residing in the physician control device 2 and to retrieve the modified prescription(s) using any suitable wired or wireless communications channel, including, but not limited to, a LAN, the Internet, a public telephone switching network, Bluetooth, WLAN and the like. Alternatively, the modified prescription(s) may be transferred to the vestibular stimulation device 1 using a portable memory device, such as an SD memory card or a USB memory stick.

The vestibular stimulation device 1 may be configured to deliver one or more thermal waveforms to the vestibular system and/or the nervous system of the patient in accordance with one or more modified prescriptions to the vestibular system and/or the nervous system of a patient. For example, as described above, the vestibular stimulation device 1 may be configured to deliver the prescribed thermal waveform(s) the vestibular system and/or the nervous system of the patient by activating one or more TEDs to warm and/or cool an earpiece inserted into an ear canal of the patient.

The physician control device 2 may be configured to generate one or more software updates. Each software update may comprise, consist essentially of or consist of a set of instructions for modifying one or more operational parameters of the vestibular stimulation device 1.

The physician control device 2 may be configured to store one or more software updates in a database residing therein and/or to relay one or more software updates to the vestibular stimulation device 1. The physician control device 2 may be configured to transmit one or more software updates to the vestibular stimulation device 1 over any suitable wired or wireless communications channel, including, but not limited to, a LAN, the Internet, a public telephone switching network, Bluetooth, WLAN and the like. Likewise, the vestibular stimulation device 1 may be configured to access a database residing in the physician control device 2 and to retrieve one or more software updates using any suitable wired or wireless communications channel, including, but not limited to, a LAN, the Internet, a public telephone switching network, Bluetooth, WLAN and the like. Alternatively, one or more software updates may be transferred to the vestibular stimulation device 1 using a portable memory device, such as an SD memory card or a USB memory stick. The software update(s) may be relayed from the physician control device 2 to the vestibular stimulation device 1 automatically (e.g., upon generation, once per week, once per month, etc.) or in response to user input.

The vestibular stimulation device 1 may be configured to modify one or more of its operational parameters responsive to receiving and/or retrieving one or more software updates from the physician control device 2. The vestibular stimulation device 1 may be configured to modify one or more of its operational parameters automatically ((e.g., upon receipt of the software update(s), once per week, once per month, etc.) or in response to user input.

As shown in FIG. 34, the vestibular stimulation system may comprise, consist essentially of or consist of a physician control device 2 operatively connected to a plurality of vestibular stimulation devices 1*a*, 1*b*, 1*c*, 1*d*.

The physician control device 2 may be configured to generate one or more thermal waveforms (i.e., to generate the parameters, indications and/or approvals of one or more thermal waveforms) and/or to store the thermal waveform(s) in a database (e.g., to store the parameters, indications and/or approvals of the thermal waveform(s) in a waveform database as described above).

The physician control device 2 may be configured to generate a plurality of prescriptions, each comprising a set of instructions for delivering one or more thermal waveforms to the vestibular system and/or the nervous system of a patient. In such embodiments, one or more of the prescriptions may comprise a set of instructions for delivering one or more of the thermal waveforms generated by the physician control device 2 to the vestibular system and/or the nervous system of a patient.

The physician control device 2 may be configured to store the prescriptions in a database residing therein (e.g., a prescription database as described above) and/or to relay each prescription to a vestibular stimulation device 1a, 1b, 1c, 1d associated with the patient for whom the prescription was generated. The physician control device 2 may be configured to transmit the prescriptions to the vestibular stimulation devices 1a, 1b, 1c, 1d over any suitable wired or wireless communications channel, including, but not limited to, a LAN, the Internet, a public telephone switching network, Bluetooth, WLAN and the like. Likewise, each of the vestibular stimulation devices 1a, 1b, 1c, 1d may be configured to access a prescription database residing in the physician control device 2 and to retrieve the prescriptions using any suitable wired or wireless communications channel, including, but not limited to, a LAN, the Internet, a public telephone switching network, Bluetooth, WLAN and the like. Alternatively, the prescriptions may be transferred to the vestibular stimulation devices 1a, 1b, 1c, 1d using one or more portable memory devices, such as SD memory cards and/or USB memory sticks.

Each of the vestibular stimulation devices 1a, 1b, 1c, 1d may be configured to deliver one or more prescribed thermal waveforms to the vestibular system and/or the nervous system of the patient for whom the prescription was generated. For example, as described above, each vestibular stimulation device 1a, 1b, 1c, 1d may be configured to deliver the prescribed thermal waveform(s) the vestibular system and/or the nervous system of the patient by activating one or more TEDs to warm and/or cool an earpiece inserted into an ear canal of the patient.

Each of the vestibular stimulation devices 1a, 1b, 1c, 1d may be configured to generate feedback data. For example, the vestibular stimulation devices 1a, 1b, 1c, 1d may comprise one or more sensors as described above, which may generate feedback data responsive to delivering the prescribed thermal waveform(s) to the vestibular system and/or the nervous system of the patient. Similarly, the vestibular stimulation devices 1a, 1b, 1c, 1d may comprise a GUI configured generate feedback data (e.g., patient feedback data) responsive to user input.

Each of the vestibular stimulation devices 1a, 1b, 1c, 1d may be configured to store feedback data in a database residing therein (e.g., a feedback database as described above) and/or to relay feedback data to the physician control device 2. The vestibular stimulation devices 1a, 1b, 1c, 1d may be configured to transmit feedback data to the physician control device 2 over any suitable wired or wireless communications channel, including, but not limited to, a LAN, the Internet, a public telephone switching network, Bluetooth, WLAN and the like. Likewise, the physician control device 2 may be configured to access one or more feedback databases residing in the vestibular stimulation devices 1a, 1b, 1c, 1d and to retrieve feedback data using any suitable wired or wireless communications channel, including, but not limited to, a LAN, the Internet, a public telephone switching network, Bluetooth, WLAN and the like. Alternatively, feedback data may be transferred to the physician control device 2 using a portable memory device, such as an SD memory card or a USB memory stick.

The physician control device 2 may be configured to analyze feedback data received and/or retrieved from one or more of the vestibular stimulation devices 1a, 1b, 1c, 1d. For example, the physician control device 2 may be configured to use the feedback data to estimate the thermal contact between one or more earpiece and the patient's ear canal(s), to calculate patient-specific time constants, to evaluate the precision with the prescribed thermal waveform(s) was/were delivered, etc.

The physician control device 2 may be configured to modify one or more thermal waveforms responsive to analyzing feedback data received and/or retrieved from one or more of the vestibular stimulation devices 1a, 1b, 1c, 1d. For example, the physician control device 2 may be configured to modify one or more parameters of a thermal waveform generated by the physician control device 2 and/or stored in a waveform database residing therein. The physician control device 2 may be configured to modify the thermal waveform(s) automatically (e.g., the physician control device 2 may be configured to automatically modify one or more thermal waveforms if/when any of its analyses indicate that such modifications are likely to improve the efficacy of the thermal waveform(s)) or responsive to user input.

The physician control device 2 may be configured to store one or more modified thermal waveforms in a database residing therein (e.g., a waveform database as described above) and/or to relay the modified thermal waveform(s) to one or more of the vestibular stimulation devices 1a, 1b, 1c, 1d. The physician control device 2 may be configured to transmit the modified thermal waveforms to the vestibular stimulation devices 1a, 1b, 1c, 1d over any suitable wired or wireless communications channel, including, but not limited to, a LAN, the Internet, a public telephone switching network, Bluetooth, WLAN and the like. Likewise, each of the vestibular stimulation devices 1a, 1b, 1c, 1d may be configured to access a waveform database residing in the physician control device 2 and to retrieve the modified thermal waveform(s) using any suitable wired or wireless communications channel, including, but not limited to, a LAN, the Internet, a public telephone switching network, Bluetooth, WLAN and the like. Alternatively, the modified thermal waveform(s) may be transferred to one or more of the vestibular stimulation devices 1a, 1b, 1c, 1d using a portable memory device, such as an SD memory card or a USB memory stick.

The physician control device 2 may be configured to modify one or more prescriptions responsive to analyzing feedback data received and/or retrieved from one or more of the vestibular stimulation devices 1a, 1b, 1c, 1d. For example, the physician control device 2 may be configured to modify one or more parameters of a prescription generated by the physician control device 2 and/or stored in a prescription database residing therein. The physician control device 2 may be configured to modify the prescription(s) automatically (e.g., the physician control device 2 may be configured to automatically modify one or more prescriptions if/when any of its analyses indicate that such modifications are likely to improve the efficacy of the prescription(s)) or responsive to user input.

The physician control device 2 may be configured to store one or more modified prescriptions in a database residing therein (e.g., a waveform database as described above) and/or to relay each of the modified prescription(s) to the vestibular stimulation device 1a, 1b, 1c, 1d associated with the patient for whom the modified prescription(s) was/were generated. The physician control device 2 may be configured to transmit the modified prescription(s) to the vestibular stimulation devices 1a, 1b, 1c, 1d over any suitable wired or wireless communications channel, including, but not limited to, a LAN, the Internet, a public telephone switching network, Bluetooth, WLAN and the like. Likewise, each of the vestibular stimulation devices 1a, 1b, 1c, 1d may be configured to access a prescription database residing in the physician control device 2 and to retrieve the modified prescription(s) associated with the patient to whom the vestibular stimulation device 1a, 1b, 1c, 1d is associated using any suitable wired or wireless communications channel, including, but not limited to, a LAN, the Internet, a public telephone switching network, Bluetooth, WLAN and the like. Alternatively, the modified prescription(s) may be transferred to the vestibular stimulation devices 1a, 1b, 1c, 1d using a portable memory device, such as an SD memory card or a USB memory stick.

Each of the vestibular stimulation devices 1a, 1b, 1c, 1d may be configured to deliver one or more thermal waveforms to the vestibular system and/or the nervous system of the patient in accordance with one or more modified prescriptions to the vestibular system and/or the nervous system of a patient. For example, as described above, the vestibular stimulation devices 1a, 1b, 1c, 1d may be configured to deliver the prescribed thermal waveform(s) the vestibular system and/or the nervous system of the patient by activating one or more TEDs to warm and/or cool an earpiece inserted into an ear canal of the patient.

The physician control device 2 may be configured to generate one or more software updates. Each software update may comprise, consist essentially of or consist of a set of instructions for modifying one or more operational parameters of the vestibular stimulation devices 1a, 1b, 1c, 1d.

The physician control device 2 may be configured to store one or more software updates in a database residing therein and/or to relay one or more software updates to one or more of the vestibular stimulation devices 1a, 1b, 1c, 1d. The physician control device 2 may be configured to transmit one or more software updates to the vestibular stimulation devices 1a, 1b, 1c, 1d over any suitable wired or wireless communications channel, including, but not limited to, a LAN, the Internet, a public telephone switching network, Bluetooth, WLAN and the like. Likewise, each of the vestibular stimulation devices 1a, 1b, 1c, 1d may be configured to access a database residing in the physician control device 2 and to retrieve one or more software updates using any suitable wired or wireless communications channel, including, but not limited to, a LAN, the Internet, a public telephone switching network, Bluetooth, WLAN and the like. Alternatively, one or more software updates may be transferred to the vestibular stimulation devices 1a, 1b, 1c, 1d using a portable memory device, such as an SD memory card or a USB memory stick. The software update(s) may be relayed from the physician control device 2 to one or more of the vestibular stimulation devices 1a, 1b, 1c, 1d automatically (e.g., upon generation, once per week, once per month, etc.) or in response to user input.

Each of the vestibular stimulation devices 1a, 1b, 1c, 1d may be configured to modify one or more of its operational parameters responsive to receiving and/or retrieving one or more software updates from the physician control device 2. The vestibular stimulation devices 1a, 1b, 1c, 1d may be configured to modify one or more of its operational parameters automatically ((e.g., upon receipt of the software update(s), once per week, once per month, etc.) or in response to user input.

Figure 35:
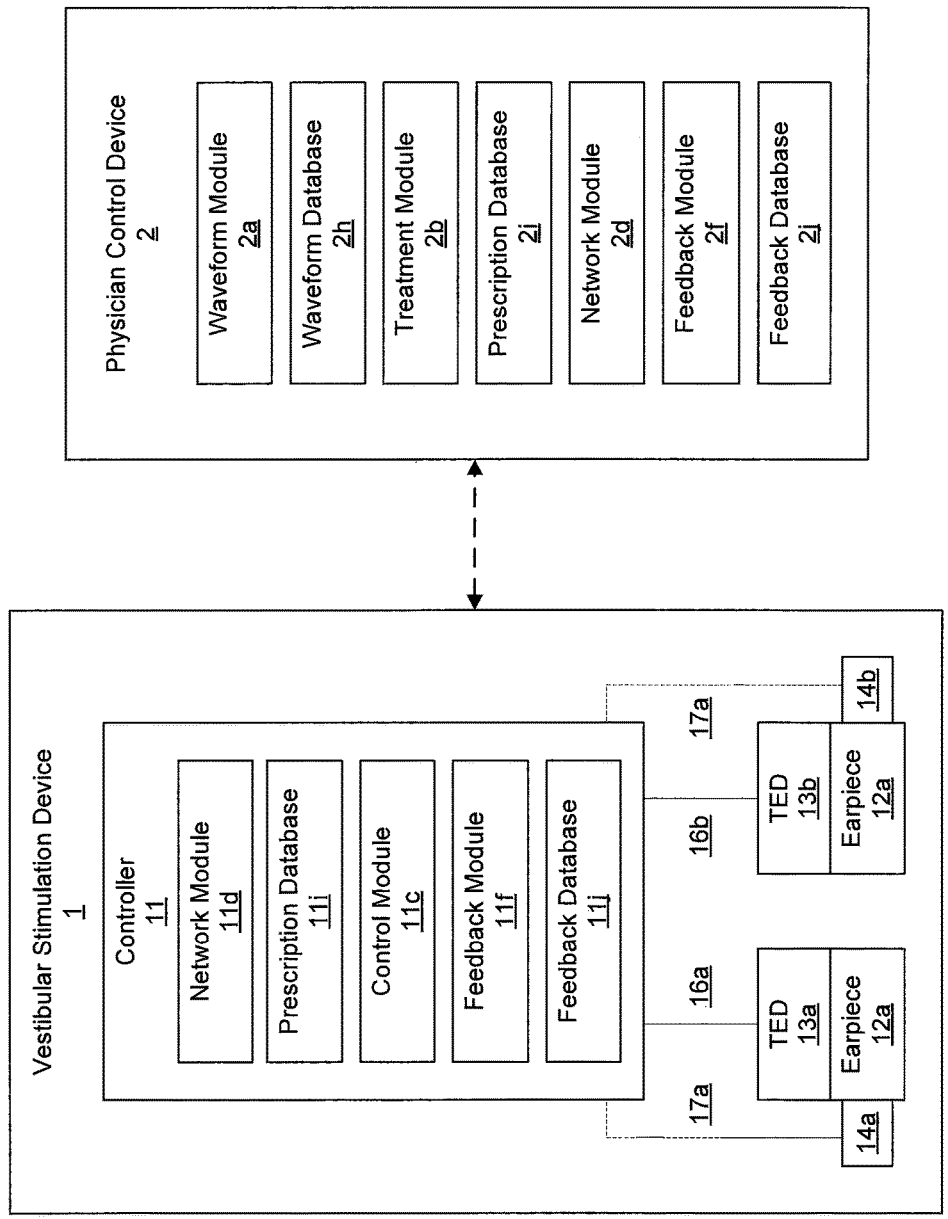
FIG. 35 is a block diagram of a vestibular stimulation system according to some embodiments of the present invention comprising a vestibular stimulation device and a physician control device.

As shown in FIG. 35, the vestibular stimulation system may comprise, consist essentially of or consist of a physician control device 2 operatively connected to a vestibular stimulation device 1 comprising a controller 11, a pair of earpieces 12a, 12b, a pair of TEDs 13a, 13b and a pair of sensors 14a, 14b, wherein each of the TEDs 13a, 13b is operatively connected to the controller 11 via a thermal stimulation lead 16a, 16b and thermally connected to one of the earpieces 12a, 12b and wherein each of the sensors 14a, 14b is operatively connected to the controller 11 via a wireless connection 17a, 17b and thermally connected to one of the earpieces 12a, 12b. In some such embodiments, the physician control device 2 comprises a waveform module 2a, a treatment module 2b, a network module 2d, a feedback module 2f, a waveform database 2h, a prescription database 2i and a feedback database 2j, and the controller comprises a control module 11c, a network module 11d, a feedback module 11f, a prescription database 11i and a feedback database 11j.

The waveform module 2a may be configured to generate one or more thermal waveforms (i.e., to generate the parameters, indications and/or approvals of one or more thermal waveforms). The physician control device 2 may be configured such that the thermal waveforms generated by the waveform module 2a are transmitted directly to the treatment module 2b and/or are stored in the waveform database 2h, from whence they may subsequently be transmitted to and/or retrieved by the treatment module 2b.

The treatment module 2b may be configured to retrieve the thermal waveforms generated by the waveform module 2a from the waveform database 2h.

The treatment module 2b may be configured to generate a prescription comprising a set of instructions for delivering one or more of the thermal waveforms generated by the waveform module 2a to the vestibular system and/or the nervous system of a patient. The physician control device 2 may be configured such that the prescription generated by the treatment module 2b is transmitted directly to the vestibular stimulation device 1 by the network module 2d residing in the physician control device 2 and/or is stored in the prescription database 2i residing in the physician control device 2, from whence it may subsequently be transmitted to and/or retrieved by the vestibular stimulation device 1.

The network module 11d residing in the controller 11 may be configured to receive and/or retrieve the prescription from the physician control device 2 and to relay the prescription to the control module 11c and/or to the prescription database 11i residing in the controller 11.

The control module 11c may be configured to retrieve the prescription from the prescription database 11i residing in the controller 11.

The control module 11c may be configured to deliver the prescribed thermal waveform(s) by activating the TEDs 13a, 13b in accordance with the prescription (i.e., by activating the TEDs 13a, 13b to by warm and/or cool the earpieces 12a, 12b so as to deliver the prescribed thermal waveform(s)).

The feedback module 11f residing in the controller 11 may be configured to receive feedback data from the TEDs 13a, 13b and/or the sensors 14a, 14b (e.g., data associated with the temperature of the earpieces 12a, 12b, the temperature of the patient's ear canals, the impedance between the earpieces 12a, 12b, etc.). The controller 11 may be configured such that the feedback data received by the feedback module 11f is transmitted directly to the physician control device 2 by the network module 11d residing in the controller 11 and/or is stored in the feedback database 11j residing in the controller 11, from whence it may subsequently be transmitted to and/or retrieved by the physician control device 2.

The network module 2d residing in the physician control device 2 may be configured to receive and/or retrieve feedback data from the vestibular stimulation device 1 and to relay the feedback data to the feedback module 2f residing in the physician control device 2 and/or to the feedback database 2j residing in the physician control device 2, from whence it may subsequently be transmitted to and/or retrieved by the feedback module 2f.

The feedback module 2f residing in the physician control device 2 may be configured to retrieve feedback data from the feedback database 2j residing in the physician control device 2.

The feedback module 2f residing in the physician control device 2 may be configured to analyze the feedback data (e.g., to estimate the thermal contact between each of the earpieces 12a, 12b and the patient's ear canals, to calculate patient-specific time constants, to evaluate the precision with the prescribed thermal waveform(s) was delivered, etc.). The physician control device 2 may be configured such that data associated with the feedback module's 2f analysis are transmitted directly to the waveform module 2a and/or the treatment module 2b and/or are stored in the feedback database 2j, from whence they may subsequently be transmitted to and/or retrieved by the waveform module 2a and/or the treatment module 2b.

The waveform module 2a may be configured to retrieve data associated with the feedback module's 2f analysis from the feedback database 2j residing in the physician control device 2.

The waveform module 2a may be configured to modify one or more of the thermal waveforms responsive to receiving and/or retrieving data associated with the feedback module's 2f analysis. The waveform module 2a may be configured to modify the thermal waveform(s) automatically (e.g., the waveform module 2a may be configured to periodically check the feedback database 2j for new analyses and to automatically modify one or more thermal waveforms if/when any analysis performed by the feedback module 2f indicates that such modifications are likely to improve the efficacy of the thermal waveform(s)) or responsive to user input. The physician control device 2 may be configured such that any modifications made by the waveform module 2a are relayed to the treatment module 2b as described above.

The treatment module 2b may be configured to retrieve data associated with the feedback module's 2f analysis from the feedback database 2j residing in the physician control device 2.

The treatment module 2b may be configured to modify, update and/or extend the prescription responsive to receiving and/or retrieving data associated with the feedback module's 2f analysis and/or to receiving and/or retrieving any modifications made by the waveform module 2a. The treatment module 2b may be configured to modify, update and/or extend the prescription automatically (e.g., the treatment module 2b may be configured to periodically check the waveform database 2h for updates and to automatically modify the prescription if/when one or more of the parameters, indications or approvals of a thermal waveform used in the prescription has been modified by the waveform module 2a) or responsive to user input. The physician control device 2 may be configured such that any modifications made by the treatment module 2b are relayed to the vestibular stimulation device 1 as described above.

As shown in FIG. 36, the vestibular stimulation system may comprise, consist essentially of or consist of a vestibular stimulation device 1 operatively connected to a patient control device 3 that is operatively connected to a physician control device 2. In some embodiments, the vestibular stimulation device 1 is also operatively connected to the physician control device 2 via an independent operative connection (i.e., independent of the patient control device 3).

The physician control device 2 may be configured to generate one or more thermal waveforms (i.e., to generate the parameters, indications and/or approvals of one or more thermal waveforms) and/or to store the thermal waveform(s) in a database (e.g., to store the parameters, indications and/or approvals of the thermal waveform(s) in a waveform database as described above).

The physician control device 2 may be configured to generate one or more prescriptions. Each prescription may comprise, consist essentially of or consist of a set of instructions for delivering one or more thermal waveforms to the vestibular system and/or the nervous system of a patient. In such embodiments, the prescription may comprise a set of instructions for delivering one or more of the thermal waveforms generated by the physician control device 2 to the vestibular system and/or the nervous system of a patient.

The physician control device 2 may be configured to store one or more prescriptions in a database residing therein (e.g., a prescription database as described above) and/or relay one or more prescriptions to the vestibular stimulation device 1 and/or the patient control device 3. The physician control device 2 may be configured to transmit one or more prescriptions to the vestibular stimulation device 1 and/or the patient control device 3 over any suitable wired or wireless communications channel, including, but not limited to, a LAN, the Internet, a public telephone switching network, Bluetooth, WLAN and the like. Likewise, the vestibular stimulation device 1 and/or the patient control device 3 may be configured to access a prescription database residing in the physician control device 2 and to retrieve one or more prescriptions using any suitable wired or wireless communications channel, including, but not limited to, a LAN, the Internet, a public telephone switching network, Bluetooth, WLAN and the like. Alternatively, one or more prescriptions may be transferred to the vestibular stimulation device 1 and/or the patient control device 3 using a portable memory device, such as an SD memory card or a USB memory stick.

The patient control device 3 may be configured to store one or more prescriptions in a database residing therein (e.g., a prescription database as described above) and/or relay one or more prescriptions to the vestibular stimulation device 1. The patient control device 3 may be configured to transmit one or more prescriptions to the vestibular stimulation device 1 over any suitable wired or wireless communications channel, including, but not limited to, a LAN, the Internet, a public telephone switching network, Bluetooth, WLAN and the like. Likewise, the vestibular stimulation device 1 may be configured to access a prescription database residing in the patient control device 3 and to retrieve one or more prescriptions using any suitable wired or wireless communications channel, including, but not limited to, a LAN, the Internet, a public telephone switching network, Bluetooth, WLAN and the like. Alternatively, one or more prescriptions may be transferred to the vestibular stimulation device 1 using a portable memory device, such as an SD memory card or a USB memory stick.

The vestibular stimulation device 1 may be configured to deliver one or more prescribed thermal waveform(s) to the vestibular system and/or the nervous system of a patient. For example, as described above, the vestibular stimulation device 1 may be configured to deliver the prescribed thermal waveform(s) the vestibular system and/or the nervous system of the patient by activating one or more TEDs to warm and/or cool an earpiece inserted into an ear canal of the patient.

The vestibular stimulation device 1 may be configured to generate feedback data. For example, the vestibular stimulation device 1 may comprise one or more sensors as described above, which may generate feedback data responsive to delivering the prescribed thermal waveform(s) to the vestibular system and/or the nervous system of the patient. Similarly, the vestibular stimulation device 1 may comprise a GUI configured generate feedback data (e.g., patient feedback data) responsive to user input.

The vestibular stimulation device 1 may be configured to store feedback data in a database residing therein (e.g., a feedback database as described above) and/or to relay feedback data to the patient control device 3 and/or the physician control device 2. The vestibular stimulation device 1 may be configured to transmit feedback data to the patient control device 3 and/or the physician control device 2 over any suitable wired or wireless communications channel, including, but not limited to, a LAN, the Internet, a public telephone switching network, Bluetooth, WLAN and the like. Likewise, the patient control device 3 and/or the physician control device 2 may be configured to access a feedback database residing in the vestibular stimulation device 1 and to retrieve feedback data using any suitable wired or wireless communications channel, including, but not limited to, a LAN, the Internet, a public telephone switching network, Bluetooth, WLAN and the like. Alternatively, feedback data may be transferred to the patient control device 3 and/or the physician control device 2 using a portable memory device, such as an SD memory card or a USB memory stick.

The patient control device 3 may be configured to supplement feedback data received and/or retrieved from the vestibular stimulation device 1 with additional feedback data (e.g., patient feedback data).

The patient control device 3 may be configured to store feedback data (including any additional feedback data generated by the patient control device 3) in a database residing therein (e.g., a feedback database as described above) and/or to relay feedback data (including any additional feedback data generated by the patient control device 3) to the physician control device 2. The patient control device 3 may be configured to transmit feedback data to the physician control device 2 over any suitable wired or wireless communications channel, including, but not limited to, a LAN, the Internet, a public telephone switching network, Bluetooth, WLAN and the like. Likewise, the physician control device 2 may be configured to access a feedback database residing in the patient control device 3 and to retrieve feedback data using any suitable wired or wireless communications channel, including, but not limited to, a LAN, the Internet, a public telephone switching network, Bluetooth, WLAN and the like. Alternatively, feedback data may be transferred to the physician control device 2 using a portable memory device, such as an SD memory card or a USB memory stick.

The physician control device 2 may be configured to analyze feedback data received and/or retrieved from the vestibular stimulation device 1 and/or the patient control device 3. For example, the physician control device 2 may be configured to use the feedback data to estimate the thermal contact between one or more earpiece and the patient's ear canal(s), to calculate patient-specific time constants, to evaluate the precision with the prescribed thermal waveform(s) was/were delivered, etc.

The physician control device 2 may be configured to modify one or more thermal waveforms responsive to analyzing feedback data received and/or retrieved from the vestibular stimulation device 1 and/or the patient control device 3. For example, the physician control device 2 may be configured to modify one or more parameters of a thermal waveform generated by the physician control device 2 and/or stored in a waveform database residing therein. The physician control device 2 may be configured to modify the thermal waveform(s) automatically (e.g., the physician control device 2 may be configured to automatically modify one or more thermal waveforms if/when any of its analyses indicate that such modifications are likely to improve the efficacy of the thermal waveform(s)) or responsive to user input.

The physician control device 2 may be configured to store one or more modified thermal waveforms in a database residing therein (e.g., a waveform database as described above) and/or to relay the modified thermal waveform(s) to the vestibular stimulation device 1 and/or the patient control device 3. The physician control device 2 may be configured to transmit the modified thermal waveform(s) to the vestibular stimulation device 1 and/or the patient control device 3 over any suitable wired or wireless communications channel, including, but not limited to, a LAN, the Internet, a public telephone switching network, Bluetooth, WLAN and the like. Likewise, the vestibular stimulation device 1 and/or the patient control device 3 may be configured to access a waveform database residing in the physician control device 2 and to retrieve the modified thermal waveform(s) using any suitable wired or wireless communications channel, including, but not limited to, a LAN, the Internet, a public telephone switching network, Bluetooth, WLAN and the like. Alternatively, the modified thermal waveform(s) may be transferred to the vestibular stimulation device 1 and/or the patient control device 3 using a portable memory device, such as an SD memory card or a USB memory stick.

The physician control device 2 may be configured to modify one or more prescriptions responsive to analyzing feedback data received and/or retrieved from the vestibular stimulation device 1 and/or the patient control device 3. For example, the physician control device 2 may be configured to modify one or more parameters of a prescription generated by the physician control device 2 and/or stored in a prescription database residing therein. The physician control device 2 may be configured to modify the prescription(s) automatically (e.g., the physician control device 2 may be configured to automatically modify one or more prescriptions if/when any of its analyses indicate that such modifications are likely to improve the efficacy of the prescription(s)) or responsive to user input.

The physician control device 2 may be configured to store one or more modified prescriptions in a database residing therein (e.g., a waveform database as described above) and/or to relay the modified thermal waveform(s) to the vestibular stimulation device 1 and/or the patient control device 3. The physician control device 2 may be configured to transmit the modified prescription(s) to the vestibular stimulation device 1 and/or the patient control device 3 over any suitable wired or wireless communications channel, including, but not limited to, a LAN, the Internet, a public telephone switching network, Bluetooth, WLAN and the like. Likewise, the vestibular stimulation device 1 and/or the patient control device 3 may be configured to access a prescription database residing in the physician control device 2 and to retrieve the modified prescription(s) using any suitable wired or wireless communications channel, including, but not limited to, a LAN, the Internet, a public telephone switching network, Bluetooth, WLAN and the like. Alternatively, the modified prescription(s) may be transferred to the vestibular stimulation device 1 and/or the patient control device 3 using a portable memory device, such as an SD memory card or a USB memory stick.

The patient control device 3 may be configured to store one or more modified prescriptions in a database residing therein (e.g., a prescription database as described above) and/or transmit one or more modified prescriptions to the vestibular stimulation device 1. The patient control device 3 may be configured to transmit the modified prescription(s) to the vestibular stimulation device 1 over any suitable wired or wireless communications channel, including, but not limited to, a LAN, the Internet, a public telephone switching network, Bluetooth, WLAN and the like. Likewise, the vestibular stimulation device 1 may be configured to access a prescription database residing in the patient control device 3 and to retrieve one or more modified prescriptions using any suitable wired or wireless communications channel, including, but not limited to, a LAN, the Internet, a public telephone switching network, Bluetooth, WLAN and the like. Alternatively, one or more modified prescriptions may be transferred to the vestibular stimulation device 1 using a portable memory device, such as an SD memory card or a USB memory stick.

The vestibular stimulation device 1 may be configured to deliver one or more thermal waveforms to the vestibular system and/or the nervous system of the patient in accordance with one or more modified prescriptions to the vestibular system and/or the nervous system of a patient. For example, as described above, the vestibular stimulation device 1 may be configured to deliver the prescribed thermal waveform(s) the vestibular system and/or the nervous system of the patient by activating one or more TEDs to warm and/or cool an earpiece inserted into an ear canal of the patient.

The physician control device 2 may be configured to generate one or more software updates. Each software update may comprise, consist essentially of or consist of a set of instructions for modifying one or more operational parameters of the vestibular stimulation device 1 and/or the patient control device 3.

The physician control device 2 may be configured to store one or more software updates in a database residing therein and/or to relay one or more software updates to the vestibular stimulation device 1 and/or the patient control device 3. The physician control device 2 may be configured to transmit one or more software updates to the vestibular stimulation device 1 and/or the patient control device 3 over any suitable wired or wireless communications channel, including, but not limited to, a LAN, the Internet, a public telephone switching network, Bluetooth, WLAN and the like. Likewise, the vestibular stimulation device 1 and/or the patient control device 3 may be configured to access a database residing in the physician control device 2 and to retrieve one or more software updates using any suitable wired or wireless communications channel, including, but not limited to, a LAN, the Internet, a public telephone switching network, Bluetooth, WLAN and the like. Alternatively, one or more software updates may be transferred to the vestibular stimulation device 1 and/or the patient control device 3 using a portable memory device, such as an SD memory card or a USB memory stick. The software update(s) may be relayed from the physician control device 2 to the vestibular stimulation device 1 and/or the patient control device 3 automatically (e.g., upon generation, once per week, once per month, etc.) or in response to user input.

The patient control device 3 may be configured to store one or more software updates in a database residing therein and/or to relay one or more software updates to the vestibular stimulation device 1. The patient control device 3 may be configured to transmit one or more software updates to the vestibular stimulation device 1 over any suitable wired or wireless communications channel, including, but not limited to, a LAN, the Internet, a public telephone switching network, Bluetooth, WLAN and the like. Likewise, the vestibular stimulation device 1 may be configured to access a database residing in the patient control device 3 and to retrieve one or more software updates using any suitable wired or wireless communications channel, including, but not limited to, a LAN, the Internet, a public telephone switching network, Bluetooth, WLAN and the like. Alternatively, one or more software updates may be transferred to the vestibular stimulation device 1 using a portable memory device, such as an SD memory card or a USB memory stick. The software update(s) may be relayed from the patient control device 3 to the vestibular stimulation device 1 automatically (e.g., upon generation, once per week, once per month, etc.) or in response to user input.

The patient control device 3 may be configured to modify one or more of its operational parameters responsive to receiving and/or retrieving one or more software updates from the physician control device 2. The patient control device 3 may be configured to modify one or more of its operational parameters automatically ((e.g., upon receipt of the software update(s), once per week, once per month, etc.) or in response to user input.

The vestibular stimulation device 1 may be configured to modify one or more of its operational parameters responsive to receiving and/or retrieving one or more software updates from the physician control device 2 and/or the patient control device 3. The vestibular stimulation device 1 may be configured to modify one or more of its operational parameters automatically ((e.g., upon receipt of the software update(s), once per week, once per month, etc.) or in response to user input. As shown in FIG. 37, the vestibular stimulation system may comprise, consist essentially of or consist of a physician control device 2 operatively connected to a plurality of patient control devices 3a, 3b, 3c, 3d, wherein each of said plurality of patient control devices 3a, 3b, 3c, 3d is operatively connected to one of a plurality of vestibular stimulation devices 1a, 1b, 1c, 1d. In some embodiments, one or more of the vestibular stimulation devices 1a, 1b, 1c, 1d is also operatively connected to the physician control device 2 via an independent operative connection (i.e., independent of the patient control device 3a, 3b, 3c, 3d with which it is associated).

The physician control device 2 may be configured to generate one or more thermal waveforms (i.e., to generate the parameters, indications and/or approvals of one or more thermal waveforms) and/or to store the thermal waveform(s) in a database (e.g., to store the parameters, indications and/or approvals of the thermal waveform(s) in a waveform database as described above).

The physician control device 2 may be configured to generate a plurality of prescriptions, each comprising a set of instructions for delivering one or more thermal waveforms to the vestibular system and/or the nervous system of a patient. In such embodiments, one or more of the prescriptions may comprise a set of instructions for delivering one or more of the thermal waveforms generated by the physician control device 2 to the vestibular system and/or the nervous system of a patient.

The physician control device 2 may be configured to store the prescriptions in a database residing therein (e.g., a prescription database as described above) and/or to relay each prescription to a vestibular stimulation device 1*a*, 1*b*, 1*c*, 1*d* and/or a patient control device 3*a*, 3*b*, 3*c*, 3*d* associated with the patient for whom the prescription was generated. The physician control device 2 may be configured to transmit the prescriptions to the vestibular stimulation devices 1*a*, 1*b*, 1*c*, 1*d* and/or a patient control devices 3*a*, 3*b*, 3*c*, 3*d* over any suitable wired or wireless communications channel, including, but not limited to, a LAN, the Internet, a public telephone switching network, Bluetooth, WLAN and the like. Likewise, each of the vestibular stimulation devices 1*a*, 1*b*, 1*c*, 1*d* and/or each of the patient control devices 3*a*, 3*b*, 3*c*, 3*d* may be configured to access a prescription database residing in the physician control device 2 and to retrieve the prescriptions using any suitable wired or wireless communications channel, including, but not limited to, a LAN, the Internet, a public telephone switching network, Bluetooth, WLAN and the like. Alternatively, the prescriptions may be transferred to the vestibular stimulation devices 1*a*, 1*b*, 1*c*, 1*d* and/or the patient control devices 3*a*, 3*b*, 3*c*, 3*d* using one or more portable memory devices, such as SD memory cards and/or USB memory sticks.

Each of the patient control devices 3*a*, 3*b*, 3*c*, 3*d* may be configured to store one or more prescriptions in a database residing therein (e.g., a prescription database as described above) and/or transmit one or more prescriptions to the vestibular stimulation device 1*a*, 1*b*, 1*c*, 1*d* with which it is associated. The patient control devices 3*a*, 3*b*, 3*c*, 3*d* may be configured to transmit the prescription(s) to the vestibular stimulation device 1*a*, 1*b*, 1*c*, 1*d* with which it is associated over any suitable wired or wireless communications channel, including, but not limited to, a LAN, the Internet, a public telephone switching network, Bluetooth, WLAN and the like. Likewise, each of the vestibular stimulation devices 1*a*, 1*b*, 1*c*, 1*d* may be configured to access a prescription database residing in the patient control device 3*a*, 3*b*, 3*c*, 3*d* with which it is associated and to retrieve one or more prescriptions using any suitable wired or wireless communications channel, including, but not limited to, a LAN, the Internet, a public telephone switching network, Bluetooth, WLAN and the like. Alternatively, one or more prescriptions may be transferred to the vestibular stimulation devices 1*a*, 1*b*, 1*c*, 1*d* using a portable memory device, such as an SD memory card or a USB memory stick.

Each of the vestibular stimulation devices 1*a*, 1*b*, 1*c*, 1*d* may be configured to deliver one or more prescribed thermal waveforms to the vestibular system and/or the nervous system of the patient for whom the prescription was generated. For example, as described above, each vestibular stimulation device 1*a*, 1*b*, 1*c*, 1*d* may be configured to deliver the prescribed thermal waveform(s) the vestibular system and/or the nervous system of the patient by activating one or more TEDs to warm and/or cool an earpiece inserted into an ear canal of the patient.

Each of the vestibular stimulation devices 1*a*, 1*b*, 1*c*, 1*d* may be configured to generate feedback data. For example, the vestibular stimulation devices 1*a*, 1*b*, 1*c*, 1*d* may comprise one or more sensors as described above, which may generate feedback data responsive to delivering the prescribed thermal waveform(s) to the vestibular system and/or the nervous system of the patient. Similarly, the vestibular stimulation devices 1*a*, 1*b*, 1*c*, 1*d* may comprise a GUI configured generate feedback data (e.g., patient feedback data) responsive to user input.

Each of the vestibular stimulation devices 1*a*, 1*b*, 1*c*, 1*d* may be configured to store feedback data in a database residing therein (e.g., a feedback database as described above) and/or to relay feedback data to the patient control device 3*a*, 3*b*, 3*c*, 3*d* with which it is associated and/or to the physician control device 2. The vestibular stimulation devices 1*a*, 1*b*, 1*c*, 1*d* may be configured to transmit feedback data to the patient control device 3*a*, 3*b*, 3*c*, 3*d* with which it is associated and/or to the physician control device 2 over any suitable wired or wireless communications channel, including, but not limited to, a LAN, the Internet, a public telephone switching network, Bluetooth, WLAN and the like. Likewise, each of the patient control devices 3*a*, 3*b*, 3*c*, 3*d* and/or to the physician control device 2 may be configured to access one or more feedback databases residing in the vestibular stimulation devices 1*a*, 1*b*, 1*c*, 1*d* and to retrieve feedback data using any suitable wired or wireless communications channel, including, but not limited to, a LAN, the Internet, a public telephone switching network, Bluetooth, WLAN and the like. Alternatively, feedback data may be transferred to the patient control devices 3*a*, 3*b*, 3*c*, 3*d* and/or the physician control device 2 using a portable memory device, such as an SD memory card or a USB memory stick.

Each of the patient control devices 3*a*, 3*b*, 3*c*, 3*d* may be configured to supplement feedback data received and/or retrieved from the vestibular stimulation device 1*a*, 1*b*, 1*c*, 1*d* with which it is associated with additional feedback data (e.g., patient feedback data).

Each of the patient control devices 3*a*, 3*b*, 3*c*, 3*d* may be configured to store feedback data (including any additional feedback data generated by the patient control device 3) in a database residing therein (e.g., a feedback database as described above) and/or to relay feedback data (including any additional feedback data generated by the patient control device 3) to the physician control device 2. The patient control devices 3*a*, 3*b*, 3*c*, 3*d* may be configured to transmit feedback data to the physician control device 2 over any suitable wired or wireless communications channel, including, but not limited to, a LAN, the Internet, a public telephone switching network, Bluetooth, WLAN and the like. Likewise, the physician control device 2 may be configured to access one or more feedback databases residing in the patient control devices 3*a*, 3*b*, 3*c*, 3*d* and to retrieve feedback data using any suitable wired or wireless communications channel, including, but not limited to, a LAN, the Internet, a public telephone switching network, Bluetooth, WLAN and the like. Alternatively, feedback data may be transferred to the physician control device 2 using a portable memory device, such as an SD memory card or a USB memory stick.

The physician control device 2 may be configured to analyze feedback data received and/or retrieved from one or more of the vestibular stimulation devices 1*a*, 1*b*, 1*c*, 1*d* and/or one or more of the patient control devices 3*a*, 3*b*, 3*c*, 3*d*. For example, the physician control device 2 may be configured to use the feedback data to estimate the thermal contact between one or more earpiece and the patient's ear canal(s), to calculate patient-specific time constants, to evaluate the precision with the prescribed thermal waveform(s) was/were delivered, etc.

The physician control device 2 may be configured to modify one or more thermal waveforms responsive to analyzing feedback data received and/or retrieved from one or more of the vestibular stimulation devices 1*a*, 1*b*, 1*c*, 1*d* and/or one or more of the patient control devices 3a, 3b, 3c, 3d. For example, the physician control device 2 may be configured to modify one or more parameters of a thermal waveform generated by the physician control device 2 and/or stored in a waveform database residing therein. The physician control device 2 may be configured to modify the thermal waveform(s) automatically (e.g., the physician control device 2 may be configured to automatically modify one or more thermal waveforms if/when any of its analyses indicate that such modifications are likely to improve the efficacy of the thermal waveform(s)) or responsive to user input.

The physician control device 2 may be configured to store one or more modified thermal waveforms in a database residing therein (e.g., a waveform database as described above) and/or to relay the modified thermal waveform(s) to one or more of the vestibular stimulation devices 1a, 1b, 1c, 1d and/or one or more of the patient control devices 3a, 3b, 3c, 3d. The physician control device 2 may be configured to transmit the modified thermal waveform(s) to one or more of the vestibular stimulation devices 1a, 1b, 1c, 1d and/or one or more of the patient control devices 3a, 3b, 3c, 3d over any suitable wired or wireless communications channel, including, but not limited to, a LAN, the Internet, a public telephone switching network, Bluetooth, WLAN and the like. Likewise, one or more of the vestibular stimulation devices 1a, 1b, 1c, 1d and/or one or more of the patient control devices 3a, 3b, 3c, 3d may be configured to access a waveform database residing in the physician control device 2 and to retrieve the modified thermal waveform(s) using any suitable wired or wireless communications channel, including, but not limited to, a LAN, the Internet, a public telephone switching network, Bluetooth, WLAN and the like. Alternatively, the modified thermal waveform(s) may be transferred to one or more of the vestibular stimulation devices 1a, 1b, 1c, 1d and/or one or more of the patient control devices 3a, 3b, 3c, 3d using a portable memory device, such as an SD memory card or a USB memory stick.

The physician control device 2 may be configured to modify one or more prescriptions responsive to analyzing feedback data received and/or retrieved from one or more of the vestibular stimulation devices 1a, 1b, 1c, 1d and/or one or more of the patient control devices 3a, 3b, 3c, 3d. For example, the physician control device 2 may be configured to modify one or more parameters of a prescription generated by the physician control device 2 and/or stored in a prescription database residing therein. The physician control device 2 may be configured to modify the prescription(s) automatically (e.g., the physician control device 2 may be configured to automatically modify one or more prescriptions if/when any of its analyses indicate that such modifications are likely to improve the efficacy of the prescription(s)) or responsive to user input.

The physician control device 2 may be configured to store one or more modified prescriptions in a database residing therein (e.g., a waveform database as described above) and/or to relay each of the modified prescription(s) to the vestibular stimulation devices 1a, 1b, 1c, 1d and/or one or more of the patient control devices 3a, 3b, 3c, 3d associated with the patient for whom the prescription was generated. The physician control device 2 may be configured to transmit the modified prescription(s) to the vestibular stimulation devices 1a, 1b, 1c, 1d and/or the patient control devices 3a, 3b, 3c, 3d over any suitable wired or wireless communications channel, including, but not limited to, a LAN, the Internet, a public telephone switching network, Bluetooth, WLAN and the like. Likewise, each of the vestibular stimulation devices 1a, 1b, 1c, 1d and/or each of the patient control devices 3a, 3b, 3c, 3d may be configured to access a prescription database residing in the physician control device 2 and to retrieve the modified prescription(s) associated with the patient to whom the vestibular stimulation device 1a, 1b, 1c, 1d and/or the patient control device 3a, 3b, 3c, 3d is associated using any suitable wired or wireless communications channel, including, but not limited to, a LAN, the Internet, a public telephone switching network, Bluetooth, WLAN and the like. Alternatively, the modified prescription(s) may be transferred to the vestibular stimulation devices 1a, 1b, 1c, 1d and/or the patient control devices 3a, 3b, 3c, 3d using a portable memory device, such as an SD memory card or a USB memory stick. Each of the patient control devices 3a, 3b, 3c, 3d may be configured to store one or more modified prescriptions in a database residing therein (e.g., a prescription database as described above) and/or transmit one or more prescriptions to the vestibular stimulation device 1a, 1b, 1c, 1d with which it is associated. The patient control devices 3a, 3b, 3c, 3d may be configured to transmit the modified prescription(s) to the vestibular stimulation device 1a, 1b, 1c, 1d with which it is associated over any suitable wired or wireless communications channel, including, but not limited to, a LAN, the Internet, a public telephone switching network, Bluetooth, WLAN and the like. Likewise, each of the vestibular stimulation devices 1a, 1b, 1c, 1d may be configured to access a prescription database residing in the patient control device 3a, 3b, 3c, 3d with which it is associated and to retrieve one or more modified prescriptions using any suitable wired or wireless communications channel, including, but not limited to, a LAN, the Internet, a public telephone switching network, Bluetooth, WLAN and the like. Alternatively, one or more modified prescriptions may be transferred to the vestibular stimulation devices 1a, 1b, 1c, 1d using a portable memory device, such as an SD memory card or a USB memory stick.

The vestibular stimulation devices 1a, 1b, 1c, 1d may be configured to deliver one or more thermal waveforms to the vestibular system and/or the nervous system of the patient in accordance with one or more modified prescriptions to the vestibular system and/or the nervous system of a patient. For example, as described above, the vestibular stimulation devices 1a, 1b, 1c, 1d may be configured to deliver the prescribed thermal waveform(s) the vestibular system and/or the nervous system of the patient by activating one or more TEDs to warm and/or cool an earpiece inserted into an ear canal of the patient.

The physician control device 2 may be configured to generate one or more software updates. Each software update may comprise, consist essentially of or consist of a set of instructions for modifying one or more operational parameters one or more of the vestibular stimulation devices 1a, 1b, 1c, 1d and/or one or more of the patient control devices 3a, 3b, 3c, 3d.

The physician control device 2 may be configured to store one or more software updates in a database residing therein and/or to relay one or more software updates to one or more of the vestibular stimulation devices 1a, 1b, 1c, 1d and/or one or more of the patient control devices 3a, 3b, 3c, 3d. The physician control device 2 may be configured to transmit one or more software updates to the vestibular stimulation devices 1a, 1b, 1c, 1d and/or the patient control devices 3a, 3b, 3c, 3d over any suitable wired or wireless communications channel, including, but not limited to, a LAN, the Internet, a public telephone switching network, Bluetooth, WLAN and the like. Likewise, each of the vestibular stimulation devices 1a, 1b, 1c, 1d and/or each of the patient control devices 3a, 3b, 3c, 3d may be configured to access a database residing in the physician control device 2 and to retrieve one or more software updates using any suitable wired or wireless communications channel, including, but not limited to, a LAN, the Internet, a public telephone switching network, Bluetooth, WLAN and the like. Alternatively, one or more software updates may be transferred to the vestibular stimulation devices 1a, 1b, 1c, 1d and/or the patient control devices 3a, 3b, 3c, 3d using a portable memory device, such as an SD memory card or a USB memory stick. The software update(s) may be relayed from the physician control device 2 to the vestibular stimulation devices 1a, 1b, 1c, 1d and/or the patient control devices 3a, 3b, 3c, 3d automatically (e.g., upon generation, once per week, once per month, etc.) or in response to user input.

Each of the patient control devices 3a, 3b, 3c, 3d may be configured to store one or more software updates in a database residing therein and/or transmit one or more software updates to the vestibular stimulation device 1a, 1b, 1c, 1d with which it is associated. The patient control devices 3a, 3b, 3c, 3d may be configured to transmit the software update(s) to the vestibular stimulation device 1a, 1b, 1c, 1d with which it is associated over any suitable wired or wireless communications channel, including, but not limited to, a LAN, the Internet, a public telephone switching network, Bluetooth, WLAN and the like. Likewise, each of the vestibular stimulation devices 1a, 1b, 1c, 1d may be configured to access a database residing in the patient control device 3a, 3b, 3c, 3d with which it is associated and to retrieve one or more software updates using any suitable wired or wireless communications channel, including, but not limited to, a LAN, the Internet, a public telephone switching network, Bluetooth, WLAN and the like. Alternatively, one or more software updates may be transferred to the vestibular stimulation devices 1a, 1b, 1c, 1d using a portable memory device, such as an SD memory card or a USB memory stick.

Each of the patient control devices 3a, 3b, 3c, 3d may be configured to modify one or more of its operational parameters responsive to receiving and/or retrieving one or more software updates from the physician control device 2. The patient control devices 3a, 3b, 3c, 3d may be configured to modify one or more of its operational parameters automatically ((e.g., upon receipt of the software update(s), once per week, once per month, etc.) or in response to user input.

Each of the vestibular stimulation devices 1a, 1b, 1c, 1d may be configured to modify one or more of its operational parameters responsive to receiving and/or retrieving one or more software updates from the physician control device 2 and/or the patient control device 3a, 3b, 3c, 3d with which it is associated. The vestibular stimulation devices 1a, 1b, 1c, 1d may be configured to modify one or more of its operational parameters automatically ((e.g., upon receipt of the software update(s), once per week, once per month, etc.) or in response to user input.

As shown in FIG. 38, in some embodiments, the vestibular stimulation system comprises, consists essentially of or consists of a physician control device 2 operatively connected to a patient control device 3 that is operatively connected to a vestibular stimulation device 1 comprising a controller 11, an earpiece 12, a TED 13, a pair of sensors 14a, 14b and a heat sink 15, wherein the TED 13 is operatively connected to the controller 11 via a thermal stimulation lead 16 and thermally connected between the earpiece 12 and the heat sink 15, wherein one of the sensors 14a is operatively connected to the controller 11 via a wireless connection 17a and thermally connected to the heat sink 15 and wherein the other sensor 14b is operatively connected to the controller 11 via a wireless connection 17b and thermally connected to the earpiece 12. In some such embodiments, the physician control device 2 comprises a waveform module 2a, a treatment module 2b, a network module 2d, a feedback module 2f, a waveform database 2h, a prescription database 2i and a feedback database 2j, the patient control device 3 comprises a network module 3d, a feedback module 3f, a prescription database 3i and a feedback database 3j and the controller comprises a control module 11c, a network module 11d and a feedback module 11f.

The waveform module 2a may be configured to generate one or more thermal waveforms (i.e., to generate the parameters, indications and/or approvals of one or more thermal waveforms). The physician control device may be configured such that the thermal waveforms generated by the waveform module 2a are transmitted directly to the treatment module 2b and/or are stored in the waveform database 2h, from whence they may subsequently be transmitted to and/or retrieved by the treatment module 2b.

The treatment module 2b may be configured to retrieve the thermal waveforms generated by the waveform module 2a from the waveform database 2h.

The treatment module 2b may be configured to generate a prescription comprising a set of instructions for delivering one or more of the thermal waveforms generated by the waveform module 2a to the vestibular system and/or the nervous system of a patient. The physician control device 2 may be configured such that the prescription generated by the treatment module 2b is transmitted directly to the patient control device 3 by the network module 2d residing in the physician control device 2 and/or is stored in the prescription database 2i residing in the physician control device 2, from whence it may subsequently be transmitted to and/or retrieved by the patient control device 3.

The network module 11d residing in the patient control device 3 may be configured to receive and/or retrieve the prescription from the physician control device 2 and to relay the prescription to the vestibular stimulation device 1 and/or to the prescription database 11i residing in the patient control device 3.

The network module 11d residing in the controller 11 may be configured to receive and/or retrieve the prescription from the patient control device 3 and to relay the prescription to the control module 11.

The control module 11c may be configured to deliver the prescribed thermal waveform(s) by activating the TED 13 in accordance with the prescription (i.e., by activating the TED 13 to by warm and/or cool the earpiece 12 so as to deliver the prescribed thermal waveform(s)).

The feedback module 11f residing in the controller 11 may be configured to receive feedback data from the TED 13 and/or the sensors 14a, 14b (e.g., data associated with the temperature of the earpiece 12, the temperature of the patient's ear canals, the temperature of the heat sink 15, etc.). The controller 11 may be configured such that the feedback data received by the feedback module 11f is transmitted directly to the patient control device 3 by the network module 11d residing in the controller 11.

The network module 3d residing in the patient control device 3 may be configured to receive feedback data from the vestibular stimulation device 1 and to relay the feedback data to the physician control device 2 and/or to the feedback database 3j residing in the patient control device 3, from whence it may subsequently be transmitted to and/or retrieved by the physician control device 2.

The patient control device 3 may be configured to supplement the feedback data received from the vestibular stimulation device 1 with additional feedback data (e.g., patient feedback data) and to relay the additional feedback data to the physician control device 2 and/or to the feedback database 3j residing in the patient control device 3, from whence it may subsequently be transmitted to and/or retrieved by the physician control device 2.

The network module 2d residing in the physician control device 2 may be configured to receive and/or retrieve feedback data from the patient control device 3 (including any additional feedback data supplied by the patient control device 3) and to relay the feedback data to the feedback module 2f residing in the physician control device 2 and/or to the feedback database 2j residing in the physician control device 2, from whence it may subsequently be transmitted to and/or retrieved by the feedback module 2f residing in the physician control device 2.

The feedback module 2f residing in the physician control device 2 may be configured to retrieve the feedback data from the feedback database 2j residing in the physician control device 2.

The feedback module 2f residing in the physician control device 2 may be configured to analyze the feedback data (e.g., to estimate the thermal contact between each of the earpiece 12a and the patient's ear canal, to calculate patient-specific time constants, to evaluate the precision with the prescribed thermal waveform(s) was delivered, etc.). The physician control device 2 may be configured such that data associated with the feedback module's 2f analysis are transmitted directly to the waveform module 2a and/or the treatment module 2b and/or are stored in the feedback database 2j, from whence they may subsequently be transmitted to and/or retrieved by the waveform module 2a and/or the treatment module 2b.

The waveform module 2a may be configured to retrieve data associated with the feedback module's 2f analysis from the feedback database 2j residing in the physician control device 2.

The waveform module 2a may be configured to modify one or more of the thermal waveforms responsive to receiving and/or retrieving data associated with the feedback module's 2f analysis. The physician control device 2 may be configured such that any modifications made by the waveform module 2a are relayed to the treatment module 2b as described above.

The treatment module 2b may be configured to retrieve data associated with the feedback module's 2f analysis from the feedback database 2j residing in the physician control device 2.

The treatment module 2b may be configured to modify, update and/or extend the prescription responsive to receiving and/or retrieving data associated with the feedback module's 2f analysis and/or to receiving and/or retrieving any modifications made by the waveform module 2a. The physician control device 2 may be configured such that any modifications made by the treatment module 2b are relayed to the vestibular stimulation device 1 and the patient control device 3 as described above.

Figure 39:
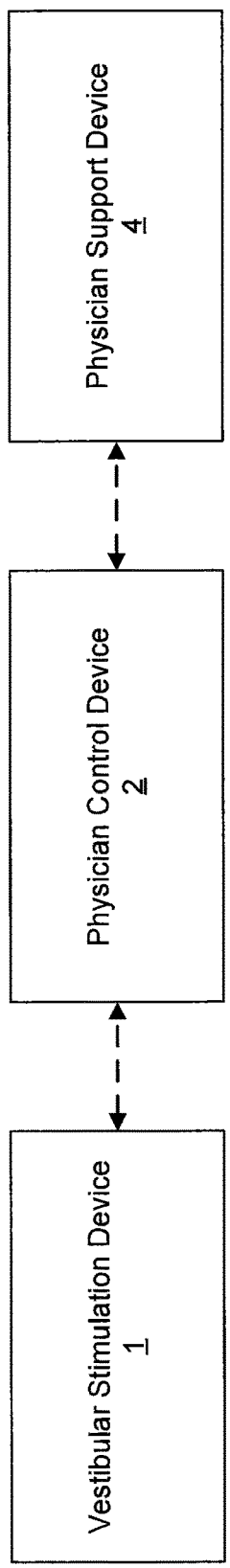
FIG. 39 is a block diagram of a vestibular stimulation system according to some embodiments of the present invention comprising a vestibular stimulation device, a physician control device and a physician support device.
Figure 40:
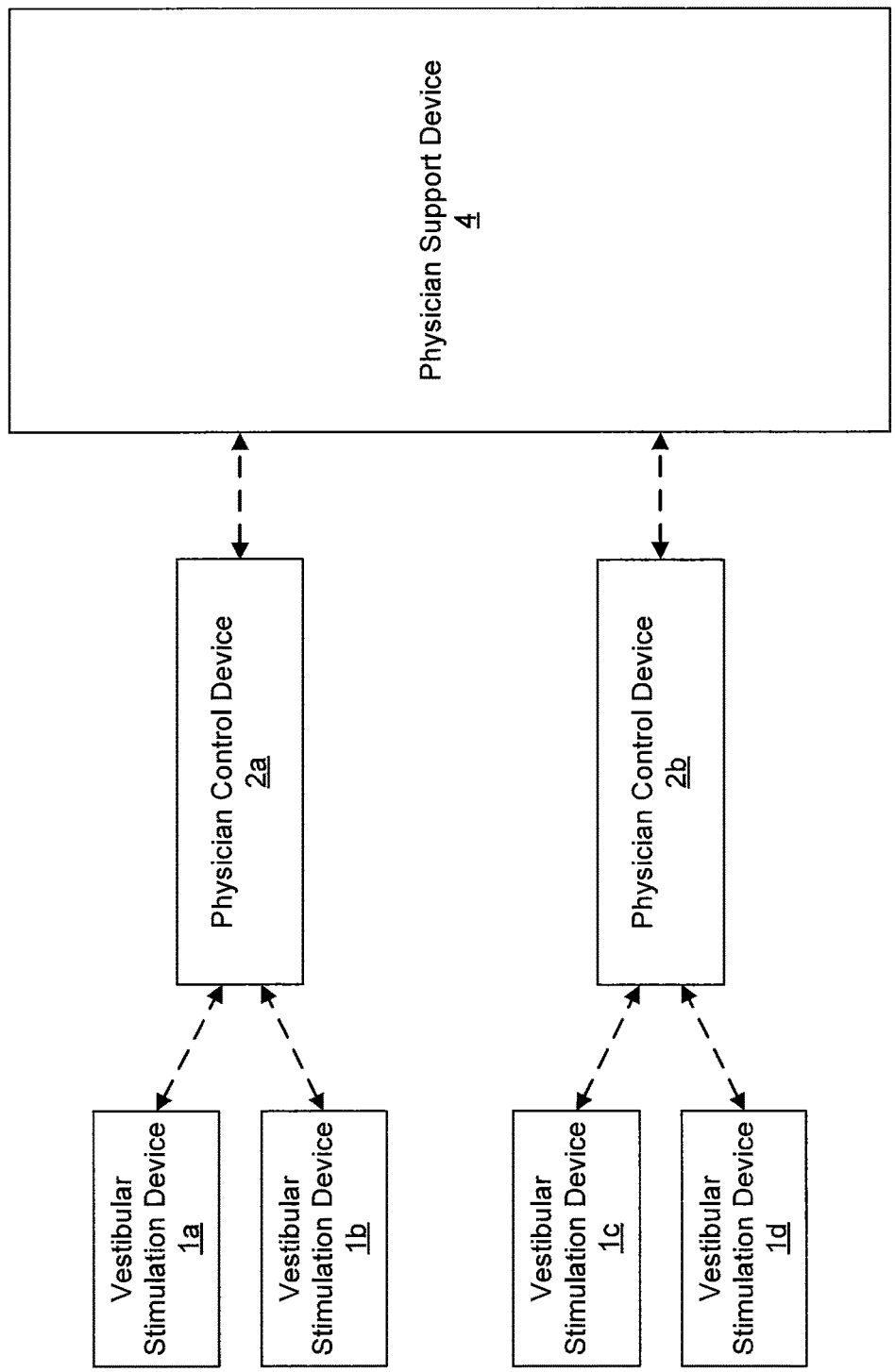
FIG. 40 is a block diagram of a vestibular stimulation system according to some embodiments of the present invention comprising a physician support device, a plurality of physician control devices and a plurality of vestibular stimulation devices.

As shown in FIG. 39 the vestibular stimulation system may comprise, consist essentially of or consist of a vestibular stimulation device 1 operatively connected to a physician control device 2 that is operatively connected to a physician support device 4.

The physician support device 4 may be configured to generate one or more thermal waveforms (i.e., to generate the parameters, indications and/or approvals of one or more thermal waveforms) and/or to store the thermal waveform(s) in a database (e.g., to store the parameters, indications and/or approvals of the thermal waveform(s) in a waveform database as described above).

The physician support device 4 may be configured to store one or more thermal waveform(s) in a database residing therein (e.g., a waveform database as described above) and/or relay one or more thermal waveforms to the physician control device 2. The physician support device 4 may be configured to transmit one or more prescriptions to the physician control device 2 over any suitable wired or wireless communications channel, including, but not limited to, a LAN, the Internet, a public telephone switching network, Bluetooth, WLAN and the like. Likewise, the physician control device 2 may be configured to access a waveform database residing in the physician support device 4 and to retrieve one or more thermal waveform(s) using any suitable wired or wireless communications channel, including, but not limited to, a LAN, the Internet, a public telephone switching network, Bluetooth, WLAN and the like. Alternatively, one or more thermal waveform(s) may be transferred to the physician control device 2 using a portable memory device, such as an SD memory card or a USB memory stick.

The physician control device 2 may be configured to generate one or more prescriptions. Each prescription may comprise, consist essentially of or consist of a set of instructions for delivering one or more thermal waveforms to the vestibular system and/or the nervous system of a patient. In such embodiments, the prescription may comprise a set of instructions for delivering one or more of the thermal waveforms generated by the physician support device 4 to the vestibular system and/or the nervous system of a patient.

The physician control device 2 may be configured to store one or more prescriptions in a database residing therein (e.g., a prescription database as described above) and/or to relay one or more prescriptions to the vestibular stimulation device 1. The physician control device 2 may be configured to transmit one or more prescriptions to the vestibular stimulation device 1 over any suitable wired or wireless communications channel, including, but not limited to, a LAN, the Internet, a public telephone switching network, Bluetooth, WLAN and the like. Likewise, the vestibular stimulation device 1 may be configured to access a prescription database residing in the physician control device 2 and to retrieve one or more prescriptions using any suitable wired or wireless communications channel, including, but not limited to, a LAN, the Internet, a public telephone switching network, Bluetooth, WLAN and the like. Alternatively, one or more prescriptions may be transferred to the vestibular stimulation device 1 using a portable memory device, such as an SD memory card or a USB memory stick.

The vestibular stimulation device 1 may be configured to deliver one or more prescribed thermal waveforms to the vestibular system and/or the nervous system of a patient. For example, as described above, the vestibular stimulation device 1 may be configured to deliver the prescribed thermal waveform(s) the vestibular system and/or the nervous system of the patient by activating one or more TEDs to warm and/or cool an earpiece inserted into an ear canal of the patient.

The vestibular stimulation device 1 may be configured to generate feedback data. For example, the vestibular stimulation device 1 may comprise one or more sensors as described above, which may generate feedback data responsive to delivering the prescribed thermal waveform(s) to the vestibular system and/or the nervous system of the patient. Similarly, the vestibular stimulation device 1 may comprise a GUI configured generate feedback data (e.g., patient feedback data) responsive to user input.

The vestibular stimulation device 1 may be configured to store feedback data in a database residing therein (e.g., a feedback database as described above) and/or to relay feedback data to the physician control device 2 and/or the physician support device 4. The vestibular stimulation device 1 may be configured to transmit feedback data to the physician control device 2 and/or the physician support device 4 over any suitable wired or wireless communications channel, including, but not limited to, a LAN, the Internet, a public telephone switching network, Bluetooth, WLAN and the like. Likewise, the physician control device 2 and/or the physician support device 4 may be configured to access a feedback database residing in the vestibular stimulation device 1 and to retrieve feedback data using any suitable wired or wireless communications channel, including, but not limited to, a LAN, the Internet, a public telephone switching network, Bluetooth, WLAN and the like. Alternatively, feedback data may be transferred to the physician control device 2 and/or the physician support device 4 using a portable memory device, such as an SD memory card or a USB memory stick.

The physician control device 2 may be configured to supplement feedback data received and/or retrieved from the vestibular stimulation device 1 with additional feedback data (e.g., physician feedback data).

The physician control device 2 may be configured to store feedback data (including any additional feedback data supplied by the physician control device 2) in a database residing therein (e.g., a feedback database as described above) and/or to relay feedback data (including any additional feedback data supplied by the physician control device 2) to the physician support device 4. The physician control device 2 may be configured to transmit feedback data to the physician support device 4 over any suitable wired or wireless communications channel, including, but not limited to, a LAN, the Internet, a public telephone switching network, Bluetooth, WLAN and the like. Likewise, the physician support device 4 may be configured to access a feedback database residing in the physician control device 2 and to retrieve feedback data using any suitable wired or wireless communications channel, including, but not limited to, a LAN, the Internet, a public telephone switching network, Bluetooth, WLAN and the like. Alternatively, feedback data may be transferred to the physician support device 4 using a portable memory device, such as an SD memory card or a USB memory stick.

The physician control device 2 may be configured to analyze feedback data received and/or retrieved from the vestibular stimulation device 1. For example, the physician control device 2 may be configured to use the feedback data to estimate the thermal contact between one or more earpiece and the patient's ear canal(s), to calculate patient-specific time constants, to evaluate the precision with the prescribed thermal waveform(s) was/were delivered, etc.

The physician support device 4 may be configured to analyze feedback data received and/or retrieved from the vestibular stimulation device 1 and/or the physician control device 2. For example, the physician support device 4 may be configured to use the feedback data to identify waveform characteristics that may be linked to increased/decreased efficacy with regard to the treatment of a given disease/disorder/injury, to identify modifications that are likely to increase the effectiveness of a given thermal waveform, class of thermal waveforms or combination of thermal waveforms; to identify new diseases/disorders/injuries for which a given thermal waveform, class of thermal waveforms, combination of thermal waveforms and/or treatment regimen may provide an effective treatment; to predict which thermal waveform(s) or combination(s) of thermal waveforms may be most effective in treating a given disease/disorder/injury; to identify thermal waveforms, classes of thermal waveforms and/or combinations of thermal waveforms that are not likely to be effective in the treatment of a given disease/disorder/injury, etc. In some embodiments, the feedback module is configured to identify new idealized thermal waveforms by identifying one or more diseases/disorders/injuries for which a thermal waveform or class of waveforms is likely to be an effective treatment (e.g., by identifying a new thermal waveform that belongs to a class of waveforms known to be effective in treating one or more diseases/disorders/injuries), to identify one or more additional diseases/disorders/injuries for which a previously identified idealized thermal waveform is likely to be an effective treatment (e.g., by identifying, in a population of patients receiving treatment with an idealized thermal waveform for treatment of a first disease/disorder/injury, one or more co-morbid diseases/disorders/injuries that also appear to be effectively treated by the idealized thermal waveform) and/or to identify one or more diseases/disorders/injuries for which a previously identified idealized thermal waveform is not likely to be an effective treatment (e.g., one or more of the diseases/disorders/injuries for which an idealized thermal waveform had previously been indicated and/or approved may be removed from the list of indications for that thermal waveform or for the class of thermal waveforms to which it belongs).

The physician support device 4 may be configured to modify one or more thermal waveforms responsive to analyzing feedback data received and/or retrieved from the vestibular stimulation device 1 and/or the physician control device 2. For example, the physician support device 4 may be configured to modify one or more parameters of a thermal waveform generated by the physician support device 4 and/or stored in a waveform database residing therein. The physician support device 4 may be configured to modify the thermal waveform(s) automatically (e.g., the physician support device 4 may be configured to automatically modify one or more thermal waveforms if/when any of its analyses indicate that such modifications are likely to improve the efficacy of the thermal waveform(s)) or responsive to user input.

The physician support device 4 may be configured to store one or more modified thermal waveforms in a database residing therein (e.g., a waveform database as described above) and/or to relay the modified thermal waveform(s) to the physician control device 2. The physician support device 4 may be configured to transmit one or more modified thermal waveforms to the physician control device 2 over any suitable wired or wireless communications channel, including, but not limited to, a LAN, the Internet, a public telephone switching network, Bluetooth, WLAN and the like. Likewise, the physician control device 2 may be configured to access a waveform database residing in the physician support device 4 and to retrieve the modified thermal waveform(s) using any suitable wired or wireless communications channel, including, but not limited to, a LAN, the Internet, a public telephone switching network, Bluetooth, WLAN and the like. Alternatively, the modified thermal waveform(s) may be transferred to the physician control device 2 using a portable memory device, such as an SD memory card or a USB memory stick.

The physician control device 2 may be configured to modify one or more prescriptions responsive to analyzing feedback data received and/or retrieved from the vestibular stimulation device 1 and/or to receiving and/or retrieving one or more modified thermal waveforms from the physician support device 4. For example, the physician control device 2 may be configured to modify one or more parameters of a prescription generated by the physician control device 2 and/or stored in a prescription database residing therein. The physician control device 2 may be configured to modify the prescription(s) automatically (e.g., the physician control device 2 may be configured to automatically modify one or more prescriptions if/when any of its analyses indicate that such modifications are likely to improve the efficacy of the prescription(s)) or responsive to user input.

The physician control device 2 may be configured to store one or more modified prescriptions in a database residing therein (e.g., a waveform database as described above) and/or to relay the modified thermal waveform(s) to the vestibular stimulation device 1. The physician control device 2 may be configured to transmit one or more modified prescriptions to the vestibular stimulation device 1 over any suitable wired or wireless communications channel, including, but not limited to, a LAN, the Internet, a public telephone switching network, Bluetooth, WLAN and the like. Likewise, the vestibular stimulation device 1 may be configured to access a prescription database residing in the physician control device 2 and to retrieve the modified prescription(s) using any suitable wired or wireless communications channel, including, but not limited to, a LAN, the Internet, a public telephone switching network, Bluetooth, WLAN and the like. Alternatively, the modified prescription(s) may be transferred to the vestibular stimulation device 1 using a portable memory device, such as an SD memory card or a USB memory stick.

The vestibular stimulation device 1 may be configured to deliver one or more thermal waveforms to the vestibular system and/or the nervous system of the patient in accordance with one or more modified prescriptions to the vestibular system and/or the nervous system of a patient. For example, as described above, the vestibular stimulation device 1 may be configured to deliver the prescribed thermal waveform(s) the vestibular system and/or the nervous system of the patient by activating one or more TEDs to warm and/or cool an earpiece inserted into an ear canal of the patient.

The physician support device 4 may be configured to generate one or more software updates. Each software update may comprise, consist essentially of or consist of a set of instructions for modifying one or more operational parameters of the vestibular stimulation device 1 and/or the physician control device 2.

The physician support device 4 may be configured to store one or more software updates in a database residing therein and/or to relay one or more software updates to the vestibular stimulation device 1 and/or the physician control device 2. The physician support device 4 may be configured to transmit one or more software updates to the vestibular stimulation device 1 and/or the physician control device 2 over any suitable wired or wireless communications channel, including, but not limited to, a LAN, the Internet, a public telephone switching network, Bluetooth, WLAN and the like. Likewise, the vestibular stimulation device 1 and/or the physician control device 2 may be configured to access a database residing in the physician support device 4 and to retrieve one or more software updates using any suitable wired or wireless communications channel, including, but not limited to, a LAN, the Internet, a public telephone switching network, Bluetooth, WLAN and the like. Alternatively, one or more software updates may be transferred to the vestibular stimulation device 1 and/or the physician control device 2 using a portable memory device, such as an SD memory card or a USB memory stick. The software update(s) may be relayed from the physician support device 4 to the vestibular stimulation device 1 and/or the physician control device 2 automatically (e.g., upon generation, once per week, once per month, etc.) or in response to user input.

The physician control device 2 may be configured to store one or more software updates in a database residing therein and/or to relay one or more software updates to the vestibular stimulation device 1. The physician control device 2 may be configured to transmit one or more software updates to the vestibular stimulation device 1 over any suitable wired or wireless communications channel, including, but not limited to, a LAN, the Internet, a public telephone switching network, Bluetooth, WLAN and the like. Likewise, the vestibular stimulation device 1 may be configured to access a database residing in the physician control device 2 and to retrieve one or more software updates using any suitable wired or wireless communications channel, including, but not limited to, a LAN, the Internet, a public telephone switching network, Bluetooth, WLAN and the like. Alternatively, one or more software updates may be transferred to the vestibular stimulation device 1 using a portable memory device, such as an SD memory card or a USB memory stick. The software update(s) may be relayed from the physician control device 2 to the vestibular stimulation device 1 automatically (e.g., upon generation, once per week, once per month, etc.) or in response to user input.

The physician control device 2 may be configured to modify one or more of its operational parameters responsive to receiving and/or retrieving one or more software updates from the physician support device 4. The physician control device 2 may be configured to modify one or more of its operational parameters automatically ((e.g., upon receipt of the software update(s), once per week, once per month, etc.) or in response to user input.

The vestibular stimulation device 1 may be configured to modify one or more of its operational parameters responsive to receiving and/or retrieving one or more software updates from the physician support device 4 and/or the physician control device 2. The vestibular stimulation device 1 may be configured to modify one or more of its operational parameters automatically ((e.g., upon receipt of the software update(s), once per week, once per month, etc.) or in response to user input.

As shown in FIG. 40, in some embodiments, the vestibular stimulation system comprises, consists essentially of or consists of a physician support device 4 operatively connected to a plurality of physician control devices 2a, 2b wherein each of said plurality of physician control devices 2a, 2b is operatively connected a plurality of vestibular stimulation devices 1a, 1b, 1c, 1d. In some embodiments, one or more of the vestibular stimulation devices 1a, 1b, 1c, 1d is also operatively connected to the physician support device 4 via an independent operative connection (i.e., independent of the physician control device 2a, 2b with which it is associated).

The physician support device 4 may be configured to generate one or more thermal waveforms (i.e., to generate the parameters, indications and/or approvals of one or more thermal waveforms) and/or to store the thermal waveform(s) in a database (e.g., to store the parameters, indications and/or approvals of the thermal waveform(s) in a waveform database as described above).

The physician support device 4 may be configured to store one or more thermal waveform(s) in a database residing therein (e.g., a waveform database as described above) and/or relay one or more thermal waveforms to one or more of the physician control devices 2a, 2b. The physician support device 4 may be configured to transmit one or more prescriptions to the physician control devices 2a, 2b over any suitable wired or wireless communications channel, including, but not limited to, a LAN, the Internet, a public telephone switching network, Bluetooth, WLAN and the like. Likewise, each of the physician control devices 2a, 2b may be configured to access a waveform database residing in the physician support device 4 and to retrieve one or more thermal waveform(s) using any suitable wired or wireless communications channel, including, but not limited to, a LAN, the Internet, a public telephone switching network, Bluetooth, WLAN and the like. Alternatively, one or more thermal waveform(s) may be transferred to the physician control devices 2a, 2b using a portable memory device, such as an SD memory card or a USB memory stick.

Each of the physician control devices 2a, 2b may be configured to generate a plurality of prescriptions, each comprising a set of instructions for delivering one or more thermal waveforms to the vestibular system and/or the nervous system of a patient. In such embodiments, one or more of the prescriptions may comprise a set of instructions for delivering one or more of the thermal waveforms generated by the physician support device 4 to the vestibular system and/or the nervous system of a patient.

Each of the physician control devices 2a, 2b may be configured to store one or more prescriptions in a database residing therein (e.g., a prescription database as described above) and/or to relay each prescription to a vestibular stimulation device 1a, 1b, 1c, 1d associated with the patient for whom the prescription was generated. The physician control devices 2a, 2b may be configured to transmit the prescriptions to the vestibular stimulation devices 1a, 1b, 1c, 1d over any suitable wired or wireless communications channel, including, but not limited to, a LAN, the Internet, a public telephone switching network, Bluetooth, WLAN and the like. Likewise, each of the vestibular stimulation devices 1a, 1b, 1c, 1d may be configured to access a prescription database residing in the physician control device 2a, 2b with which it is associated and to retrieve the prescriptions using any suitable wired or wireless communications channel, including, but not limited to, a LAN, the Internet, a public telephone switching network, Bluetooth, WLAN and the like. Alternatively, the prescriptions may be transferred to the vestibular stimulation devices 1a, 1b, 1c, 1d using one or more portable memory devices, such as SD memory cards and/or USB memory sticks.

Each of the vestibular stimulation devices 1a, 1b, 1c, 1d may be configured to deliver one or more prescribed thermal waveforms to the vestibular system and/or the nervous system of the patient for whom the prescription was generated. For example, as described above, each vestibular stimulation device 1a, 1b, 1c, 1d may be configured to deliver the prescribed thermal waveform(s) the vestibular system and/or the nervous system of the patient by activating one or more TEDs to warm and/or cool an earpiece inserted into an ear canal of the patient.

Each of the vestibular stimulation devices 1a, 1b, 1c, 1d may be configured to store feedback data in a database residing therein (e.g., a feedback database as described above) and/or to relay feedback data to the physician control device 2a, 2b with which it is associated and/or to the physician support device 4. Each of the vestibular stimulation devices 1a, 1b, 1c, 1d may be configured to transmit feedback data to the physician control device 2a, 2b with which it is associated and/or to the physician support device 4 over any suitable wired or wireless communications channel, including, but not limited to, a LAN, the Internet, a public telephone switching network, Bluetooth, WLAN and the like. Likewise, each of the physician control devices 2a, 2b and/or to the physician support device 4 may be configured to access one or more feedback databases residing in the vestibular stimulation devices 1a, 1b, 1c, 1d and to retrieve feedback data using any suitable wired or wireless communications channel, including, but not limited to, a LAN, the Internet, a public telephone switching network, Bluetooth, WLAN and the like. Alternatively, feedback data may be transferred to the physician control devices 2a, 2b and/or to the physician support device 4 using a portable memory device, such as an SD memory card or a USB memory stick.

Each of the physician control devices 2a, 2b may be configured to supplement feedback data received and/or retrieved from the vestibular stimulation device 1a, 1b, 1c, 1d with which it is associated with additional feedback data (e.g., physician feedback data).

Each of the physician control devices 2a, 2b may be configured to store feedback data (including any additional feedback data supplied by the physician control devices 2a, 2b) in a database residing therein (e.g., a feedback database as described above) and/or to relay feedback data (including any additional feedback data supplied by the physician control devices 2a, 2b) to the physician support device 4. The physician control devices 2a, 2b 2 may be configured to transmit feedback data to the physician support device 4 over any suitable wired or wireless communications channel, including, but not limited to, a LAN, the Internet, a public telephone switching network, Bluetooth, WLAN and the like. Likewise, the physician support device 4 may be configured to access one or more feedback databases residing in the physician control devices 2a, 2b and to retrieve feedback data using any suitable wired or wireless communications channel, including, but not limited to, a LAN, the Internet, a public telephone switching network, Bluetooth, WLAN and the like. Alternatively, feedback data may be transferred to the physician support device 4 using a portable memory device, such as an SD memory card or a USB memory stick.

Each of the physician control devices 2a, 2b may be configured to analyze feedback data received and/or retrieved from the vestibular stimulation device 1a, 1b, 1c, 1d with which it is associated. For example, the physician control devices 2a, 2b may be configured to use the feedback data to estimate the thermal contact between one or more earpiece and the patient's ear canal(s), to calculate patient-specific time constants, to evaluate the precision with the prescribed thermal waveform(s) was/were delivered, etc.

The physician support device 4 may be configured to analyze feedback data received and/or retrieved from the vestibular stimulation devices 1a, 1b, 1c, 1d and/or the physician control devices 2a, 2b. For example, the physician support device 4 may be configured to use the feedback data to identify waveform characteristics that may be linked to increased/decreased efficacy with regard to the treatment of a given disease/disorder/injury, to identify modifications that are likely to increase the effectiveness of a given thermal waveform, class of thermal waveforms or combination of thermal waveforms; to identify new diseases/disorders/injuries for which a given thermal waveform, class of thermal waveforms, combination of thermal waveforms and/or treatment regimen may provide an effective treatment; to predict which thermal waveform(s) or combination(s) of thermal waveforms may be most effective in treating a given disease/disorder/injury; to identify thermal waveforms, classes of thermal waveforms and/or combinations of thermal waveforms that are not likely to be effective in the treatment of a given disease/disorder/injury, etc. In some embodiments, the feedback module is configured to identify new idealized thermal waveforms by identifying one or more diseases/disorders/injuries for which a thermal waveform or class of waveforms is likely to be an effective treatment (e.g., by identifying a new thermal waveform that belongs to a class of waveforms known to be effective in treating one or more diseases/disorders/injuries), to identify one or more additional diseases/disorders/injuries for which a previously identified idealized thermal waveform is likely to be an effective treatment (e.g., by identifying, in a population of patients receiving treatment with an idealized thermal waveform for treatment of a first disease/disorder/injury, one or more co-morbid diseases/disorders/injuries that also appear to be effectively treated by the idealized thermal waveform) and/or to identify one or more diseases/disorders/injuries for which a previously identified idealized thermal waveform is not likely to be an effective treatment (e.g., one or more of the diseases/disorders/injuries for which an idealized thermal waveform had previously been indicated and/or approved may be removed from the list of indications for that thermal waveform or for the class of thermal waveforms to which it belongs).

The physician support device 4 may be configured to modify one or more thermal waveforms responsive to analyzing feedback data received and/or retrieved from the vestibular stimulation devices 1a, 1b, 1c, 1d and/or the physician control devices 2a, 2b. For example, the physician support device 4 may be configured to modify one or more parameters of a thermal waveform generated by the physician support device 4 and/or stored in a waveform database residing therein. The physician support device 4 may be configured to modify the thermal waveform(s) automatically (e.g., the physician support device 4 may be configured to automatically modify one or more thermal waveforms if/when any of its analyses indicate that such modifications are likely to improve the efficacy of the thermal waveform(s)) or responsive to user input.

The physician support device 4 may be configured to store one or more modified thermal waveforms in a database residing therein (e.g., a waveform database as described above) and/or to relay the modified thermal waveform(s) to one or more of the physician control devices 2a, 2b. The physician support device 4 may be configured to transmit one or more modified thermal waveforms to one or more of the physician control devices 2a, 2b over any suitable wired or wireless communications channel, including, but not limited to, a LAN, the Internet, a public telephone switching network, Bluetooth, WLAN and the like. Likewise, each of the physician control devices 2a, 2b may be configured to access a waveform database residing in the physician support device 4 and to retrieve the modified thermal waveform(s) using any suitable wired or wireless communications channel, including, but not limited to, a LAN, the Internet, a public telephone switching network, Bluetooth, WLAN and the like. Alternatively, the modified thermal waveform(s) may be transferred to the physician control devices 2a, 2b using a portable memory device, such as an SD memory card or a USB memory stick.

Each of the physician control devices 2a, 2b may be configured to modify one or more prescriptions responsive to analyzing feedback data received and/or retrieved from the vestibular stimulation device 1a, 1b, 1c, 1d with which it is associated and/or to receiving and/or retrieving one or more modified thermal waveforms from the physician support device 4. For example, the physician control devices 2a, 2b may be configured to modify one or more parameters of a prescription generated by the physician control devices 2a, 2b and/or stored in a prescription database residing therein. The physician control devices 2a, 2b may be configured to modify the prescription(s) automatically (e.g., the physician control devices 2a, 2b may be configured to automatically modify one or more prescriptions if/when any of its analyses indicate that such modifications are likely to improve the efficacy of the prescription(s)) or responsive to user input.

Each of the physician control devices 2a, 2b may be configured to store one or more modified prescriptions in a database residing therein (e.g., a waveform database as described above) and/or to relay the modified thermal waveform(s) to the vestibular stimulation device 1a, 1b, 1c, 1d with which it is associated. The physician control devices 2a, 2b may be configured to transmit one or more modified prescriptions to the vestibular stimulation device 1a, 1b, 1c, 1d with which it is associated over any suitable wired or wireless communications channel, including, but not limited to, a LAN, the Internet, a public telephone switching network, Bluetooth, WLAN and the like. Likewise, each of the vestibular stimulation devices 1a, 1b, 1c, 1d may be configured to access a prescription database residing in the physician control device 2a, 2b with which it is associated and to retrieve the modified prescription(s) using any suitable wired or wireless communications channel, including, but not limited to, a LAN, the Internet, a public telephone switching network, Bluetooth, WLAN and the like. Alternatively, the modified prescription(s) may be transferred to the vestibular stimulation devices 1a, 1b, 1c, 1d using a portable memory device, such as an SD memory card or a USB memory stick.

Each of the vestibular stimulation devices 1a, 1b, 1c, 1d may be configured to deliver one or more thermal waveforms to the vestibular system and/or the nervous system of the patient in accordance with one or more modified prescriptions to the vestibular system and/or the nervous system of a patient. For example, as described above, the vestibular stimulation device 1 may be configured to deliver the prescribed thermal waveform(s) the vestibular system and/or the nervous system of the patient by activating one or more TEDs to warm and/or cool an earpiece inserted into an ear canal of the patient.

The physician support device 4 may be configured to generate one or more software updates. Each software update may comprise, consist essentially of or consist of a set of instructions for modifying one or more operational parameters one or more of the vestibular stimulation devices 1a, 1b, 1c, 1d and/or one or more of the physician control devices 2a, 2b.

The physician support device 4 may be configured to store one or more software updates in a database residing therein and/or to relay one or more software updates to one or more of the vestibular stimulation devices 1a, 1b, 1c, 1d and/or one or more of the physician control devices 2a, 2b. The physician support device 4 may be configured to transmit one or more software updates to the vestibular stimulation devices 1a, 1b, 1c, 1d and/or the physician control devices 2a, 2b over any suitable wired or wireless communications channel, including, but not limited to, a LAN, the Internet, a public telephone switching network, Bluetooth, WLAN and the like. Likewise, each of the vestibular stimulation devices 1a, 1b, 1c, 1d and/or each of the physician control devices 2a, 2b may be configured to access a database residing in the physician support device 4 and to retrieve one or more software updates using any suitable wired or wireless communications channel, including, but not limited to, a LAN, the Internet, a public telephone switching network, Bluetooth, WLAN and the like. Alternatively, one or more software updates may be transferred to the vestibular stimulation devices 1a, 1b, 1c, 1d and/or the physician control devices 2a, 2b using a portable memory device, such as an SD memory card or a USB memory stick. The software update(s) may be relayed from the physician support device 4 to the vestibular stimulation devices 1a, 1b, 1c, 1d and/or the physician control devices 2a, 2b automatically (e.g., upon generation, once per week, once per month, etc.) or in response to user input.

Each of the physician control devices 2a, 2b may be configured to store one or more software updates in a database residing therein and/or transmit one or more software updates to one or more of the vestibular stimulation devices 1a, 1b, 1c, 1d with which it is associated. The physician control devices 2a, 2b may be configured to transmit the software update(s) to one or more of the vestibular stimulation devices 1a, 1b, 1c, 1d with which it is associated over any suitable wired or wireless communications channel, including, but not limited to, a LAN, the Internet, a public telephone switching network, Bluetooth, WLAN and the like. Likewise, each of the vestibular stimulation devices 1a, 1b, 1c, 1d may be configured to access a database residing in the physician control device 2a, 2b with which it is associated and to retrieve one or more software updates using any suitable wired or wireless communications channel, including, but not limited to, a LAN, the Internet, a public telephone switching network, Bluetooth, WLAN and the like. Alternatively, one or more software updates may be transferred to the vestibular stimulation devices 1a, 1b, 1c, 1d using a portable memory device, such as an SD memory card or a USB memory stick.

Each of the physician control devices 2a, 2b may be configured to modify one or more of its operational parameters responsive to receiving and/or retrieving one or more software updates from the physician support device 4. The physician control devices 2a, 2b may be configured to modify one or more of its operational parameters automatically ((e.g., upon receipt of the software update(s), once per week, once per month, etc.) or in response to user input.

Each of the vestibular stimulation devices 1a, 1b, 1c, 1d may be configured to modify one or more of its operational parameters responsive to receiving and/or retrieving one or more software updates from the physician support device 4 and/or the physician control device 2a, 2b with which it is associated. The vestibular stimulation devices 1a, 1b, 1c, 1d may be configured to modify one or more of its operational parameters automatically ((e.g., upon receipt of the software update(s), once per week, once per month, etc.) or in response to user input.

Figure 41:
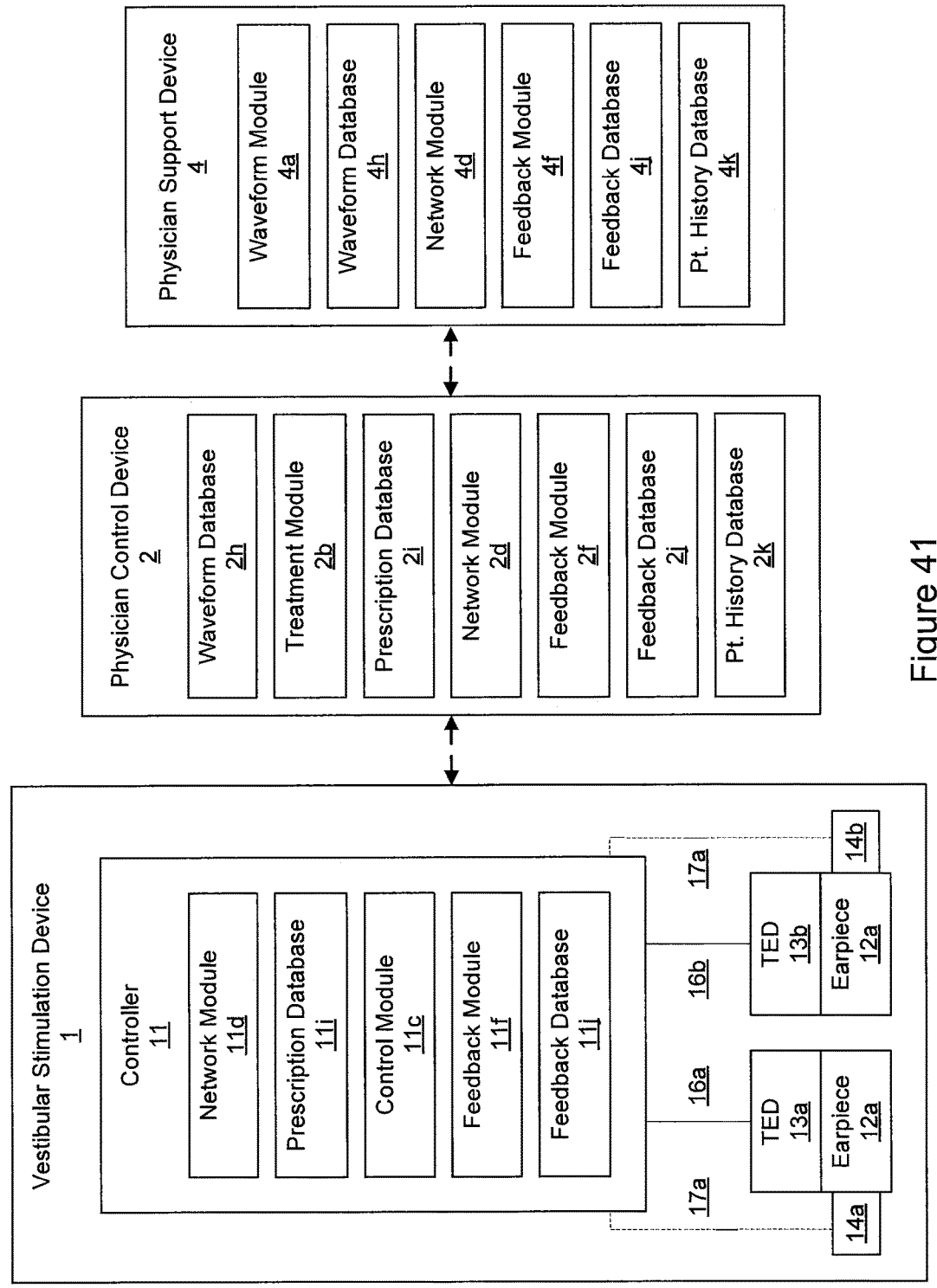
FIG. 41 is a block diagram of a vestibular stimulation system according to some embodiments of the present invention comprising a vestibular stimulation device, a physician control device and a physician support device.

As shown in FIG. 41, in some embodiments, the vestibular stimulation system comprises, consists essentially of or consists of a physician support device 4, a physician control device 2 and a vestibular stimulation device 1 comprising a controller 11, a pair of earpieces 12a, 12b, a pair of TEDs 13a, 13b and a pair of sensors 14a, 14b, wherein each of the TEDs 13a, 13b is operatively connected to the controller 11 via a thermal stimulation lead 16a, 16b and thermally connected to one of the earpieces 12a, 12b and wherein each of the sensors 14a, 14b is operatively connected to the controller 11 via a wireless connection 17a, 17b and thermally connected to one of the earpieces 12a, 12b. In some such embodiments, the physician support device 4 comprises a waveform module 4a, a network module 4d, a feedback module 4f, a waveform database 4h, a feedback database 4j and a patient history database 4k; the physician control device 2 comprises a treatment module 2b, a network module 2d, a feedback module 2f, a waveform database 2h, a prescription database 2i, a feedback database 2j and a patient history database 2k and the controller comprises a control module 11c, a network module 11d, a feedback module 11f, a prescription database 11i and a feedback database 11j.

The waveform module 4a may be configured to generate one or more thermal waveforms (i.e., to generate the parameters, indications and/or approvals of one or more thermal waveforms). The physician support device 4 may be configured such that the thermal waveforms generated by the waveform module 4a are transmitted directly to the physician control device 2 by the network module residing in the physician support device 4 and/or are stored in the waveform database 4h residing in the physician support device 4, from whence they may subsequently be transmitted to and/or retrieved by the physician control device 2.

The network module 2d residing in the physician control device 2 may be configured to receive and/or retrieve thermal waveforms generated by the waveform module 4a from the physician support device 4 and to relay the thermal waveforms to the treatment module 2b and/or to the waveform database 2h residing in the physician control device 2, from whence they may subsequently be transmitted to and/or retrieved by the treatment module 2b.

The treatment module 2b may be configured to retrieve the thermal waveforms generated by the waveform module 4a from the waveform database 2h residing in the physician control device 2 and/or from the waveform database 4h residing in the physician support device 4.

The treatment module 2b may be configured to generate a prescription comprising a set of instructions for delivering one or more of the thermal waveforms generated by the waveform module 4a to the vestibular system and/or the nervous system of a patient. The physician control device 2 may be configured such that the prescription generated by the treatment module 2b is transmitted directly to the vestibular stimulation device 1 by the network module 2d residing in the physician control device 2 and/or is stored in the prescription database 2i residing in the physician control device 2, from whence it may subsequently be transmitted to and/or retrieved by the vestibular stimulation device 1.

The network module 11d residing in the controller 11 may be configured to receive and/or retrieve the prescription from the physician control device 2 and to relay the prescription to the control module 11c and/or to the prescription database 11i residing in the controller 11.

The control module 11c may be configured to retrieve the prescription from the prescription database 11i residing in the controller 11.

The control module 11c may be configured to deliver the prescribed thermal waveform(s) by activating the TEDs 13a, 13b in accordance with the prescription (i.e., by activating the TEDs 13a, 13b to by warm and/or cool the earpieces 12a, 12b so as to deliver the prescribed thermal waveform(s)).

The feedback module 11f residing in the controller 11 may be configured to receive feedback data from the TEDs 13a, 13b and/or the sensors 14a, 14b (e.g., data associated with the temperature of the earpieces 12a, 12b, the temperature of the patient's ear canals, the impedance between the earpieces 12a, 12b, etc.). The controller 11 may be configured such that the feedback data received by the feedback module 11f is transmitted directly to the physician control device 2 and/or the physician support device 4 by the network module 11d residing in the controller 11 and/or is stored in the feedback database 11j residing in the controller 11, from whence it may subsequently be transmitted to and/or retrieved by the physician control device 2 and/or the physician support device 4.

The network module 2d residing in the physician control device 2 may be configured to receive and/or retrieve feedback data from the vestibular stimulation device 1 and to relay the feedback data to the physician support device 4, to the feedback module 2f residing in the physician control device 2 and/or to the feedback database 2j residing in the physician control device 2, from whence they may subsequently be transmitted to and/or retrieved by the physician support device 4 and/or the feedback module 2f residing in the physician control device 2.

The physician control device 2 may be configured to supplement the feedback data received and/or retrieved from the vestibular stimulation device 1 with additional feedback data (e.g., physician comments regarding the effectiveness of a given thermal waveform, class of thermal waveforms, combination of thermal waveforms, etc.) and to relay the additional feedback data to the physician support device 4, to the feedback module 2f residing in the physician control device 2 and/or to the feedback database 2j residing in the physician control device 2, from whence they may subsequently be transmitted to and/or retrieved by the physician support device 4 and/or the feedback module 2f residing in the physician control device 2.

The feedback module 2f residing in the physician control device 2 may be configured to retrieve feedback data (including any additional feedback data supplied by the physician control device 2) from the feedback database 2j residing in the physician control device 2.

The feedback module 2f residing in the physician control device 2 may be configured to analyze the feedback data (e.g., to estimate the thermal contact between each of the earpieces 12a, 12b and the patient's ear canals, to calculate patient-specific time constants, to evaluate the precision with the prescribed thermal waveform(s) was delivered, etc.). The physician control device 2 may be configured such that data associated with the feedback module's 2f analysis are transmitted to the physician support device 4 and/or to the feedback database 2j residing in the physician control device 2, from whence they may subsequently be transmitted to and/or retrieved by the physician support device 4.

The network module 4d residing in the physician support device 4 may be configured to receive and/or retrieve feedback data (including any additional feedback data supplied by the physician control device 2 and/or data associated with any analysis performed by the feedback module 2f residing in the physician control device 2) from the physician control device 2 and to relay the feedback data to the feedback module 4f residing in the physician support device 4 and/or to the feedback database 4j residing in the physician support device 4, from whence they may subsequently be transmitted to and/or retrieved by the feedback module 4f residing in the physician support device 4.

The physician control device 2 may be configured to generate and/or modify patient information (e.g., information related to a patient's identity, medical history, current symptoms, current prescriptions, etc.). The physician control device 2 may be configured to transmit patient information to the physician control device 4 and/or to the patient history database 2k residing in the physician control device 2, from whence it may subsequently be transmitted to and/or retrieved by the physician support device 4.

The network module 4d residing in the physician support device 4 may be configured to receive and/or retrieve patient information from the physician control device 2 and to relay the patient information to the feedback module 4f residing in the physician support device 4 and/or to the patient history database 4k residing in the physician support device 4, from whence it may subsequently be transmitted to and/or retrieved by the feedback module 4f residing in the physician support device 4.

The feedback module 4f residing in the physician support device 4 may be configured to analyze the feedback data and/or the patient information (e.g., to identify modifications that are likely to increase the effectiveness of a given thermal waveform, class of thermal waveforms or combination of thermal waveforms). The physician support device 4 may be configured such that data associated with the feedback module's 4f analysis are transmitted to the physician control device 2, to the waveform module 4a and/or to the feedback database 4j residing in the physician support device 4, from whence they may subsequently be transmitted to and/or retrieved by the physician control device 2 and/or the waveform module 4a.

The network module 2d residing in the physician control device 2 may be configured to receive and/or retrieve data associated with the feedback module's 4f analysis from the physician support device 4 and to relay that data to the treatment module 2b and/or to the feedback database 2j residing in the physician control device 2, from whence they may subsequently be transmitted to and/or retrieved by the treatment module 2b.

The waveform module 4a may be configured to retrieve data associated with the feedback module's 4f analysis from the feedback database 4j residing in the physician support device 4.

The waveform module 4a may be configured to modify one or more of the thermal waveforms responsive to receiving and/or retrieving data associated with the feedback module's 4f analysis (e.g., by modifying one or more of the parameters, indications and/or approvals of a thermal waveform). The waveform module 4a may be configured to modify the thermal waveform(s) automatically (e.g., the waveform module 4a may be configured to periodically check the feedback database 4j for new analyses and to automatically modify one or more thermal waveforms if/when any analysis performed by the feedback module 4f indicates that such modifications are likely to improve the efficacy of the thermal waveform(s)) or responsive to user input. The physician support device 4 may be configured such that any modifications made by the waveform module 4a are relayed to the physician control device 2 as described above.

The treatment module 2b may be configured to retrieve data associated with the feedback module's 2f analysis from the feedback database 2j residing in the physician control device 2 and/or to retrieve any modifications made by the waveform module 4a from the waveform database 2h residing in the physician control device 2 and/or from the waveform database residing in the physician support device 4.

The treatment module 2b may be configured to modify, update and/or extend the prescription responsive to receiving and/or retrieving data associated with the feedback module's 2f analysis and/or to receiving and/or retrieving any modifications made by the waveform module 2a. The treatment module 2b may be configured to modify, update and/or extend the prescription automatically (e.g., the treatment module 2b may be configured to periodically check the waveform database 2h for updates and to automatically modify the prescription if/when one or more of the parameters, indications or approvals of a thermal waveform used in the prescription has been modified by the waveform module 4a) or responsive to user input. The physician control device 2 may be configured such that any modifications made by the treatment module 2b are relayed to the vestibular stimulation device 1 as described above.

As shown in FIG. 42 the vestibular stimulation system may comprise, consist essentially of or consist of a vestibular stimulation device 1 operatively connected to a physician control device 2 that is operatively connected to a physician support device 4, which is itself operatively connected to a registry 5.

The registry 5 may be configured to store data associated with one or more thermal waveforms (e.g., one or more idealized thermal waveforms) in a database residing therein (e.g., to store the parameters, indications and/or approvals of the thermal waveform(s) in a waveform database as described above) and/or to relay data associated with one or more thermal waveforms to the physician support device 4. The registry 5 may be configured to transmit one or more thermal waveforms to the physician support device 4 over any suitable wired or wireless communications channel, including, but not limited to, a LAN, the Internet, a public telephone switching network, Bluetooth, WLAN and the like. Likewise, the physician support device 4 may be configured to access a waveform database residing in the registry 5 and to retrieve one or more thermal waveform(s) using any suitable wired or wireless communications channel, including, but not limited to, a LAN, the Internet, a public telephone switching network, Bluetooth, WLAN and the like. Alternatively, one or more thermal waveform(s) may be transferred to the physician support device 4 using a portable memory device, such as an SD memory card or a USB memory stick.

The physician support device 4 may be configured to modify one or more of the thermal waveforms received/retrieved from the registry 5 (i.e., to modify one or more of the parameters, indications and/or approvals of one or more thermal waveforms) and/or to store the modified thermal waveform(s) in a database (e.g., to store the parameters, indications and/or approvals of the modified thermal waveform(s) in a waveform database as described above).

The physician support device 4 may be configured to store one or more thermal waveform(s) (including the modified thermal waveforms discussed above) in a database residing therein (e.g., a waveform database as described above) and/or relay one or more thermal waveforms to the physician control device 2. The physician support device 4 may be configured to transmit one or more prescriptions to the physician control device 2 over any suitable wired or wireless communications channel, including, but not limited to, a LAN, the Internet, a public telephone switching network, Bluetooth, WLAN and the like. Likewise, the physician control device 2 may be configured to access a waveform database residing in the physician support device 4 and to retrieve one or more thermal waveform(s) using any suitable wired or wireless communications channel, including, but not limited to, a LAN, the Internet, a public telephone switching network, Bluetooth, WLAN and the like. Alternatively, one or more thermal waveform(s) may be transferred to the physician control device 2 using a portable memory device, such as an SD memory card or a USB memory stick.

The physician control device 2 may be configured to generate one or more prescriptions. Each prescription may comprise, consist essentially of or consist of a set of instructions for delivering one or more thermal waveforms to the vestibular system and/or the nervous system of a patient. In such embodiments, the prescription may comprise a set of instructions for delivering one or more of the thermal waveforms generated by the physician support device 4 to the vestibular system and/or the nervous system of a patient.

The physician control device 2 may be configured to store one or more prescriptions in a database residing therein (e.g., a prescription database as described above) and/or to relay one or more prescriptions to the vestibular stimulation device 1. The physician control device 2 may be configured to transmit one or more prescriptions to the vestibular stimulation device 1 over any suitable wired or wireless communications channel, including, but not limited to, a LAN, the Internet, a public telephone switching network, Bluetooth, WLAN and the like. Likewise, the vestibular stimulation device 1 may be configured to access a prescription database residing in the physician control device 2 and to retrieve one or more prescriptions using any suitable wired or wireless communications channel, including, but not limited to, a LAN, the Internet, a public telephone switching network, Bluetooth, WLAN and the like. Alternatively, one or more prescriptions may be transferred to the vestibular stimulation device 1 using a portable memory device, such as an SD memory card or a USB memory stick.

The vestibular stimulation device 1 may be configured to deliver one or more prescribed thermal waveforms to the vestibular system and/or the nervous system of a patient. For example, as described above, the vestibular stimulation device 1 may be configured to deliver the prescribed thermal waveform(s) the vestibular system and/or the nervous system of the patient by activating one or more TEDs to warm and/or cool an earpiece inserted into an ear canal of the patient.

The vestibular stimulation device 1 may be configured to generate feedback data. For example, the vestibular stimulation device 1 may comprise one or more sensors as described above, which may generate feedback data responsive to delivering the prescribed thermal waveform(s) to the vestibular system and/or the nervous system of the patient. Similarly, the vestibular stimulation device 1 may comprise a GUI configured generate feedback data (e.g., patient feedback data) responsive to user input.

The vestibular stimulation device 1 may be configured to store feedback data in a database residing therein (e.g., a feedback database as described above) and/or to relay feedback data to the physician control device 2, the physician support device 4 and/or the registry 5. The vestibular stimulation device 1 may be configured to transmit feedback data to the physician control device 2, the physician support device 4 and/or the registry 5 over any suitable wired or wireless communications channel, including, but not limited to, a LAN, the Internet, a public telephone switching network, Bluetooth, WLAN and the like. Likewise, the physician control device 2, the physician support device 4 and/or the registry 5 may be configured to access a feedback database residing in the vestibular stimulation device 1 and to retrieve feedback data using any suitable wired or wireless communications channel, including, but not limited to, a LAN, the Internet, a public telephone switching network, Bluetooth, WLAN and the like. Alternatively, feedback data may be transferred to the physician control device 2, the physician support device 4 and/or the registry 5 using a portable memory device, such as an SD memory card or a USB memory stick.

The physician control device 2 may be configured to supplement feedback data received and/or retrieved from the vestibular stimulation device 1 with additional feedback data (e.g., physician feedback data).

The physician control device 2 may be configured to analyze feedback data received and/or retrieved from the vestibular stimulation device 1. For example, the physician control device 2 may be configured to use the feedback data to estimate the thermal contact between one or more earpiece and the patient's ear canal(s), to calculate patient-specific time constants, to evaluate the precision with the prescribed thermal waveform(s) was/were delivered, etc.

The physician control device 2 may be configured to store feedback data (including any additional feedback data supplied by the physician control device 2 and any data associated with the analysis described above) in a database residing therein (e.g., a feedback database as described above) and/or to relay feedback data (including any additional feedback data supplied by the physician control device 2 and any data associated with the analysis described above) to the physician support device 4 and/or the registry 5. The physician control device 2 may be configured to transmit feedback data to the physician support device 4 and/or the registry 5 over any suitable wired or wireless communications channel, including, but not limited to, a LAN, the Internet, a public telephone switching network, Bluetooth, WLAN and the like. Likewise, the physician support device 4 and/or the registry 5 may be configured to access a feedback database residing in the physician control device 2 and to retrieve feedback data using any suitable wired or wireless communications channel, including, but not limited to, a LAN, the Internet, a public telephone switching network, Bluetooth, WLAN and the like. Alternatively, feedback data may be transferred to the physician support device 4 and/or the registry 5 using a portable memory device, such as an SD memory card or a USB memory stick.

The physician support device 4 may be configured to supplement feedback data received and/or retrieved from the vestibular stimulation device 1 and/or the physician control device 2 with additional feedback data (e.g., physician feedback data).

The physician support device 4 may be configured to analyze feedback data received and/or retrieved from the vestibular stimulation device 1 and/or the physician control device 2. For example, the physician support device 4 may be configured to use the feedback data to identify waveform characteristics that may be linked to increased/decreased efficacy with regard to the treatment of a given disease/disorder/injury, to identify modifications that are likely to increase the effectiveness of a given thermal waveform, class of thermal waveforms or combination of thermal waveforms; to identify new diseases/disorders/injuries for which a given thermal waveform, class of thermal waveforms, combination of thermal waveforms and/or treatment regimen may provide an effective treatment; to predict which thermal waveform(s) or combination(s) of thermal waveforms may be most effective in treating a given disease/disorder/injury; to identify thermal waveforms, classes of thermal waveforms and/or combinations of thermal waveforms that are not likely to be effective in the treatment of a given disease/disorder/injury, etc. In some embodiments, the feedback module is configured to identify new idealized thermal waveforms by identifying one or more diseases/disorders/injuries for which a thermal waveform or class of waveforms is likely to be an effective treatment (e.g., by identifying a new thermal waveform that belongs to a class of waveforms known to be effective in treating one or more diseases/disorders/injuries), to identify one or more additional diseases/disorders/injuries for which a previously identified idealized thermal waveform is likely to be an effective treatment (e.g., by identifying, in a population of patients receiving treatment with an idealized thermal waveform for treatment of a first disease/disorder/injury, one or more co-morbid diseases/disorders/injuries that also appear to be effectively treated by the idealized thermal waveform) and/or to identify one or more diseases/disorders/injuries for which a previously identified idealized thermal waveform is not likely to be an effective treatment (e.g., one or more of the diseases/disorders/injuries for which an idealized thermal waveform had previously been indicated and/or approved may be removed from the list of indications for that thermal waveform or for the class of thermal waveforms to which it belongs).

The physician support device 4 may be configured to store feedback data (including any additional feedback data supplied by the physician support device 4 and any data associated with the analysis described above) in a database residing therein (e.g., a feedback database as described above) and/or to relay feedback data (including any additional feedback data supplied by the physician support device 4 and any data associated with the analysis described above) to the registry 5. The physician support device 4 may be configured to transmit feedback data to the registry 5 over any suitable wired or wireless communications channel, including, but not limited to, a LAN, the Internet, a public telephone switching network, Bluetooth, WLAN and the like. Likewise, the registry 5 may be configured to access a feedback database residing in the physician support device 4 and to retrieve feedback data using any suitable wired or wireless communications channel, including, but not limited to, a LAN, the Internet, a public telephone switching network, Bluetooth, WLAN and the like. Alternatively, feedback data may be transferred to the registry 5 using a portable memory device, such as an SD memory card or a USB memory stick.

The physician support device 4 may be configured to modify one or more thermal waveforms responsive to analyzing feedback data received and/or retrieved from the vestibular stimulation device 1 and/or the physician control device 2. For example, the physician support device 4 may be configured to modify one or more parameters of the thermal waveform(s) received/retrieved from the registry 5. The physician support device 4 may be configured to modify the thermal waveform(s) automatically (e.g., the physician support device 4 may be configured to automatically modify one or more thermal waveforms if/when any of its analyses indicate that such modifications are Rely to improve the efficacy of the thermal waveform(s)) or responsive to user input.

The physician support device 4 may be configured to store one or more modified thermal waveforms in a database residing therein (e.g., a waveform database as described above) and/or to relay the modified thermal waveform(s) to the physician control device 2 and/or the registry 5. The physician support device 4 may be configured to transmit one or more modified thermal waveforms to the physician control device 2 and/or the registry 5 over any suitable wired or wireless communications channel, including, but not limited to, a LAN, the Internet, a public telephone switching network, Bluetooth, WLAN and the like. Likewise, the physician control device 2 and/or the registry 5 may be configured to access a waveform database residing in the physician support device 4 and to retrieve the modified thermal waveform(s) using any suitable wired or wireless communications channel, including, but not limited to, a LAN, the Internet, a public telephone switching network, Bluetooth, WLAN and the like. Alternatively, the modified thermal waveform(s) may be transferred to the physician control device 2 and/or the registry 5 using a portable memory device, such as an SD memory card or a USB memory stick.

The physician control device 2 may be configured to modify one or more prescriptions responsive to analyzing feedback data received and/or retrieved from the vestibular stimulation device 1 and/or to receiving and/or retrieving one or more modified thermal waveforms from the physician support device 4. For example, the physician control device 2 may be configured to modify one or more parameters of a prescription generated by the physician control device 2 and/or stored in a prescription database residing therein. The physician control device 2 may be configured to modify the prescription(s) automatically (e.g., the physician control device 2 may be configured to automatically modify one or more prescriptions if/when any of its analyses indicate that such modifications are likely to improve the efficacy of the prescription(s)) or responsive to user input.

The physician control device 2 may be configured to store one or more modified prescriptions in a database residing therein (e.g., a waveform database as described above) and/or to relay the modified thermal waveform(s) to the vestibular stimulation device 1. The physician control device 2 may be configured to transmit one or more modified prescriptions to the vestibular stimulation device 1 over any suitable wired or wireless communications channel, including, but not limited to, a LAN, the Internet, a public telephone switching network, Bluetooth, WLAN and the like. Likewise, the vestibular stimulation device 1 may be configured to access a prescription database residing in the physician control device 2 and to retrieve the modified prescription(s) using any suitable wired or wireless communications channel, including, but not limited to, a LAN, the Internet, a public telephone switching network, Bluetooth, WLAN and the like. Alternatively, the modified prescription(s) may be transferred to the vestibular stimulation device 1 using a portable memory device, such as an SD memory card or a USB memory stick.

The vestibular stimulation device 1 may be configured to deliver one or more thermal waveforms to the vestibular system and/or the nervous system of the patient in accordance with one or more modified prescriptions to the vestibular system and/or the nervous system of a patient. For example, as described above, the vestibular stimulation device 1 may be configured to deliver the prescribed thermal waveform(s) the vestibular system and/or the nervous system of the patient by activating one or more TEDs to warm and/or cool an earpiece inserted into an ear canal of the patient.

The registry 5 may be configured to generate one or more software updates. Each software update may comprise, consist essentially of or consist of a set of instructions for modifying one or more operational parameters of the vestibular stimulation device 1, the physician control device 2 and/or the physician support device 4.

The registry 5 may be configured to store one or more software updates in a database residing therein and/or to relay one or more software updates to the vestibular stimulation device 1, the physician control device 2 and/or the physician support device 4. The registry 5 may be configured to transmit one or more software updates the vestibular stimulation device 1, the physician control device 2 and/or the physician support device 4 over any suitable wired or wireless communications channel, including, but not limited to, a LAN, the Internet, a public telephone switching network, Bluetooth, WLAN and the like. Likewise, the vestibular stimulation device 1, the physician control device 2 and/or the physician support device 4 may be configured to access a database residing in the registry 5 and to retrieve one or more software updates using any suitable wired or wireless communications channel, including, but not limited to, a LAN, the Internet, a public telephone switching network, Bluetooth, WLAN and the like. Alternatively, one or more software updates may be transferred to the vestibular stimulation device 1, the physician control device 2 and/or the physician support device 4 using a portable memory device, such as an SD memory card or a USB memory stick. The software update(s) may be relayed from the registry 5 to the vestibular stimulation device 1, the physician control device 2 and/or the physician support device 4 automatically (e.g., upon generation, once per week, once per month, etc.) or in response to user input.

The physician support device 4 may be configured to store one or more software updates in a database residing therein and/or to relay one or more software updates to the vestibular stimulation device 1 and/or the physician control device 2. The physician support device 4 may be configured to transmit one or more software updates to the vestibular stimulation device 1 and/or the physician control device 2 over any suitable wired or wireless communications channel, including, but not limited to, a LAN, the Internet, a public telephone switching network, Bluetooth, WLAN and the like. Likewise, the vestibular stimulation device 1 and/or the physician control device 2 may be configured to access a database residing in the physician support device 4 and to retrieve one or more software updates using any suitable wired or wireless communications channel, including, but not limited to, a LAN, the Internet, a public telephone switching network, Bluetooth, WLAN and the like. Alternatively, one or more software updates may be transferred to the vestibular stimulation device 1 and/or the physician control device 2 using a portable memory device, such as an SD memory card or a USB memory stick. The software update(s) may be relayed from the physician support device 4 to the vestibular stimulation device 1 and/or the physician control device 2 automatically (e.g., upon generation, once per week, once per month, etc.) or in response to user input.

The physician control device 2 may be configured to store one or more software updates in a database residing therein and/or to relay one or more software updates to the vestibular stimulation device 1. The physician control device 2 may be configured to transmit one or more software updates to the vestibular stimulation device 1 over any suitable wired or wireless communications channel, including, but not limited to, a LAN, the Internet, a public telephone switching network, Bluetooth, WLAN and the like. Likewise, the vestibular stimulation device 1 may be configured to access a database residing in the physician control device 2 and to retrieve one or more software updates using any suitable wired or wireless communications channel, including, but not limited to, a LAN, the Internet, a public telephone switching network, Bluetooth, WLAN and the like. Alternatively, one or more software updates may be transferred to the vestibular stimulation device 1 using a portable memory device, such as an SD memory card or a USB memory stick. The software update(s) may be relayed from the physician control device 2 to the vestibular stimulation device 1 automatically (e.g., upon generation, once per week, once per month, etc.) or in response to user input.

The physician control device 2 may be configured to modify one or more of its operational parameters responsive to receiving and/or retrieving one or more software updates from the physician support device 4. The physician control device 2 may be configured to modify one or more of its operational parameters automatically ((e.g., upon receipt of the software update(s), once per week, once per month, etc.) or in response to user input.

The vestibular stimulation device 1 may be configured to modify one or more of its operational parameters responsive to receiving and/or retrieving one or more software updates from the physician support device 4 and/or the physician control device 2. The vestibular stimulation device 1 may be configured to modify one or more of its operational parameters automatically ((e.g., upon receipt of the software update(s), once per week, once per month, etc.) or in response to user input. As shown in FIG. 43, in some embodiments, the vestibular stimulation system comprises, consists essentially of or consists of a registry 5 operatively connected to a plurality of physician control devices 2a, 2b wherein each of said plurality of physician control devices 2a, 2b is operatively connected a plurality of vestibular stimulation devices 1a, 1b, 1c, 1d. In some embodiments, one or more of the vestibular stimulation devices 1a, 1b, 1c, 1d is also operatively connected to the physician support device 4 via an independent operative connection (i.e., independent of the physician control device 2a, 2b with which it is associated).

The registry 5 may be configured to store one or more thermal waveforms (e.g., one or more idealized thermal waveforms) in a database residing therein (e.g., to store the parameters, indications and/or approvals of the thermal waveform(s) in a waveform database as described above) and/or to relay data associated with one or more thermal waveforms to one or more of the physician control devices 2a, 2b. The registry 5 may be configured to transmit one or more thermal waveforms to the physician control devices 2a, 2b over any suitable wired or wireless communications channel, including, but not limited to, a LAN, the Internet, a public telephone switching network, Bluetooth, WLAN and the like. Likewise, each of the physician control devices 2a, 2b may be configured to access a waveform database residing in the registry 5 and to retrieve one or more thermal waveform(s) using any suitable wired or wireless communications channel, including, but not limited to, a LAN, the Internet, a public telephone switching network, Bluetooth, WLAN and the like. Alternatively, one or more thermal waveform(s) may be transferred to the physician control devices 2a, 2b using a portable memory device, such as an SD memory card or a USB memory stick.

Each of the physician control devices 2a, 2b may be configured to generate one or more thermal waveforms (i.e., to generate the parameters, indications and/or approvals of one or more thermal waveforms) and/or to store the thermal waveform(s) in a database (e.g., to store the parameters, indications and/or approvals of the thermal waveform(s) in a waveform database as described above).

Each of the physician control devices 2a, 2b may be configured to modify one or more of the thermal waveforms received/retrieved from the registry 5 (i.e., to modify one or more of the parameters, indications and/or approvals of one or more thermal waveforms) and/or to store the modified thermal waveform(s) in a database (e.g., to store the parameters, indications and/or approvals of the modified thermal waveform(s) in a waveform database as described above).

Each of the physician control devices 2a, 2b may be configured to generate a plurality of prescriptions, each comprising a set of instructions for delivering one or more thermal waveforms to the vestibular system and/or the nervous system of a patient. In such embodiments, one or more of the prescriptions may comprise a set of instructions for delivering one or more of the thermal waveforms generated by the physician support device 4 to the vestibular system and/or the nervous system of a patient.

Each of the physician control devices 2a, 2b may be configured to store one or more prescriptions in a database residing therein (e.g., a prescription database as described above) and/or to relay each prescription to a vestibular stimulation device 1a, 1b, 1c, 1d associated with the patient for whom the prescription was generated. The physician control devices 2a, 2b may be configured to transmit the prescriptions to the vestibular stimulation devices 1a, 1b, 1c, 1d over any suitable wired or wireless communications channel, including, but not limited to, a LAN, the Internet, a public telephone switching network, Bluetooth, WLAN and the like. Likewise, each of the vestibular stimulation devices 1a, 1b, 1c, 1d may be configured to access a prescription database residing in the physician control device 2a, 2b with which it is associated and to retrieve the prescriptions using any suitable wired or wireless communications channel, including, but not limited to, a LAN, the Internet, a public telephone switching network, Bluetooth, WLAN and the like. Alternatively, the prescriptions may be transferred to the vestibular stimulation devices 1a, 1b, 1c, 1d using one or more portable memory devices, such as SD memory cards and/or USB memory sticks.

Each of the vestibular stimulation devices 1a, 1b, 1c, 1d may be configured to deliver one or more prescribed thermal waveforms to the vestibular system and/or the nervous system of the patient for whom the prescription was generated. For example, as described above, each vestibular stimulation device 1a, 1b, 1c, 1d may be configured to deliver the prescribed thermal waveform(s) the vestibular system and/or the nervous system of the patient by activating one or more TEDs to warm and/or cool an earpiece inserted into an ear canal of the patient.

Each of the vestibular stimulation devices 1a, 1b, 1c, 1d may be configured to store feedback data in a database residing therein (e.g., a feedback database as described above) and/or to relay feedback data to the physician control device 2a, 2b with which it is associated and/or to the registry 5. Each of the vestibular stimulation devices 1a, 1b, 1c, 1d may be configured to transmit feedback data to the physician control device 2a, 2b with which it is associated and/or to the registry 5 over any suitable wired or wireless communications channel, including, but not limited to, a LAN, the Internet, a public telephone switching network, Bluetooth, WLAN and the like. Likewise, each of the physician control devices 2a, 2b and/or to the registry 5 may be configured to access one or more feedback databases residing in the vestibular stimulation devices 1a, 1b, 1c, 1d and to retrieve feedback data using any suitable wired or wireless communications channel, including, but not limited to, a LAN, the Internet, a public telephone switching network, Bluetooth, WLAN and the like. Alternatively, feedback data may be transferred to the physician control devices 2a, 2b and/or to the registry 5 using a portable memory device, such as an SD memory card or a USB memory stick.

Each of the physician control devices 2a, 2b may be configured to supplement feedback data received and/or retrieved from the vestibular stimulation device 1a, 1b, 1c, 1d with which it is associated with additional feedback data (e.g., physician feedback data).

Each of the physician control devices 2a, 2b may be configured to analyze feedback data received and/or retrieved from the vestibular stimulation device 1a, 1b, 1c, 1d with which it is associated. For example, the physician control devices 2a, 2b may be configured to use the feedback data to identify waveform characteristics that may be linked to increased/decreased efficacy with regard to the treatment of a given disease/disorder/injury, to identify modifications that are likely to increase the effectiveness of a given thermal waveform, class of thermal waveforms or combination of thermal waveforms; to identify new diseases/disorders/injuries for which a given thermal waveform, class of thermal waveforms, combination of thermal waveforms and/or treatment regimen may provide an effective treatment; to predict which thermal waveform(s) or combination(s) of thermal waveforms may be most effective in treating a given disease/disorder/injury; to identify thermal waveforms, classes of thermal waveforms and/or combinations of thermal waveforms that are not likely to be effective in the treatment of a given disease/disorder/injury, etc. In some embodiments, the feedback module is configured to identify new idealized thermal waveforms by identifying one or more diseases/disorders/injuries for which a thermal waveform or class of waveforms is likely to be an effective treatment (e.g., by identifying a new thermal waveform that belongs to a class of waveforms known to be effective in treating one or more diseases/disorders/injuries), to identify one or more additional diseases/disorders/injuries for which a previously identified idealized thermal waveform is likely to be an effective treatment (e.g., by identifying, in a population of patients receiving treatment with an idealized thermal waveform for treatment of a first disease/disorder/injury, one or more co-morbid diseases/disorders/injuries that also appear to be effectively treated by the idealized thermal waveform) and/or to identify one or more diseases/disorders/injuries for which a previously identified idealized thermal waveform is not likely to be an effective treatment (e.g., one or more of the diseases/disorders/injuries for which an idealized thermal waveform had previously been indicated and/or approved may be removed from the list of indications for that thermal waveform or for the class of thermal waveforms to which it belongs).

Each of the physician control devices 2a, 2b may be configured to store feedback data (including any additional feedback data supplied by the physician control devices 2a, 2b) in a database residing therein (e.g., a feedback database as described above) and/or to relay feedback data (including any additional feedback data supplied by the physician control devices 2a, 2b) to the registry 5. The physician control devices 2a, 2b 2 may be configured to transmit feedback data to the registry 5 over any suitable wired or wireless communications channel, including, but not limited to, a LAN, the Internet, a public telephone switching network, Bluetooth, WLAN and the like. Likewise, the registry 5 may be configured to access one or more feedback databases residing in the physician control devices 2a, 2b and to retrieve feedback data using any suitable wired or wireless communications channel, including, but not limited to, a LAN, the Internet, a public telephone switching network, Bluetooth, WLAN and the like. Alternatively, feedback data may be transferred to the registry 5 using a portable memory device, such as an SD memory card or a USB memory stick.

Each of the physician control devices 2a, 2b may be configured to modify one or more thermal waveforms responsive to analyzing feedback data received and/or retrieved from the vestibular stimulation devices with which it is associated 1a, 1b, 1c, 1d. For example, the physician control devices 2a, 2b may be configured to modify one or more parameters of the thermal waveform(s) received/retrieved from the registry 5. The physician control devices 2a, 2b may be configured to modify the thermal waveform(s) automatically (e.g., the physician support device 4 may be configured to automatically modify one or more thermal waveforms if/when any of its analyses indicate that such modifications are likely to improve the efficacy of the thermal waveform(s)) or responsive to user input.

Each of the physician control devices 2a, 2b may be configured to store one or more modified thermal waveforms in a database residing therein (e.g., a waveform database as described above) and/or to relay the modified thermal waveform(s) to one or more of the vestibular stimulation devices 1a, 1b, 1c, 1d with which it is associated and/or to the registry 5. The physician control devices 2a, 2b may be configured to transmit one or more modified thermal waveforms to one or more of the physician control devices 2a, 2b and/or the registry 5 over any suitable wired or wireless communications channel, including, but not limited to, a LAN, the Internet, a public telephone switching network, Bluetooth, WLAN and the like. Likewise, each of the vestibular stimulation devices 1a, 1b, 1c, 1d and/or the registry 5 may be configured to access a waveform database residing in one or more of the physician control devices 2a, 2b and to retrieve the modified thermal waveform(s) using any suitable wired or wireless communications channel, including, but not limited to, a LAN, the Internet, a public telephone switching network, Bluetooth, WLAN and the like. Alternatively, the modified thermal waveform(s) may be transferred to the vestibular stimulation devices 1a, 1b, 1c, 1d with which it is associated and/or the registry 5 using a portable memory device, such as an SD memory card or a USB memory stick.

Each of the physician control devices 2a, 2b may be configured to modify one or more prescriptions responsive to analyzing feedback data received and/or retrieved from the vestibular stimulation device 1a, 1b, 1c, 1d with which it is associated and/or to modifying one or more modified thermal waveforms. For example, the physician control devices 2a, 2b may be configured to modify one or more parameters of a prescription stored in a prescription database residing therein. The physician control devices 2a, 2b may be configured to modify the prescription(s) automatically (e.g., the physician control devices 2a, 2b may be configured to automatically modify one or more prescriptions if/when any of its analyses indicate that such modifications are likely to improve the efficacy of the prescription(s)) or responsive to user input.

Each of the physician control devices 2a, 2b may be configured to store one or more modified prescriptions in a database residing therein (e.g., a waveform database as described above) and/or to relay the modified thermal waveform(s) to the vestibular stimulation device 1a, 1b, 1c, 1d with which it is associated and/or to the registry 5. The physician control devices 2a, 2b may be configured to transmit one or more modified prescriptions to the vestibular stimulation device 1a, 1b, 1c, 1d and/or the registry 5 with which it is associated over any suitable wired or wireless communications channel, including, but not limited to, a LAN, the Internet, a public telephone switching network, Bluetooth, WLAN and the like. Likewise, each of the vestibular stimulation devices 1a, 1b, 1c, 1d and/or the registry 5 may be configured to access a prescription database residing in the physician control device 2a, 2b with which it is associated and to retrieve the modified prescription(s) using any suitable wired or wireless communications channel, including, but not limited to, a LAN, the Internet, a public telephone switching network, Bluetooth, WLAN and the like. Alternatively, the modified prescription(s) may be transferred to the vestibular stimulation devices 1a, 1b, 1c, 1d and/or the registry 5 using a portable memory device, such as an SD memory card or a USB memory stick.

Each of the vestibular stimulation devices 1a, 1b, 1c, 1d may be configured to deliver one or more thermal waveforms to the vestibular system and/or the nervous system of the patient in accordance with one or more modified prescriptions to the vestibular system and/or the nervous system of a patient. For example, as described above, the vestibular stimulation devices 1a, 1b, 1c, 1d may be configured to deliver the prescribed thermal waveform(s) the vestibular system and/or the nervous system of the patient by activating one or more TEDs to warm and/or cool an earpiece inserted into an ear canal of the patient.

The registry 5 may be configured to generate one or more software updates. Each software update may comprise, consist essentially of or consist of a set of instructions for modifying one or more operational parameters one or more of the vestibular stimulation devices 1a, 1b, 1c, 1d and/or one or more of the physician control devices 2a, 2b.

The registry 5 may be configured to store one or more software updates in a database residing therein and/or to relay one or more software updates to one or more of the vestibular stimulation devices 1a, 1b, 1c, 1d and/or one or more of the physician control devices 2a, 2b. The physician support device 4 may be configured to transmit one or more software updates to the vestibular stimulation devices 1a, 1b, 1c, 1d and/or the physician control devices 2a, 2b over any suitable wired or wireless communications channel, including, but not limited to, a LAN, the Internet, a public telephone switching network, Bluetooth, WLAN and the like. Likewise, each of the vestibular stimulation devices 1a, 1b, 1c, 1d and/or each of the physician control devices 2a, 2b may be configured to access a database residing in the registry 5 and to retrieve one or more software updates using any suitable wired or wireless communications channel, including, but not limited to, a LAN, the Internet, a public telephone switching network, Bluetooth, WLAN and the like. Alternatively, one or more software updates may be transferred to the vestibular stimulation devices 1a, 1b, 1c, 1d and/or the physician control devices 2a, 2b using a portable memory device, such as an SD memory card or a USB memory stick. The software update(s) may be relayed from the registry 5 to the vestibular stimulation devices 1a, 1b, 1c, 1d and/or the physician control devices 2a, 2b automatically (e.g., upon generation, once per week, once per month, etc.) or in response to user input.

Each of the physician control devices 2a, 2b may be configured to store one or more software updates in a database residing therein and/or transmit one or more software updates to one or more of the vestibular stimulation devices 1a, 1b, 1c, 1d with which it is associated. The physician control devices 2a, 2b may be configured to transmit the software update(s) to one or more of the vestibular stimulation devices 1a, 1b, 1c, 1d with which it is associated over any suitable wired or wireless communications channel, including, but not limited to, a LAN, the Internet, a public telephone switching network, Bluetooth, WLAN and the like. Likewise, each of the vestibular stimulation devices 1a, 1b, 1c, 1d may be configured to access a database residing in the physician control device 2a, 2b with which it is associated and to retrieve one or more software updates using any suitable wired or wireless communications channel, including, but not limited to, a LAN, the Internet, a public telephone switching network, Bluetooth, WLAN and the like. Alternatively, one or more software updates may be transferred to the vestibular stimulation devices 1a, 1b, 1c, 1d using a portable memory device, such as an SD memory card or a USB memory stick.

Each of the physician control devices 2a, 2b may be configured to modify one or more of its operational parameters responsive to receiving and/or retrieving one or more software updates from the registry 5. The physician control devices 2a, 2b may be configured to modify one or more of its operational parameters automatically ((e.g., upon receipt of the software update(s), once per week, once per month, etc.) or in response to user input.

Each of the vestibular stimulation devices 1a, 1b, 1c, 1d may be configured to modify one or more of its operational parameters responsive to receiving and/or retrieving one or more software updates from the registry 5 and/or the physician control device 2a, 2b with which it is associated. The vestibular stimulation devices 1a, 1b, 1c, 1d may be configured to modify one or more of its operational parameters automatically ((e.g., upon receipt of the software update(s), once per week, once per month, etc.) or in response to user input.

As shown in FIG. 44, in some embodiments, the vestibular stimulation system comprises, consists essentially of or consists of a registry 5, a physician control device 2 and a vestibular stimulation device 1 comprising a controller 11, a pair of earpieces 12a, 12b, a pair of TEDs 13a, 13b and a pair of sensors 14a, 14b, wherein each of the TEDs 13a, 13b is operatively connected to the controller 11 via a thermal stimulation lead 16a, 16b and thermally connected to one of the earpieces 12a, 12b and wherein each of the sensors 14a, 14b is operatively connected to the controller 11 via a wireless connection 17a, 17b and thermally connected to one of the earpieces 12a, 12b. In some such embodiments, the registry 5 comprises a network module 4d, a waveform database 4h, a prescription database 4i, a feedback database 4j and a patient history database 4k; the physician control device 2 comprises a waveform module 2a, a treatment module 2b, a network module 2d, a feedback module 2f, a waveform database 2h, a prescription database 2i, a feedback database 2j and a patient history database 2k and the controller comprises a control module 11c, a network module 11d, a feedback module 11f, a prescription database 11i and a feedback database 11j.

The registry 5 may be configured to relay one or more thermal waveforms (e.g., idealized thermal waveforms) to the physician control device 2 (i.e., data associated with the parameters, indications and/or approvals of one or more thermal waveforms may be transferred from the registry 5 to the physician control device 2). For example, the registry 5 may be configured such that the thermal waveform(s) are transmitted directly to the physician control device 2 by the network module 5d residing in the registry 5 and/or are stored in the waveform database 5h residing in the registry 5, from whence they may subsequently be transmitted to and/or retrieved by the physician control device 2.

The network module 2d residing in the physician control device 2 may be configured to receive and/or retrieve one or more thermal waveforms from the physician registry 5 and to relay the thermal waveforms to the treatment module 2b and/or to the waveform database 2h residing in the physician control device 2, from whence they may subsequently be transmitted to and/or retrieved by the treatment module 2b.

The waveform module 2a may be configured to modify one or more of the thermal waveforms received/retrieved from the registry 5 (i.e., to modify one or more of the parameters, indications and/or approvals of one or more of the thermal waveforms received/retrieved from the registry 5). The physician control device 2 may be configured such that the modified thermal waveforms generated by the waveform module 4a are transmitted directly to the treatment module 2b by the network module 2d residing in the physician control device 2 and/or are stored in the waveform database 2h residing in the physician control device 2, from whence they may subsequently be transmitted to and/or retrieved by the treatment module 2b.

The treatment module 2b may be configured to retrieve one or more of the thermal waveforms received/retrieved from the registry 5 and/or one or more of the modified thermal waveforms generated by the waveform module 2a from the waveform database 2h residing in the physician control device 2 and/or from the waveform database 5h residing in the registry 5.

The treatment module 2b may be configured to generate a prescription comprising a set of instructions for delivering one or more of the thermal waveforms received/retrieved from the registry 5 and/or one or more of the modified thermal waveforms generated by the waveform module 2a to the vestibular system and/or the nervous system of a patient. The physician control device 2 may be configured such that the prescription generated by the treatment module 2b is transmitted directly to the vestibular stimulation device 1 and/or the registry 5 by the network module 2d residing in the physician control device 2 and/or is stored in the prescription database 2i residing in the physician control device 2, from whence it may subsequently be transmitted to and/or retrieved by the vestibular stimulation device 1 and/or the registry 5.

The network module 5d residing in the registry 5 may be configured to receive and/or retrieve the prescription from the physician control device 2 and to relay the prescription to the prescription database 5i residing in the registry 5.

The network module 11d residing in the controller 11 may be configured to receive and/or retrieve the prescription from the physician control device 2 and to relay the prescription to the control module 11c and/or to the prescription database 11i residing in the controller 11.

The control module 11c may be configured to retrieve the prescription from the prescription database 11i residing in the controller 11.

The control module 11c may be configured to deliver the prescribed thermal waveform(s) by activating the TEDs 13a, 13b in accordance with the prescription (i.e., by activating the TEDs 13a, 13b to by warm and/or cool the earpieces 12a, 12b so as to deliver the prescribed thermal waveform(s)).

The feedback module 11f residing in the controller 11 may be configured to receive feedback data from the TEDs 13a, 13b and/or the sensors 14a, 14b (e.g., data associated with the temperature of the earpieces 12a, 12b, the temperature of the patient's ear canals, the impedance between the earpieces 12a, 12b, etc.). The controller 11 may be configured such that the feedback data received by the feedback module 11f is transmitted directly to the physician control device 2 and/or the registry 5 by the network module 11d residing in the controller 11 and/or is stored in the feedback database 11j residing in the controller 11, from whence it may subsequently be transmitted to and/or retrieved by the physician control device 2 and/or the registry 5.

The network module 2d residing in the physician control device 2 may be configured to receive and/or retrieve feedback data from the vestibular stimulation device 1 and to relay the feedback data to the registry 5, to the feedback module 2f residing in the physician control device 2 and/or to the feedback database 2j residing in the physician control device 2, from whence they may subsequently be transmitted to and/or retrieved by the registry 5 and/or the feedback module 2f residing in the physician control device 2.

The physician control device 2 may be configured to supplement the feedback data received and/or retrieved from the vestibular stimulation device 1 with additional feedback data (e.g., physician comments regarding the effectiveness of a given thermal waveform, class of thermal waveforms, combination of thermal waveforms, etc.) and to relay the additional feedback data to the registry 5, to the feedback module 2f residing in the physician control device 2 and/or to the feedback database 2j residing in the physician control device 2, from whence they may subsequently be transmitted to and/or retrieved by the registry 5 and/or the feedback module 2f residing in the physician control device 2.

The feedback module 2f residing in the physician control device 2 may be configured to retrieve feedback data (including any additional feedback data supplied by the physician control device 2) from the feedback database 2j residing in the physician control device 2.

The feedback module 2f residing in the physician control device 2 may be configured to analyze the feedback data (e.g., to estimate the thermal contact between each of the earpieces 12a, 12b and the patient's ear canals, to calculate patient-specific time constants, to evaluate the precision with the prescribed thermal waveform(s) was delivered, etc.). The physician control device 2 may be configured such that data associated with the feedback module's 2f analysis are transmitted to the registry 5 and/or to the feedback database 2j residing in the physician control device 2, from whence they may subsequently be transmitted to and/or retrieved by the registry 5.

The network module 5d residing in the registry 5 may be configured to receive and/or retrieve feedback data (including any additional feedback data supplied by the physician control device 2 and/or data associated with any analysis performed by the feedback module 2f residing in the physician control device 2) from the physician control device 2 and to relay the feedback data to the feedback database 5j residing in the registry 5.

The waveform module 2a may be configured to modify one or more of the thermal waveforms responsive to receiving and/or retrieving data associated with the feedback module's 2f analysis (e.g., by modifying one or more of the parameters, indications and/or approvals of a thermal waveform). The waveform module 2a may be configured to modify the thermal waveform(s) automatically (e.g., the waveform module 2a may be configured to periodically check the feedback database 2j for new analyses and to automatically modify one or more thermal waveforms if/when any analysis performed by the feedback module 2f indicates that such modifications are likely to improve the efficacy of the thermal waveform(s)) or responsive to user input. The physician control device 2 may be configured such that any modifications made by the waveform module 2a are transmitted to the registry 5 and/or the waveform database 2h residing in the physician control device 2, from whence they may subsequently be transmitted to and/or retrieved by the registry 5.

The treatment module 2b may be configured to retrieve data associated with the feedback module's 2f analysis from the feedback database 2j residing in the physician control device 2 and/or to retrieve any modifications made by the waveform module 2a from the waveform database 2h residing in the physician control device 2 and/or from the waveform database residing in the registry 5.

The network module 5d residing in the registry 5 may be configured to receive and/or retrieve one or more modified thermal waveforms from the physician control device 2 and to relay the modified thermal waveform(s) to the waveform database 5h residing in the registry 5.

The treatment module 2b may be configured to modify, update and/or extend the prescription responsive to receiving and/or retrieving data associated with the feedback module's 2f analysis and/or to receiving and/or retrieving any modifications made by the waveform module 2a. The treatment module 2b may be configured to modify, update and/or extend the prescription automatically (e.g., the treatment module 2b may be configured to periodically check the waveform database 2h for updates and to automatically modify the prescription if/when one or more of the parameters, indications or approvals of a thermal waveform used in the prescription has been modified by the waveform module 4a) or responsive to user input. The physician control device 2 may be configured such that any modifications made by the treatment module 2b are relayed to the vestibular stimulation device 1 as described above and/or are transmitted to the registry 5 and/or the prescription database 2i residing in the physician control device 2, from whence they may subsequently be transmitted to and/or retrieved by the registry 5.

The network module 5d residing in the registry 5 may be configured to receive and/or retrieve one or more modified prescriptions from the physician control device 2 and to relay the modified prescription(s) to the prescription database 5i residing in the registry 5.

The physician control device 2 may be configured to generate and/or modify patient information (e.g., information related to a patient's identity, medical history, current symptoms, current prescriptions, etc.). The physician control device 2 may be configured to transmit patient information to the registry 5 and/or to the patient history database 2k residing in the physician control device 2, from whence it may subsequently be transmitted to and/or retrieved by the registry 5.

The network module 5d residing in the registry 5 may be configured to receive and/or retrieve patient information from the physician control device 2 and to relay the patient information to the patient history database 5k residing in the registry 5.

One of skill in the art will appreciate that one or more telemedicine modules may be incorporated into the vestibular stimulation systems described above to facilitate and/or control communications between the vestibular stimulation devices, patient control devices, physician control devices, physician support devices and/or registries. For example, a first telemedicine module may be operatively connected to a physician control device to ensure that prescriptions transmitted to a vestibular stimulation device comply with patient privacy regulations and a second telemedicine module may be operatively connected to the vestibular stimulation device to ensure that feedback data transmitted to the physician control device likewise comply with patient privacy regulations. Similarly, a first telemedicine module may be operatively connected to a physician control device to ensure that feedback data transmitted to a physician support device comply with patient privacy regulations and a second telemedicine module may be operatively connected to the physician support device to ensure that any analysis transmitted to the physician control device likewise complies with patient privacy regulations.

Delivering Thermal Waveforms

As noted above, the present invention provides a method of delivering one or more thermal waveforms (e.g., one or more actively controlled, time-varying thermal waveforms) to the vestibular system and/or the nervous system of a patient.

In some embodiments, the method comprises, consists essentially of or consists of generating a prescription comprising a set of instructions for delivering one or more thermal waveforms to the vestibular system and/or the nervous system of a patient and delivering the prescribed thermal waveform(s) to the patient using a vestibular stimulation device. Any suitable vestibular stimulation device may be used to deliver the prescribed thermal waveform(s), including, but not limited to, a vestibular stimulation device as described above. In some embodiments, the prescription comprises a set of instructions for delivering one or more thermal waveforms to the left ear canal of a patient and for delivering one or more thermal waveforms to the right ear canal of a patient.

In some embodiments, the prescription is generated and delivered using the same vestibular stimulation device.

Figure 45:
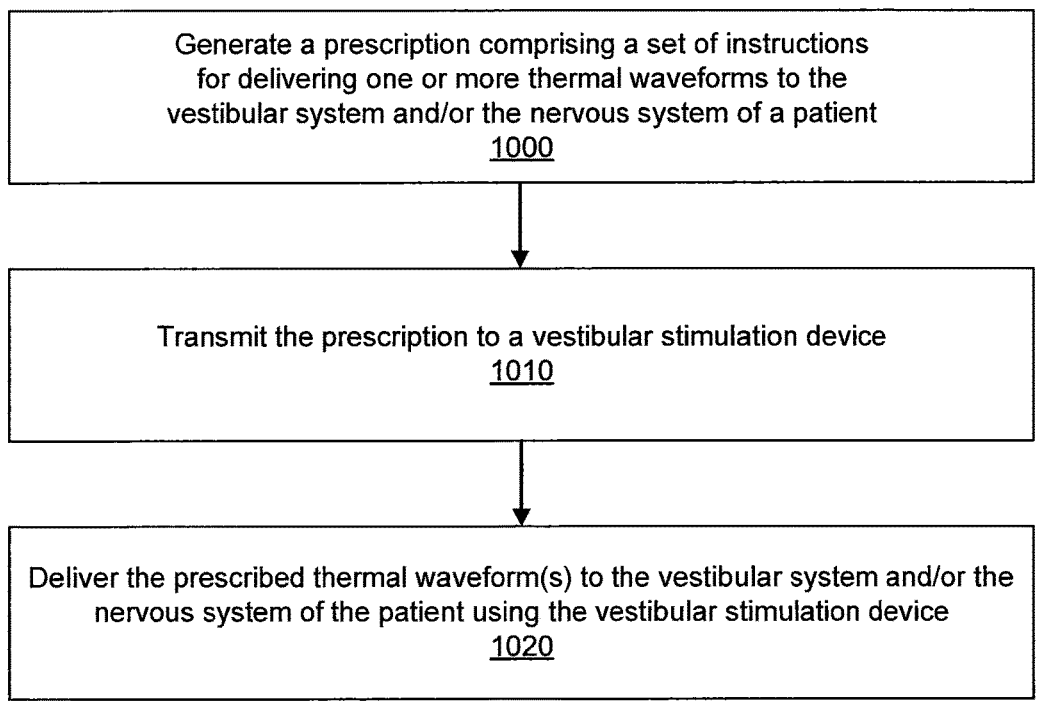
FIG. 45 is a block diagram illustrating a method of delivering one or more thermal waveforms to the vestibular system and/or the nervous system of a patient according to some embodiments of the present invention.

In some embodiments, the prescription is generated by a physician control device and delivered using a vestibular stimulation device. Any suitable physician control device may be used to generate the prescription, including, but not limited to, a physician control device as described above. As shown in FIG. 45, in such embodiments, the method may comprise generating a prescription comprising a set of instructions for the delivery of one or more thermal waveforms to the vestibular system and/or the nervous system of a patient 1000, transmitting the prescription to a vestibular stimulation device 1010 and delivering the prescribed thermal waveform(s) using the vestibular stimulation device 1020. The prescription may be transmitted to the vestibular stimulation device directly from the physician control device that generated the prescription or via an intermediate device (e.g., a patient control device or a telemedicine module, as described above). As discussed above, the prescription may be transmitted to the vestibular stimulation device over any suitable wired or wireless communications channel, including, but not limited to, a LAN, the Internet, a public telephone switching network, Bluetooth, WLAN and the like. Alternatively, the prescription may be uploaded to the vestibular stimulation device using a portable memory device, such as an SD memory card or a USB memory stick.

In some embodiments, the method comprises generating one or more thermal waveforms. Thermal waveforms may be generated using any suitable means, including, but not limited to, a waveform module as described above. For example, a physician support device as described above may be used to generate the parameters, indications and/or approvals of one or more thermal waveforms (e.g., idealized thermal waveforms).

In some embodiments, the method comprises modifying one or more thermal waveforms. Thermal waveforms may be modified using any suitable means, including, but not limited to, a waveform module as described above. For example, a physician support device as described above may be used to modify the parameters, indications and/or approvals of one or more thermal waveforms (e.g., idealized thermal waveforms).

In some embodiments, the method comprises storing one or more thermal waveforms in a database. Thermal waveforms may be stored in any suitable database, including, but not limited to, a waveform database as described above. For example, one or more thermal waveforms may be stored in a waveform database residing in a physician support device as described above, a waveform database residing in a physician control device as described above and/or a waveform database residing in a portable memory device (e.g., an SD memory card).

In some embodiments, the method comprises updating a waveform database. The waveform database may be updated using any suitable means, including, but not limited to, a waveform module as described above. The waveform database may be updated automatically. The waveform database may be updated at any suitable interval (e.g., daily, weekly, monthly, etc.). For example, a waveform database residing in a physician support device as described above may be automatically updated in response to analyses performed by a feedback module residing in the physician support device.

In some embodiments, the method comprises selecting one or more thermal waveforms. Thermal waveforms may be selected using any suitable means, including, but not limited to, a treatment module as described above. Thermal waveforms may be selected, from any suitable source, including, but not limited to, a waveform database as described above. For example, a physician control device as described above may be used to select one or more thermal waveforms (e.g., idealized thermal waveforms) from a waveform database residing in the physician control, a waveform database residing in a physician support device as described above and/or a waveform database residing in a portable memory device (e.g., an SD memory card).

In some embodiments, the method comprises generating one or more instructions for delivering one or more thermal waveforms to the vestibular system and/or the nervous system of a patient. Instructions for delivering one or more thermal waveforms to the vestibular system and/or the nervous system of a patient may be generated using any suitable means, including, but not limited to, a treatment module as described above. For example, a physician control device as described above may be used to generate instructions as to which thermal waveform(s) is/are to be delivered to the patient, when each thermal waveform is to be delivered to the patient, whether each thermal waveform is to be delivered to the right and/or the left ear canal of the patient, how long the treatment schedule is to last, how many treatments may be administered in a given day/week/month, etc.

In some embodiments, the method comprises modifying instructions for delivering one or more thermal waveforms to the vestibular system and/or the nervous system of a patient. Instructions for delivering one or more thermal waveforms to the vestibular system and/or the nervous system of a patient may be modified using any suitable means, including, but not limited to, a treatment module as described above. For example, a physician control device as described above may be used to modify which thermal waveform(s) is/are to be delivered to a patient, when each thermal waveform is to be delivered to the patient, whether each thermal waveform is to be delivered to the right and/or the left ear canal of the patient, how long the treatment schedule is to last, how many treatments may be administered in a given day/week/month, etc.

In some embodiments, the method comprises storing one or more instructions for delivering one or more thermal waveforms to the vestibular system and/or the nervous system of a patient. Instructions for delivering one or more thermal waveforms to the vestibular system and/or the nervous system of a patient may be stored in any suitable database, including, but not limited to, a prescription database as described above. For example, one or more instructions for delivering one or more thermal waveforms to the vestibular system and/or the nervous system of a patient may be stored in a prescription database residing in a physician support device as described above, a prescription database residing in a physician control device as described above and/or a prescription database residing in a portable memory device (e.g., an SD memory card).

In some embodiments, the method comprises selecting one or more instructions for delivering one or more thermal waveforms to the vestibular system and/or the nervous system of a patient. Instructions for delivering one or more thermal waveforms to the vestibular system and/or the nervous system of a patient maybe selected from any suitable source, including, but not limited to, a prescription database as described above. For example, a physician control device as described above may be used to select one or more instructions for delivering one or more thermal waveforms to the vestibular system and/or the nervous system of a patient from a prescription database residing in the physician control, a prescription database residing in a physician support device as described above and/or a prescription database residing in a portable memory device (e.g., an SD memory card).

In some embodiments, generating a prescription comprises receiving user input and generating a prescription responsive to said user input. User input may include, but is not limited to, selection of one or more thermal waveform parameters (e.g., shape, frequency, amplitude, duration, etc.), selection of one or more thermal waveforms from a database (e.g., a waveform database residing in the device used to generate the prescription), modification of one or more thermal waveform parameters, generation of one or, more instructions for delivering one or more thermal waveforms to the vestibular system and/or the nervous system of a patient, modification of one or more instructions for delivering one or more thermal waveforms to the vestibular system and/or the nervous system of a patient and selection of one or more instructions for delivering one or more thermal waveforms to the vestibular system and/or the nervous system of a patient. Any suitable means may be used to receive user input, including, but not limited to, a GUI module as described above.

In some embodiments, the method further comprises monitoring the patient's response to the prescribed thermal waveform(s), modifying the prescription based upon the patient's response to the prescribed thermal waveform(s) and delivering one or more thermal waveforms to the vestibular system and/or the nervous system of the patient in accordance with the modified prescription. The prescription may be modified in any suitable manner, including, but not limited to, adding/deleting thermal waveforms, changing one or more of the parameters (e.g., shape, frequency, amplitude, duration, etc.) the prescribed thermal waveform(s) and changing one or more of the parameters of delivery (e.g., how often each of the prescribed thermal waveforms is delivered, what time of day each of the thermal waveforms is delivered, etc.).

Figure 46:
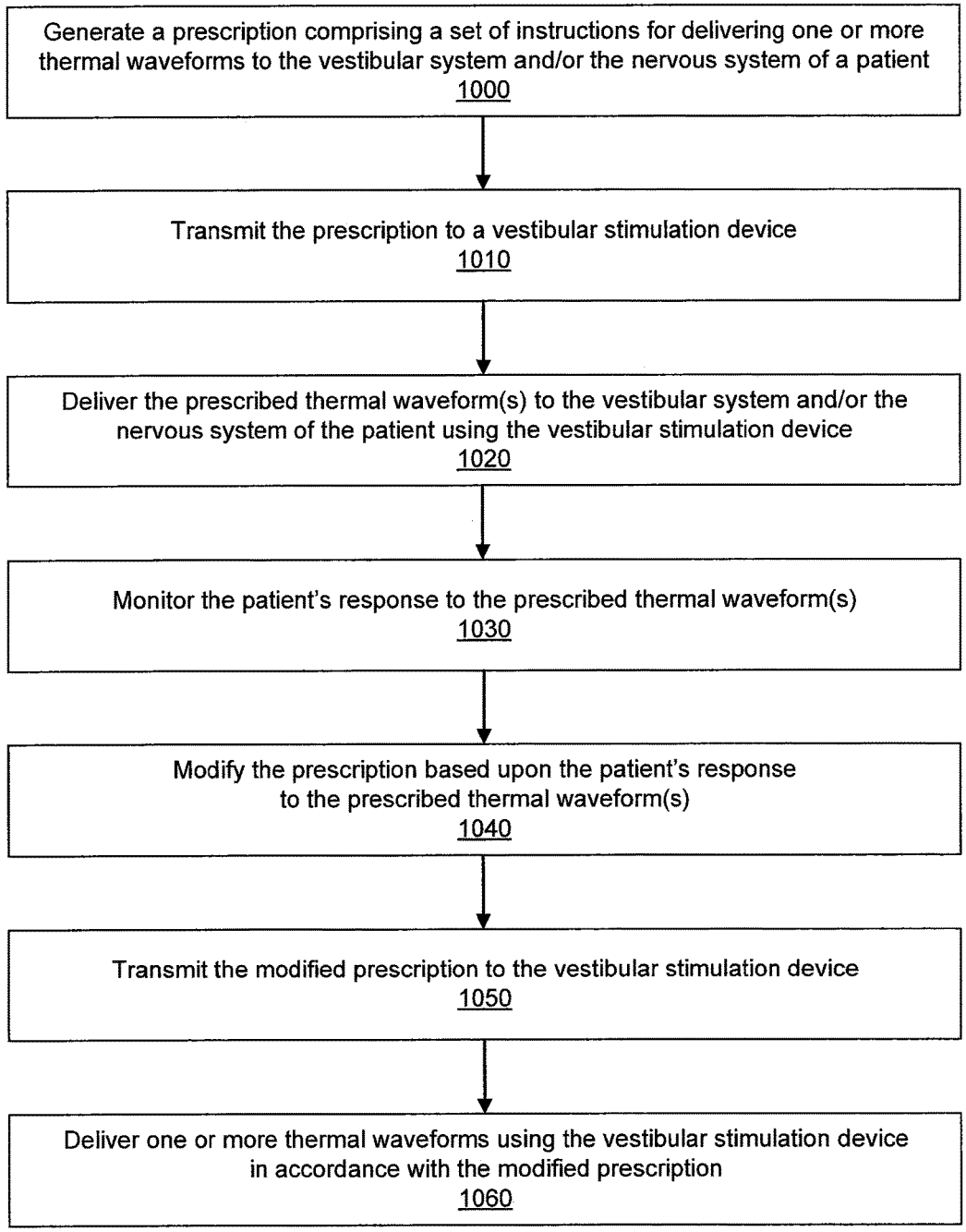
FIG. 46 is a block diagram illustrating a method of delivering one or more thermal waveforms to the vestibular system and/or the nervous system of a patient according to some embodiments of the present invention.

In some such embodiments, the prescription is modified by a physician control device and delivered using a vestibular stimulation device. Any suitable physician control device may be used to generate the prescription, including, but not limited to, a physician control device as described above. As shown in FIG. 46, the method may generating a prescription comprising a set of instruction for the delivery of one or more thermal waveforms to the vestibular system and/or the nervous system of a patient 1000, transmitting the prescription to a vestibular stimulation device 1010, delivering the prescribed thermal waveform(s) to the vestibular system and/or the nervous system of the patient using the vestibular stimulation device 1020, monitoring the patient's response to the prescribed thermal waveform(s) 1030, modifying the prescription based upon the patient's response to the prescribed thermal waveform(s) 1040, delivering the modified prescription to the vestibular stimulation device 1050 and delivering one or more thermal waveforms to the vestibular system and/or the nervous system of the patient using the vestibular stimulation and/or the nervous system of the patient according to the modified prescription 1060.

In some embodiments, the method further comprises monitoring the patient's response to the thermal waveform(s) delivered according to the modified prescription, modifying the prescription based upon the patient's response to the thermal waveform(s) delivered according to the modified prescription and delivering one or more thermal waveforms to the vestibular system and/or the nervous system of the patient in accordance with the newly-modified prescription. Such monitoring and modification may be performed as often as is feasible and/or desired.

Updating a Waveform Database

As noted above, the present invention provides a method of updating a database comprising one or more thermal waveforms (e.g., idealized thermal waveforms).

In some embodiments, the method comprises analyzing data (e.g., data associated with the delivery of one or more thermal waveforms, patient feedback data, physician feedback data and patient information) and updating a waveform database responsive to said analysis. In some embodiments, the method comprises modifying one or more parameters, indications and/or approvals of one or more thermal waveforms (e.g., idealized thermal waveforms) responsive to analyzing data associated with the delivery of one or more thermal waveforms. In some embodiments, the method comprises modifying one or more parameters, indications and/or approvals of one or more thermal waveforms (e.g., idealized thermal waveforms) responsive to analyzing patient feedback data. In some embodiments, the method comprises modifying one or more parameters, indications and/or approvals of one or more thermal waveforms (e.g., idealized thermal waveforms) responsive to analyzing physician feedback data. In some embodiments, the method comprises modifying one or more parameters, indications and/or approvals of one or more thermal waveforms (e.g., idealized thermal waveforms) responsive to analyzing patient information.

Analyzing data may comprise the analysis of data from any suitable source, including, but not limited to, a feedback database as described above and a patient history database as described above. For example, analyzing data may comprise the analysis of data from a feedback database residing in a vestibular stimulation device as described above, a feedback database residing in a patient control device as described above, a feedback database residing in a physician control device as described above, a feedback database residing in a physician support device as described above, a feedback database residing in a portable memory device (e.g., an SD memory card), a patient history database residing in a vestibular stimulation device as described above, a patient history database residing in a patient control device as described above, a patient history database residing in a physician control device as described above, a patient history database residing in a physician support device as described above and a patient history database residing in a portable memory device (e.g., an SD memory card).

Any suitable analysis may be carried out, including, but not limited to, identifying waveform modifications that are likely to increase the effectiveness of a given thermal waveform, class of thermal waveforms or combination of thermal waveforms; identifying new diseases/disorders/injuries for which a given thermal waveform, class of thermal waveforms, combination of thermal waveforms and/or treatment regimen may provide an effective treatment; predicting which thermal waveform(s) may be most effective in treating a given disease/disorder/disorder (in patients of a given age, sex, etc., for example); identifying thermal waveforms, classes of thermal waveforms and/or combinations of thermal waveforms that are not likely to be effective in the treatment of a given disease/disorder/injury; identify waveform characteristics that may be linked to increased/decreased efficacy with regard to the treatment of a given disease/disorder/injury.

In some embodiments, the waveform database is automatically updated in response to analysis of data associated with the delivery of one or more thermal waveforms, patient feedback data, physician feedback data and/or patient information (i.e., no user input is required to trigger the update).

The database may be updated by adding one or more thermal waveforms, modifying the parameters (e.g., shape, frequency, amplitude and duration), indications and/or approvals of one or more of the thermal waveforms in the database and/or deleting one or more of the thermal waveforms from the database.

The present invention is explained in greater detail in the following non-limiting Examples.

Example 1

Long Duration Square Wave Administration

A male subject in his forties and good health, nave to CVS, was administered cold CVS to his right ear in a square waveform pattern. The pattern was of cooling to 10 degrees Centigrade (as compared to normal body temperature of about 37 degrees Centigrade) as a "step" function or "square wave" with one symmetric square wave being delivered for a time period of 20 minutes. The subject was observed by others to be slurring his words, and was asked to remain seated for a time of two hours following the treatment session as a precaution. Otherwise, no long-term deleterious effects were observed.

Example 2

Sawtooth Wave Administration

The same subject described in EXAMPLE 1 was subsequently treated by administering cold CVS to the right ear in a sawtooth waveform pattern of cooling to 20 degrees Centigrade (as compared to normal body temperature of about 37 degrees Centigrade) in a symmetric sawtooth waveform pattern, without gaps, at a frequency of one cycle or waveform every five minutes, for a total duration of approximately 10 minutes and a delivery of a first and second waveform. Unlike the situation with the square wave pattern described in Example 1, the subject continued to perceive the temperature cycling up and down.

Example 3

Maximum Waveform Amplitude

The same subject described in Examples 1-2 was administered cold CVS to the right ear as a sawtooth cooling waveform at different amplitudes in a titration study. A maximum perceived sensation of cyclic cooling was perceived at a peak amplitude of about 17 degrees Centigrade (or cooling from normal body temperature to a temperature of about 20 degrees Centigrade). Cooling beyond this did not lead to additional gains in the sensation of cyclic cooling perceived by the subject.

Example 4

Minimum Waveform Amplitude

Modeling of the human vestibular system indicates that the cupula (the structure within the semicircular canals pushed by the movement of fluid therein and which contain hair cells that convert the mechanical distortion to electrical signals in the vestibular nerve), is stimulated by CVS at chilling temperatures of 5 or 7 degrees Centigrade below body temperature.

Example 5

Maximum Waveform Frequency

Modeling of the human vestibular system indicates that a slew rate faster than 20 degrees Centigrade per minute (which would enable one 20 degree Centigrade waveform every two minutes) is not useful because the human body cannot adapt to temperature changes at a more rapid rate. While maximum frequency is dependent in part on other factors such as waveform amplitude, a maximum frequency of about one cycle every one to two minutes is indicated.

Example 6

Minimum Waveform Frequency

Modeling of the human vestibular system indicates that a continuous, time-varying waveform is most effective in stimulating the vestibular system, as stagnation and adaptation of the cupula is thereby minimized. While minimum frequency is dependent in part on other factors such as the waveform amplitude, a minimum frequency of about one cycle every ten to twenty minutes is indicated.

Example 7

Treatment Session Duration

To permit delivery of at least a first and second waveform, a duration of at least one or two minutes is preferred. As noted above and below, results have been reported by patients with treatment durations of ten and twenty minutes. Hence, as a matter of convenience, a treatment session duration of not more than 30 or 40 minutes is preferred (though longer sessions may be desired for some conditions, such as acute care situations).

Example 8

Treatment of Migraine Headache with Sawtooth Waveforms

A female patient in her early fifties with a long standing history of migraine suffered an acute migraine episode with symptoms that consisted of a pounding headache, nausea, phonophobia, and photophobia. Right ear cold CVS was performed using the sawtooth waveform, essentially as described in Example 2 above, with a temperature maximum of 17 degrees Centigrade (chilling from body temperature) for 10 minutes (for a total delivery of two cycles). At the conclusion of the treatment the patient reported that her headache and associated symptoms were no longer present. At a reassessment one day later, the patient reported that the headache had not returned.

Example 9

Treatment of Diabetes with Sawtooth Waveforms

The same subject described in examples 1-3 suddenly developed an episode of extreme urination (10 liters per day), thirst for ice water, and associated fatigue. Urinary testing suggested the onset of diabetes mellitus, for which there was strong family history.

The patient's initial weight as taken at his primary care physician indicated a recent 20 pound weight loss. The first attempt to obtain a glucose reading from the patient resulted in an out of range result (this result typically occurs with glucose levels in excess of 600 mg/dl). The patient was hospitalized and received hydration and IV insulin therapy. The patient's first glucose level after this treatment was 700 mg/dl. The glucose level were brought down to approximately 350 and treatment with an oral antihyperglycemic agent was initiated.

Follow-up care after hospital discharge with the subject's primary care physician. expanded the oral antihyperglycemic agent therapy to include both metformin and JANU-VIA™ sitagliptin. In addition, a strict exercise program of 30-45 minutes 5 to 6 days per week and diet control were instituted. Daily glucose levels via finger stick were taken 2 to 3 times per day.

At this point the patient's baseline hemoglobin A1c (Hb A1c) level was 9.8%, as compared to normal levels of 5 to 6%.

The patient then began daily treatment with CVS. The treatment was carried out for a time of ten minutes, once a day for about a month, after which the treatment was continued two to three times a week for three additional months (with each treatment session being about 10 minutes in duration). The CVS was delivered to the patient's right ear, as a sawtooth cooling waveform as described in Example 2. At the conclusion of these treatments, the patient's HB A1c level was 5.3%. As a result, the patient was removed from all hypoglemic agents.

Most oral antihyperglycemic agents lower a patient's Hb A1c level by approximately 1 to 2% (see generally S. Inzucchi, *Oral Antihyperglycemic Therapy for Type 2 Dia-* betes, JAMA 287:360-372 (Jan. 16, 2002)). In contrast, this patient's initial value was 9.5, and dropped to 5.3.

Example 10

Alternate Waveform Shapes

Figure 47A:
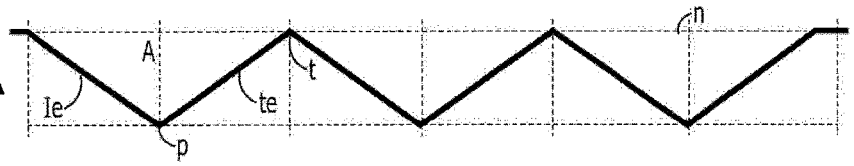
FIGS. 47A-47F are schematic diagrams of various non-limiting examples of thermal waveforms that may be delivered using the devices, systems and methods of the present invention. While each line A through F illustrates several cycles of a given frequency and waveform shape, note that "waveform" herein generally refers to a single cycle of a given frequency and waveform shape.

The sawtooth waveform described in the examples above was symmetric and linear, as illustrated in FIG. 47A, where line dashed line "n" represents the subject's normal body temperature (typically about 37 degrees Centigrade). Modeling of the vestibular system indicates that waveforms of similar amplitude and frequency, but with a variation in shape, are also effective, such as the "logarithmic" or "convex" waveform of FIG. 47B, and the "exponential" or "concave" waveform of FIG. 47C. All waveforms generally include a leading edge ("le"), a trailing edge ("te"), a peak ("p") and a trough ("t").

Figure 47B:
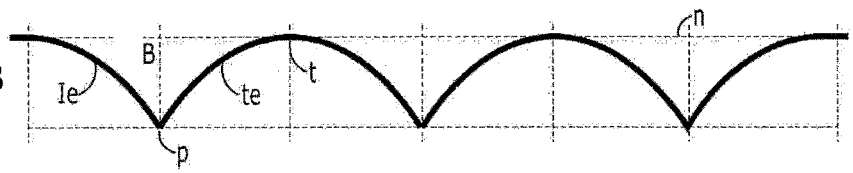
Figure 47C:
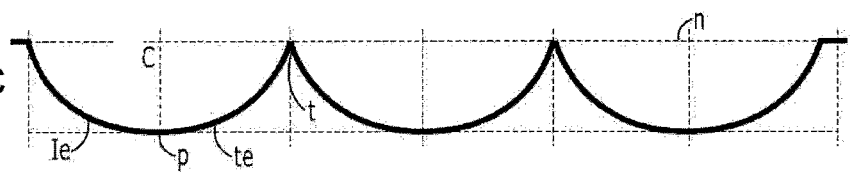
Figure 47D:
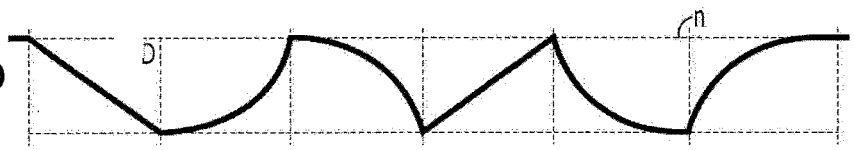

While FIGS. 47A through 47C all show three consecutive waveforms of the same shape, amplitude, and frequency, the consecutive waveforms can be varied in shape as shown in FIG. 47D, and can be varied in amplitude or duration as well (preferably each consecutive waveform within the parameters noted above), to produce still additional waveforms and sequences of waveforms which are useful in carrying out the present invention.

Figure 47E:
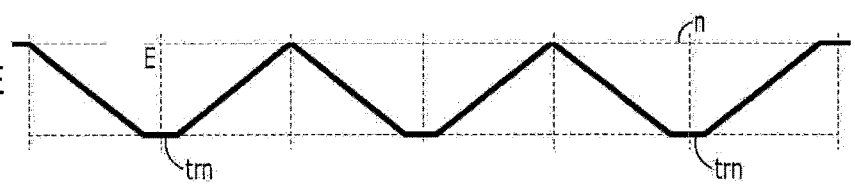
Figure 47F:
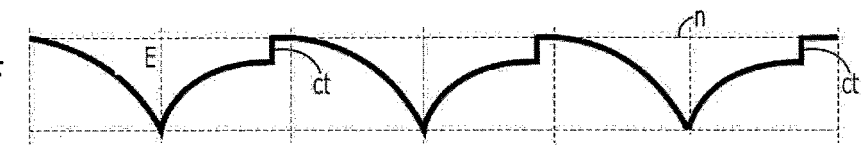

In addition, while the waveforms of FIGS. 47A through 47D are shown as continuous, minor disruptions can be included therein, such as truncations ("trn"; for example, as shown in FIG. 47E) or vertical cuts ("ct"; for example, as shown in FIG. 47F) to produce still additional waveforms and sequences of waveforms which are useful in carrying out the present invention.

The peak for all waveforms of FIGS. 47A-47F is cooling by 17 degrees Centigrade from normal body temperature to a temperature of 20 degrees Centigrade, and the trough for all waveforms is a return to normal body temperature, giving an amplitude of 17 degrees Centigrade. The frequency for all illustrated waveforms is 1 cycle (or one complete waveform) every five minutes. While 3 cycles of the same waveform are illustrated for clarity, note that in some of the examples above only two cycles are delivered over a total treatment or session duration of ten minutes.

Example 11

Patient Orientation

It was noted that a patient who was sitting up (watching television) and receiving a cold CVS treatment reported perceiving a different effect than perceived in prior sessions. Upon reclining to about 45 degrees, she did receive the earlier effect.

The "standard" angle of recline for diagnostic CVS is about 60 degrees (or equivalently 30 degrees above horizontal). The reason for this positioning is that the "horizontal" SCC is tilted up by about 30 degrees (higher on rostal side) (More recent x-ray measurements put the angle at closer to 20+/−7 degrees.) The intent with diagnostic CVS is to reorient the horizontal SCC so that it is substantially vertical, thus maximizing the effect of the convective flow set up by calorics.

Hence, if the subject is reclined to about 20 degrees above horizontal (and supine), then a cold stimulus leads to inhibition or a phasic rate less than the tonic rate. For a warm stimulus, this situation is reversed (phasic rate increases above tonic).

Further, cold simulation tends to activate principally the contralateral brain structures whereas hot leads to principally ipsilateral activation. For example, in V. Marcelli et al. (EUR. J. RADIOL. 70(2):312-6 (2009)), the authors did a left ear, cold stimulation by water irrigation and saw right-side activation in the brainstem, cerebellum, etc. The patient was presumably nearly reclined in the MRI magnet.

Empirical tests and modeling indicate that approximately 20 degrees Centigrade absolute cooling (17 degrees Centigrade below body temperature) is the lower limit beyond which the cupula is maximally deformed and therefore the phasic rate change is maximal. On the warming side, more than about 7 degrees Centigrade or so above body temperature becomes uncomfortable. This level of temperature heating within the ear canal will not lead to maximal deformation of the cupula. Therefore, there is an asymmetry in terms of ability to span the full frequency spectrum of phasic firing rates. However, the increase in the phasic firing rate is not constrained in the manner of a decrease—that is, the phasic firing rite can only approach zero, relative to the tonic rate of roughly 100 Hz, whereas the phasic rate can exceed 200 Hz.

Since inverting the patient changes the sign of the inhibitory/excitatory motion of the cupula, the following can be seen: Using a cold stimulus, of 20 degrees Centigrade absolute, but now orient the patient so that his head is tilted forward by from 75 to 20 degrees from the vertical position. This will invert the horizontal SCC relative to the image above and now the cold stimulus will result in an excitatory increase in the phasic firing rate. For clarity, tilting the head forward by 20 degrees makes the horizontal SCC substantially horizontal. Tilting beyond that now starts to invert it so that at 110 degrees (tilted forward), the horizontal SCC will be in a vertical orientation, but now 180 degrees flipped from what is used in conventional diagnostic CVS. So, the "general rule" for treatment of having the patient reclined by 45-90 degrees can be expanded to include "tilted forward" by 75-120 degrees.

Thus a protocol is seen where, using only cold stimulus, one can cover the entire range of phasic firing rates simply by reorienting the patient at the appropriate points during the time course of treatment.

Note that this type of inversion should also lead to an inversion in the side of the brain that is primarily activated. Specifically, if cold stimulation leads to principally contralateral activation in the "rightside up" orientation, then it should lead to principally ipsilateral activation in the "upside down" orientation.

Example 12

Thermal Modeling of Caloric Vestibular Stimulation

Equation (4) of Proctor et al. (ACTA OTOLARYNGOL. 79:425-435 (1975)) can be extended for an arbitrary sequence of heating and/or cooling steps. Equation (4) is a fairly simple usage of the 1-dimensional diffusion equation. Therefore, the model is not exact. The temperature difference across the horizontal canal (i.e., the thermal driving gradient) is approximated:

$$\Delta T = \frac{A_1}{\sqrt{t}} e^{-B/t} + \frac{A_2}{\sqrt{t-t_1}} e^{-B/(t-t_1)} + \ldots + \frac{A_n}{\sqrt{t-t_n}} e^{-B/(t-t_n)} \quad (1)$$

-continued $$A_n = \frac{-LT_n}{\sqrt{\pi a}}$$

where: and $$B = \frac{x^2}{4a}$$

L=distance across horizontal canal (mm); default=6

$T_n$=difference between applied temperature and previous temperature (degrees Centigrade)

a="thermal diffusivity" of temporal bone (mm2/sec); this may vary in patients, but compact bone paths will dominate the thermal. The literature lists values from 0.14-0.25, but this is based on the onset of nystagmus as the "stimulation time." Marcelli et al. showed a much faster, actual brainstem activation time after CVS, which did not relate to the onset of nystagmus. Literature estimates for the thermal diffusivity of hard bone range from 0.45-0.55 to 1.6. A value of 0.5 is assumed here, based on x-rays of the compact, wet bone in the region of interest.

x=the effective thermal distance (mm) between external ear canal and the edge of horizontal semicircular canal; default=7.5 mm ΔT=the temperature difference across the semicircular canal (degrees Centigrade); distal minus proximal temperature.

$t_n$=time at which new stimulus starts.

Default values for the constants are listed next to the definitions. CVS application times that are short compared to the response time of the patient may not be very different from a longer pulse at a lower temperature due to thermal smoothing effects. Literature reports of the maximum phasic firing rate are about 100 Hz. That is, +/−100 Hz away from the tonic firing rate, which is on the order of 100 Hz. The maximum deformation of the cupula at its center is, correspondingly, about 77 microns. Thermal gradients that imply a deformation greater than this value would tend to lead to saturation of the phasic firing rate. At the other end of the scale, the minimum detectable volume change in the SCC is on the order of 25 picoliters and this corresponds to a change in the phasic rate of roughly 0.5 Hz. This indicates a minimum temperature gradient across the SCC of ~0.02 degrees Centigrade. The obvious requirement is that the body's homeostatic temperature regulation must ensure a constant temperature across the 6 mm wide canal to a value on that order.

Another simplification used in the model was to ignore the temperature dependence of the bulk coefficient of thermal expansion of water (with the simplifying assumption that endolymph has roughly the thermal properties of water). This assumption will lead to an apparent saturation of the phasic firing rate at higher temperature (roughly 27 degrees Centigrade) than will actually occur. Below body temperature, the phasic rate may not saturate until the lower 20's.

The volume of the horizontal SCC is estimated to be: 3.2E-3 cc. The change in volume due to a temperature difference ΔT is: 3.8E-4*3.2E-3*ΔT=1.22E-6 ΔT.

The volume of the "lens" of the cupula when deformed to its maximal (saturation of the phasic firing rate) extent is roughly: 4.4E-6 cc Therefore, the change in the phasic rate: Δf=27.7*ΔT in Hz.

The relationship between the applied thermal waveform and the phasic firing rate of the afferents of the vestibular branch of the 8th cranial nerve can thus be modeled for a square waveform stimulus (such as in Example 1 above), and for a time-varying, saw tooth, waveform stimulus (such as in Example 2 above).

It was noted that there is little distortion of the time-varying waveform of, as compared to the square waveform, because the body can track the more gradual temperature changes.

There is a tendency for the values to skew a small amount vertically (e.g., the temperature delta goes slightly above body temp at points). This effect appears to be non-physical and is simply a limit of the approximate model employed. The same appears true of the firing rate going positive.

The "tips" of the sawtooth waveforms appear to exceed the maximum change in phasic firing rate of 100 Hz (this is seen in the square wave as well). This may be because the coefficient of thermal expansion of the endolymph changes with temperature and was not corrected in the model above. This would result in an overestimate of the firing rate for a given temperature in the plot. Therefore, the firing rate may not, in fact, saturate (i.e., will stay below a delta of 100 HZ) at 20 C. The loss of a sense of improvement reported in Example 3 above for temperatures below about 17 to 20 degrees Centigrade may be due to the cupula of the vestibular canal "pegging" (achieving its maximal physical distortion) and the firing rate saturating.

Example 13

Treatment of Chronic Migraines and Refractory Depression

A female subject was a headache sufferer with a 10-year history of debilitating, chronic migraines, the last five being refractory. She had failed all pharmaceutical interventions. The patient underwent an occipital nerve stimulator implant for headaches, with good symptom-management for approximately one year, at which point the device was no longer effective. Co-morbid with her migraine headaches was depression, which was only partially responsive to pharmaceutical management. Subject was placed on disability from her employment.

The subject was treated using a five-day therapy paradigm consisting of daily treatments comprising a square waveform pattern of cooling to 20 degrees Centigrade, at a frequency of one cycle every ten minutes, for a total duration of ten minutes while the patient was in a reclined position of thirty degrees above horizontal. Video images of the subject were captured before, during and after each treatment session and were used to assess the effectiveness of the treatment (e.g., by assessing the patient's mood).

For all active, in-process migraine episodes, within 5-15 minutes after completion of a treatment, subject experienced pain attenuation. Chronic headache indication was alleviated on the $4^{th}$ day of treatment, with concurrent progressive improvement in her mood over the course of the five days. The treatment course peaked at day 5. The subject became pain-free, with complete resolution of mood symptoms. She remained pain-free for 63 days after the therapy was completed, at which time her migraine headaches began to recur, but without return of clinical mood symptoms.

The five-day therapy paradigm was repeated. The subject responded more quickly to this second longitudinal therapy, with her chronic headaches disappearing on the $3^{rd}$ day of treatment. She remained pain-free for five weeks.

Later, the patient was treated with a sawtooth waveform (lower temperature of 20 degrees Centigrade) employing a daily treatment duration of 10 minutes. By the end of the treatment week, the patient was pain free (using a 0-3 pain scale where 3 is severe, 2 is moderate, 1 is mild, and zero is no pain). Charted pain scores (not shown) showed improvement after treatment. All CVS treatments were to the right ear using cold stimulation. Additionally, after each treatment week, the patient stayed pain free for times varying from 2-9 weeks. The patient additionally reported feelings of high energy and resolution of co-morbid depression.

Example 14

Treatment-Associated Dizziness in Migraine Patient

The same subject described in example 8 had right ear CVS treatment using a heating, to approximately 42-43 degrees, sawtooth waveform for 10 minutes, with a contiguous repeat for an additional 10 minutes. The treatment was effective in resolving her acute migraine pain. Additionally, the treatment had a soporific effect but also caused slight dizziness. The subject did not note the feeling of dizziness in example 8 using cold stimulation.

Example 15

Treatment of Cluster Headache and Treatment-Associated Dizziness

The same subject described in example 1 underwent the same CVS treatment described in example 14. He too reported a feeling of slight dizziness that was not apparent during cold CVS stimulation.

Example 16

Vestibular Migraine Treatment in Female Patient

A female subject in her late 30's had a history of migraine with associated vertigo (vestibular migraine). The subject has a history of vestibular dysfunction and slight co-morbid depression. The subject was treated on a near daily basis, between 20-40 minutes per day, with cold stimulation (down to 20 degrees Centigrade) CVS before switching to warm CVS, with a maximum temperature of 48 degrees Centigrade. All CVS treatments used a sawtooth pattern with left-ear stimulation due to more severe vestibular dysfunction in the right ear. This subject did not note dizziness as a side effect of the warm CVS treatment, suggesting that her vestibular system, due to dysfunction, is more immune to CVS (and thus she must treat more aggressively to gain benefit). A parent of the subject commented on a change in the subject's speech and "spirit" during phone conversations while using cold CVS. The switch to warm CVS resulted in additional mood and motivational elements. Colleagues commented on enhanced interpersonal interactions and an increased sense of confidence. The subject stated: "for the last couple of year I've felt as if my brain has burnt out, it feels so much better since the warm treatments."

Example 17

Vestibular Migraine Treatment in Male Patient

A male in his 40's developed sudden onset migraine with vestibular dysfunction that led to effective disability and inability to go to work. The subject was not helped by medications and sought the advice of multiple physicians at two prominent academic research hospitals. The subject was treated on a near daily basis for 10-20 minutes a day with cold CVS (down to 20 degrees Centigrade) CVS before switching to warm CVS, with a maximum temperature of 42 degrees Centigrade. The subject, like the subject in example 16, did not experience dizziness with the introduction of warm CVS treatments, possibly associated with the vestibular dysfunction accompanying his migraines. CVS treatments are soporific for this patient. The subject's wife notes a pronounced change since CVS treatments were started. Whereas prior to CVS treatment the subject was loath to get out of bed, since CVS treatment the subject has returned to part-time work with his employer.

Example 18

Treatment of Diabetic Patient with Warm Sawtooth Stimulation

The same subject described in example 9 switched from cold CVS to warm CVS for the control of his type II diabetes. He treated with a sawtooth waveform that oscillated between 34 and 43 degrees Centigrade. The average heating slew rate was typically above 40 degrees Centigrade/min and the average cooling slew rate was typically greater than 10 degrees Centigrade/min. Since commencing CVS therapy, the subject has stopped taking medications, which were previously necessary to maintain serum glucose near a normal range. At the time of diagnosis, the subject's Ale value was 9.8. At the time shown at the end of the chart below, that value was reduced to 5.6 (again, with no medications). Ale is viewed as a better long-term marker of diabetes control than serum glucose (it doesn't fluctuate). The normal range is about 4-6. For diabetics, the recommendation is that anything below 7 is a good target. A record of the subject's serum glucose readings (not shown) indicated possible additional improvement realized with the switch from cold to warm CVS in terms of reduced variability. The subject also had a gingival abscess during the period shown and such infections can lead to oxidative stress and impaired glucose control (see generally J. Southerland et al., Diabetes and Periodontal Infection: Making the Connection, *Clinical Diabetes* 23, 171-178 (2005)). The infection did not disrupt the subject's glucose maintenance.

Glucose readings taken at 7 AM and 10 PM; CVS treatment in evening. Treatment 1: 34 to 17 degree C. sawtooth waveform, 20 minute duration. Treatment 2: 34 to 43 degree C. sawtooth waveform, two 20 minute treatment per day. Glucose levels are more controlled with treatment 2. No other diabetes medications were in use during the testing period. The subject reported that the warm sawtooth CVS differed slightly from the cold sawtooth CVS in that it appeared to have increased potency as noted by the feeling of increased dizziness and mild nausea, which appear consistently with each treatment. Glucose levels tend to drop 10-30 points approximately 60 minutes or more after the treatment. The subject reported that combining exercise in proximity to the TNM therapy appeared to cause a glucose decrease of 30 to 50 points.

Example 19

Treatment of PTSD Patient

A male in his mid 60's was wounded three times as a Medic in Vietnam and had a history of post-traumatic stress disorder. His manner is described as introverted and his mood depressive. After the commencement of cold CVS treatments, the subject's wife reported that he started becoming more extroverted. She reported that "she did not know who this person was speaking to her this morning"; that he was planning getting together with friends; that usually he would only do this if forced; that he expressed interest in going to Africa for a photo safari; that she started thinking "where is my husband?" After a second treatment, the subject reported continuous sleep throughout the night (usually he would usually wake up 3-4 times). He commented that "insomniacs should use this." The subject reported feeling energized. The subject was usually unable to recall dreams, but awoke with visual flashback of events in Vietnam, not unpleasant just old visual memories, and returned to sleep. The subject traditionally avoided driving but now is driving with substantially less hesitation. The subject is a serious amateur painter and both the subject and his spouse report significant positive developments in his painting style and productivity since commencement of his CVS. Upon interruption of CVS therapy, PTSD symptoms gradually returned almost to baseline one week after CVS stopped.

Example 20

Treatment of Diabetes in a PTSD Patient

The patient of example 19 has type II diabetes. After the commencement of CVS therapy he became much more responsive to oral hypoglycemics, has had to cut dose significantly (data not shown).

Example 21

Alternative Waveforms in Treatment of Diabetes and Cluster Headaches

The patient described in example 18 above was administered three different waveform CVS stimuli, as follows:
A: Cooling, by approximately 22-23 degrees, with a spike waveform for 10 minutes with a contiguous repeat for an additional 10 minutes.
B: Heating, to approximately 42-43 degrees, with a spike waveform for 10 with a contiguous repeat for an additional 10 minutes.
C: Cooling, to approximately 22-23 degrees, with a spike waveform for 10 minutes as illustrated in connection with A above, followed immediately by heating, to approximately 42-43 degrees, with a spike waveform for 10 minutes as illustrated in connection with "B" above.
The treatments seemed to have a bimodal pattern of efficacy based upon cooling or heat cycles. Both modes seem to induce a sense of motion and mild nausea associated with enhanced therapeutic efficacy for the treatment of cluster headaches and the stabilization of type II diabetes in this subject. Pattern A appeared to be the most efficacious. Increasing cycle times to thirty minutes does not appear to confer an additional benefit.

Example 22

Induction of Prolonged Nystagmus by Waveform CVS

Nystagmus is the name given to involuntary eye movements enabled by the so-called vestibulo-ocular reflex (VOR). CVS provides an artificial means to activate the VOR. By tilting the head (~20 degrees above the horizontal), the horizontal SCC is placed in a vertical orientation. Creating a differential temperature across this canal results in convection currents that act to displace the cupula. Warm CVS leads to cupular displacement such that the phasic firing rate increases whereas cold CVS leads to a decrease in the firing rate. Further, warm CVS results in nystagmus that is manifested by a rapid movement of the eyes towards the simulated ear. Cold CVS results in the rapid phase of nystamus away from the stimulated ear. Therefore, by noting the existence and the direction of nystagmus, one may determine that the VOR is being activated and whether the phasic firing rate is greater than or less than the tonic firing rate.

The use of continuous CVS irrigation or stimulation at a constant temperature will induce nystagmus, but after a time on the order of 2-3 minutes (e.g., Bock et al., *Vestibular adaptation to long-term stimuli*, BIOL. CYBERNETICS 33:77-79 (1979)), the cupula will adapt to its new, displaced position and the phasic firing rate will return to the tonic rate. Thus nystagmus will effectively cease and the vestibular nerve afferents will no longer be stimulated.

It is an aspect of the current invention that the use of time-varying thermal waveforms enables the persistent stimulation of the vestibular nerve afferents, beyond the time period at which adaptation to a constant thermal stimulus occurs. In this example, the present invention has been used to generate nystagmus over a 12 minute period as measured by videonystagmography and by electronystagmography. A sawtooth cooling waveform going between temperatures of 34 to 20 degrees Centigrade was applied to the right ear of a subject who was reclined such that his head was ~20 degrees above the horizontal. Electronystagmography was used to measure the movement of his eyes, and demonstrated the existence of nystagmus both early in a 12 minute period and near the end of the 12 minute period (data not shown).

Example 23

Effect of CVS on Regional Cerebral Blood Flow (rCBF)

The purpose of this Example is to find a robust marker of successful CVS induction of relevance to neurological treatments. The study is being performed on rats using a modified version of a dual ear CVS unit. Specifically, ear bars that are connected to TEC's are placed in the ear canals of rats that have been anesthetized. The device has dual ear stimulation capability.

Methods and Results: Single Ear CVS:
Rat #9 received a sawtooth waveform in the right ear that oscillated between 36 and 14 degrees Centigrade for 60 minutes (not shown). The rat was anesthetized with isoflurane. It should be noted that anesthesia may lessen the effects of CVS to a degree. The rat was oriented horizontally, which places the horizontal semicircular canal in the vestibular bodies at a roughly 30 degree tilt upwards on the anterior side. After the end of the 60 minute right ear stimulation, the same caloric waveform was then applied to the left ear. The response of the regional cerebral blood flow was measured on the right parietal region of the skull via a laser Doppler probe affixed to the skull. Roughly 30 minutes after the start of right ear CVS, the oscillation in blood flow became pronounced. The period of the sawtooth temperature waveform is 1.9 minutes. As observed (using nearest neighbor averaging), the period of the modulation in blood flow is longer, by about 30 seconds on average (data not shown). This suggests that the driving force (the CVS) leads to modulation of the blood flow via a mechanism that stays in a non-equilibrium state. That is, the rat's response does not simply match the period of the CVS waveform and is instead adapting to it dynamically. At the end of right ear CVS, the oscillations stop. Roughly 35-40 minutes after the start of left ear CVS, clear oscillations once again appear, though diminished in amplitude relative to right ear stimulation. This is presumably due to the fact that left ear stimulation has a weaker effect on blood flow in the right portion of the brain. Serrador et al. (*BMC Neuroscience* 10, 119 (2009)) note that "connections have been found between the vestibular nuclei and the fastigial nucleus . . . followed by vasodilatory connections to the cerebral vessels."

Control Run:

The Vestibular stimulation device was placed on the rat, but was not activated. No oscillations in rCBF were seen (the downward drift in the flow data is due to a slight shift in the baseline of the probe).

Dual Ear, Same Waveform:

Rat #12 had CVS delivered to both right and left ears simultaneously (not shown). The waveforms were not tied in phase and tended to become out of phase during the bulk of the 60 minute treatment period. No modulations in rCBF were manifested (data not shown).

The dual ear stimulation data suggest that the application of the same waveform to both ears simultaneously acted to cancel out any net modulatory effect on rCBF. However, it is still the case that the same stimulation was given to the vestibular nuclei as when only single ear CVS was used. Nystagmus, would also not appear if the same CVS stimulation were applied to both ears since the phenomenon, mediated by the vestibulo-ocular reflex (VOR), requires a differential input to the two horizontal SCC's. Thus the absence of rCBF modulation does not mean that the fastigial nuclei (both nuclei for dual ear CVS) are not being stimulated. Rather, their combined activation yields no net effect on rCBF. Since modulation of rCBF is not a necessary aspect of CVS induced neuroprotection (it is a marker of CVS induction), CVS therapy may actually be as or more effective with dual ear stimulation.

Dual Ear, Different Waveforms:

Run 17 simultaneously applied a 34 to 44 C sawtooth waveform to the right ear (period of ~40 seconds) and a 34 to 13 C sawtooth (period ~1.7 min) to the left ear (not shown). In this case, flow modulations were seen and they persisted well past the end of the CVS treatment period (not shown). In this case the flow effect, with different temperatures applied, not only was present but continued to oscillate after the end of the active CVS treatment.

Discussion:

The vestibular systems of all mammals act in the same way. Therefore, the results of the rat study discussed above have implications for human CVS therapy as well. The conclusion from the study is that the most likely cause of the modulation seen in rCBF is that CVS does stimulate the fastigial nucleus in the cerebellum.

Example 24

EEG in Rats as a Metric of CVS Efficacy

EEG is useful in identifying cortical activation associated with CVS. Therefore, EEG is useful as a non-invasive means to titrate CVS therapy. This report summarizes EEG data acquired in a rat study.

Methods and Results:

The report on regional cerebral blood flow changes in a rat during various CVS treatments has been generated. In this summary, EEG electrodes were placed in the scalp of the rat, differential pairs being applied on either side of the midline of the skull. (data not shown).

Discussion:

The activity observed in the theta band was markedly different between the 3 states. For the low flow state, activity was depressed. The high flow peaks were shifted to lower frequencies as compared to the baseline (pre-CVS). In the 0-40 Hz plot, the high and low flow peaks in the low-30 Hz range overlap whereas the baseline peak is shifted (this is likely due to a difference in somatosensory perception during CVS versus pre-CVS). The sensitivity of EEG spectra to the details of CVS delivery suggest that EEG is an effective tool for evaluating the difference between CVS waveforms and for titrating them.

Example 25

Heart Rate Variability (HRV) as a Metric of CVS Efficacy

Heart rate variability seems to be a significant marker of health and systems for measuring it non-invasively are becoming common. This report describes the use of the ithlete, a commercial HRV measurement instrument that runs as an smartphone software program, or "app."

Methods and Results:

The subject is a 40-45 year old male diagnosed with seasonal cluster headaches. The device used to measure HRV is the ithlete (HRV Fit Ltd., Hants UK)) which uses an iPhone as the recording/readout device and a chest strap with sensors that monitor heart rate. The HRV parameter is calculated via a proprietary algorithm that takes the raw heart rate data as input. Note: of course there are many devices that will measure HRV and the ithlete was chosen only as a low cost and convenient system. Proper HRV is used as a metric of proper cardiac health (good health implies adequately high HRV; e.g., Malik, *Heart rate variability: standards of measurement, physiological interpretation, and clinical use*, EUR. HEART J. 17:354 (1996)). For example, Gujjar et al. have linked HRV and outcomes after acute severe stroke ("Heart rate variability and outcome in acute severe stroke," Neurocritical Care, vol. 1, pg. 347, 2004).

The CVS treatment was a 42 degrees Centigrade sawtooth wave applied to the left ear and a 17 degrees Centigrade sawtooth applied to the right ear. The treatment lasted for 10 minutes. HRV data were recorded immediately after the end of the treatment. HRV is a dimensionless measure. During the October $24^{th}$ test, average HRV dropped by 30% and on October $28^{th}$ by 27% (data not shown).

Discussion:

HRV is proposed as a marker of effective CVS induction and could thus be used as a tool for titrating CVS dosing. Pathological conditions (such as cluster headaches discussed here) can lead to elevated HRV levels. Other pathological conditions, e.g., cardiac insufficiencies, are often associated with abnormally low HRV values (for that individual).

Example 26

Treatment of Fibromyalgia

A subject (also female, age 50-55) was diagnosed with fibromyalgia 3 years ago. Multiple allopathic and homeopathic interventions provided no substantive relief. The subject has co-morbid migraine headaches.

Methods and Results:

The subject underwent CVS treatment in the right ear, with a 17 degree C. sawtooth waveform.

From September 13-19 the subject stopped CVS treatment due to significant pain and inability to function. On September 20 the subject began treatments twice per day, sometimes using a $3^{rd}$ daily treatment using the CVS parameters listed above. She realized an improvement in both migraine pain and pain from fibromyalgia. In the September 28-30 timeframe thunderstorms seemed to trigger additional migraine pain, but this abated over the following days until her pain level was barely noticeable.

The subject commented upon starting twice-a-day treatments: "I'm writing to report excellent results using 2 treatments. Last night I tried 2 consecutive treatments, and I felt great! Like I'd been to a spa and had a relaxing massage and soak in the hot tub."

The subject reported on September $26^{th}$: "This weekend I was able to work with [husband] getting 14 new bushes in the yard and picking out new paint at Lowe's to repaint the shutters on the house. I'm so very hopeful and happy. Gardening is a shared passion for us, and the first two years here, I wasn't able to even water the plants, so the ones left are real survivors! I feel like you are giving me my life back, and giving [husband] his wife back."

When the subject's spouse was asked if the Vestibular stimulation device was truly helpful he responded: "Nothing in the last 3 years had helped before this."

After October 6, the unit was retrieved. The subject has since returned to baseline.

Example 27

Treatment of Peripheral Neuropathy

A female subject underwent spinal surgery and sustained damage to the spinal cord. Thereafter she has had intractable peripheral neuropathy (foot pain) over a roughly 4 month period that had not responded to analgesics. The subject has obtained relief using CVS, with the extent and duration of relief depending on the device used and the waveform details.

Methods and Results:

The subject underwent CVS treatment with the following chronology:

i. Dual ear CVS unit: L-ear, sawtooth, 34 to 20 degrees Centigrade; R-ear, sawtooth, 34 to 42 degrees Centigrade, 10 min. therapy. The treatment made her very sleepy (deep sleep for 20 min). Within 30 minutes, she was pain free and stayed so for 3 days, which was extraordinary for her.

ii. Single (right) ear CVS unit, sawtooth, 34 to 17 degrees Centigrade, 10 min therapy. She realized about a 50% reduction in pain level that lasted around 2 hours.

iii. Single (right) ear CVS unit, long (single rise) square wave, 34 to 48 degrees Centigrade, 10 min. She finds that the single ear, warm treatment is better than single ear, cold treatment. She must use the device several times a day to achieve pain relief.

iv. Dual ear CVS unit, L-ear 17 degrees Centigrade square wave, R-ear 44 degrees Centigrade sawtooth, 10 min. Deep sleep for 45 min (at 5 PM). Foot pain ceased.

Discussion:

The subject received extended (multiple day) pain relief from one 10 min session using dual ear CVS. Single ear CVS, using a sawtooth waveform (slower slew rate) and an early device (basically a single cold/warm square wave), led to partial pain reduction for a time limited to hours. Therefore, the dual ear CVS treatment was superior to single ear for pain reduction. This subject and another have stated that the mixed waveform, dual ear (e.g., example 4) results in more significant subjective sensations (deep relaxation/sleep for this subject, increased nausea for the other). It is unclear with this single case if the mixed waveform treatment leads to increased pain reduction efficacy (both dual ear treatments were significant).

Example 28

Single Ear Treatment of Episodic Migraine

This Example evaluates the feasibility of using a portable CVS unit in a home setting over a month or more. The hypothesis was that daily CVS treatment would reduce the overall pain level and frequency of headaches.

Methods and Results:

The subject is a 50-55 year old female with a history of 6-8 migraine headache days per month (a month is taken as 28 days when reporting on migraine frequency). The subject used a right-ear Vestibular stimulation device and a sawtooth waveform that went from 34 degrees Centigrade to 17 degrees Centigrade with a period of roughly 1.7 minutes. The duration of the treatment was 10 minutes per session (daily sessions, moving to every other day after about 2 weeks of treatment). The average slew rate for heating was 40 degrees Centigrade/minute and the average slew rate for cooling was 14 degrees Centigrade/minute.

The subject experienced a decrease in pain over the first week of therapy. (pain score data not shown). In the 40 days past the one week transitionary period, the subject had only one migraine headache (again, to qualify as a migraine it must be at a pain level of 6 or more on a scale of zero to ten and last for 4 hours or more). The one headache occurred during unusual stress associated with a transatlantic trip and disruption of work schedule upon her return. The subject also noted a subjective improvement in co-morbid depression over the treatment period.

Example 29

Titration of CVS Therapy for Type II Diabetes

The intent of this report is to show experimental evidence of the control of glucose levels by adjusting the frequency with which CVS is used in a subject with type II diabetes.

Methods and Results:

The subject is a 40-45 year old male diagnosed with type II diabetes within the last two years. As reported earlier, the subject has been able to forego the use of medications to control serum glucose levels, using CVS therapy instead. Recently, the subject has started using dual ear CVS, with a warm time-varying waveform applied to one ear and a cold time-varying waveform applied to the other. The dual ear therapy reduced the frequency with which the subject needed to use CVS in order to control serum glucose levels (data not shown). Dual ear CVS was used with a 17 degrees Centigrade square wave for the right ear and a 42 degrees Centigrade sawtooth on the left ear. Each point in the graph represents a daily measurement (consistent time during each day). The red lines show when CVS was used. As the glucose levels were tracked, they would tend to move up in between CVS treatments, thus signaling when another treatment should be applied. This feedback method should be able to be extended to other patients, using their specific glucose levels to titrate frequency and intensity of CVS treatments. This subject remains off any other medications to control glucose levels.

Discussion:

This is an update report to supplement accounts from this subject already included in the Examples above, and further shows that serum glucose is a useful metric for CVS titration.

Example 30

CVS Intensity for Different Waveforms

As the CVS treatment device has evolved, we have moved from single to dual ear stimulation and have increased the slew rate to allow waveforms to be played out at a higher frequency. This report lists subjective metrics that can be used to assess the strength of CVS stimulation for a given subject.

Methods and Results:

The subject is a 40-45 year old male using CVS therapy chronically for type II diabetes and seasonal cluster headaches. He ranks the level of intensity of the CVS experience as follows:

single ear:
  daily treatments were required to control cluster headaches and serum glucose levels typical treatment is a cold sawtooth wave going between 34 and 17 degrees Centigrade
dual ear, same waveform shape, warm and cold:
only 1-3 treatments per week are needed to control cluster headaches and serum glucose
  typical waveform is a sawtooth going from 34 to 42-44 degrees Centigrade in one ear and 34 to 17 degrees Centigrade in the other ear.
Not much subjective difference compared with single ear during treatment
  More pronounced dizziness upon standing
  Nausea more persistent
  Faster, more complete responses for increased pain level
  Blurred vision for 3-5 minutes (possibly nystagmus)
dual ear, different waveform shape, warm and cold:
only 1-3 treatments per week are needed to control cluster headaches and serum glucose
  typical waveform is a sawtooth going from 34 to 42-44 degrees Centigrade in one ear and a square wave in the other ear going from 34 to 17-20 degrees Centigrade.
  most potent of all types tried in terms of pain mitigation and positive mood effects (side effects do not outweigh additional benefits)
    ii. sleep inducing
    iii. nausea while in horizontal position
    iv. significant nausea and brief period of poor postural control upon standing
    v. persistent feeling of head fullness Discussion:

The most significant metrics for CVS therapy for pain patients is its effects on pain level and relative side effects. This report recounts observations by one subject that can serve as a paradigm for how other patients can be assessed in the clinic. The right titration will involve an on-going assessment of effects on symptoms (e.g., pain) and minimization of unwanted, lasting side effects (for clarity, the side effects reported above are transient). There are tradeoffs that patients can make between efficacy with more intense side effects balanced against less frequent need to treat.

The following parameters can be varied in a dual ear system:
  temperature (magnitude and sign with respect to body temperature);
  waveform shape;
  frequency of waveform(s); if they are different frequencies, they could be commensurate and beat frequencies could be established;
  relative phase of waveforms (e.g., in phase or some degree of being out of phase if they have the same frequency); and
  variable frequency during the course of a treatment (each side).

The Vestibular stimulation device can be programmed, in principal, to play out a different combination every day, thus frustrating any tendency of the VS of the patient to adapt to a given therapeutic waveform. This is a principal advantage of dual ear over single ear CVS.

Example 31

Treatment of Sleep Disorders/Insomnia with CVS

A common report from users of the Vestibular stimulation device is that they have beneficial effects in terms of sleeping soundly. It is known (e.g., Horii et al., J. NEUROPHYSIOL. 70:1822 (1993)) that CVS does activate the hypothalamus. The hypothalamus in turn controls the sleep/wake cycle in mammals.

Methods and Results:

The reports of the soporific effects of CVS with subjects is variable and subjective. Listing the claims by subjects in order of frequency:
  i. a relaxed feeling right after the completion of a CVS treatment;
  ii. report of having an exceptionally complete sleep cycle on the night following a CVS treatment; and
  iii. a very powerful soporific effect that resulted in the subject falling asleep during a 10-20 minute CVS treatment and staying asleep for up to several hours.

Examples of Each of the Observations Listed Above:
  iv. A small pilot clinical trial was performed at a private headache clinic on patients who were being treated for migraine headache. The CVS waveform used was a sawtooth, right ear only, with the temperature oscillating between 34 and 17 degrees Centigrade. None of the subjects fell asleep during the 10 minute CVS treatment, but commonly reported being relaxed in a way that was greater than what they would feel when lying down, in a similar position, for the same amount of time.
  v. A male, age 50-55 acting as a normal test subject used single ear (right) CVS, sawtooth waveform oscillating between 34 and 17 degrees Centigrade. He reported pleasant drowsiness after the 10 minute therapy session and then reported that he'd slept exceptionally soundly that night.
  vi. A subject using CVS for foot pain (see previous Example on this subject) used a dual ear Vestibular stimulation device: L-ear, sawtooth, 34 to 20 degrees Centigrade; R-ear, sawtooth, 34 to 42 degrees Centigrade, 10 min. therapy. The treatment made her very sleepy (deep sleep for 20 min). Then again: dual ear, L-ear 17 degrees Centigrade square wave, R-ear 44 degrees Centigrade sawtooth, 10 min. Deep sleep for 45 min (at 5 PM) and had to be awakened.

In all cases, subjects reported restful sleep versus "forced" sleep and they reported no ill side effects.

Example 32

Single Ear CVS Treatment of Pediatric Epilepsy

The intent with this study was to evaluate using the Gen 2.0 CVS unit (left ear only, same earpiece but different (less powerful) TEC (thermoelectric cooler or Peltier cooler) than will be used in Gen 3 device) in a single session to observe any effects on spike activity in epileptic patients as monitored by EEG.

Methods and Results:

The subjects were treated with a sawtooth waveform that went from 34 degrees Centigrade to 17 degrees Centigrade (left ear only). Note that the actual temperature profile was not the same for all patients. For patient 3, the average slew rate on heating was around 14-15 degrees Centigrade/min and the cooling rate dropped from about 5.8 degrees Centigrade/min to 4.5 degrees Centigrade/min (not shown). It can be seen that more time was required to in the second "dip" to get to 17 degrees Centigrade. This is due to insufficient power in the Gen 2.0 Vestibular stimulation device.

For patient 4, the inadequate power of the unit is even more apparent. The average heating slew rate was about the same as with patient 3, but the cooling rate started at 4.2 degrees Centigrade/min and dropped to 3.6/min (not shown). The device failed to reach the 17 degrees Centigrade target temperature.

The spike rate was measured by continuous EEG before CVS treatment and after CVS treatment (data not shown). The decrease in spike rate lasted from 1-2 hours for each of the four patients. The reduction in spiking ranges from 21-32%.

Discussion:

despite the underperformance of the Gen 2.0 model, primarily caused by an older, less powerful TEC and the lack of a cooling fan on the heat sink, demonstrable effects were seen in all 4 patients in terms of a reduction in spike activity that persisted past the end of the CVS treatment session. At this time, we don't have the ability to try a more advanced device (e.g., Gen 2.5) with these patients. A logical course would be to treat the patients longitudinally to see if the effects of CVS could be made more lasting. Despite the challenge of performing CVS on this population (age range from 6-10 years old), it was accomplished and there were no side effects of the treatment.

The foregoing is illustrative of the present invention, and is not to be construed as limiting thereof. The invention is defined by the following claims, with equivalents of the claims to be included herein.

That which is claimed:

1. A vestibular stimulation device comprising:
   an earpiece;
   a thermoelectric device (TED) thermally coupled to said earpiece; and
   a controller operatively connected to said TED, said controller comprising:
   a prescription comprising a set of instructions for delivering one or more thermal waveforms to the vestibular system and/or the nervous system of a patient; and
   a control module configured to activate said TED to deliver the prescribed thermal waveform(s), wherein the prescribed thermal waveform(s) are configured to treat Parkinson's disease in a subject in need of treatment thereof.

2. The vestibular stimulation device of claim 1, wherein the one or more thermal waveforms are configured to maintain a vestibular stimulation that is sufficient to alter a vestibular phasic firing rate to thereby induce nystagmus over a period of more than three minutes.

3. The vestibular stimulation device of claim 1, wherein said set of instructions for delivering one or more thermal waveforms to at least one of the vestibular system and the nervous system of a patient is stored in a prescription database.

4. The vestibular stimulation device of claim 3, wherein said prescription database reside(s) in a device selected from the group consisting of a patient control device, a physician control device, a physician support device and a registry.

5. The vestibular stimulation device of claim 4, wherein said prescription database resides in a registry that comprises prescriptions from at least one of one or more physician control devices and one or more physician support devices.

6. The vestibular stimulation device of claim 3, wherein said waveform database reside(s) in a device selected from the group consisting of a patient control device, a physician control device, a physician support device and a registry.

7. The vestibular stimulation device of claim 1, wherein said vestibular stimulation device further comprises a sensor operatively connected to said controller, said sensor configured to transmit data associated with the temperature of the earpiece to said controller.

8. The vestibular stimulation device of claim 7, wherein said control module is configured to use said data associated with the temperature of the earpiece to ensure that the appropriate one or more thermal waveforms are delivered to the vestibular system and the nervous system of said patient.

9. The vestibular stimulation device of claim 8, wherein using said data associated with the temperature of the earpiece to ensure that the appropriate one or more thermal waveforms are delivered to at least one of the vestibular system and the nervous system of said patient comprises adjusting an activation signal used to drive said TED responsive to said data associated with the temperature of the earpiece.

10. The vestibular stimulation device of claim 9, wherein said sensor repeatedly transmits data associated with the temperature of the earpiece to said controller and wherein said controller repeatedly adjusts the activation signal used to drive said TED.

11. The vestibular stimulation device of claim 9, wherein said controller is configured to shut down if the temperature of the earpiece drops below a low temperature threshold or exceeds a high temperature threshold.

12. The vestibular stimulation device of claim 1, wherein said controller is configured such that the patient is prevented from at least one of modifying and deleting said prescription.

13. The vestibular stimulation device of claim 1, wherein the set of instructions for delivering one or more thermal waveforms comprising the prescription includes instructions for providing a plurality of spaced-apart treatment sessions over a defined period of time.

14. The vestibular stimulation device of claim 1, wherein the set of instructions for delivering one or more thermal waveforms comprising the prescription includes an expiration time after which the controller prohibits delivery of the one or more thermal waveforms.

15. A vestibular stimulation device comprising:
an earpiece;
a thermoelectric device (TED) thermally coupled to said earpiece; and
a controller operatively connected to said TED, said controller comprising:
    a prescription comprising a set of instructions for delivering one or more thermal waveforms to the vestibular system and/or the nervous system of a patient; and
    a control module configured to activate said TED to deliver the prescribed thermal waveform(s), wherein the prescribed thermal waveform(s) are configured to treat headache in a subject in need of treatment thereof.

16. A method of delivering one or more thermal waveforms to at least one of the vestibular system and the nervous system of a patient, comprising: generating a prescription comprising a set of instructions for delivering one or more thermal waveforms to at least one of the vestibular system and the nervous system of said subject; and delivering the prescribed thermal waveform(s) to at least one of the vestibular system and the nervous system of the patient using a vestibular stimulation device,), wherein the prescribed thermal waveform(s) are configured to treat Parkinson's in a subject in need of treatment thereof.

17. The method of claim 16, wherein the prescribed thermal waveforms are configured to maintain a vestibular stimulation that is sufficient to alter a vestibular phasic firing rate to thereby induce nystagmus over a period of more than three minutes.

18. A method of delivering one or more thermal waveforms to at least one of the vestibular system and the nervous system of a patient, comprising: generating a prescription comprising a set of instructions for delivering one or more thermal waveforms to at least one of the vestibular system and the nervous system of said subject; and delivering the prescribed thermal waveform(s) to at least one of the vestibular system and the nervous system of the patient using a vestibular stimulation device,), wherein the prescribed thermal waveform(s) are configured to treat headache in a subject in need of treatment thereof.

19. The method of claim 18, wherein the prescribed thermal waveforms are configured to maintain a vestibular stimulation that is sufficient to alter a vestibular phasic firing rate to thereby induce nystagmus over a period of more than three minutes.

20. The method of claim 18, wherein said vestibular stimulation device is a vestibular stimulation device according to claim 1.

* * * * *

UNITED STATES PATENT AND TRADEMARK OFFICE
CERTIFICATE OF CORRECTION

PATENT NO. : 10,478,331 B2
APPLICATION NO. : 15/379612
DATED : November 19, 2019
INVENTOR(S) : Rogers et al.

It is certified that error appears in the above-identified patent and that said Letters Patent is hereby corrected as shown below:

In the Specification

Column 160, Line 49: Please correct "nave" to read -- naïve --

Column 168, Line 31: Please correct "Ale" to read -- A1c --

Column 168, Line 33: Please correct "Ale" to read -- A1c --

Signed and Sealed this
First Day of September, 2020

Andrei Iancu
*Director of the United States Patent and Trademark Office*